(12) United States Patent
Rosen et al.

(10) Patent No.: US 7,906,119 B1
(45) Date of Patent: *Mar. 15, 2011

(54) ANTIBODIES AGAINST PROTECTIVE ANTIGEN

(75) Inventors: Craig A. Rosen, Pasadena, MD (US); Michael W. Laird, San Ramon, CA (US); Reiner L. Gentz, Belo Horizonte (BR)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/421,139

(22) Filed: Apr. 9, 2009

Related U.S. Application Data

(63) Continuation of application No. 10/602,727, filed on Jun. 25, 2003, now Pat. No. 7,601,351.

(60) Provisional application No. 60/391,162, filed on Jun. 26, 2002, provisional application No. 60/406,339, filed on Aug. 28, 2002, provisional application No. 60/417,305, filed on Oct. 10, 2002, provisional application No. 60/426,360, filed on Nov. 15, 2002, provisional application No. 60/434,807, filed on Dec. 20, 2002, provisional application No. 60/438,004, filed on Jan. 6, 2003, provisional application No. 60/443,858, filed on Jan. 31, 2003, provisional application No. 60/443,781, filed on Jan. 31, 2003, provisional application No. 60/454,613, filed on Mar. 17, 2003, provisional application No. 60/468,651, filed on May 8, 2003.

(51) Int. Cl.
*A61K 39/395* (2006.01)
*C07K 16/00* (2006.01)

(52) U.S. Cl. ............... 424/141.1; 424/150.1; 530/388.4

(58) Field of Classification Search .................. None
See application file for complete search history.

(56) References Cited

U.S. PATENT DOCUMENTS

| | | | |
|---|---|---|---|
| 5,525,338 A | 6/1996 | Goldenberg |
| 5,591,631 A | 1/1997 | Leppla et al. |
| 5,604,201 A | 2/1997 | Thomas et al. |
| 5,650,154 A | 7/1997 | Meeusen et al. |
| 5,677,274 A | 10/1997 | Leppla et al. |
| 5,698,405 A | 12/1997 | Goldenberg |
| 5,792,462 A | 8/1998 | Johnston et al. |
| 5,840,312 A | 11/1998 | Mock et al. |
| 5,846,741 A | 12/1998 | Griffiths et al. |
| 6,022,855 A | 2/2000 | Thomas et al. |
| 6,156,558 A | 12/2000 | Johnston et al. |
| 6,180,356 B1 | 1/2001 | London et al. |
| 6,224,870 B1 | 5/2001 | Segal |
| 6,267,966 B1 | 7/2001 | Baillie |
| 6,316,006 B1 | 11/2001 | Worsham et al. |
| 6,329,156 B1 | 12/2001 | Cirino et al. |
| 6,348,450 B1 | 2/2002 | Tang et al. |
| 6,387,665 B1 | 5/2002 | Ivins et al. |
| 6,432,409 B1 | 8/2002 | Humphreys et al. |
| 6,436,933 B1 | 8/2002 | Rideout et al. |
| 6,448,016 B1 | 9/2002 | Rastogi et al. |
| 6,495,143 B2 | 12/2002 | Lee et al. |
| 6,503,906 B1 | 1/2003 | Lee |
| 6,521,235 B2 | 2/2003 | Johnston et al. |
| 6,531,135 B1 | 3/2003 | Johnston et al. |
| 6,541,010 B1 | 4/2003 | Johnston et al. |
| 6,569,630 B1 | 5/2003 | Vivekananda et al. |
| 6,592,872 B1 | 7/2003 | Klimpel et al. |
| 6,632,436 B2 | 10/2003 | Segal |
| 6,632,640 B1 | 10/2003 | Lee et al. |
| 6,706,963 B2 | 3/2004 | Gaudiana et al. |
| 6,716,823 B1 | 4/2004 | Tang et al. |
| 6,770,479 B1 | 8/2004 | Lee et al. |
| 6,828,110 B2 | 12/2004 | Lee et al. |
| 6,884,588 B1 | 4/2005 | Rastogi et al. |
| 6,913,756 B1 | 7/2005 | Kearney |
| 6,916,474 B2 | 7/2005 | Harvey et al. |
| 6,916,479 B2 | 7/2005 | Embrechts et al. |
| 6,962,702 B2 | 11/2005 | Hansen et al. |
| 6,979,449 B1 | 12/2005 | Mock |
| 7,037,503 B2 | 5/2006 | Collier et al. |
| 7,052,872 B1 | 5/2006 | Hansen et al. |
| 7,074,405 B1 | 7/2006 | Hansen et al. |
| 7,074,913 B2 | 7/2006 | Young et al. |
| 7,083,945 B1 | 8/2006 | Chen et al. |
| 7,094,571 B2 | 8/2006 | Harvey et al. |
| 7,097,965 B2 | 8/2006 | Klimpel et al. |
| 7,138,103 B2 | 11/2006 | Goldenberg et al. |
| 7,176,275 B2 | 2/2007 | Bogoch et al. |
| 7,179,645 B2 | 2/2007 | Humphreys et al. |
| 7,189,800 B2 | 3/2007 | Bogoch et al. |
| 7,201,912 B2 | 4/2007 | Park et al. |
| 7,205,274 B2 | 4/2007 | Humphreys et al. |
| 7,235,235 B2 | 6/2007 | Johnston et al. |
| 7,252,993 B2 | 8/2007 | Keener |
| 7,261,900 B2 | 8/2007 | Leppla et al. |

(Continued)

FOREIGN PATENT DOCUMENTS

EP    0 934 953 A2    8/1999

(Continued)

OTHER PUBLICATIONS

"Anthrax," Internet publication by National Organization of Rare Disorders (NORD), 2001.
"Anthrax: Current, comprehensive information on pathogenesis, microbiology, epidemiology, diagnosis, treatment, and prophylaxis," published by Center for Infectious Disease Research & Policy (CIDRAP) Academic Health Center—University of Minnesota (Jul. 23, 2003).
"Anthrax", Chapter 19 of *Epidemiology & Prevention of Vaccine-Preventable Diseases*, Centers for Disease Control and Prevention, 7th ed., Washington, DC: Public Health Foundation, 2002.

(Continued)

*Primary Examiner* — Patricia A Duffy

(57) ABSTRACT

The present invention relates to antibodies and related molecules that specifically bind to protective antigen of *Bacillus anthracis* (PA). Such antibodies have uses, for example, in the prevention and treatment of anthrax and anthrax toxin poisoning. The invention also relates to nucleic acid molecules encoding anti-PA antibodies, vectors and host cells containing these nucleic acids, and methods for producing the same.

44 Claims, 7 Drawing Sheets

U.S. PATENT DOCUMENTS

| | | | |
|---|---|---|---|
| 7,282,580 B2 | 10/2007 | Singh et al. |
| 7,329,738 B1 | 2/2008 | Lee et al. |
| 7,355,027 B2 | 4/2008 | Brehm et al. |
| 7,374,888 B2 | 5/2008 | Valkirs et al. |
| 7,387,772 B1 | 6/2008 | Hansen et al. |
| 7,405,320 B2 | 7/2008 | McBride et al. |
| 7,414,121 B2 | 8/2008 | Hansen et al. |
| 7,420,028 B2 | 9/2008 | Bogoch et al. |
| 7,429,381 B2 | 9/2008 | Hansen et al. |
| 7,438,909 B2 | 10/2008 | Morrow et al. |
| 7,442,373 B2 | 10/2008 | Morrow et al. |
| 7,442,761 B2 | 10/2008 | Bogoch et al. |
| 7,452,963 B2 | 11/2008 | Bogoch et al. |
| 7,456,264 B2 | 11/2008 | Keler et al. |
| 7,491,404 B2 | 2/2009 | Mock |
| 7,504,202 B2 | 3/2009 | Cullum et al. |
| 7,504,425 B2 | 3/2009 | Xiong et al. |
| 7,541,334 B2 | 6/2009 | Humphreys et al. |
| 7,560,110 B2 | 7/2009 | Goldenberg et al. |
| 7,563,439 B2 | 7/2009 | Hansen et al. |
| 7,601,351 B1 | 10/2009 | Rosen et al. |
| 7,611,866 B2 | 11/2009 | Georgiou et al. |
| 7,618,783 B2 | 11/2009 | Mangold et al. |
| 7,674,880 B2 | 3/2010 | Bogoch et al. |
| 2001/0031264 A1 | 10/2001 | Segal |
| 2002/0034512 A1 | 3/2002 | Ivins et al. |
| 2002/0039588 A1 | 4/2002 | Collier et al. |
| 2002/0048590 A1 | 4/2002 | Klimpel et al. |
| 2002/0051791 A1 | 5/2002 | Galloway et al. |
| 2002/0082386 A1 | 6/2002 | Mangold et al. |
| 2002/0120106 A1 | 8/2002 | Bogoch et al. |
| 2002/0142002 A1 | 10/2002 | Galloway et al. |
| 2002/0197272 A1 | 12/2002 | Galloway et al. |
| 2003/0003109 A1 | 1/2003 | Galloway et al. |
| 2003/0059937 A1 | 3/2003 | Ruben et al. |
| 2003/0118591 A1 | 6/2003 | Levy |
| 2003/0198595 A1 | 10/2003 | Goldenberg et al. |
| 2003/0235594 A1 | 12/2003 | Humphreys et al. |
| 2004/0009178 A1 | 1/2004 | Bowdish et al. |
| 2004/0009182 A1 | 1/2004 | Myers et al. |
| 2004/0014707 A1 | 1/2004 | Cirino et al. |
| 2004/0028695 A1 | 2/2004 | Park et al. |
| 2004/0058881 A1 | 3/2004 | Humphreys et al. |
| 2004/0166120 A1 | 8/2004 | Thomas et al. |
| 2004/0170967 A1 | 9/2004 | Lee et al. |
| 2004/0171121 A1 | 9/2004 | Leppla et al. |
| 2004/0235136 A1 | 11/2004 | Singh et al. |
| 2004/0258699 A1 | 12/2004 | Bowdish et al. |
| 2005/0106647 A1 | 5/2005 | Harvey et al. |
| 2005/0123900 A1 | 6/2005 | Dimitrov et al. |
| 2005/0136049 A1 | 6/2005 | Ledbetter et al. |
| 2005/0267294 A1 | 12/2005 | Harvey et al. |
| 2005/0281830 A1 | 12/2005 | Morrow et al. |
| 2005/0287149 A1 | 12/2005 | Keler et al. |
| 2006/0002947 A1 | 1/2006 | Humphreys et al. |
| 2006/0121045 A1 | 6/2006 | Iverson et al. |
| 2007/0020281 A1 | 1/2007 | Kearney |
| 2007/0065913 A1 | 3/2007 | Chen et al. |
| 2007/0099267 A1 | 5/2007 | Harvey et al. |
| 2007/0259387 A1 | 11/2007 | Kearney |
| 2008/0305122 A1 | 12/2008 | Humphreys et al. |
| 2009/0110700 A1 | 4/2009 | Mock |
| 2009/0202553 A1 | 8/2009 | Morrow et al. |

FOREIGN PATENT DOCUMENTS

| | | |
|---|---|---|
| EP | 1 382 615 A1 | 1/2004 |
| GB | 2 400 851 A | 10/2004 |
| WO | WO-94/16073 A3 | 7/1994 |
| WO | WO94/18332 A2 | 8/1994 |
| WO | WO-96/37616 A1 | 11/1996 |
| WO | WO-98/11914 A1 | 3/1998 |
| WO | WO-99/08713 A1 | 2/1999 |
| WO | WO-99/36507 A1 | 7/1999 |
| WO | WO-99/45391 A1 | 9/1999 |
| WO | WO-99/55842 A1 | 11/1999 |
| WO | WO99/57266 A2 | 11/1999 |
| WO | WO00/02522 A3 | 1/2000 |
| WO | WO-00/02523 A2 | 1/2000 |
| WO | WO-00/02524 A2 | 1/2000 |
| WO | WO-00/66179 A1 | 11/2000 |
| WO | WO-01/21193 A1 | 3/2001 |
| WO | WO01/45639 A2 | 6/2001 |
| WO | WO-01/49823 A3 | 7/2001 |
| WO | WO01/58956 A2 | 8/2001 |
| WO | WO01/82788 A3 | 11/2001 |
| WO | WO-01/83561 A3 | 11/2001 |
| WO | WO02/04646 A1 | 1/2002 |
| WO | WO-02/34886 A3 | 5/2002 |
| WO | WO-02/056910 A1 | 7/2002 |
| WO | WO 02/096467 A2 | 12/2002 |
| WO | WO-02/100340 A2 | 12/2002 |
| WO | WO03/010316 A1 | 2/2003 |
| WO | WO-03/070920 A1 | 8/2003 |
| WO | WO-03/076568 A3 | 9/2003 |
| WO | WO03/087129 A2 | 10/2003 |
| WO | WO03/087378 A1 | 10/2003 |
| WO | WO-03/092630 A3 | 11/2003 |
| WO | WO2004/002415 A2 | 1/2004 |
| WO | WO2004/003139 A2 | 1/2004 |
| WO | WO2004/024067 A2 | 3/2004 |
| WO | WO-2004/030616 A3 | 4/2004 |
| WO | WO2004/037861 A2 | 5/2004 |
| WO | WO-2004/041864 A3 | 5/2004 |
| WO | WO2004/056874 A2 | 7/2004 |
| WO | WO2004/072117 A2 | 8/2004 |
| WO | WO-2004/110362 A3 | 12/2004 |
| WO | WO2004/113522 A1 | 12/2004 |
| WO | WO2005/000884 A1 | 1/2005 |
| WO | WO2005/004791 A2 | 1/2005 |
| WO | WO2005/007804 A2 | 1/2005 |
| WO | WO-2005/017148 A1 | 2/2005 |
| WO | WO-2005/019409 A3 | 3/2005 |
| WO | WO-2005/023177 A3 | 3/2005 |
| WO | WO2005/034841 A2 | 4/2005 |
| WO | WO-2005/056052 A1 | 6/2005 |
| WO | WO-2005/095988 A3 | 10/2005 |
| WO | WO-2006/076410 A3 | 7/2006 |
| WO | WO-2006/137938 A2 | 12/2006 |

OTHER PUBLICATIONS

"Summary of Notifiable Diseases—United States, 2001," in *Morbidity & Mortality Weekly Report*, published by Centers for Disease Control & Prevention, 50(53):1-108 (May 2, 2003) (selected pages).

"Suspected Cutaneous Anthrax in a Laboratory Worker—Texas, 2002," in *Morbidity & Mortality Weekly Report*, published by Centers for Disease Control & Prevention, 51(13):279-281 (Apr. 5, 2002).

"The Anthrax Vaccine: Is It Safe? Does It Work?," Joellenbeck et al., eds., Committee to Assess the Safety and Efficacy of the Anthrax Vaccine, Medical Follow-Up Agency, Institute of Medicine, National Academy Press, Washington, D.C. (Mar. 2002) (4 pp).

"Update: Investigation of Bioterrorism-Related Anthrax and Interim Guidelines for Clinical Evaluation of Persons with Possible Anthrax," in *Morbidity & Mortality Weekly Report*, published by Centers for Disease Control & Prevention, 50(43):941-948 (Nov. 2, 2001).

Abramova et al., "Pathology of inhalational anthrax in 42 cases from the Sverdlovsk outbreak of 1979," *Proc. Natl. Acad. Sci. USA*, 90:2291-2294 (Mar. 1993).

Anthrax Fact Sheet. Internet publication by Office of Communications & Public Liaison, National Institute of Allergy and Infectious Diseases (May 2002).

Athamna et al., "In vitro susceptibility of *Bacillus anthracis* to various antibacterial agents and their time-kill activity," *J. Antimicrobiol. Chemother.*, 53:247-251 (2004).

Barakat et al., "Fatal Inhalational Anthrax in a 94-Year-Old Connecticut Woman," *JAMA*, 287:863-868 (Feb. 20, 2002).

Barnard, et al., "Vaccination against Anthrax with Attenuated Recombinant Strains of *Bacillus anthracis* That Produce Protective Antigen," *Infect. Immun.*, 67:562-567 (Feb. 1999).

Beauregard et al., "Proteolytic activation of receptor-bound anthrax protective antigen on macrophages promotes its internalization," *Cell. Microbiol.*, 2:251-258 (2000).

BioPort, Inc., Anthrax Vaccine Adsorbed (Biothrax™) Product Insert (Jan. 31, 2002).
Bohannon, John, "From Bioweapons Backwater to Main Attraction," *Science*, 300:414-415 (Apr. 18, 2003).
Bradley et al., "Identification of the cellular receptor for anthrax toxin," *Nature*, 414:225-229 (Nov. 8, 2001).
Bregenholt, S. and J. Haurum, "Pathogen-specific recombinant human polyclonal antibodies: biodefence applications," *Expert Opin. Biol. Ther.*, 4:387-396 (2004).
Brook et al., "In vitro resistance of *Bacillus anthracis* Sterne to doxycycline, macrolides and quinolones," *Int. J. Antimicrob. Agents*, 18:559-562 (2001).
Brossier et al., "Role of Toxin Functional Domains in Anthrax Pathogenesis," *Infect. Immun.*, 68:1781-1786 (Apr. 2000).
Brossier et al., "Anthrax Spores Make an Essential Contribution to Vaccine Efficacy," *Infect. Immun.*, 70:661-664 (Feb. 2002).
Casadevall, A., "Antibodies for defense against biological attack," *Nature Biotech.*, 20:114 (Feb. 2002).
Casadevall, A., "Passive Antibody Administration (Immediate Immunity) as a Specific Defense against Biological Weapons," *Emerg. Infect. Dis.*, 8:833-841 (Aug. 2002).
Casbohm et al., "Flow cytometric analysis of protective antigen-stimulated T cell cytokine production and proliferation in rhesus macaques challenged with aerosolized *Bacillus anthracis* spores," presented at Proceedings of the 45th Annual Meeting and ToxExpo, Society of Toxicology (SOT), San Diego, CA, Mar. 5-9, 2006 (poster).
Chang et al., Endemic, Notifiable Bioterrorism-Related Diseases, United States, 1992-1999, *Emerg. Infect. Dis.*, 9:556-564 (May 2003).
Chaudry et al., Quickening the pace of anthrax research: three advances point towards possible therapies, *Trends Microbiol.*, 10:58-62 (Feb. 2002).
Cieslak, T.J. and E.M. Eitzen, "Clinical and Epidemiologic Principles of Anthrax," *Emerg. Infect. Dis.*, 5:552-555 (Jul.-Aug. 1999).
Cirino et al., "Disruption of Anthrax Toxin Binding with the Use of Human Antibodies and Competitive Inhibitors," *Infect. Immun.*, 67:2957-2963 (Jun. 1999).
Coker et al., "*Bacillus anthracis* Virulence in Guinea Pigs Vaccinated with Anthrax Vaccine Adsorbed is Linked to Plasmid Quantities and Clonality," *J. Clin. Microbiol.*, 41:1212-1218 (Mar. 2003).
Cui et al., "Lethality during continuous anthrax lethal toxin infusion is associated with circulatory shock but not inflammatory cytokine or nitric oxide release in rats," *Am. J. Physiol. Regul. Integr. Comp. Physiol.*, 286:R699-R709 (2004).
Cui et al., "Late Treatment with a Protective Antigen-Directed Monoclonal Antibody Improves Hemodynamic Function and Survival in a Lethal Toxin-Infused Rat Model of Anthrax Sepsis," *J. Infect. Dis.*, 191:422-434 (2005).
Cunningham et al., "Mapping the lethal factor and edema factor binding sites on oligomeric anthrax protective antigen," *PNAS*, 99:7049-7053 (May 14, 2002).
Dixon et al., "Anthrax," *N. Engl. J. Med.*, 341:815-826 (Sep. 9, 1999).
Escuyer, V. and R.J. Collier, "Anthrax Protective Antigen Interacts with a Specific Receptor on the Surface of CHO-K1 Cells," *Infect. Immun.*, 59:3381-3386 (Oct. 1991).
Ezzell et al., "Immunoelectrophoretic Analysis, Toxicity, and Kinetics of in Vitro Production of the Protective Antigen and Lethal Factor Components of *Bacillus anthracis* Toxin," *Infect. Immun.*, 45:761-767 (Sep. 1984).
Ezzell, J.W. and T.G. Abshire, "Serum protease cleavage of *Bacillus anthracis* protective antigen," *J. Gen. Microbiol.*, 138:543-549 (1992).
Farchaus et al., "Fermentation, Purification, and Characterization of Protective Antigen from a Recombinant, Avirulent Strain of *Bacillus anthracis*," *Appl. Environ. Microbiol.*, 64:982-991 (Mar. 1998).
Fellows et al., "Efficacy of a human anthrax vaccine in guinea pigs, rabbits, and rhesus macaques against challenge by *Bacillus anthracis* isolates of diverse geographical origin," *Vaccine*, 19:3241-3247 (2001).
Friedlander, A.M., "Chapter 22: Anthrax," in *Textbook of Military Medicine: Medical Aspects of Chemical and Biological Warfare*. Specialty eds: Sidell, F.R., et al., (The Office of the Surgeon General at TMM Publications, Borden Institute, Walter Reed Army Medical Center, Washington, DC) pp. 467-478 (1997).
Friedlander, A.M., "Anthrax: Clinical Features, Pathogenesis, and Potential Biological Warfare Threat," *Curr. Clinic. Topics Infect. Dis.*, 20:335-349 (2000).
Friedlander, A.M., "Tackling anthrax," *Nature*, 414:160-161 (Nov. 8, 2001).
Friedlander et al., "Postexposure Prophylaxis against Experimental Inhalation Anthrax," *J. Infect. Dis.*, 167:1239-1243 (May 1993).
Friedlander et al., "Anthrax Vaccine Evidence for Safety and Efficacy Against Inhalational Anthrax," *JAMA*, 282:2104-2106 (Dec. 8, 1999).
Geier, M.R. and D.A. Geier, "Gastrointestinal Adverse Reactions Following Anthrax Vaccination: An Analysis of the Vaccine Adverse Events Reporting System (VAERS) Database," *Hepato-Gastroenterol.*, 51:762-767 (2004).
Gordon et al., "Inhibitors of Receptor-Mediated Endocytosis Block the Entry of *Bacillus anthracis* Adenylate Cyclase Toxin but Not That of *Bordetella pertussis* Adenylate Cyclase Toxin," *Infect. Immun.*, 56:1066-1069 (May 1988).
Hanna et al., "On the role of macrophages in anthrax," *Proc. Natl. Acad. Sci. USA*, 90:10198-10201 (Nov. 1993).
Hering et al., "Validation of the anthrax lethal toxin neutralization assay," *Biologicals*, 32:17-27 (2004).
Holty et al., "Systematic Review: A Century of Inhalational Anthrax Cases from 1900 to 2005," *Ann. Intern. Med.* 144:270-280 (2006).
Inglesby et al., "Anthrax as a Biological Weapon, 2002 Updated Recommendations for Management," *JAMA*, 287:2236-2252 (May 1, 2002); (reprinted with corrections as set forth in *JAMA* 288:1849 (Oct. 16, 2002)).
Ivins et al., "Comparative efficacy of experimental anthrax vaccine candidates against inhalation anthrax in rhesus macaques," *Vaccine*, 16:1141-1148 (1998).
Ivins et al., "Influence of Body Weight on Response of Fischer 344 Rats to Anthrax Lethal Toxin," *Appl. Environ. Microbiol.*, 55:2098-2100 (Aug. 1989).
Ivins et al., "Efficacy of a standard human anthrax vaccine against *Bacillus anthracis* aerosol spore challenge in rhesus monkeys," *Salisbury Medical Bulletin*, Special Supplement No. 87, pp. 125-126 (1996).
Jefferds, et al., "Adherence to Antimicrobial Inhalational Anthrax Prophylaxis among Postal Workers, Washington, D.C., 2001," *Emerg. Infect. Dis.*, 8:1138-1144 (Oct. 2002).
Jernigan et al., "Bioterrorism-Related Inhalational Anthrax: The First 10 Cases Reported in the United States," *Emerg. Infect. Dis.*, 7:933-944 (Nov.-Dec. 2001).
Jernigan et al., "Investigation of Bioterrorism-Related Anthrax, United States, 2001: Epidemiologic Findings," *Emerg. Infect. Dis.*, 8:1019-1028 (Oct. 2002).
Klimpel et al., "Anthrax toxin protective antigen is activated by a cell surface protease with the sequence specificity and catalytic properties of furin," *Proc. Natl. Acad. Sci. USA*, 89:10277-10281 (Nov. 1992).
Kobiler et al., "Efficiency of Protection of Guinea Pigs against Infection with *Bacillus anthracis* Spores by Passive Immunization," *Infect. Immun.*, 70:544-550 (Feb. 2002).
Langermann et al., "Therapeutic Potential of Dominant Negative Inhibitor (DNI) Following Spore Challenge in New Zealand White (NZW) Rabbits," presented at $44^{th}$ Interscience Conference on Antimicrobial Agents & Chemotherapy (ICAAC), Washington, DC, Oct. 30-Nov. 2, 2004 (abstract only).
Leppla, S.H., "Anthrax toxin edema factor: A bacterial adenylate cyclase that increases cyclic AMP concentrations in eukaryotic cells," *Proc. Natl. Acad. Sci. USA*, 79:3162-3166 (May 1982).
Leppla, S.H., "A dominant-negative therapy for anthrax," *Nature Med.*, 7:659-660 (Jun. 2001).
Leppla et al., "Development of an improved vaccine for anthrax," *J. Clin. Invest.*, 110:141-144 (Jul. 2002).
Little, S.F. and B.F. Ivins, "Molecular Pathogenesis of *Bacillus anthracis* Infection," *Microbes Infect.*, 2:131-139 (1999).
Little et al., "Production and Characterization of Monoclonal Antibodies against the Lethal Factor Component of *Bacillus anthracis* Lethal Toxin," *Infect. Immun.*, 58:1606-1613 (Jun. 1990).

Little et al., "Characterization of lethal factor binding and cell receptor binding domains of protective antigen of *Bacillus anthracis* using monoclonal antibodies," *Microbiology*, 142:707-715 (1996).
Little et al., "Passive Protection by Polyclonal Antibodies against *Bacillus anthracis* Infection in Guinea Pigs," *Infect. Immun.*, 65:5171-5175 (Dec. 1997).
Little et al., "Defining a serological correlate of protection in rabbits for a recombinant anthrax vaccine," *Vaccine*, 22:422-430 (2004).
Mahan et al., "Anthrax Vaccination and Self-reported Symptoms, Functional Status, and Medical Conditions in the National Health Survey of Gulf War Era Veterans and Their Families," *Ann. Epidemiol.*, 14:81-88 (2004).
Marcus et al., "Contribution of Immunological Memory to Protective Immunity Conferred by a *Bacillus anthracis* Protective Antigen-Based Vaccine," *Infect Immun.*, 72:3471-3477 (Jun. 2004).
Maynard et al., "Protection against anthrax toxin by recombinant antibody fragments correlates with antigen affinity," *Nature Biotech.*, 20:597-601 (Jun. 2002).
Meselson et al., "The Sverdlovsk Anthrax Outbreak of 1979," *Science*, 266:1202-1208 (Nov. 18, 1994).
Milne, J.C. and R.J. Collier, "pH-dependent permeabilization of the plasma membrane of mammalian cells by anthrax protective antigen," *Mol. Microbiol.*, 10:647-653 (1993).
Mogridge et al., "The lethal and edema factors of anthrax toxin bind only to oligomeric forms of the protective antigen," *PNAS*, 99:7045-7048 (May 14, 2002).
Mohamed et al., "A High-Affinity Monoclonal Antibody to Anthrax Protective Antigen Passively Protects Rabbits before and after Aerosolized *Bacillus anthracis* Spore Challenge," *Infect. Immun.*, 73:795-802 (Feb. 2005).
Mourez et al., "Designing a polyvalent inhibitor of anthrax toxin," *Nature Biotech.*, 19:958-961 (Oct. 2001).
Okinaka et al., "Sequence and Organization of pXO1, the Large *Bacillus anthracis* Plasmid Harboring the Anthrax Toxin Genes," *J. Bacteriol.*, 181:6509-6515 (Oct. 1999).
Pezard et al., "Contribution of Individual Toxin Components to Virulence of *Bacillus anthracis*," *Infect. Immun*., 59:3472-3477 (Oct. 1991).
Pezard et al., "Protective Immunity Induced by *Bacillus anthracis* Toxin-Deficient Strains," *Infect. Immun.*, 63:1369-1372 (Apr. 1995).
Pitt et al., "In vitro correlate of immunity in a rabbit model of inhalational anthrax," *Vaccine*, 19:4768-4773 (2001).
Price et al., "Genetic Diversity in the Protective Antigen Gene of *Bacillus anthracis*," *J. Bacteriol.*, 181:2358-2362 (Apr. 1999).
Quinn et al., "Functional Mapping of Anthrax Toxin Lethal Factor by In-frame Insertion Mutagenesis," *J. Biol. Chem.*, 266:20124-20130 (Oct. 25, 1991).
Quinn et al., "Specific, Sensitive, and Quantitative Enzyme-Linked Immunosorbent Assay for Human Immunoglobulin G Antibodies to Anthrax Toxin Protective Antigen," *Emerg. Infect. Dis.*, 8:1103-1110 (Oct. 2002).
Ramirez et al., "Production, recovery and immunogenicity of the protective antigen from a recombinant strain of *Bacillus anthracis*," *J. Indust. Microbiol. Biotech.*, 28:232-238 (2002).
Read et al., "Comparative Genome Sequencing for Discovery of Novel Polymorphisms in *Bacillus anthracis*," *Science*, 296:2028-2033 (Jun. 14, 2002).
Reed et al., "Mapping of Antibody Responses to the Protective Antigen of *Bacillus anthracis* by Flow Cytometric Analysis," *Cytometry*, 49:1-7 (2002).
Reuveny et al., "Search for Correlates of Protective Immunity Conferred by Anthrax Vaccine," *Infect. Immun.*, 69:2888-2893 (May 2001).
Russell, P.K., "Vaccines in Civilian Defense Against Bioterrorism," *Emerg. Infect. Dis.*, 5:531-533 (Jul.-Aug. 1999).
Sabourin et al., "Short Duration Ciprofloxacin® Therapy Provides High Protection to Non-Human Primates Challenged With Aerosolized *B. anthracis* Spores," presented at *Bacillus* Act Conference-2005, Santa Fe, NM, Sep. 25-29, 2006 (abstract only).
Saile et al., "Control of Anthrax Toxin Gene Expression by the Transition State Regulator *abrB*," *J. Bacteriol.*, 184:370-380 (Jan. 2002).
Sastry et al., "Identification of *Bacillus anthracis* by a simple protective antigen-specific mAb dot-ELISA," *J. Med. Microbiol.*, 52:47-49 (2003).
Sawada-Hirai et al., "Human anti-anthrax protective antigen neutralizing monoclonal antibodies derived from donors vaccinated with anthrax vaccine adsorbed," *J. Immune Based Therapies and Vaccines*, 2:5 (2004).
Scobie et al., "Human capillary morphogenesis protein 2 functions as an anthrax toxin receptor," *PNAS*, 100:5170-5174 (Apr. 29, 2003).
Sellman et al., "Point Mutations in Anthrax Protective Antigen That Block Translocation," *J. Biol. Chem.* 276:8371-8376 (Mar. 16, 2001).
Sellman et al., "Dominant-Negative Mutants of a Toxin Subunit: An Approach to Therapy of Anthrax," *Science*, 292:695-697 (Apr. 27, 2001).
Shepard et al., "Antimicrobial Postexposure Phophylaxis for Anthrax: Adverse Events and Adherence," *Emerg. Infect. Dis.*, 8:1124-1132 (Oct. 2002).
Singh et al., "The Carboxyl-terminal End of Protective Antigen is Required for Receptor Binding and Anthrax Toxin Activity," *J. Biol. Chem.*, 266:15493-15497 (Aug. 15, 1991).
Singh et al., "Study of Immunization against Anthrax with the Purified Recombinant Protective Antigen of *Bacillus anthracis*," *Infect. Immun.*, 66:3447-3448 (Jul. 1998).
Singh et al., "A Dominant Negative Mutant of *Bacillus anthracis* Protective Antigen Inhibits Anthrax Toxin Action in Vivo," *J. Biol. Chem.*, 276:22090-22094 (Jun. 22, 2001).
Subramanian et al., "A Phase 1 Study of PAmAb, a Fully Human Monoclonal Antibody against *Bacillus anthracis* Protective Antigen, in Healthy Volunteers," *Clin. Infect. Dis.*, 41:12-20 (Jul. 1, 2005).
Swartz, M.N., "Recognition and Management of Anthrax—An Update," *N. Engl. J. Med.*, 345:1621-1626 (Nov. 29, 2001).
Vasconcelos et al., "Pathology of Inhalation Anthrax in Cynomolgus Monkeys (*Macaca fascicularis*)," *Lab. Invest.*, 83:1201-1209 (Aug. 2003).
Vaughan et al., "Human Antibodies with Sub-nanomolar Affinities Isolated from a Large Non-immunized Phage Display Library," *Nature Biotech.*, 14:309-314 (Mar. 1996).
Vietri et al., "Short-course postexposure antibiotic prophylaxis combined with vaccination protects against experimental inhalational anthrax infection," presented at Proceedings of the 43rd Annual Meeting of Infectious Diseases Society of America (IDSA) San Francisco, CA, Oct. 6-9, 2006 (poster).
Vodkin, M.H. and S.H. Leppla., "Cloning of the Protective Antigen Gene of *Bacillus anthracis*," *Cell*, 34:693-697 (Sep. 1983).
Wein et al., "Emergency response to an anthrax attack," *PNAS*, 100:4346-4351 (Apr. 1, 2003).
Welkos et al., "Sequence and analysis of the DNA encoding protective antigen of *Bacillus anthracis*," *Gene*, 69:287-300 (1988).
Welkos et al., "Non-toxigenic derivatives of the Ames strain of *Bacillus anthracis* are fully virulent for mice: role of plasmid pX02 and chromosome in strain-dependent virulence," *Microb. Pathog.*, 14:381-388 (1993).
Welkos et al., "The role of antibodies to *Bacillus anthracis* and anthrax toxin components in inhibiting the early stages of infection by anthrax spores," *Microbiology*, 147:1677-1685 (2001).
Welkos et al., "In-vitro characterisation of the phagocytosis and fate of anthrax spores in macrophages and the effects of anti-PA antibody," *J. Med. Microbiol.*, 51:821-831 (2002).
Wild et al., "Human antibodies from immunized donors are protective against anthrax toxin in vivo," *Nature Biotech.*, 21:1305-1306 (Nov. 2003).
Williams et al., "Anthrax Postexposure Prophylaxis in Postal Workers, Connecticut, 2001," *Emerg. Infect. Dis.*, 8:1133-1137 (Oct. 2002).
Young, J.A.T. and R.J. Collier, "Attacking anthrax," *Sci. Am.*, 286:48-50, 54-59 (2002).
Zaucha et al., "The Pathology of Experimental Anthrax in Rabbits Exposed by Inhalation and Subcutaneous Inoculation," *Arch. Pathol. Lab. Med.*, 122:982-992 (1998).

Zhou et al., "Human antibodies against spores of the genus *Bacillus*: A model study for detection of and protection against anthrax and the bioterrorist threat," *PNAS*, 99:5241-5246 (Apr. 16, 2002).

Zilinskas, R. A., "Iraq's Biological Weapons-The Past as Future?," *JAMA*, 278:418-424 (Aug. 6, 1997).

Bendig, M.M., "Humanization of Rodent Monoclonal Antibodies by CDR Grafting" *Methods: A Companion to Methods in Enzymology*, 8:83-93 (1995).

Migone et al., "Raxibacumab for the Treatment of Inhalational Anthrax," N. Engl. J. Med. 361(2):135-144 (Jul. 9, 2009).

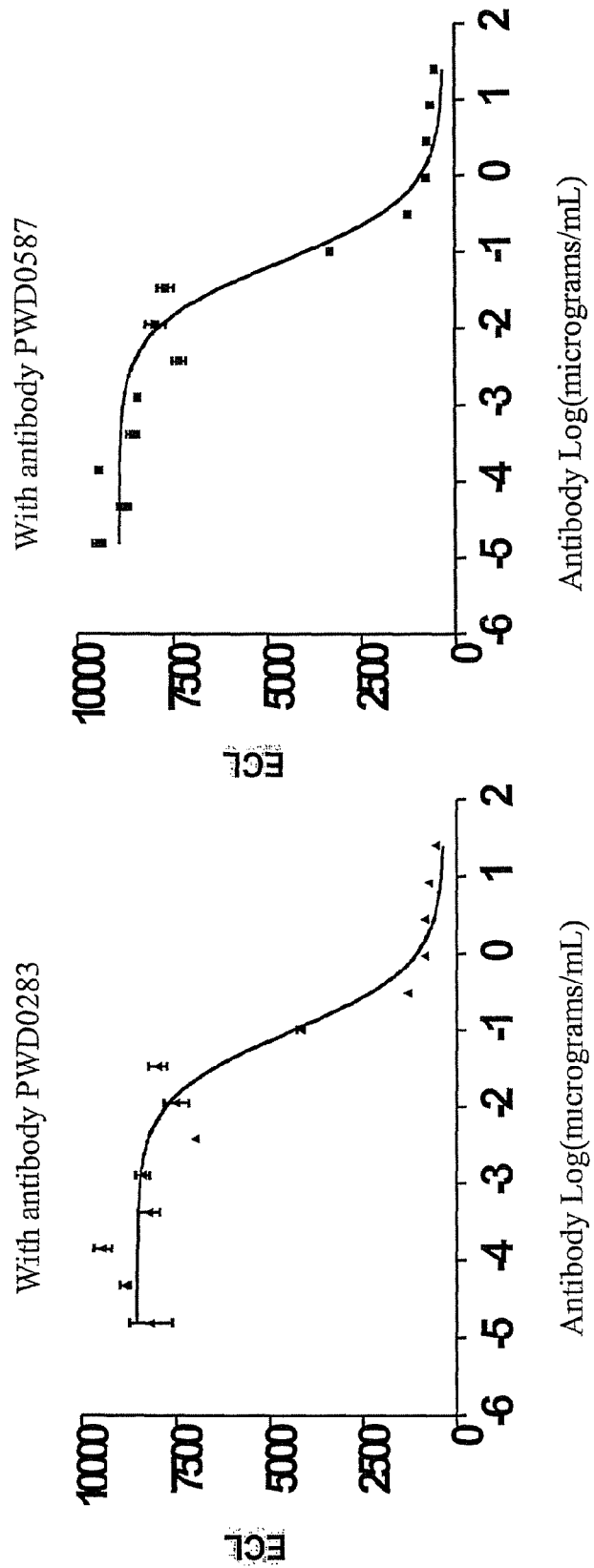
Figure 1: Inhibition of PA-ATR binding

Figure 2: Binding of Biotinylated PA to Cells as Determined by Flow Cytometry
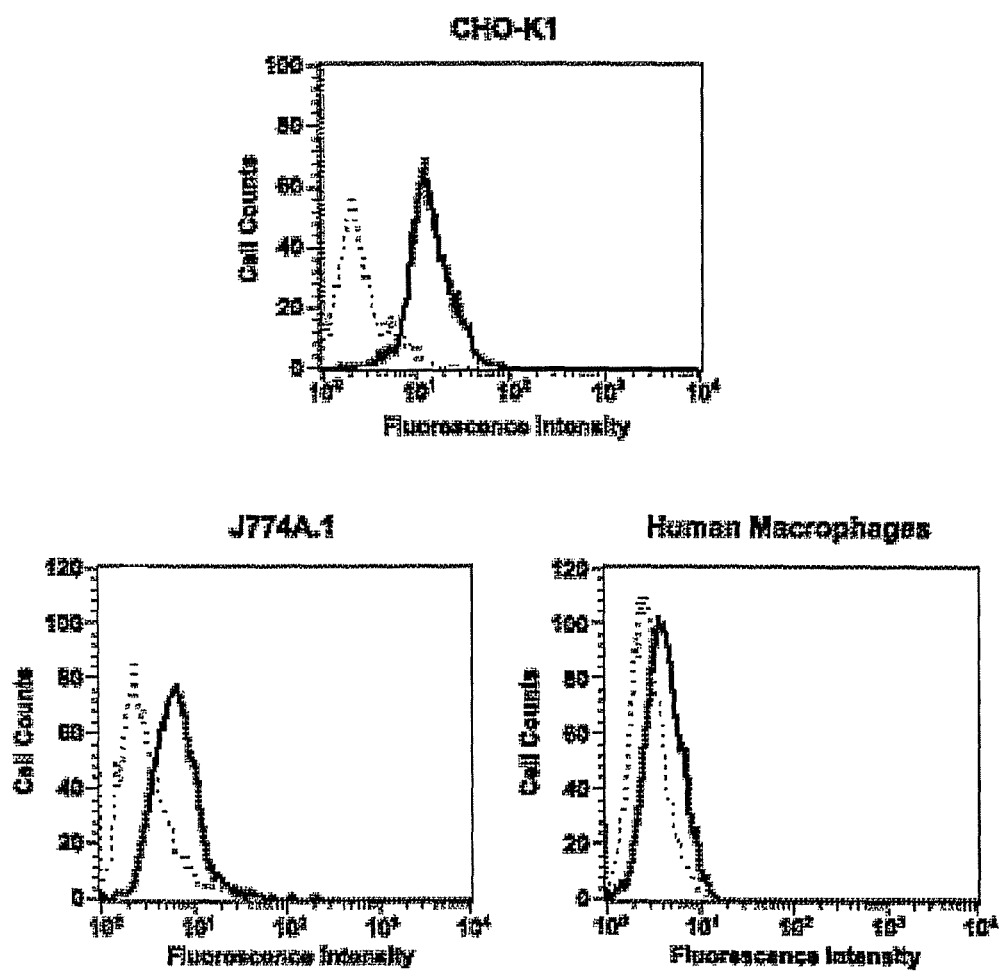

Figure 3: Rubidium Release Assay
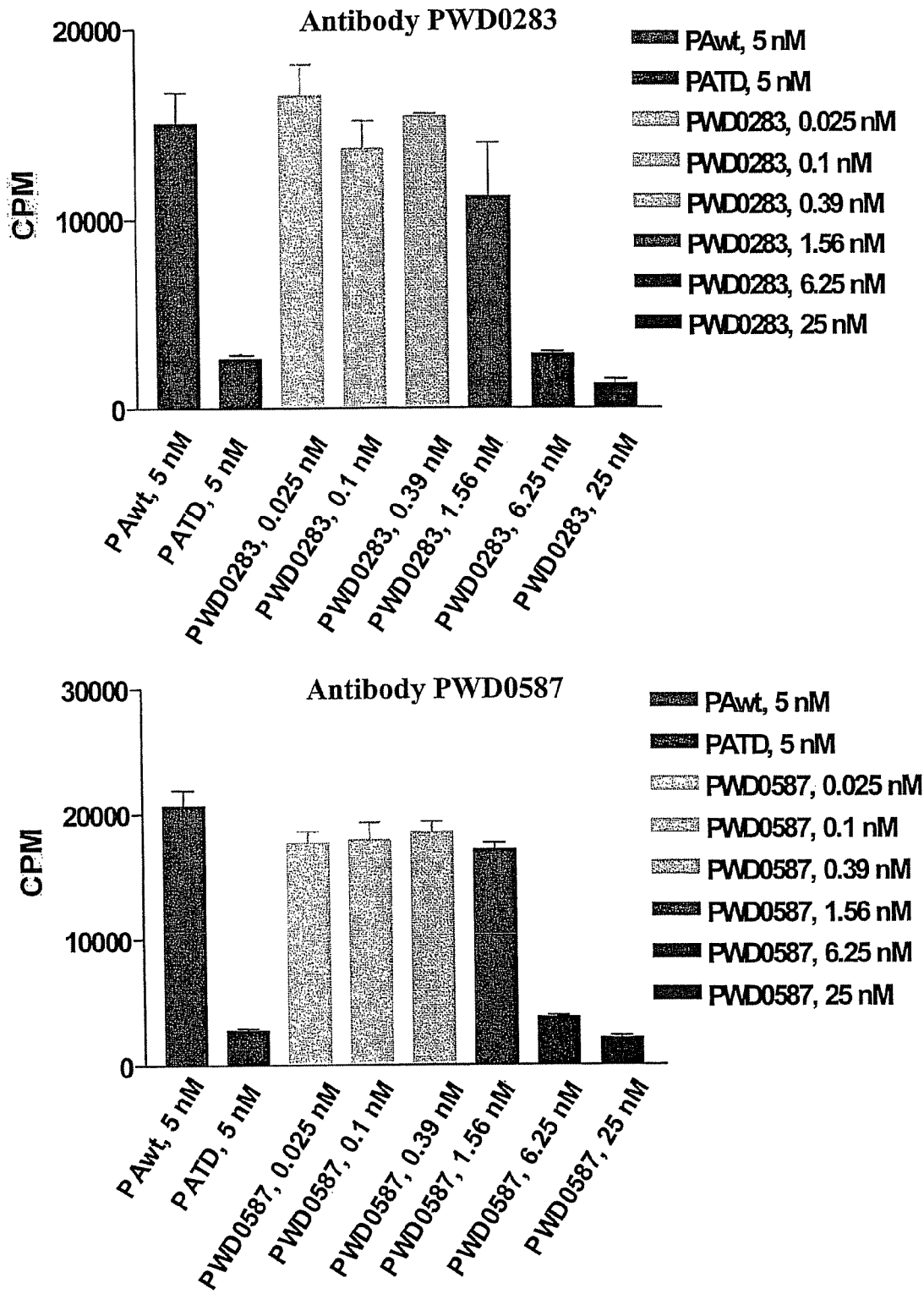

Figure 4: Inhibition Of Cell Killing
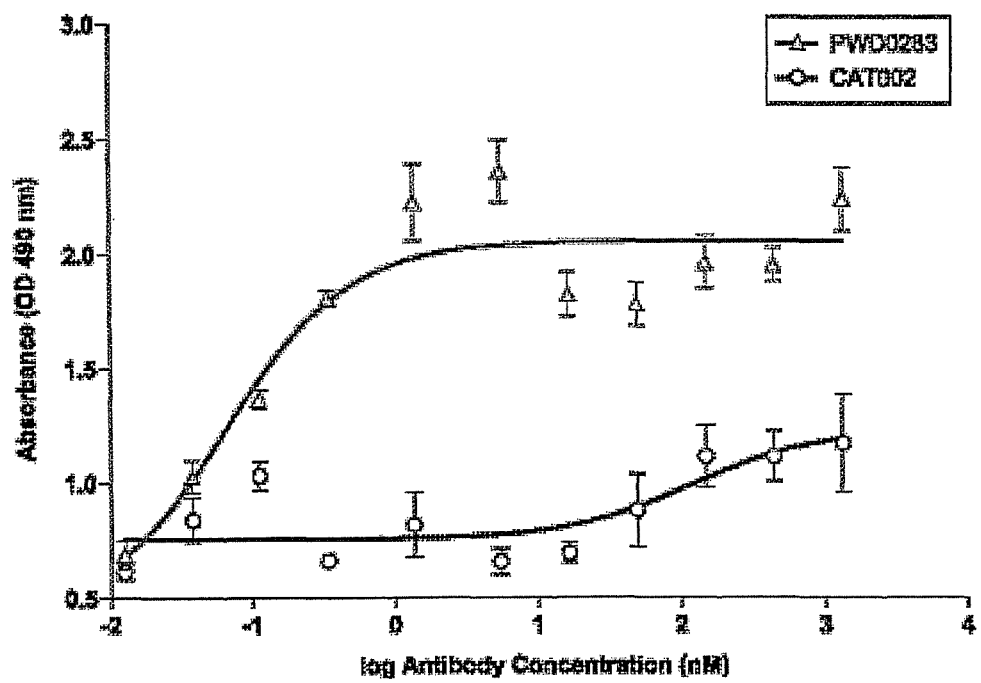
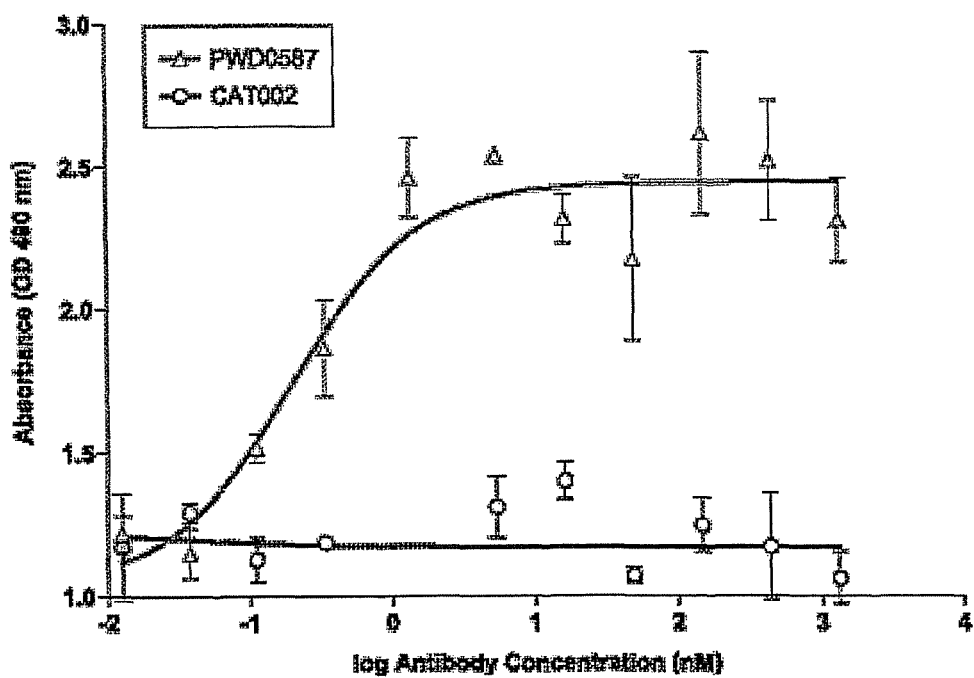

Figure 5: Effect of Prophylactic Administration of Anti-PA Monoclonal Antibodies 60 Minutes Prior to Lethal Toxin Exposure

Figure 6
Survival Curves of New Zealand White Rabbits After
Inhalational Exposure to Lethal Dose of *B. anthracis spores.*

Figure 7
Survival Curves of Cynomolgus Monkeys After
Inhalational Exposure to Lethal Dose of *B. anthracis spores.*

SEQUENCE LISTING

```
<160> NUMBER OF SEQ ID NOS: 535

<210> SEQ ID NO 1
<211> LENGTH: 2295
<212> TYPE: DNA
<213> ORGANISM: Bacillus anthracis
<220> FEATURE:
<221> NAME/KEY: CDS
<222> LOCATION: (1)..(2295)

<400> SEQUENCE: 1 atg aaa aag cgt aaa gtt ctg atc ccg ctg atg gct ctg tct acc atc      48
Met Lys Lys Arg Lys Val Leu Ile Pro Leu Met Ala Leu Ser Thr Ile
1               5                   10                  15 ctg gtt tct agc acc ggt aac ctg gaa gta atc cag gct gaa gtt aaa      96
Leu Val Ser Ser Thr Gly Asn Leu Glu Val Ile Gln Ala Glu Val Lys
            20                  25                  30 cag gaa aac cgt ctg ctc aac gaa tct gag tct tcc tct cag ggc ctg     144
Gln Glu Asn Arg Leu Leu Asn Glu Ser Glu Ser Ser Ser Gln Gly Leu
        35                  40                  45
```

| | | | | | | | | | | | | | | | | |
|---|---|---|---|---|---|---|---|---|---|---|---|---|---|---|---|---|
| ctg | ggt | tac | tat | ttc | tct | gac | ctg | aac | ttc | cag | gca | ccg | atg | gtt | gta | 192 |
| Leu | Gly | Tyr | Tyr | Phe | Ser | Asp | Leu | Asn | Phe | Gln | Ala | Pro | Met | Val | Val | |
| | 50 | | | | 55 | | | | | 60 | | | | | | |
| act | tct | tcc | acc | acc | ggc | gac | ctg | tct | att | ccg | tct | tct | gaa | ctg | gag | 240 |
| Thr | Ser | Ser | Thr | Thr | Gly | Asp | Leu | Ser | Ile | Pro | Ser | Ser | Glu | Leu | Glu | |
| 65 | | | | | 70 | | | | | 75 | | | | | 80 | |
| aac | atc | ccg | tct | gaa | aac | cag | tac | ttc | cag | tct | gct | atc | tgg | tct | ggt | 288 |
| Asn | Ile | Pro | Ser | Glu | Asn | Gln | Tyr | Phe | Gln | Ser | Ala | Ile | Trp | Ser | Gly | |
| | | | | 85 | | | | | 90 | | | | | 95 | | |
| ttc | att | aaa | gtt | aag | aaa | tct | gac | gaa | tac | acc | ttc | gct | act | tct | gca | 336 |
| Phe | Ile | Lys | Val | Lys | Lys | Ser | Asp | Glu | Tyr | Thr | Phe | Ala | Thr | Ser | Ala | |
| | | | | 100 | | | | | 105 | | | | | 110 | | |
| gat | aac | cac | gtt | act | atg | tgg | gta | gac | gac | cag | gaa | gtt | atc | aac | aaa | 384 |
| Asp | Asn | His | Val | Thr | Met | Trp | Val | Asp | Asp | Gln | Glu | Val | Ile | Asn | Lys | |
| | | | 115 | | | | | 120 | | | | | 125 | | | |
| gct | tct | aac | tct | aac | aaa | atc | cgt | ctg | gaa | aaa | ggc | cgt | ctg | tac | cag | 432 |
| Ala | Ser | Asn | Ser | Asn | Lys | Ile | Arg | Leu | Glu | Lys | Gly | Arg | Leu | Tyr | Gln | |
| | | 130 | | | | | 135 | | | | | 140 | | | | |
| atc | aag | att | caa | tac | caa | cgt | gaa | aac | ccg | acc | gag | aaa | ggt | ctg | gac | 480 |
| Ile | Lys | Ile | Gln | Tyr | Gln | Arg | Glu | Asn | Pro | Thr | Glu | Lys | Gly | Leu | Asp | |
| 145 | | | | | 150 | | | | | 155 | | | | | 160 | |
| ttc | aaa | ctg | tac | tgg | acc | gac | tct | cag | aac | aag | aaa | gaa | gtt | atc | tct | 528 |
| Phe | Lys | Leu | Tyr | Trp | Thr | Asp | Ser | Gln | Asn | Lys | Lys | Glu | Val | Ile | Ser | |
| | | | | 165 | | | | | 170 | | | | | 175 | | |
| tcc | gac | aac | ctg | cag | ctg | ccg | gaa | ctg | aaa | cag | aaa | tct | tcc | aac | tct | 576 |
| Ser | Asp | Asn | Leu | Gln | Leu | Pro | Glu | Leu | Lys | Gln | Lys | Ser | Ser | Asn | Ser | |
| | | | 180 | | | | | 185 | | | | | 190 | | | |
| cgt | aaa | aag | cgt | tct | act | tct | gct | ggt | ccg | acc | gtt | ccg | gac | cgt | gat | 624 |
| Arg | Lys | Lys | Arg | Ser | Thr | Ser | Ala | Gly | Pro | Thr | Val | Pro | Asp | Arg | Asp | |
| | | 195 | | | | | 200 | | | | | 205 | | | | |
| aac | gac | ggt | att | ccg | gac | tct | ctg | gaa | gtt | gaa | ggc | tac | acc | gta | gac | 672 |
| Asn | Asp | Gly | Ile | Pro | Asp | Ser | Leu | Glu | Val | Glu | Gly | Tyr | Thr | Val | Asp | |
| 210 | | | | | 215 | | | | | 220 | | | | | | |
| gtt | aaa | aac | aaa | cgt | acc | ttc | ctg | tct | ccg | tgg | atc | tct | aac | atc | cac | 720 |
| Val | Lys | Asn | Lys | Arg | Thr | Phe | Leu | Ser | Pro | Trp | Ile | Ser | Asn | Ile | His | |
| 225 | | | | | 230 | | | | | 235 | | | | | 240 | |
| gaa | aag | aaa | ggt | ctg | acc | aaa | tac | aaa | tct | tcc | ccg | gag | aaa | tgg | tct | 768 |
| Glu | Lys | Lys | Gly | Leu | Thr | Lys | Tyr | Lys | Ser | Ser | Pro | Glu | Lys | Trp | Ser | |
| | | | | 245 | | | | | 250 | | | | | 255 | | |
| acc | gct | tct | gat | ccg | tac | tct | gac | ttc | gaa | aaa | gtt | act | ggt | cgt | atc | 816 |
| Thr | Ala | Ser | Asp | Pro | Tyr | Ser | Asp | Phe | Glu | Lys | Val | Thr | Gly | Arg | Ile | |
| | | | 260 | | | | | 265 | | | | | 270 | | | |
| gac | aaa | aac | gtt | tct | ccg | gaa | gct | cgt | cac | ccg | ctg | gta | gca | gcg | tac | 864 |
| Asp | Lys | Asn | Val | Ser | Pro | Glu | Ala | Arg | His | Pro | Leu | Val | Ala | Ala | Tyr | |
| | | 275 | | | | | 280 | | | | | 285 | | | | |
| ccg | atc | gtt | cac | gtt | gac | atg | gaa | aac | att | atc | ctg | tct | aaa | aac | gaa | 912 |
| Pro | Ile | Val | His | Val | Asp | Met | Glu | Asn | Ile | Ile | Leu | Ser | Lys | Asn | Glu | |
| | 290 | | | | | 295 | | | | | 300 | | | | | |
| gac | cag | tct | acc | cag | aac | acc | gac | tct | caa | act | cgt | acc | atc | tct | aaa | 960 |
| Asp | Gln | Ser | Thr | Gln | Asn | Thr | Asp | Ser | Gln | Thr | Arg | Thr | Ile | Ser | Lys | |
| 305 | | | | | 310 | | | | | 315 | | | | | 320 | |
| aac | acc | tct | acc | tct | cgt | act | cac | acc | tct | gaa | gtt | cac | ggt | aac | gct | 1008 |
| Asn | Thr | Ser | Thr | Ser | Arg | Thr | His | Thr | Ser | Glu | Val | His | Gly | Asn | Ala | |
| | | | | 325 | | | | | 330 | | | | | 335 | | |
| gag | gtt | cac | gct | tct | ttc | ttt | gac | atc | ggt | ggc | tct | gta | tct | gct | ggt | 1056 |
| Glu | Val | His | Ala | Ser | Phe | Phe | Asp | Ile | Gly | Gly | Ser | Val | Ser | Ala | Gly | |
| | | | 340 | | | | | 345 | | | | | 350 | | | |
| ttc | tct | aac | tct | aac | tct | tct | acc | gtt | gca | atc | gac | cac | tct | ctg | tct | 1104 |
| Phe | Ser | Asn | Ser | Asn | Ser | Ser | Thr | Val | Ala | Ile | Asp | His | Ser | Leu | Ser | |
| | | 355 | | | | | 360 | | | | | 365 | | | | |

-continued

| | | |
|---|---|---|
| ctg gct ggt gaa cgt acc tgg gct gaa act atg ggc ctg aac acc gca<br>Leu Ala Gly Glu Arg Thr Trp Ala Glu Thr Met Gly Leu Asn Thr Ala<br>370                        375                    380 | 1152 |
| gac acc gct cgt ctg aac gct aac atc cgt tac gtt aac acc ggc acc<br>Asp Thr Ala Arg Leu Asn Ala Asn Ile Arg Tyr Val Asn Thr Gly Thr<br>385                     390                    395                   400 | 1200 |
| gct ccg atc tac aac gtt ctg ccg act acc tct ctg gta ctg ggt aaa<br>Ala Pro Ile Tyr Asn Val Leu Pro Thr Thr Ser Leu Val Leu Gly Lys<br>                    405                    410                   415 | 1248 |
| aac cag acc ctg gca acc atc aaa gct aag gaa aac cag ctg tct cag<br>Asn Gln Thr Leu Ala Thr Ile Lys Ala Lys Glu Asn Gln Leu Ser Gln<br>             420                    425                   430 | 1296 |
| atc ctg gct ccg aac aac tac tat ccg tct aaa aac ctg gct ccg att<br>Ile Leu Ala Pro Asn Asn Tyr Tyr Pro Ser Lys Asn Leu Ala Pro Ile<br>                    435                    440                   445 | 1344 |
| gca ctg aac gct cag gac gac ttc tct tcc acc ccg atc act atg aac<br>Ala Leu Asn Ala Gln Asp Asp Phe Ser Ser Thr Pro Ile Thr Met Asn<br>450                          455                    460 | 1392 |
| tac aac cag ttc ctg gaa ctg gag aaa acc aaa cag ctg cgt ctg gac<br>Tyr Asn Gln Phe Leu Glu Leu Glu Lys Thr Lys Gln Leu Arg Leu Asp<br>465                        470                    475                   480 | 1440 |
| acc gac cag gtt tac ggt aac atc gct acc tac aac ttc gaa aac ggt<br>Thr Asp Gln Val Tyr Gly Asn Ile Ala Thr Tyr Asn Phe Glu Asn Gly<br>                    485                    490                   495 | 1488 |
| cgt gtt cgt gta gac acc ggc tct aac tgg tct gaa gtt ctg ccg cag<br>Arg Val Arg Val Asp Thr Gly Ser Asn Trp Ser Glu Val Leu Pro Gln<br>             500                    505                   510 | 1536 |
| atc cag gaa acc act gct cgt att atc ttc aac ggt aaa gac ctg aac<br>Ile Gln Glu Thr Thr Ala Arg Ile Ile Phe Asn Gly Lys Asp Leu Asn<br>                    515                    520                   525 | 1584 |
| ctg gtt gaa cgt cgt atc gct gca gta aac ccg tct gac ccg ctg gaa<br>Leu Val Glu Arg Arg Ile Ala Ala Val Asn Pro Ser Asp Pro Leu Glu<br>530                          535                    540 | 1632 |
| acc act aaa ccg gac atg acc ctg aaa gaa gct ctg aaa atc gct ttc<br>Thr Thr Lys Pro Asp Met Thr Leu Lys Glu Ala Leu Lys Ile Ala Phe<br>545                          550                    555                   560 | 1680 |
| ggt ttc aac gaa ccg aac ggc aac ctg cag tac cag ggt aaa gat atc<br>Gly Phe Asn Glu Pro Asn Gly Asn Leu Gln Tyr Gln Gly Lys Asp Ile<br>                      565                    570                   575 | 1728 |
| acc gaa ttc gac ttt aac ttc gac cag caa acc tct cag aac atc aaa<br>Thr Glu Phe Asp Phe Asn Phe Asp Gln Gln Thr Ser Gln Asn Ile Lys<br>                    580                    585                   590 | 1776 |
| aac cag ctg gct gaa ctg aac gct acc aac atc tac acc gtt ctg gac<br>Asn Gln Leu Ala Glu Leu Asn Ala Thr Asn Ile Tyr Thr Val Leu Asp<br>             595                    600                   605 | 1824 |
| aaa atc aag ctg aac gct aaa atg aac att ctg atc cgt gat aaa cgt<br>Lys Ile Lys Leu Asn Ala Lys Met Asn Ile Leu Ile Arg Asp Lys Arg<br>610                          615                    620 | 1872 |
| ttc cac tac gac cgt aac aac atc gct gtt ggt gct gac gaa tct gta<br>Phe His Tyr Asp Arg Asn Asn Ile Ala Val Gly Ala Asp Glu Ser Val<br>625                          630                    635                   640 | 1920 |
| gtt aaa gaa gct cac cgt gag gtt atc aac tct tcc acc gaa ggt ctg<br>Val Lys Glu Ala His Arg Glu Val Ile Asn Ser Ser Thr Glu Gly Leu<br>                      645                    650                   655 | 1968 |
| ctc ctg aac atc gac aaa gat att cgt aaa atc ctg tct ggt tac atc<br>Leu Leu Asn Ile Asp Lys Asp Ile Arg Lys Ile Leu Ser Gly Tyr Ile<br>                    660                    665                   670 | 2016 |
| gtt gaa atc gaa gac acc gag ggc ctg aaa gaa gtt atc aac gac cgt<br>Val Glu Ile Glu Asp Thr Glu Gly Leu Lys Glu Val Ile Asn Asp Arg<br>             675                    680                   685 | 2064 |

```
tac gat atg ctg aac atc tct tcc ctg cgt cag gac ggt aaa acc ttc    2112
Tyr Asp Met Leu Asn Ile Ser Ser Leu Arg Gln Asp Gly Lys Thr Phe
        690                 695                 700 atc gac ttc aaa aag tac aac gat aaa ctg ccg ctg tac atc tct aac    2160
Ile Asp Phe Lys Lys Tyr Asn Asp Lys Leu Pro Leu Tyr Ile Ser Asn
705                 710                 715                 720 ccg aac tac aaa gta aac gtt tac gct gtt acc aaa gaa aac acc att    2208
Pro Asn Tyr Lys Val Asn Val Tyr Ala Val Thr Lys Glu Asn Thr Ile
                725                 730                 735 atc aac ccg tct gaa aac ggt gac acc tct acc aac ggt atc aaa aag    2256
Ile Asn Pro Ser Glu Asn Gly Asp Thr Ser Thr Asn Gly Ile Lys Lys
            740                 745                 750 atc ctg atc ttc tct aag aaa ggc tac gaa atc ggt taa                2295
Ile Leu Ile Phe Ser Lys Lys Gly Tyr Glu Ile Gly
        755                 760
```

<210> SEQ ID NO 2
<211> LENGTH: 764
<212> TYPE: PRT
<213> ORGANISM: Bacillus anthracis

<400> SEQUENCE: 2

```
Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
```

-continued

```
             275                 280                 285
Pro Ile Val His Val Asp Met Glu Asn Ile Ile Leu Ser Lys Asn Glu
290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
                325                 330                 335
Glu Val His Ala Ser Phe Phe Asp Ile Gly Gly Ser Val Ser Ala Gly
                340                 345                 350
Phe Ser Asn Ser Asn Ser Ser Thr Val Ala Ile Asp His Ser Leu Ser
                355                 360                 365
Leu Ala Gly Glu Arg Thr Trp Ala Glu Thr Met Gly Leu Asn Thr Ala
370                 375                 380
Asp Thr Ala Arg Leu Asn Ala Asn Ile Arg Tyr Val Asn Thr Gly Thr
385                 390                 395                 400
Ala Pro Ile Tyr Asn Val Leu Pro Thr Thr Ser Leu Val Leu Gly Lys
                405                 410                 415
Asn Gln Thr Leu Ala Thr Ile Lys Ala Lys Glu Asn Gln Leu Ser Gln
                420                 425                 430
Ile Leu Ala Pro Asn Asn Tyr Tyr Pro Ser Lys Asn Leu Ala Pro Ile
                435                 440                 445
Ala Leu Asn Ala Gln Asp Asp Phe Ser Ser Thr Pro Ile Thr Met Asn
450                 455                 460
Tyr Asn Gln Phe Leu Glu Leu Glu Lys Thr Lys Gln Leu Arg Leu Asp
465                 470                 475                 480
Thr Asp Gln Val Tyr Gly Asn Ile Ala Thr Tyr Asn Phe Glu Asn Gly
                485                 490                 495
Arg Val Arg Val Asp Thr Gly Ser Asn Trp Ser Glu Val Leu Pro Gln
                500                 505                 510
Ile Gln Glu Thr Thr Ala Arg Ile Ile Phe Asn Gly Lys Asp Leu Asn
                515                 520                 525
Leu Val Glu Arg Arg Ile Ala Ala Val Asn Pro Ser Asp Pro Leu Glu
                530                 535                 540
Thr Thr Lys Pro Asp Met Thr Leu Lys Glu Ala Leu Lys Ile Ala Phe
545                 550                 555                 560
Gly Phe Asn Glu Pro Asn Gly Asn Leu Gln Tyr Gln Gly Lys Asp Ile
                565                 570                 575
Thr Glu Phe Asp Phe Asn Phe Asp Gln Gln Thr Ser Gln Asn Ile Lys
                580                 585                 590
Asn Gln Leu Ala Glu Leu Asn Ala Thr Asn Ile Tyr Thr Val Leu Asp
                595                 600                 605
Lys Ile Lys Leu Asn Ala Lys Met Asn Ile Leu Ile Arg Asp Lys Arg
                610                 615                 620
Phe His Tyr Asp Arg Asn Asn Ile Ala Val Gly Ala Asp Glu Ser Val
625                 630                 635                 640
Val Lys Glu Ala His Arg Glu Val Ile Asn Ser Ser Thr Glu Gly Leu
                645                 650                 655
Leu Leu Asn Ile Asp Lys Asp Ile Arg Lys Ile Leu Ser Gly Tyr Ile
                660                 665                 670
Val Glu Ile Glu Asp Thr Glu Gly Leu Lys Glu Val Ile Asn Asp Arg
                675                 680                 685
Tyr Asp Met Leu Asn Ile Ser Ser Leu Arg Gln Asp Gly Lys Thr Phe
                690                 695                 700
```

```
Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
            725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 3
<211> LENGTH: 368
<212> TYPE: PRT
<213> ORGANISM: Homo sapiens

<400> SEQUENCE: 3

Met Ala Thr Ala Glu Arg Arg Ala Leu Gly Ile Gly Phe Gln Trp Leu
1               5                   10                  15

Ser Leu Ala Thr Leu Val Leu Ile Cys Ala Gly Gln Gly Gly Arg Arg
            20                  25                  30

Glu Asp Gly Gly Pro Ala Cys Tyr Gly Gly Phe Asp Leu Tyr Phe Ile
        35                  40                  45

Leu Asp Lys Ser Gly Ser Val Leu His His Trp Asn Glu Ile Tyr Tyr
50                  55                  60

Phe Val Glu Gln Leu Ala His Lys Phe Ile Ser Pro Gln Leu Arg Met
65                  70                  75                  80

Ser Phe Ile Val Phe Ser Thr Arg Gly Thr Thr Leu Met Lys Leu Thr
                85                  90                  95

Glu Asp Arg Glu Gln Ile Arg Gln Gly Leu Glu Glu Leu Gln Lys Val
            100                 105                 110

Leu Pro Gly Gly Asp Thr Tyr Met His Glu Gly Phe Glu Arg Ala Ser
        115                 120                 125

Glu Gln Ile Tyr Tyr Glu Asn Arg Gln Gly Tyr Arg Thr Ala Ser Val
130                 135                 140

Ile Ile Ala Leu Thr Asp Gly Glu Leu His Glu Asp Leu Phe Phe Tyr
145                 150                 155                 160

Ser Glu Arg Glu Ala Asn Arg Ser Arg Asp Leu Gly Ala Ile Val Tyr
                165                 170                 175

Cys Val Gly Val Lys Asp Phe Asn Glu Thr Gln Leu Ala Arg Ile Ala
            180                 185                 190

Asp Ser Lys Asp His Val Phe Pro Val Asn Asp Gly Phe Gln Ala Leu
        195                 200                 205

Gln Gly Ile Ile His Ser Ile Leu Lys Lys Ser Cys Ile Glu Ile Leu
210                 215                 220

Ala Ala Glu Pro Ser Thr Ile Cys Ala Gly Glu Ser Phe Gln Val Val
225                 230                 235                 240

Val Arg Gly Asn Gly Phe Arg His Ala Arg Asn Val Asp Arg Val Leu
                245                 250                 255

Cys Ser Phe Lys Ile Asn Asp Ser Val Thr Leu Asn Glu Lys Pro Phe
            260                 265                 270

Ser Val Glu Asp Thr Tyr Leu Leu Cys Pro Ala Pro Ile Leu Lys Glu
        275                 280                 285

Val Gly Met Lys Ala Ala Leu Gln Val Ser Met Asn Asp Gly Leu Ser
290                 295                 300

Phe Ile Ser Ser Ser Val Ile Ile Thr Thr Thr His Cys Ser Asp Gly
305                 310                 315                 320
```

```
Ser Ile Leu Ala Ile Ala Leu Leu Ile Leu Phe Leu Leu Ala Leu
                325                 330                 335

Ala Leu Leu Trp Trp Phe Trp Pro Leu Cys Cys Thr Val Ile Ile Lys
            340                 345                 350

Glu Val Pro Pro Pro Ala Glu Glu Ser Glu Glu Asn Lys Ile Lys
        355                 360                 365

<210> SEQ ID NO 4
<211> LENGTH: 800
<212> TYPE: PRT
<213> ORGANISM: Bacillus anthracis

<400> SEQUENCE: 4

Met Thr Arg Asn Lys Phe Ile Pro Asn Lys Phe Ser Ile Ile Ser Phe
1               5                   10                  15

Ser Val Leu Leu Phe Ala Ile Ser Ser Gln Ala Ile Glu Val Asn
            20                  25                  30

Ala Met Asn Glu His Tyr Thr Glu Ser Asp Ile Lys Arg Asn His Lys
            35                  40                  45

Thr Glu Lys Asn Lys Thr Glu Lys Glu Lys Phe Lys Asp Ser Ile Asn
        50                  55                  60

Asn Leu Val Lys Thr Glu Phe Thr Asn Glu Thr Leu Asp Lys Ile Gln
65                  70                  75                  80

Gln Thr Gln Asp Leu Leu Lys Lys Ile Pro Lys Asp Val Leu Glu Ile
                85                  90                  95

Tyr Ser Glu Leu Gly Gly Glu Ile Tyr Phe Thr Asp Ile Asp Leu Val
            100                 105                 110

Glu His Lys Glu Leu Gln Asp Leu Ser Glu Glu Lys Asn Ser Met
            115                 120                 125

Asn Ser Arg Gly Glu Lys Val Pro Phe Ala Ser Arg Phe Val Phe Glu
130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
            180                 185                 190

Leu Asn Leu Ile Lys Ser Leu Ser Asp Asp Ser Asp Ser Ser Asp Leu
            195                 200                 205

Leu Phe Ser Gln Lys Phe Lys Glu Lys Leu Glu Leu Asn Asn Lys Ser
        210                 215                 220

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
                245                 250                 255

Leu Glu Leu Tyr Ala Pro Asp Met Phe Glu Tyr Met Asn Lys Leu Glu
            260                 265                 270

Lys Gly Gly Phe Glu Lys Ile Ser Glu Ser Leu Lys Lys Glu Gly Val
        275                 280                 285

Glu Lys Asp Arg Ile Asp Val Leu Lys Gly Glu Lys Ala Leu Lys Ala
    290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
                325                 330                 335
```

```
Asn Leu Ile Lys Ser Gly Val Ala Thr Lys Gly Leu Asn Val His Gly
                340                 345                 350

Lys Ser Ser Asp Trp Gly Pro Val Ala Gly Tyr Ile Pro Phe Asp Gln
            355                 360                 365

Asp Leu Ser Lys Lys His Gly Gln Gln Leu Ala Val Glu Lys Gly Asn
        370                 375                 380

Leu Glu Asn Lys Lys Ser Ile Thr Glu His Glu Gly Glu Ile Gly Lys
385                 390                 395                 400

Ile Pro Leu Lys Leu Asp His Leu Arg Ile Glu Glu Leu Lys Glu Asn
                405                 410                 415

Gly Ile Ile Leu Lys Gly Lys Lys Glu Ile Asp Asn Gly Lys Lys Tyr
            420                 425                 430

Tyr Leu Leu Glu Ser Asn Asn Gln Val Tyr Glu Phe Arg Ile Ser Asp
        435                 440                 445

Glu Asn Asn Glu Val Gln Tyr Lys Thr Lys Glu Gly Lys Ile Thr Val
    450                 455                 460

Leu Gly Glu Lys Phe Asn Trp Arg Asn Ile Glu Val Met Ala Lys Asn
465                 470                 475                 480

Val Glu Gly Val Leu Lys Pro Leu Thr Ala Asp Tyr Asp Leu Phe Ala
                485                 490                 495

Leu Ala Pro Ser Leu Thr Glu Ile Lys Lys Gln Ile Pro Gln Lys Glu
            500                 505                 510

Trp Asp Lys Val Val Asn Thr Pro Asn Ser Leu Glu Lys Gln Lys Gly
        515                 520                 525

Val Thr Asn Leu Leu Ile Lys Tyr Gly Ile Glu Arg Lys Pro Asp Ser
    530                 535                 540

Thr Lys Gly Thr Leu Ser Asn Trp Gln Lys Gln Met Leu Asp Arg Leu
545                 550                 555                 560

Asn Glu Ala Val Lys Tyr Thr Gly Tyr Thr Gly Gly Asp Val Val Asn
                565                 570                 575

His Gly Thr Glu Gln Asp Asn Glu Glu Phe Pro Glu Lys Asp Asn Glu
            580                 585                 590

Ile Phe Ile Ile Asn Pro Glu Gly Glu Phe Ile Leu Thr Lys Asn Trp
        595                 600                 605

Glu Met Thr Gly Arg Phe Ile Glu Lys Asn Ile Thr Gly Lys Asp Tyr
    610                 615                 620

Leu Tyr Tyr Phe Asn Arg Ser Tyr Asn Lys Ile Ala Pro Gly Asn Lys
625                 630                 635                 640

Ala Tyr Ile Glu Trp Thr Asp Pro Ile Thr Lys Ala Lys Ile Asn Thr
                645                 650                 655

Ile Pro Thr Ser Ala Glu Phe Ile Lys Asn Leu Ser Ser Ile Arg Arg
            660                 665                 670

Ser Ser Asn Val Gly Val Tyr Lys Asp Ser Gly Asp Lys Asp Glu Phe
        675                 680                 685

Ala Lys Lys Glu Ser Val Lys Lys Ile Ala Gly Tyr Leu Ser Asp Tyr
    690                 695                 700

Tyr Asn Ser Ala Asn His Ile Phe Ser Gln Glu Lys Lys Arg Lys Ile
705                 710                 715                 720

Ser Ile Phe Arg Gly Ile Gln Ala Tyr Asn Glu Ile Glu Asn Val Leu
                725                 730                 735

Lys Ser Lys Gln Ile Ala Pro Glu Tyr Lys Asn Tyr Phe Gln Tyr Leu
            740                 745                 750

Lys Glu Arg Ile Thr Asn Gln Val Gln Leu Leu Leu Thr His Gln Lys
        755                 760                 765
```

```
Ser Asn Ile Glu Phe Lys Leu Leu Tyr Lys Gln Leu Asn Phe Thr Glu
    770             775                 780

Asn Glu Thr Asp Asn Phe Glu Val Phe Gln Lys Ile Ile Asp Glu Lys
785             790                 795                 800

<210> SEQ ID NO 5
<211> LENGTH: 809
<212> TYPE: PRT
<213> ORGANISM: Bacillus anthracis

<400> SEQUENCE: 5

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
            20                  25                  30

Gly Ala Gly Gly His Gly Asp Val Gly Met His Val Lys Glu Lys Glu
        35                  40                  45

Lys Asn Lys Asp Glu Asn Lys Arg Lys Asp Glu Glu Arg Asn Lys Thr
    50                  55                  60

Gln Glu Glu His Leu Lys Glu Ile Met Lys His Ile Val Lys Ile Glu
65              70                  75                  80

Val Lys Gly Glu Glu Ala Val Lys Lys Glu Ala Ala Glu Lys Leu Leu
            85                  90                  95

Glu Lys Val Pro Ser Asp Val Leu Glu Met Tyr Lys Ala Ile Gly Gly
            100                 105                 110

Lys Ile Tyr Ile Val Asp Gly Asp Ile Thr Lys His Ile Ser Leu Glu
        115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205

Thr Ile Lys Asn Ala Ser Asp Ser Asp Gly Gln Asp Leu Leu Phe Thr
    210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
        275                 280                 285

Leu Glu Glu Leu Lys Asp Gln Arg Met Leu Ser Arg Tyr Glu Lys Trp
    290                 295                 300

Glu Lys Ile Lys Gln His Tyr Gln His Trp Ser Asp Ser Leu Ser Glu
305                 310                 315                 320

Glu Gly Arg Gly Leu Leu Lys Lys Leu Gln Ile Pro Ile Glu Pro Lys
                325                 330                 335

Lys Asp Asp Ile Ile His Ser Leu Ser Gln Glu Glu Lys Glu Leu Leu
            340                 345                 350
```

-continued

Lys Arg Ile Gln Ile Asp Ser Ser Asp Phe Leu Ser Thr Glu Glu Lys
        355                 360                 365
Glu Phe Leu Lys Lys Leu Gln Ile Asp Ile Arg Asp Ser Leu Ser Glu
        370                 375                 380
Glu Glu Lys Glu Leu Leu Asn Arg Ile Gln Val Asp Ser Ser Asn Pro
385                 390                 395                 400
Leu Ser Glu Lys Glu Lys Glu Phe Leu Lys Lys Leu Lys Leu Asp Ile
                405                 410                 415
Gln Pro Tyr Asp Ile Asn Gln Arg Leu Gln Asp Thr Gly Gly Leu Ile
                420                 425                 430
Asp Ser Pro Ser Ile Asn Leu Asp Val Arg Lys Gln Tyr Lys Arg Asp
            435                 440                 445
Ile Gln Asn Ile Asp Ala Leu Leu His Gln Ser Ile Gly Ser Thr Leu
        450                 455                 460
Tyr Asn Lys Ile Tyr Leu Tyr Glu Asn Met Asn Ile Asn Asn Leu Thr
465                 470                 475                 480
Ala Thr Leu Gly Ala Asp Leu Val Asp Ser Thr Asp Asn Thr Lys Ile
                485                 490                 495
Asn Arg Gly Ile Phe Asn Glu Phe Lys Lys Asn Phe Lys Tyr Ser Ile
                500                 505                 510
Ser Ser Asn Tyr Met Ile Val Asp Ile Asn Glu Arg Pro Ala Leu Asp
            515                 520                 525
Asn Glu Arg Leu Lys Trp Arg Ile Gln Leu Ser Pro Asp Thr Arg Ala
        530                 535                 540
Gly Tyr Leu Glu Asn Gly Lys Leu Ile Leu Gln Arg Asn Ile Gly Leu
545                 550                 555                 560
Glu Ile Lys Asp Val Gln Ile Ile Lys Gln Ser Glu Lys Glu Tyr Ile
                565                 570                 575
Arg Ile Asp Ala Lys Val Val Pro Lys Ser Lys Ile Asp Thr Lys Ile
                580                 585                 590
Gln Glu Ala Gln Leu Asn Ile Asn Gln Glu Trp Asn Lys Ala Leu Gly
            595                 600                 605
Leu Pro Lys Tyr Thr Lys Leu Ile Thr Phe Asn Val His Asn Arg Tyr
        610                 615                 620
Ala Ser Asn Ile Val Glu Ser Ala Tyr Leu Ile Leu Asn Glu Trp Lys
625                 630                 635                 640
Asn Asn Ile Gln Ser Asp Leu Ile Lys Lys Val Thr Asn Tyr Leu Val
                645                 650                 655
Asp Gly Asn Gly Arg Phe Val Phe Thr Asp Ile Thr Leu Pro Asn Ile
                660                 665                 670
Ala Glu Gln Tyr Thr His Gln Asp Glu Ile Tyr Glu Gln Val His Ser
            675                 680                 685
Lys Gly Leu Tyr Val Pro Glu Ser Arg Ser Ile Leu Leu His Gly Pro
        690                 695                 700
Ser Lys Gly Val Glu Leu Arg Asn Asp Ser Glu Gly Phe Ile His Glu
705                 710                 715                 720
Phe Gly His Ala Val Asp Asp Tyr Ala Gly Tyr Leu Leu Asp Lys Asn
                725                 730                 735
Gln Ser Asp Leu Val Thr Asn Ser Lys Lys Phe Ile Asp Ile Phe Lys
            740                 745                 750
Glu Glu Gly Ser Asn Leu Thr Ser Tyr Gly Arg Thr Asn Glu Ala Glu
        755                 760                 765
Phe Phe Ala Glu Ala Phe Arg Leu Met His Ser Thr Asp His Ala Glu

-continued

```
                770                 775                 780
Arg Leu Lys Val Gln Lys Asn Ala Pro Lys Thr Phe Gln Phe Ile Asn
785                 790                 795                 800

Asp Gln Ile Lys Phe Ile Ile Asn Ser
                805

<210> SEQ ID NO 6
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 6
caggtgcagc tggtgcagtc tgg                                            23

<210> SEQ ID NO 7
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 7
caggtcaact taagggagtc tgg                                            23

<210> SEQ ID NO 8
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 8
gaggtgcagc tggtggagtc tgg                                            23

<210> SEQ ID NO 9
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 9
caggtgcagc tgcaggagtc ggg                                            23

<210> SEQ ID NO 10
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 10
gaggtgcagc tgttgcagtc tgc                                            23

<210> SEQ ID NO 11
<211> LENGTH: 23
<212> TYPE: DNA
<213> ORGANISM: Artificial sequence
<220> FEATURE:
<223> OTHER INFORMATION: PCR primer useful for amplifying VH and VL
```

-continued

```
domains

<400> SEQUENCE: 11
caggtacagc tgcagcagtc agg                                               23

<210> SEQ ID NO 12
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 12
tgaggagacg gtgaccaggg tgcc                                              24

<210> SEQ ID NO 13
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 13
tgaagagacg gtgaccattg tccc                                              24

<210> SEQ ID NO 14
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 14
tgaggagacg gtgaccaggg ttcc                                              24

<210> SEQ ID NO 15
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 15
tgaggagacg gtgaccgtgg tccc                                              24

<210> SEQ ID NO 16
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 16
gacatccaga tgacccagtc tcc                                               23

<210> SEQ ID NO 17
<211> LENGTH: 23
<212> TYPE: DNA
<213> ORGANISM: Artificial sequence
<220> FEATURE:
<223> OTHER INFORMATION: PCR primer useful for amplifying VH and VL
      domains
```

```
<400> SEQUENCE: 17
gatgttgtga tgactcagtc tcc                                          23

<210> SEQ ID NO 18
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 18
gatattgtga tgactcagtc tcc                                          23

<210> SEQ ID NO 19
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 19
gaaattgtgt tgacgcagtc tcc                                          23

<210> SEQ ID NO 20
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 20
gacatcgtga tgacccagtc tcc                                          23

<210> SEQ ID NO 21
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 21
gaaacgacac tcacgcagtc tcc                                          23

<210> SEQ ID NO 22
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 22
gaaattgtgc tgactcagtc tcc                                          23

<210> SEQ ID NO 23
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 23
```

-continued

```
cagtctgtgt tgacgcagcc gcc                                              23

<210> SEQ ID NO 24
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 24
cagtctgccc tgactcagcc tgc                                              23

<210> SEQ ID NO 25
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 25
tcctatgtgc tgactcagcc acc                                              23

<210> SEQ ID NO 26
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 26
tcttctgagc tgactcagga ccc                                              23

<210> SEQ ID NO 27
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 27
cacgttatac tgactcaacc gcc                                              23

<210> SEQ ID NO 28
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 28
caggctgtgc tcactcagcc gtc                                              23

<210> SEQ ID NO 29
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 29
aattttatgc tgactcagcc cca                                              23
```

```
<210> SEQ ID NO 30
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 30
acgtttgatt tccaccttgg tccc                                          24

<210> SEQ ID NO 31
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 31
acgtttgatc tccagcttgg tccc                                          24

<210> SEQ ID NO 32
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 32
acgtttgata tccactttgg tccc                                          24

<210> SEQ ID NO 33
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 33
acgtttgatc tccaccttgg tccc                                          24

<210> SEQ ID NO 34
<211> LENGTH: 24
<212> TYPE: DNA
<213> ORGANISM: Artificial sequence
<220> FEATURE:
<223> OTHER INFORMATION: PCR primer useful for amplifying VH and VL
      domains

<400> SEQUENCE: 34
acgtttaatc tccagtcgtg tccc                                          24

<210> SEQ ID NO 35
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 35
cagtctgtgt tgacgcagcc gcc                                           23

<210> SEQ ID NO 36
```

```
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 36
cagtctgccc tgactcagcc tgc                                              23

<210> SEQ ID NO 37
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 37
tcctatgtgc tgactcagcc acc                                              23

<210> SEQ ID NO 38
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 38
tcttctgagc tgactcagga ccc                                              23

<210> SEQ ID NO 39
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 39
cacgttatac tgactcaacc gcc                                              23

<210> SEQ ID NO 40
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 40
caggctgtgc tcactcagcc gtc                                              23

<210> SEQ ID NO 41
<211> LENGTH: 23
<212> TYPE: DNA
<213> ORGANISM: Artificial sequence
<220> FEATURE:
<223> OTHER INFORMATION: PCR primer useful for amplifying VH and VL
      domains

<400> SEQUENCE: 41
aattttatgc tgactcagcc cca                                              23

<210> SEQ ID NO 42
<211> LENGTH: 489
<212> TYPE: PRT
```

-continued

<213> ORGANISM: Homo sapiens

<400> SEQUENCE: 42

```
Met Val Ala Glu Arg Ser Pro Ala Arg Ser Pro Gly Ser Trp Leu Phe
1               5                   10                  15

Pro Gly Leu Trp Leu Leu Val Leu Ser Gly Pro Gly Gly Leu Leu Arg
            20                  25                  30

Ala Gln Glu Gln Pro Ser Cys Arg Arg Ala Phe Asp Leu Tyr Phe Val
        35                  40                  45

Leu Asp Lys Ser Gly Ser Val Ala Asn Asn Trp Ile Glu Ile Tyr Asn
    50                  55                  60

Phe Val Gln Gln Leu Ala Glu Arg Phe Val Ser Pro Glu Met Arg Leu
65                  70                  75                  80

Ser Phe Ile Val Phe Ser Ser Gln Ala Thr Ile Ile Leu Pro Leu Thr
                85                  90                  95

Gly Asp Arg Gly Lys Ile Ser Lys Gly Leu Glu Asp Leu Lys Arg Val
            100                 105                 110

Ser Pro Val Gly Glu Thr Tyr Ile His Glu Gly Leu Lys Leu Ala Asn
        115                 120                 125

Glu Gln Ile Gln Lys Ala Gly Gly Leu Lys Thr Ser Ser Ile Ile Ile
    130                 135                 140

Ala Leu Thr Asp Gly Lys Leu Asp Gly Leu Val Pro Ser Tyr Ala Glu
145                 150                 155                 160

Lys Glu Ala Lys Ile Ser Arg Ser Leu Gly Ala Ser Val Tyr Cys Val
                165                 170                 175

Gly Val Leu Asp Phe Glu Gln Ala Gln Leu Glu Arg Ile Ala Asp Ser
            180                 185                 190

Lys Glu Gln Val Phe Pro Val Lys Gly Gly Phe Gln Ala Leu Lys Gly
        195                 200                 205

Ile Ile Asn Ser Ile Leu Ala Gln Ser Cys Thr Glu Ile Leu Glu Leu
    210                 215                 220

Gln Pro Ser Ser Val Cys Val Gly Glu Glu Phe Gln Ile Val Leu Ser
225                 230                 235                 240

Gly Arg Gly Phe Met Leu Gly Ser Arg Asn Gly Ser Val Leu Cys Thr
                245                 250                 255

Tyr Thr Val Asn Glu Thr Tyr Thr Thr Ser Val Lys Pro Val Ser Val
            260                 265                 270

Gln Leu Asn Ser Met Leu Cys Pro Ala Pro Ile Leu Asn Lys Ala Gly
        275                 280                 285

Glu Thr Leu Asp Val Ser Val Ser Phe Asn Gly Gly Lys Ser Val Ile
    290                 295                 300

Ser Gly Ser Leu Ile Val Thr Ala Thr Glu Cys Ser Asn Gly Ile Ala
305                 310                 315                 320

Ala Ile Ile Val Ile Leu Val Leu Leu Leu Leu Gly Ile Gly Leu
                325                 330                 335

Met Trp Trp Phe Trp Pro Leu Cys Cys Lys Val Val Ile Lys Asp Pro
            340                 345                 350

Pro Pro Pro Pro Pro Ala Pro Lys Glu Glu Glu Glu Pro Leu
        355                 360                 365

Pro Thr Lys Lys Trp Pro Thr Val Asp Ala Ser Tyr Tyr Gly Gly Arg
    370                 375                 380

Gly Val Gly Gly Ile Lys Arg Met Glu Val Arg Trp Gly Asp Lys Gly
385                 390                 395                 400

Ser Thr Glu Glu Gly Ala Arg Leu Glu Lys Ala Lys Asn Ala Val Val
```

```
                            405                 410                 415
Lys Ile Pro Glu Glu Thr Glu Glu Pro Ile Arg Pro Arg Pro Arg
                420                 425                 430

Pro Lys Pro Thr His Gln Pro Pro Gln Thr Lys Trp Tyr Thr Pro Ile
            435                 440                 445

Lys Gly Arg Leu Asp Ala Leu Trp Ala Leu Leu Arg Arg Gln Tyr Asp
        450                 455                 460

Arg Val Ser Leu Met Arg Pro Gln Glu Gly Asp Glu Val Cys Ile Trp
465                 470                 475                 480

Glu Cys Ile Glu Lys Glu Leu Thr Ala
                485

<210> SEQ ID NO 43
<211> LENGTH: 8
<212> TYPE: PRT
<213> ORGANISM: Artificial Sequence
<220> FEATURE:
<223> OTHER INFORMATION: FLAG tag

<400> SEQUENCE: 43

Asp Tyr Lys Asp Asp Asp Asp Lys
1               5

<210> SEQ ID NO 44
<211> LENGTH: 137
<212> TYPE: PRT
<213> ORGANISM: Homo sapiens
<220> FEATURE:
<223> OTHER INFORMATION: human mature J chain

<400> SEQUENCE: 44

Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135

<210> SEQ ID NO 45
<211> LENGTH: 137
<212> TYPE: PRT
<213> ORGANISM: Artificial sequence
<220> FEATURE:
<223> OTHER INFORMATION: Mutant form of human mature J chain with C134S
      mutation compared to wild type Mature form of human J chain (SEQ
      ID NO:44)

<400> SEQUENCE: 45

Gln Glu Asp Glu Arg Ile Val Leu Val Asp Asn Lys Cys Lys Cys Ala
```

```
                1               5                  10                  15
Arg Ile Thr Ser Arg Ile Ile Arg Ser Ser Glu Asp Pro Asn Glu Asp
                20                  25                  30

Ile Val Glu Arg Asn Ile Arg Ile Ile Val Pro Leu Asn Asn Arg Glu
                35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
                100                 105                 110

Val Val Pro Leu Val Tyr Gly Gly Glu Thr Lys Met Val Glu Thr Ala
                115                 120                 125

Leu Thr Pro Asp Ala Ser Tyr Pro Asp
                130                 135
```

<210> SEQ ID NO 46
<211> LENGTH: 112
<212> TYPE: PRT
<213> ORGANISM: Artificial sequence
<220> FEATURE:
<223> OTHER INFORMATION: Mutant form of human mature J chain with amino
      acids 113-137 deleted compared to wild type Mature form of human J
      chain (SEQ ID NO:44)

<400> SEQUENCE: 46

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
                20                  25                  30

Ile Val Glu Arg Asn Ile Arg Ile Ile Val Pro Leu Asn Asn Arg Glu
                35                  40                  45

Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
                100                 105                 110
```

<210> SEQ ID NO 47
<211> LENGTH: 137
<212> TYPE: PRT
<213> ORGANISM: Artificial sequence
<220> FEATURE:
<223> OTHER INFORMATION: Mutant form of human mature J chain with C109S
      and C134S mutation compared to wild type mature form of human J
      chain (SEQ ID NO:44)

<400> SEQUENCE: 47

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
                20                  25                  30

Ile Val Glu Arg Asn Ile Arg Ile Ile Val Pro Leu Asn Asn Arg Glu
                35                  40                  45
```

```
Asn Ile Ser Asp Pro Thr Ser Pro Leu Arg Thr Arg Phe Val Tyr His
    50                  55                  60

Leu Ser Asp Leu Cys Lys Lys Cys Asp Pro Thr Glu Val Glu Leu Asp
 65                  70                  75                  80

Asn Gln Ile Val Thr Ala Thr Gln Ser Asn Ile Cys Asp Glu Asp Ser
                     85                  90                  95

Ala Thr Glu Thr Cys Tyr Thr Tyr Asp Arg Asn Lys Ser Tyr Thr Ala
                100                 105                 110

Val Val Pro Leu Val Tyr Gly Gly Glu Thr Lys Met Val Glu Thr Ala
                115                 120                 125

Leu Thr Pro Asp Ala Ser Tyr Pro Asp
                130                 135

<210> SEQ ID NO 48
<211> LENGTH: 248
<212> TYPE: PRT
<213> ORGANISM: Artificial sequence
<220> FEATURE:
<223> OTHER INFORMATION: PWB2447 scFv

<400> SEQUENCE: 48

Gln Val Gln Leu Val Glu Ser Gly Gly Gly Val Val Gln Ser Gly Gly
 1               5                  10                  15

Ser Leu Arg Leu Ser Cys Ser Ala Ser Gly Phe Thr Phe Ser Asp Tyr
                20                  25                  30

Gly Met His Trp Val Arg Gln Ala Pro Gly Lys Gly Leu Glu Trp Val
             35                  40                  45

Ala Val Val Ser Tyr Asp Gly Ser Asn Ile Tyr Tyr Ile Asp Ser Val
 50                  55                  60

Lys Gly Arg Phe Thr Ile Ser Arg Asp Asp Ser Lys Asn Thr Leu Tyr
 65                  70                  75                  80

Leu Gln Met Asn Ser Leu Arg Ala Glu Asp Thr Ala Leu Tyr Tyr Cys
                85                  90                  95

Ala Lys Ala Gly Arg Arg Thr Gln Leu Gln Pro Arg Asp Phe Leu Phe
                100                 105                 110

Glu Tyr Trp Gly Gln Gly Thr Leu Val Thr Val Ser Ser Gly Gly Gly
            115                 120                 125

Gly Ser Gly Gly Gly Gly Ser Gly Gly Gly Gly Ser Ser Glu Leu Thr
        130                 135                 140

Gln Asp Pro Ala Val Ser Val Ala Leu Gly Gln Thr Val Arg Ile Thr
145                 150                 155                 160

Cys Gln Gly Asp Ser Leu Arg Ser Tyr Tyr Ala Ser Trp Tyr Gln Gln
                165                 170                 175

Lys Pro Gly Gln Ala Pro Val Leu Val Ile Tyr Gly Lys Asn Asn Arg
                180                 185                 190

Pro Ser Gly Ile Pro Asp Arg Phe Ser Gly Ser Ser Ser Gly Asn Thr
            195                 200                 205

Ala Ser Leu Thr Ile Thr Gly Ala Gln Ala Glu Asp Glu Ala Asp Tyr
        210                 215                 220

Tyr Cys Asn Ser Arg Asp Ser Ser Gly Asn His Val Val Phe Gly Gly
225                 230                 235                 240

Gly Thr Lys Leu Thr Val Leu Gly
                245

<210> SEQ ID NO 49
<211> LENGTH: 251
<212> TYPE: PRT
```

```
<213> ORGANISM: Artificial sequence
<220> FEATURE:
<223> OTHER INFORMATION: PWC2004 scFv

<400> SEQUENCE: 49

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Met Phe Thr Gly Tyr
                20                  25                  30

Tyr Met His Trp Val Arg Gln Ala Pro Gly Gln Gly Leu Glu Trp Met
            35                  40                  45

Gly Trp Ile Lys Pro Tyr Ser Gly Gly Thr Asn Tyr Ala Gln Lys Phe
50                  55                  60

His Asp Arg Val Thr Met Thr Arg Asp Thr Ser Ile Ser Thr Ala Tyr
65                  70                  75                  80

Met Glu Val Met Arg Leu Thr Ser Asp Ser Ala Val Phe Tyr Cys
                85                  90                  95

Ala Arg Ser Arg Tyr Ser Ser Pro Phe Arg Gly Gly Leu Asp Val
            100                 105                 110

Trp Gly Arg Gly Thr Met Val Thr Val Ser Ser Gly Gly Gly Ser
            115                 120                 125

Gly Gly Gly Gly Ser Gly Gly Gly Ser Ala Gln Ala Val Leu Thr
            130                 135                 140

Gln Pro Ser Ser Val Ser Gly Ala Pro Gly Gln Arg Val Thr Ile Ser
145                 150                 155                 160

Cys Thr Gly Ser Ser Ser Asn Ile Gly Asp Gly Tyr Asp Val His Trp
                165                 170                 175

Tyr Gln Gln Leu Pro Gly Thr Ala Pro Lys Leu Leu Ile Tyr Gly Asn
            180                 185                 190

Thr Asn Arg Pro Ser Gly Val Pro Asp Arg Phe Ser Gly Ser Lys Ser
        195                 200                 205

Asp Thr Ser Ala Ser Leu Ala Ile Thr Gly Leu Gln Val Glu Asp Glu
    210                 215                 220

Ala Asp Tyr Phe Cys His Ser Tyr Asp Ser Ser Ile Ser Gly Trp Ile
225                 230                 235                 240

Phe Gly Gly Gly Thr Lys Val Thr Val Leu Gly
                245                 250

<210> SEQ ID NO 50
<211> LENGTH: 246
<212> TYPE: PRT
<213> ORGANISM: Artificial sequence
<220> FEATURE:
<223> OTHER INFORMATION: PWD0283 scFv

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Thr Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95
Ala Arg Val Gly Gly Ala Ile Arg Phe Asp Ser Trp Gly Arg Gly Thr
                100                 105                 110

Leu Val Thr Val Ser Ser Gly Gly Gly Ser Gly Gly Gly Gly Ser
                115                 120                 125

Gly Gly Gly Gly Ser Ala Leu Ser Tyr Glu Leu Thr Gln Pro Pro Ser
            130                 135                 140

Ala Ser Glu Thr Pro Gly Gln Arg Val Ser Ile Ser Cys Ser Gly Gly
145                 150                 155                 160

Thr Ser Asn Ile Gly Ser Asn Thr Ile Asn Trp Tyr Gln Gln Val Pro
                165                 170                 175

Gly Thr Ala Pro Lys Leu Leu Ile Tyr Phe Asn Asn Arg Arg Pro Ala
                180                 185                 190

Gly Val Pro Ala Arg Phe Ser Ala Ser Lys Ser Gly Thr Ser Ala Ser
                195                 200                 205

Leu Thr Ile Ser Gly Leu Gln Ser Glu Asp Ala Asp Tyr Tyr Cys
                210                 215                 220

Ser Ala Trp Asp Asp Ser Leu Ser Gly Val Val Phe Gly Gly Gly Thr
225                 230                 235                 240

Lys Leu Thr Val Leu Gly
                245
```

<210> SEQ ID NO 51
<211> LENGTH: 244
<212> TYPE: PRT
<213> ORGANISM: Artificial sequence
<220> FEATURE:
<223> OTHER INFORMATION: PWD0323 scFv

<400> SEQUENCE: 51

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ile Trp Gly Arg Phe Glu Tyr Trp Gly Arg Gly Thr Thr
                100                 105                 110

Val Thr Val Ser Ser Gly Gly Gly Gly Ser Gly Gly Gly Gly Ser Gly
                115                 120                 125

Gly Gly Gly Ser Ala Gln Ala Val Leu Thr Gln Pro Ser Ser Ala Ser
            130                 135                 140

Gly Thr Pro Gly Gln Arg Val Thr Ile Ser Cys Ser Gly Ser Ser Ser
145                 150                 155                 160

Asn Ile Gly Thr Asn Thr Val Asn Trp Tyr Gln Gln Leu Pro Gly Thr
                165                 170                 175

Ala Pro Lys Leu Leu Ile Phe Ser Asn Asn Gln Arg Pro Ser Gly Val
                180                 185                 190

Pro Asp Arg Phe Ser Gly Ser Lys Ser Gly Pro Ser Ala Ser Leu Ala
                195                 200                 205
```

```
Ile Ser Gly Leu Gln Ser Glu Asp Glu Ala Asp Tyr Tyr Cys Ala Ala
    210                 215                 220

Trp Asp Asp Arg Leu Asn Gly Tyr Val Phe Gly Thr Gly Thr Lys Leu
225                 230                 235                 240

Thr Val Leu Gly

<210> SEQ ID NO 52
<211> LENGTH: 244
<212> TYPE: PRT
<213> ORGANISM: Artificial sequence
<220> FEATURE:
<223> OTHER INFORMATION: PWD0422 scFv

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gln Ala Phe Ala Arg Phe Glu Phe Trp Gly Arg Gly Thr Leu
            100                 105                 110

Val Thr Val Ser Ser Gly Gly Gly Gly Ser Gly Gly Gly Gly Ser Gly
        115                 120                 125

Gly Gly Gly Ser Ala Gln Ser Val Val Thr Gln Pro Pro Ser Val Ser
    130                 135                 140

Gly Thr Pro Gly Gln Arg Val Thr Ile Ser Cys Ser Gly Ser Ser Ser
145                 150                 155                 160

Asn Ile Gly Thr Asn Thr Val Asn Trp Tyr Gln Gln Leu Pro Gly Thr
                165                 170                 175

Ala Pro Lys Leu Leu Ile Tyr Ser Asn Asn Gln Arg Pro Ser Gly Val
            180                 185                 190

Pro Asp Arg Phe Ser Gly Ser Lys Ser Gly Thr Ser Ala Ser Val Ala
        195                 200                 205

Ile Ser Gly Leu Gln Ser Glu Asp Glu Ala Asp Tyr Tyr Cys Ser Ser
    210                 215                 220

Trp Asp Asp Ser Leu Asn Gly Val Val Phe Gly Gly Gly Thr Lys Leu
225                 230                 235                 240

Thr Val Leu Gly

<210> SEQ ID NO 53
<211> LENGTH: 244
<212> TYPE: PRT
<213> ORGANISM: Artificial sequence
<220> FEATURE:
<223> OTHER INFORMATION: PWD0587 scFv

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                         20                  25                  30
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ile Trp Gly Arg Phe Glu Tyr Trp Gly Arg Gly Thr Thr
            100                 105                 110

Val Thr Val Ser Ser Gly Gly Gly Ser Gly Gly Gly Gly Ser Gly
        115                 120                 125

Gly Gly Gly Ser Ala Gln Ser Val Leu Thr Gln Pro Pro Ser Ala Ser
        130                 135                 140

Gly Thr Pro Gly Gln Arg Val Thr Ile Ser Cys Ser Gly Ser Ser Ser
145                 150                 155                 160

Asn Ile Gly Ser Asn Thr Val Asn Trp Tyr Gln Gln Leu Pro Gly Thr
                165                 170                 175

Ala Pro Lys Leu Leu Ile Tyr Ser Asn Asn Gln Arg Pro Ser Gly Val
            180                 185                 190

Pro Asp Arg Phe Ser Gly Ser Lys Ser Gly Thr Ser Ala Ser Leu Ala
            195                 200                 205

Ile Ser Gly Leu Gln Ser Glu Asp Glu Ala Asp Tyr Tyr Cys Ala Ala
        210                 215                 220

Trp Asp Asp Ser Leu Asn Gly Val Val Phe Gly Gly Thr Lys Leu
225                 230                 235                 240

Thr Val Leu Gly

<210> SEQ ID NO 54
<211> LENGTH: 248
<212> TYPE: PRT
<213> ORGANISM: Artificial sequence
<220> FEATURE:
<223> OTHER INFORMATION: PWD0791 scFv

<400> SEQUENCE: 54

Glu Val Gln Leu Leu Glu Ser Gly Gly Gly Leu Leu Gln Pro Gly Gly
1               5                   10                  15

Ser Leu Arg Leu Ser Cys Ala Ala Ser Gly Phe Ser Phe Ile Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asp His Lys Trp Asp Leu Pro Phe Asp Tyr Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Ala Leu Ser Tyr Val Leu Thr Gln Pro
        130                 135                 140
```

```
Pro Ser Ala Ser Gly Thr Pro Gly Gln Arg Val Val Ser Cys Ser
145                 150                 155                 160

Gly Gly Ser Ser Asn Ile Gly Lys Asn Pro Val Thr Trp Tyr Gln His
                165                 170                 175

Leu Pro Gly Thr Ala Pro Lys Leu Leu Ile Ser Arg Asn Thr Gln Arg
            180                 185                 190

Pro Ser Gly Val Pro Asp Arg Phe Ser Gly Ser Lys Ser Gly Thr Ser
        195                 200                 205

Ala Ser Leu Ala Ile Ser Gly Leu Gln Ser Glu Asp Glu Ala Asp Tyr
    210                 215                 220

Tyr Cys Ala Ala Trp Asp Asp Ser Leu Lys Gly Trp Val Phe Gly Gly
225                 230                 235                 240

Gly Thr Lys Leu Thr Val Leu Gly
                245

<210> SEQ ID NO 55
<211> LENGTH: 244
<212> TYPE: PRT
<213> ORGANISM: Artificial sequence
<220> FEATURE:
<223> OTHER INFORMATION: PHD2222 scFv

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Ile Trp Gly Arg Phe Glu Tyr Trp Gly Arg Gly Thr Thr
            100                 105                 110

Val Thr Val Ser Ser Gly Gly Gly Gly Ser Gly Gly Gly Gly Ser Gly
        115                 120                 125

Gly Gly Gly Ser Ala Gln Ser Val Leu Thr Gln Pro Pro Ser Ala Ser
130                 135                 140

Gly Thr Pro Gly Gln Arg Val Thr Ile Ser Cys Ser Gly Ser Ser Ser
145                 150                 155                 160

Asn Ile Gly Ser Asn Thr Val Asn Trp Tyr Gln Gln Leu Pro Gly Thr
                165                 170                 175

Ala Pro Lys Leu Leu Ile Tyr Ser Asn Asn Gln Arg Pro Ser Gly Val
            180                 185                 190

Pro Asp Arg Phe Ser Gly Ser Lys Ser Gly Thr Ser Ala Ser Leu Ala
        195                 200                 205

Val Ser Gly Leu Gln Ser Glu Asp Glu Ala Asp Tyr Tyr Cys Ala Ala
    210                 215                 220

Trp Asp Asp Ser Leu Asn Gly Val Val Phe Gly Gly Gly Thr Lys Leu
225                 230                 235                 240

Thr Val Leu Gly

<210> SEQ ID NO 56
```

<211> LENGTH: 244
<212> TYPE: PRT
<213> ORGANISM: Artificial sequence
<220> FEATURE:
<223> OTHER INFORMATION: PHD2581 scFv

<400> SEQUENCE: 56

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gln Ile Trp Gly Arg Phe Glu Tyr Trp Gly Lys Gly Thr Met
            100                 105                 110
Val Thr Val Ser Ser Gly Gly Gly Gly Ser Gly Gly Gly Gly Ser Gly
        115                 120                 125
Gly Gly Gly Ser Ala Gln Ser Val Leu Thr Gln Pro Pro Ser Ala Ser
    130                 135                 140
Gly Thr Pro Gly Gln Arg Val Thr Ile Ser Cys Ser Gly Ser Ser Ser
145                 150                 155                 160
Asn Ile Gly Ser Asn Thr Val Asn Trp Tyr Gln Gln Leu Pro Gly Thr
                165                 170                 175
Ala Pro Lys Leu Leu Ile Tyr Ser Asn Asn Gln Arg Pro Ser Gly Val
            180                 185                 190
Pro Asp Arg Phe Ser Gly Ser Lys Ser Gly Thr Ser Ala Ser Leu Ala
        195                 200                 205
Ile Ser Gly Leu Gln Ser Glu Asp Glu Ala Asp Tyr Tyr Cys Ala Ala
    210                 215                 220
Trp Asp Asp Ser Leu Asn Gly Val Val Phe Gly Gly Gly Thr Lys Leu
225                 230                 235                 240
Thr Val Leu Gly
```

<210> SEQ ID NO 57
<211> LENGTH: 744
<212> TYPE: DNA
<213> ORGANISM: Artificial sequence
<220> FEATURE:
<223> OTHER INFORMATION: DNA encoding PWB2447 scFv

<400> SEQUENCE: 57

```
caggtgcagc tggtggagtc tgggggaggc gtggtccagt ctggggggtc cctgaggctc        60
tcctgttcag cgtctggatt caccttcagt gactatggca tgcactgggt ccgccaggct       120
ccaggcaagg ggctggagtg ggtggcagtc gtgtcatatg atggaagtaa tatatactat       180
atagactccg tgaagggccg tttcaccatc tccagagacg attccaagaa cacgctttat       240
ctccaaatga acagcctgag agctgaggac acggctctgt attactgtgc gaaagctggg       300
aggcgaaccc aattacaacc cagagacttt cttttttgagt actggggcca aggaaccctg       360
gtcaccgtct cgagtggtgg aggcggttca ggcggaggtg gcagcggcgg tggcggatcg       420
tctgagctga ctcaggaccc tgctgtgtct gtggccttgg gacagacagt caggatcaca       480
```

| | |
|---|---:|
| tgccaaggag acagcctcag aagctattat gcaagctggt accagcagaa gccaggacag | 540 |
| gcccctgtac ttgtcatcta cggtaaaaac aaccggccct cagggatccc agaccgattc | 600 |
| tctggctcca gctcaggaaa cacagcttcc ttgaccatca ctggggctca ggcggaagat | 660 |
| gaggctgact attactgtaa ctcccgggac agcagtggta accatgtggt attcggcgga | 720 |
| gggaccaagc tgaccgtcct aggt | 744 |

<210> SEQ ID NO 58
<211> LENGTH: 753
<212> TYPE: DNA
<213> ORGANISM: Artificial sequence
<220> FEATURE:
<223> OTHER INFORMATION: DNA encoding PWC2004 scFv

<400> SEQUENCE: 58

| | |
|---|---:|
| caggtccagc tggtgcagtc tggggctgag gtgaggaagc ctggggcctc agtgaaggtc | 60 |
| tcctgcaagg cttctggata catgttcacc ggctactata tgcactgggt gcgacaggcc | 120 |
| cctggacaag gcttgagtg gatgggatgg atcaagcctt acagtggtgg cacaaactat | 180 |
| gcacagaagt tccacgacag ggtcaccatg accaggggaca cgtccatcag cacagcctac | 240 |
| atggaggtga tgaggctgac atctgacgac agcgccgtgt tttactgtgc gagaagccgc | 300 |
| tatagcagca gccctttag ggggggtttg gacgtctggg gccagggac aatggtcacc | 360 |
| gtctcgagtg gaggcggcgg ttcaggcgga ggtggctctg gcggtggcgg aagtgcacag | 420 |
| gctgtgctga ctcagccgtc ctcagtgtct ggggccccag gcagagggt caccatctcc | 480 |
| tgcactggga gcagctccaa catcggggac ggttatgatg tccactggta tcagcaactt | 540 |
| ccaggaacag ccccccaaact cctcatctat ggtaacacta tcggccctc agggggtccct | 600 |
| gaccgattct ctggctccaa gtctgacacc tctgcctccc tggccatcac tgggctccag | 660 |
| gttgaggatg aggctgatta tttctgccac tcctatgaca gcagtatcag tggctggatt | 720 |
| ttcggcggag ggaccaaggt caccgtccta ggt | 753 |

<210> SEQ ID NO 59
<211> LENGTH: 738
<212> TYPE: DNA
<213> ORGANISM: Artificial sequence
<220> FEATURE:
<223> OTHER INFORMATION: DNA encoding PWD0283 scFv

<400> SEQUENCE: 59

| | |
|---|---:|
| gaggtgcagc tgttggagtc tgggggaggc ttggtacagc ctggggggtc cctgagactc | 60 |
| tcctgtgcag cctctggatt cacctttagc agctatgcca cgagctgggt ccgccaggct | 120 |
| ccagggaagg ggctggagtg ggtctcagct attagtggta gtggtggtag cacatactac | 180 |
| gcagactccg tgaagggccg gttcaccatc tccagagaca attccaagaa cacgctgtat | 240 |
| ctgcaaatga acagcctgag agccgaggac acggccgtgt attactgtgc gagagtgggg | 300 |
| ggagccattc gctttgactc ctggggcagg gaaccctgg tcaccgtctc gagtggaggc | 360 |
| ggcggttcag gcggaggtgg ctctggcggt ggcggaagtg cactttccta tgagctgact | 420 |
| cagccaccct cagcgtctga gacccccggg cagagggtct ccatctcttg ttctggaggc | 480 |
| acctcgaaca tcggatccaa cactatcaac tggtaccagc aggtcccagg aacgccccc | 540 |
| aaactactca tctattttaa taatcggcgg cccgcagggg tccctgcccg attttctgcc | 600 |
| tccaagtctg gcacctcagc ctccctgacc atcagtgggc tccagtctga ggatgaggct | 660 |
| gactattatt gttcagcatg ggatgacagc ctgagtggcg tggtgttcgg cggagggacc | 720 |

```
aagctgaccg tcctaggt                                                      738

<210> SEQ ID NO 60
<211> LENGTH: 732
<212> TYPE: DNA
<213> ORGANISM: Artificial sequence
<220> FEATURE:
<223> OTHER INFORMATION: DNA encoding PWD0323 scFv

<400> SEQUENCE: 60
gaggtgcagc tgttggagtc tgggggaggc ttggtacagc ctgggggtc cctgagactc          60 tcctgtgcag cctctggatt cacctttagc agctatgcca tgagctgggt ccgccaggct        120
ccagggaagg gctggagtg gtctcagct attagtggta gtggtggtag cacatactac          180
gcagactccg tgaagggccg gttcaccatc tccagagaca attccaagaa cacgctgtat        240
ctgcaaatga acagcctgag agccgaggac acggccgtgt attactgtgc gaggcaaatc        300 tgggacgat tgaatattg ggggaggggg accacgtca ccgtctcgag tggaggcggc           360
ggttcaggcg gaggtggctc tggcggtggc ggaagtgcac aggctgtgct gactcagccg        420
tcctcagcgt ctgggacccc cgggcagagg gtcaccatct cttgttctgg aagcagctcc        480
aacatcggaa ctaatactgt aaactggtac caacagctcc caggaacggc ccccaaactc        540
ctcatcttta gtaataatca acggccctca ggggtccctg accgattctc tggctccaag        600 tctggccct cagcctccct ggccatcagt ggactccagt ccgaggatga ggctgattat         660
tactgtgcag catgggatga caggctgaat ggttatgtct tcggaactgg gaccaagctg        720
accgtcctag gt                                                            732

<210> SEQ ID NO 61
<211> LENGTH: 732
<212> TYPE: DNA
<213> ORGANISM: Artificial sequence
<220> FEATURE:
<223> OTHER INFORMATION: DNA encoding PWD0422 scFv

<400> SEQUENCE: 61
gaggtgcagc tgttggagtc tgggggaggc ttggtacagc ctgggggtc cctgagactc          60 tcctgtgcag cctctggatt cacctttagc agctatgcca tgagctgggt ccgccaggct        120
ccagggaagg gctggagtg gtctcagct attagtggta gtggtggtag cacatactac          180
gcagactccg tgaagggccg gttcaccatc tccagagaca attccaagaa cacgctgtat        240
ctgcaaatga acagcctgag agccgaggac acggccgtgt attactgtgc gacccaggcc       300
tttgctcgtt tcgagttttg gggcggggc accctggtca ccgtctcgag tggaggcggc        360
ggttcaggcg gaggtggctc tggcggtggc ggaagtgcac agtctgtcgt gacgcagccg        420
ccctcagtgt ctgggacccc cgggcagagg gtcaccatct cttgttctgg aagcagctcc       480
aacatcggaa ctaatactgt aaactggtac caacaactcc caggaacggc ccccaaactc       540
ctcatctata gtaataatca gcgaccctca ggggtccctg accgattctc tggctccaag       600
tctggcacct cagcctccgt ggccatcagt gggctccagt ctgaggatga ggctgattac       660
tactgttctt catgggatga cagcctgaat ggcgtcgtgt tcggcggagg gaccaagctg       720
accgtcctag gt                                                            732

<210> SEQ ID NO 62
<211> LENGTH: 732
<212> TYPE: DNA
<213> ORGANISM: Artificial sequence
```

```
<220> FEATURE:
<223> OTHER INFORMATION: DNA encoding PWD0587 scFv

<400> SEQUENCE: 62
gaggtgcagc tgttggagtc tggggggaggc ttggtacagc ctgggggtc cctgagactc      60 tcctgtgcag cctctggatt cacctttagc agctatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat     240
ctgcaaatga acagcctgag agccgaggac acggccgtgt attactgtgc gaggcaaata    300
tggggacgat ttgaatattg ggggcggggg accacgtca ccgtctcgag tggaggcggc     360
ggttcaggcg gaggtggctc tggcggtggc ggaagtgcac agtctgtgct gactcagcca     420
ccctcagcgt ctgggacccc cggcagagg gtcaccatct cttgttctgg aagcagctcc     480
aacatcggaa gtaatactgt aaactggtac cagcagctcc caggaacggc ccccaaactc     540
ctcatctata gtaataatca gcggccctca ggggtccctg accgattctc tggctccaag    600
tctggcacct cagcctccct ggccatcagt gggctccagt ctgaggatga ggctgattat    660
tactgtgcag catgggatga cagcctgaat ggagtggtat tcggcggagg gaccaagctg    720
accgtcctag gt                                                        732

<210> SEQ ID NO 63
<211> LENGTH: 744
<212> TYPE: DNA
<213> ORGANISM: Artificial sequence
<220> FEATURE:
<223> OTHER INFORMATION: DNA encoding PWD0791 scFv

<400> SEQUENCE: 63
gaggtgcagc tgttggagtc tggggggaggc ttgttacagc ctgggggtc cctgagactc      60 tcctgtgcag cctctggatt ctctttatc agctatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat     240
ctgcaaatga acagcctgag agccgaggac acggccgtgt attactgtgc cagagtggac    300
cataaatggg aacctacccctt tgactactgg ggccgaggca ccctggtcac cgtctcgagt    360
ggaggcggcg gttcaggcgg aggtggctct ggcggtggcg gaagtgcact ttcctatgtg     420
ctgactcagc caccctcagc gtctggaacc ccgggcaga gggtcgtcgt ctcttgttct    480
gggggcagct ccaacatcgg aaaaaatcct gtaacctggt atcagcacct cccaggaacg   540 gccccaaac tcctcatctc tagaaatact cagcggccct caggagtccc tgaccgattc    600
tctggctcca agtctggcac gtcagcctcc ctggccatca gtgggctcca gtctgaggat    660
gaggctgatt attactgtgc agcatgggat gacagcctca agggctgggt gttcggcgga    720
gggaccaagc tgaccgtcct aggt                                           744

<210> SEQ ID NO 64
<211> LENGTH: 732
<212> TYPE: DNA
<213> ORGANISM: Artificial sequence
<220> FEATURE:
<223> OTHER INFORMATION: DNA encoding PHD2222 scFv

<400> SEQUENCE: 64
gaggtgcagc tgttggagtc tggggggaggc ttggtacagc ctgggggtc cctgagactc      60 tcctgtgcag cctctggatt cacctttagc agctatgcca tgagctgggt ccgccaggct    120
```

```
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaggcaaatc    300
tggggacgct ttgaatattg ggggcggggg accacggtca ccgtctcgag tggaggcggc    360
ggttcaggcg gaggtggctc tggcggtggc ggaagtgcac agtctgtgct gactcagcca    420
ccctcagcgt ctgggacccc cgggcagagg gtcaccatct cttgttctgg aagcagctcc    480
aacatcggaa gtaatactgt aaactggtac cagcagctcc caggaacggc ccccaaactc    540
ctcatctata gtaataatca gcggccctca ggggtccctg accgattctc tggctccaag    600
tctggcacct cagcctccct ggccgtcagt gggctccagt ctgaggatga ggctgattat    660
tactgtgcag catgggatga cagcctgaat ggtgtggtat tcggcggagg gaccaagctg    720
accgtcctag gt    732
```

<210> SEQ ID NO 65
<211> LENGTH: 732
<212> TYPE: DNA
<213> ORGANISM: Artificial sequence
<220> FEATURE:
<223> OTHER INFORMATION: DNA encoding PHD2581 sequence

<400> SEQUENCE: 65

```
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaggcaaatc    300
tggggacgat ttgaatattg gggcaaaggg acaatggtca ccgtctcgag tggaggcggc    360
ggttcaggcg gaggtggctc tggcggtggc ggaagtgcac agtctgtgct gactcagcca    420
ccctcagcgt ctgggacccc cgggcagagg gtcaccatct cttgttctgg aagcagctcc    480
aacatcggaa gtaatactgt aaactggtac cagcagctcc caggaacggc ccccaaactc    540
ctcatctata gtaataatca gcggccctca ggggtccctg accgattctc tggctccaag    600
tctggcacct cagcctccct ggccatcagt gggctccagt ctgaggatga ggctgattat    660
tactgtgcgg catgggatga cagcctgaat ggtgtggtat tcggcggagg gaccaagctg    720
accgtcctag gt    732
```

<210> SEQ ID NO 66
<211> LENGTH: 10
<212> TYPE: PRT
<213> ORGANISM: Homo sapiens

<400> SEQUENCE: 66

His Ser Pro Gly Asp Tyr Ala Phe Asp Tyr
1               5                   10

<210> SEQ ID NO 67
<211> LENGTH: 10
<212> TYPE: PRT
<213> ORGANISM: Homo sapiens

<400> SEQUENCE: 67

His Ser Pro Gly Asp Tyr Ala Phe Asp Tyr
1               5                   10

```
<210> SEQ ID NO 68
<211> LENGTH: 10
<212> TYPE: PRT
<213> ORGANISM: Homo sapiens

<400> SEQUENCE: 68

His Ser Pro Gly Asp Tyr Ala Phe Asp Tyr
1               5                   10

<210> SEQ ID NO 69
<211> LENGTH: 16
<212> TYPE: PRT
<213> ORGANISM: Homo sapiens

<400> SEQUENCE: 69

Ala Gly Arg Arg Thr Gln Leu Gln Pro Arg Asp Phe Leu Phe Glu Tyr
1               5                   10                  15

<210> SEQ ID NO 70
<211> LENGTH: 16
<212> TYPE: PRT
<213> ORGANISM: Homo sapiens

<400> SEQUENCE: 70

Ala Gly Arg Arg Thr Gln Leu Gln Pro Arg Asp Phe Leu Phe Glu Tyr
1               5                   10                  15

<210> SEQ ID NO 71
<211> LENGTH: 16
<212> TYPE: PRT
<213> ORGANISM: Homo sapiens

<400> SEQUENCE: 71

Ala Gly Arg Arg Thr Gln Leu Gln Pro Arg Asp Phe Leu Phe Glu Tyr
1               5                   10                  15

<210> SEQ ID NO 72
<211> LENGTH: 16
<212> TYPE: PRT
<213> ORGANISM: Homo sapiens

<400> SEQUENCE: 72

Ala Gly Arg Arg Thr Gln Leu Gln Pro Arg Asp Phe Leu Phe Glu Tyr
1               5                   10                  15

<210> SEQ ID NO 73
<211> LENGTH: 16
<212> TYPE: PRT
<213> ORGANISM: Homo sapiens

<400> SEQUENCE: 73

Ala Gly Arg Arg Thr Gln Leu Gln Pro Arg Asp Phe Leu Phe Glu Tyr
1               5                   10                  15

<210> SEQ ID NO 74
<211> LENGTH: 10
<212> TYPE: PRT
<213> ORGANISM: Homo sapiens

<400> SEQUENCE: 74

His Ser Pro Gly Asp Tyr Ala Phe Asp Tyr
1               5                   10

<210> SEQ ID NO 75
```

```
<211> LENGTH: 10
<212> TYPE: PRT
<213> ORGANISM: Homo sapiens

<400> SEQUENCE: 75

His Ser Pro Gly Asp Tyr Ala Phe Asp Tyr
1               5                   10

<210> SEQ ID NO 76
<211> LENGTH: 12
<212> TYPE: PRT
<213> ORGANISM: Homo sapiens

<400> SEQUENCE: 76

Ala Ser Tyr Leu Ser Thr Ser Ser Leu Asp Tyr
1               5                   10

<210> SEQ ID NO 77
<211> LENGTH: 12
<212> TYPE: PRT
<213> ORGANISM: Homo sapiens

<400> SEQUENCE: 77

Ala Ser Tyr Leu Ser Thr Ser Ser Leu Asp Tyr
1               5                   10

<210> SEQ ID NO 78
<211> LENGTH: 16
<212> TYPE: PRT
<213> ORGANISM: Homo sapiens

<400> SEQUENCE: 78

Ala Gly Arg Arg Thr Gln Leu Gln Pro Arg Asp Phe Leu Phe Glu Tyr
1               5                   10                  15

<210> SEQ ID NO 79
<211> LENGTH: 16
<212> TYPE: PRT
<213> ORGANISM: Homo sapiens

<400> SEQUENCE: 79

Asp Leu Asp Ser Ser Thr Ile Pro His Arg Glu Tyr Gly Met Asp Val
1               5                   10                  15

<210> SEQ ID NO 80
<211> LENGTH: 16
<212> TYPE: PRT
<213> ORGANISM: Homo sapiens

<400> SEQUENCE: 80

Ala Gly Arg Arg Thr Gln Leu Gln Pro Arg Asp Phe Leu Phe Glu Tyr
1               5                   10                  15

<210> SEQ ID NO 81
<211> LENGTH: 16
<212> TYPE: PRT
<213> ORGANISM: Homo sapiens

<400> SEQUENCE: 81

Ala Gly Arg Arg Thr Gln Leu Gln Pro Arg Asp Phe Leu Phe Glu Tyr
1               5                   10                  15

<210> SEQ ID NO 82
<211> LENGTH: 16
<212> TYPE: PRT
<213> ORGANISM: Homo sapiens
```

-continued

<400> SEQUENCE: 82

Ala Gly Arg Arg Thr Gln Leu Gln Pro Arg Asp Phe Leu Phe Glu Tyr
1               5                   10                  15

<210> SEQ ID NO 83
<211> LENGTH: 12
<212> TYPE: PRT
<213> ORGANISM: Homo sapiens

<400> SEQUENCE: 83

Ala Ser Asn Leu Ser Thr Ser Ser Ser Leu Asp Tyr
1               5                   10

<210> SEQ ID NO 84
<211> LENGTH: 10
<212> TYPE: PRT
<213> ORGANISM: Homo sapiens

<400> SEQUENCE: 84

Ser Gly Ser Ser Trp Ser His Phe Asp Phe
1               5                   10

<210> SEQ ID NO 85
<211> LENGTH: 14
<212> TYPE: PRT
<213> ORGANISM: Homo sapiens

<400> SEQUENCE: 85

Gly Ser Pro Thr Gly Asp Leu Asn Val Asp Val Phe Asp Tyr
1               5                   10

<210> SEQ ID NO 86
<211> LENGTH: 10
<212> TYPE: PRT
<213> ORGANISM: Homo sapiens

<400> SEQUENCE: 86

His Ser Pro Gly Asp Tyr Ala Phe Asp Tyr
1               5                   10

<210> SEQ ID NO 87
<211> LENGTH: 13
<212> TYPE: PRT
<213> ORGANISM: Homo sapiens

<400> SEQUENCE: 87

Val Arg Asp Ile Arg Pro Gly Asp Tyr Ala Phe Asp Tyr
1               5                   10

<210> SEQ ID NO 88
<211> LENGTH: 16
<212> TYPE: PRT
<213> ORGANISM: Homo sapiens

<400> SEQUENCE: 88

Ala Gly Arg Arg Thr Gln Leu Gln Pro Arg Asp Phe Leu Phe Glu Tyr
1               5                   10                  15

<210> SEQ ID NO 89
<211> LENGTH: 10
<212> TYPE: PRT
<213> ORGANISM: Homo sapiens

<400> SEQUENCE: 89

```
His Ser Pro Gly Asp Tyr Ala Phe Asp Tyr
1               5                   10

<210> SEQ ID NO 90
<211> LENGTH: 12
<212> TYPE: PRT
<213> ORGANISM: Homo sapiens

<400> SEQUENCE: 90

Ala Ser Tyr Leu Ser Thr Ser Pro Ser Leu Asp Tyr
1               5                   10

<210> SEQ ID NO 91
<211> LENGTH: 16
<212> TYPE: PRT
<213> ORGANISM: Homo sapiens

<400> SEQUENCE: 91

Ala Gly Arg Arg Thr Gln Leu Gln Pro Arg Asp Phe Leu Phe Glu Tyr
1               5                   10                  15

<210> SEQ ID NO 92
<211> LENGTH: 10
<212> TYPE: PRT
<213> ORGANISM: Homo sapiens

<400> SEQUENCE: 92

His Ser Pro Gly Asp Tyr Ala Phe Asp Tyr
1               5                   10

<210> SEQ ID NO 93
<211> LENGTH: 16
<212> TYPE: PRT
<213> ORGANISM: Homo sapiens

<400> SEQUENCE: 93

Ala Gly Arg Arg Thr Gln Leu Gln Pro Arg Asp Phe Leu Phe Glu Tyr
1               5                   10                  15

<210> SEQ ID NO 94
<211> LENGTH: 10
<212> TYPE: PRT
<213> ORGANISM: Homo sapiens

<400> SEQUENCE: 94

Ser Gly Ser Ser Trp Ser His Phe Asp Phe
1               5                   10

<210> SEQ ID NO 95
<211> LENGTH: 16
<212> TYPE: PRT
<213> ORGANISM: Homo sapiens

<400> SEQUENCE: 95

Ala Gly Arg Arg Thr Gln Leu Pro Pro Arg Asp Phe Leu Phe Glu His
1               5                   10                  15

<210> SEQ ID NO 96
<211> LENGTH: 10
<212> TYPE: PRT
<213> ORGANISM: Homo sapiens

<400> SEQUENCE: 96

His Ser Pro Gly Asp Tyr Ala Phe Asp Tyr
1               5                   10
```

```
<210> SEQ ID NO 97
<211> LENGTH: 12
<212> TYPE: PRT
<213> ORGANISM: Homo sapiens

<400> SEQUENCE: 97

Ala Ser Asn Leu Ser Thr Ser Pro Ser Leu Asp Tyr
1               5                   10

<210> SEQ ID NO 98
<211> LENGTH: 16
<212> TYPE: PRT
<213> ORGANISM: Homo sapiens

<400> SEQUENCE: 98

Ala Gly Arg Arg Thr Gln Leu Gln Pro Ile Asp Phe Leu Phe Glu Tyr
1               5                   10                  15

<210> SEQ ID NO 99
<211> LENGTH: 16
<212> TYPE: PRT
<213> ORGANISM: Homo sapiens

<400> SEQUENCE: 99

Ala Gly Arg Arg Thr Gln Leu Gln Pro Arg Asp Phe Leu Phe Glu Tyr
1               5                   10                  15

<210> SEQ ID NO 100
<211> LENGTH: 10
<212> TYPE: PRT
<213> ORGANISM: Homo sapiens

<400> SEQUENCE: 100

His Ser Pro Gly Asp Tyr Ala Phe Asp Tyr
1               5                   10

<210> SEQ ID NO 101
<211> LENGTH: 16
<212> TYPE: PRT
<213> ORGANISM: Homo sapiens

<400> SEQUENCE: 101

Ala Gly Arg Arg Thr Gln Leu Gln Pro Arg Asp Phe Leu Phe Glu Tyr
1               5                   10                  15

<210> SEQ ID NO 102
<211> LENGTH: 17
<212> TYPE: PRT
<213> ORGANISM: Homo sapiens

<400> SEQUENCE: 102

Gly Ser Gly Tyr Ser Gly Tyr Asp Phe Pro Tyr Tyr Tyr Gly Met Asp
1               5                   10                  15

Val

<210> SEQ ID NO 103
<211> LENGTH: 16
<212> TYPE: PRT
<213> ORGANISM: Homo sapiens

<400> SEQUENCE: 103

Ala Gly Arg Arg Thr Gln Leu Gln Pro Arg Asp Phe Leu Phe Glu Tyr
1               5                   10                  15
```

```
<210> SEQ ID NO 104
<211> LENGTH: 16
<212> TYPE: PRT
<213> ORGANISM: Homo sapiens

<400> SEQUENCE: 104

Ala Gly Arg Arg Thr Gln Leu Gln Pro Arg Asp Phe Leu Phe Glu Tyr
1               5                   10                  15

<210> SEQ ID NO 105
<211> LENGTH: 16
<212> TYPE: PRT
<213> ORGANISM: Homo sapiens

<400> SEQUENCE: 105

Ala Gly Arg Arg Thr Gln Leu Gln Pro Arg Asp Phe Leu Phe Glu Tyr
1               5                   10                  15

<210> SEQ ID NO 106
<211> LENGTH: 16
<212> TYPE: PRT
<213> ORGANISM: Homo sapiens

<400> SEQUENCE: 106

Ala Gly Arg Arg Thr Gln Leu Gln Pro Arg Asp Phe Leu Phe Glu Tyr
1               5                   10                  15

<210> SEQ ID NO 107
<211> LENGTH: 11
<212> TYPE: PRT
<213> ORGANISM: Homo sapiens

<400> SEQUENCE: 107

Asp Ser Ser Ser Gly Trp Phe Phe Ile Asp Tyr
1               5                   10

<210> SEQ ID NO 108
<211> LENGTH: 13
<212> TYPE: PRT
<213> ORGANISM: Homo sapiens

<400> SEQUENCE: 108

Ala Arg Asp Ser Ser Ser Gly Trp Phe Phe Ile Asp Tyr
1               5                   10

<210> SEQ ID NO 109
<211> LENGTH: 11
<212> TYPE: PRT
<213> ORGANISM: Homo sapiens

<400> SEQUENCE: 109

Asp Ser Ser Ser Gly Trp Phe Phe Ile Asp Tyr
1               5                   10

<210> SEQ ID NO 110
<211> LENGTH: 11
<212> TYPE: PRT
<213> ORGANISM: Homo sapiens

<400> SEQUENCE: 110

Asp Ser Ser Ser Gly Trp Phe Phe Ile Asp Tyr
1               5                   10

<210> SEQ ID NO 111
<211> LENGTH: 11
<212> TYPE: PRT
```

<213> ORGANISM: Homo sapiens

<400> SEQUENCE: 111

Asp Ser Ser Ser Gly Trp Phe Phe Ile Asp Tyr
1               5                   10

<210> SEQ ID NO 112
<211> LENGTH: 11
<212> TYPE: PRT
<213> ORGANISM: Homo sapiens

<400> SEQUENCE: 112

Asp Ser Ser Ser Gly Trp Phe Phe Ile Asp Tyr
1               5                   10

<210> SEQ ID NO 113
<211> LENGTH: 11
<212> TYPE: PRT
<213> ORGANISM: Homo sapiens

<400> SEQUENCE: 113

Asp Ser Ser Ser Gly Trp Phe Phe Ile Asp Tyr
1               5                   10

<210> SEQ ID NO 114
<211> LENGTH: 11
<212> TYPE: PRT
<213> ORGANISM: Homo sapiens

<400> SEQUENCE: 114

Asp Ser Ser Ser Gly Trp Phe Phe Ile Asp Tyr
1               5                   10

<210> SEQ ID NO 115
<211> LENGTH: 11
<212> TYPE: PRT
<213> ORGANISM: Homo sapiens

<400> SEQUENCE: 115

Asp Ser Ser Ser Gly Trp Phe Phe Ile Asp Tyr
1               5                   10

<210> SEQ ID NO 116
<211> LENGTH: 11
<212> TYPE: PRT
<213> ORGANISM: Homo sapiens

<400> SEQUENCE: 116

Asp Ser Ser Ser Gly Trp Phe Phe Ile Asp Tyr
1               5                   10

<210> SEQ ID NO 117
<211> LENGTH: 11
<212> TYPE: PRT
<213> ORGANISM: Homo sapiens

<400> SEQUENCE: 117

Asp Ser Ser Ser Gly Trp Phe Phe Ile Asp Tyr
1               5                   10

<210> SEQ ID NO 118
<211> LENGTH: 14
<212> TYPE: PRT
<213> ORGANISM: Homo sapiens

<400> SEQUENCE: 118

Ser Arg Tyr Ser Ser Ser Pro Phe Arg Gly Gly Leu Asp Val
1               5                   10

<210> SEQ ID NO 119
<211> LENGTH: 14
<212> TYPE: PRT
<213> ORGANISM: Homo sapiens

<400> SEQUENCE: 119

Ser Arg Tyr Ser Ser Ser Pro Phe Arg Gly Gly Leu Asp Val
1               5                   10

<210> SEQ ID NO 120
<211> LENGTH: 14
<212> TYPE: PRT
<213> ORGANISM: Homo sapiens

<400> SEQUENCE: 120

Ser Arg Tyr Ser Ser Ser Pro Phe Arg Gly Gly Leu Asp Val
1               5                   10

<210> SEQ ID NO 121
<211> LENGTH: 14
<212> TYPE: PRT
<213> ORGANISM: Homo sapiens

<400> SEQUENCE: 121

Ser Arg Tyr Ser Ser Ser Pro Phe Arg Gly Gly Leu Asp Val
1               5                   10

<210> SEQ ID NO 122
<211> LENGTH: 14
<212> TYPE: PRT
<213> ORGANISM: Homo sapiens

<400> SEQUENCE: 122

Ser Arg Tyr Ser Ser Ser Pro Phe Arg Gly Gly Leu Asp Val
1               5                   10

<210> SEQ ID NO 123
<211> LENGTH: 14
<212> TYPE: PRT
<213> ORGANISM: Homo sapiens

<400> SEQUENCE: 123

Ser Arg Tyr Ser Ser Ser Pro Phe Arg Gly Gly Leu Asp Val
1               5                   10

<210> SEQ ID NO 124
<211> LENGTH: 14
<212> TYPE: PRT
<213> ORGANISM: Homo sapiens

<400> SEQUENCE: 124

Ser Arg Tyr Ser Ser Ser Pro Phe Arg Gly Gly Leu Asp Val
1               5                   10

<210> SEQ ID NO 125
<211> LENGTH: 14
<212> TYPE: PRT
<213> ORGANISM: Homo sapiens

<400> SEQUENCE: 125

Ser Arg Tyr Ser Ser Ser Pro Phe Arg Gly Gly Leu Asp Val
1               5                   10

<210> SEQ ID NO 126
<211> LENGTH: 14
<212> TYPE: PRT
<213> ORGANISM: Homo sapiens

<400> SEQUENCE: 126

Ser Arg Tyr Ser Ser Ser Pro Phe Arg Gly Gly Leu Asp Val
1               5                   10

<210> SEQ ID NO 127
<211> LENGTH: 14
<212> TYPE: PRT
<213> ORGANISM: Homo sapiens

<400> SEQUENCE: 127

Ser Arg Tyr Ser Ser Ser Pro Phe Arg Gly Gly Leu Asp Val
1               5                   10

<210> SEQ ID NO 128
<211> LENGTH: 10
<212> TYPE: PRT
<213> ORGANISM: Homo sapiens

<400> SEQUENCE: 128

Ser Ser Ser Gly Cys Leu Phe Ile Asp Tyr
1               5                   10

<210> SEQ ID NO 129
<211> LENGTH: 14
<212> TYPE: PRT
<213> ORGANISM: Homo sapiens

<400> SEQUENCE: 129

Ser Arg Tyr Ser Ser Ser Pro Phe Arg Gly Gly Leu Asp Val
1               5                   10

<210> SEQ ID NO 130
<211> LENGTH: 14
<212> TYPE: PRT
<213> ORGANISM: Homo sapiens

<400> SEQUENCE: 130

Ser Arg Tyr Ser Ser Ser Pro Phe Arg Gly Gly Leu Asp Val
1               5                   10

<210> SEQ ID NO 131
<211> LENGTH: 11
<212> TYPE: PRT
<213> ORGANISM: Homo sapiens

<400> SEQUENCE: 131

Asp Ser Ser Ser Gly Trp Phe Phe Ile Asp Tyr
1               5                   10

<210> SEQ ID NO 132
<211> LENGTH: 14
<212> TYPE: PRT
<213> ORGANISM: Homo sapiens

<400> SEQUENCE: 132

Ser Arg Tyr Ser Ser Ser Pro Phe Arg Gly Gly Leu Asp Val
1               5                   10

<210> SEQ ID NO 133

```
<211> LENGTH: 14
<212> TYPE: PRT
<213> ORGANISM: Homo sapiens

<400> SEQUENCE: 133

Ser Arg Tyr Ser Ser Ser Pro Phe Arg Gly Gly Leu Asp Val
1               5                   10

<210> SEQ ID NO 134
<211> LENGTH: 14
<212> TYPE: PRT
<213> ORGANISM: Homo sapiens

<400> SEQUENCE: 134

Ser Arg Tyr Ser Ser Ser Pro Phe Arg Gly Gly Leu Asp Val
1               5                   10

<210> SEQ ID NO 135
<211> LENGTH: 9
<212> TYPE: PRT
<213> ORGANISM: Homo sapiens

<400> SEQUENCE: 135

Asp Ser Ser Ser Gly Trp Phe Phe Ile
1               5

<210> SEQ ID NO 136
<211> LENGTH: 10
<212> TYPE: PRT
<213> ORGANISM: Homo sapiens

<400> SEQUENCE: 136

Ser Ser Ser Gly Trp Leu Phe Ile Asp Tyr
1               5                   10

<210> SEQ ID NO 137
<211> LENGTH: 14
<212> TYPE: PRT
<213> ORGANISM: Homo sapiens

<400> SEQUENCE: 137

Ser Arg Tyr Ser Ser Ser Pro Phe Arg Gly Gly Leu Asp Val
1               5                   10

<210> SEQ ID NO 138
<211> LENGTH: 14
<212> TYPE: PRT
<213> ORGANISM: Homo sapiens

<400> SEQUENCE: 138

Ser Arg Tyr Ser Ser Ser Pro Phe Arg Gly Gly Leu Asp Val
1               5                   10

<210> SEQ ID NO 139
<211> LENGTH: 11
<212> TYPE: PRT
<213> ORGANISM: Homo sapiens

<400> SEQUENCE: 139

Asp Ser Ser Ser Gly Trp Phe Phe Ile Asp Tyr
1               5                   10

<210> SEQ ID NO 140
<211> LENGTH: 11
<212> TYPE: PRT
<213> ORGANISM: Homo sapiens
```

<400> SEQUENCE: 140

Asp Ser Ser Ser Gly Trp Phe Phe Ile Asp Tyr
1               5                   10

<210> SEQ ID NO 141
<211> LENGTH: 14
<212> TYPE: PRT
<213> ORGANISM: Homo sapiens

<400> SEQUENCE: 141

Ser Arg Tyr Ser Ser Pro Phe Arg Gly Gly Leu Asp Val
1               5                   10

<210> SEQ ID NO 142
<211> LENGTH: 11
<212> TYPE: PRT
<213> ORGANISM: Homo sapiens

<400> SEQUENCE: 142

Asp Ser Ser Ser Gly Trp Phe Phe Ile Asp Tyr
1               5                   10

<210> SEQ ID NO 143
<211> LENGTH: 13
<212> TYPE: PRT
<213> ORGANISM: Homo sapiens

<400> SEQUENCE: 143

Thr Tyr Pro Tyr Gly Gly Gly Thr Tyr Ala Phe Asp Tyr
1               5                   10

<210> SEQ ID NO 144
<211> LENGTH: 5
<212> TYPE: PRT
<213> ORGANISM: Homo sapiens

<400> SEQUENCE: 144

Asn Ala Phe Asp Tyr
1               5

<210> SEQ ID NO 145
<211> LENGTH: 12
<212> TYPE: PRT
<213> ORGANISM: Homo sapiens

<400> SEQUENCE: 145

Ser Ala Lys Ser Gly Trp Lys Ser Thr Phe Asp Val
1               5                   10

<210> SEQ ID NO 146
<211> LENGTH: 11
<212> TYPE: PRT
<213> ORGANISM: Homo sapiens

<400> SEQUENCE: 146

Asp Ser Ser Ser Gly Trp Leu Phe Ile Asp Tyr
1               5                   10

<210> SEQ ID NO 147
<211> LENGTH: 14
<212> TYPE: PRT
<213> ORGANISM: Homo sapiens

<400> SEQUENCE: 147

Ser Arg Tyr Ser Ser Ser Pro Phe Arg Gly Gly Leu Asp Val
1               5                   10

<210> SEQ ID NO 148
<211> LENGTH: 14
<212> TYPE: PRT
<213> ORGANISM: Homo sapiens

<400> SEQUENCE: 148

Ser Arg Tyr Ser Ser Ser Pro Phe Arg Gly Gly Leu Asp Val
1               5                   10

<210> SEQ ID NO 149
<211> LENGTH: 11
<212> TYPE: PRT
<213> ORGANISM: Homo sapiens

<400> SEQUENCE: 149

Asp Ser Ser Ser Gly Trp Leu Phe Ile Asp Tyr
1               5                   10

<210> SEQ ID NO 150
<211> LENGTH: 11
<212> TYPE: PRT
<213> ORGANISM: Homo sapiens

<400> SEQUENCE: 150

Asp Ser Ser Ser Gly Trp Leu Phe Ile Asp Tyr
1               5                   10

<210> SEQ ID NO 151
<211> LENGTH: 14
<212> TYPE: PRT
<213> ORGANISM: Homo sapiens

<400> SEQUENCE: 151

Ser Arg Tyr Ser Ser Ser Pro Phe Arg Gly Gly Leu Asp Val
1               5                   10

<210> SEQ ID NO 152
<211> LENGTH: 8
<212> TYPE: PRT
<213> ORGANISM: Homo sapiens

<400> SEQUENCE: 152

Gln Met Ile Met Ala Ala Arg Cys
1               5

<210> SEQ ID NO 153
<211> LENGTH: 9
<212> TYPE: PRT
<213> ORGANISM: Homo sapiens

<400> SEQUENCE: 153

Asp Ser Ser Ser Gly Trp Phe Phe Ile
1               5

<210> SEQ ID NO 154
<211> LENGTH: 9
<212> TYPE: PRT
<213> ORGANISM: Homo sapiens

<400> SEQUENCE: 154

Asp Ser Ser Ser Gly Trp Phe Phe Ile
1               5

```
<210> SEQ ID NO 155
<211> LENGTH: 11
<212> TYPE: PRT
<213> ORGANISM: Homo sapiens

<400> SEQUENCE: 155

Val Asp His Lys Trp Asp Leu Pro Phe Asp Tyr
1               5                   10

<210> SEQ ID NO 156
<211> LENGTH: 11
<212> TYPE: PRT
<213> ORGANISM: Homo sapiens

<400> SEQUENCE: 156

Val Asp His Lys Trp Asp Leu Pro Phe Asp Tyr
1               5                   10

<210> SEQ ID NO 157
<211> LENGTH: 11
<212> TYPE: PRT
<213> ORGANISM: Homo sapiens

<400> SEQUENCE: 157

Val Asp His Lys Trp Asp Leu Pro Phe Asp Tyr
1               5                   10

<210> SEQ ID NO 158
<211> LENGTH: 11
<212> TYPE: PRT
<213> ORGANISM: Homo sapiens

<400> SEQUENCE: 158

Val Asp His Lys Trp Asp Leu Pro Phe Asp Tyr
1               5                   10

<210> SEQ ID NO 159
<211> LENGTH: 14
<212> TYPE: PRT
<213> ORGANISM: Homo sapiens

<400> SEQUENCE: 159

Leu Leu Arg Gly Gly Ser Thr Tyr Leu Asp Ala Phe Asp Asn
1               5                   10

<210> SEQ ID NO 160
<211> LENGTH: 14
<212> TYPE: PRT
<213> ORGANISM: Homo sapiens

<400> SEQUENCE: 160

Leu Leu Arg Gly Gly Ser Thr Tyr Leu Asp Ala Phe Asp Asn
1               5                   10

<210> SEQ ID NO 161
<211> LENGTH: 7
<212> TYPE: PRT
<213> ORGANISM: Homo sapiens

<400> SEQUENCE: 161

Gly Trp Gly Val Phe Asp Ile
1               5

<210> SEQ ID NO 162
<211> LENGTH: 11
```

```
<212> TYPE: PRT
<213> ORGANISM: Homo sapiens

<400> SEQUENCE: 162

Val Asp His Asn Trp Asp Leu Pro Phe Asp Tyr
1               5                   10

<210> SEQ ID NO 163
<211> LENGTH: 11
<212> TYPE: PRT
<213> ORGANISM: Homo sapiens

<400> SEQUENCE: 163

Val Asp His Asn Trp Asp Leu Pro Phe Asp Tyr
1               5                   10

<210> SEQ ID NO 164
<211> LENGTH: 11
<212> TYPE: PRT
<213> ORGANISM: Homo sapiens

<400> SEQUENCE: 164

Val Asp His Asn Trp Asp Leu Pro Phe Asp Tyr
1               5                   10

<210> SEQ ID NO 165
<211> LENGTH: 11
<212> TYPE: PRT
<213> ORGANISM: Homo sapiens

<400> SEQUENCE: 165

Val Asp His Asn Trp Asp Leu Pro Phe Asp Tyr
1               5                   10

<210> SEQ ID NO 166
<211> LENGTH: 11
<212> TYPE: PRT
<213> ORGANISM: Homo sapiens

<400> SEQUENCE: 166

Val Asp His Asn Trp Asp Leu Pro Phe Asp Tyr
1               5                   10

<210> SEQ ID NO 167
<211> LENGTH: 11
<212> TYPE: PRT
<213> ORGANISM: Homo sapiens

<400> SEQUENCE: 167

Val Asp His Asn Trp Asp Leu Pro Phe Asp Tyr
1               5                   10

<210> SEQ ID NO 168
<211> LENGTH: 11
<212> TYPE: PRT
<213> ORGANISM: Homo sapiens

<400> SEQUENCE: 168

Val Asp His Asn Trp Asp Leu Pro Phe Asp Tyr
1               5                   10

<210> SEQ ID NO 169
<211> LENGTH: 11
<212> TYPE: PRT
<213> ORGANISM: Homo sapiens
```

```
<400> SEQUENCE: 169

Val Asp His Asn Trp Asp Leu Pro Phe Asp Tyr
1               5                   10

<210> SEQ ID NO 170
<211> LENGTH: 11
<212> TYPE: PRT
<213> ORGANISM: Homo sapiens

<400> SEQUENCE: 170

Val Asp His Asn Trp Asp Leu Pro Phe Asp Tyr
1               5                   10

<210> SEQ ID NO 171
<211> LENGTH: 11
<212> TYPE: PRT
<213> ORGANISM: Homo sapiens

<400> SEQUENCE: 171

Val Asp His Asn Trp Asp Leu Pro Phe Asp Tyr
1               5                   10

<210> SEQ ID NO 172
<211> LENGTH: 11
<212> TYPE: PRT
<213> ORGANISM: Homo sapiens

<400> SEQUENCE: 172

Val Asp His Asn Trp Asp Leu Pro Phe Asp Tyr
1               5                   10

<210> SEQ ID NO 173
<211> LENGTH: 11
<212> TYPE: PRT
<213> ORGANISM: Homo sapiens

<400> SEQUENCE: 173

Val Asp His Asn Trp Asp Leu Pro Phe Asp Tyr
1               5                   10

<210> SEQ ID NO 174
<211> LENGTH: 11
<212> TYPE: PRT
<213> ORGANISM: Homo sapiens

<400> SEQUENCE: 174

Val Asp His Asn Trp Asp Leu Pro Phe Asp Tyr
1               5                   10

<210> SEQ ID NO 175
<211> LENGTH: 11
<212> TYPE: PRT
<213> ORGANISM: Homo sapiens

<400> SEQUENCE: 175

Val Asp His Lys Trp Asp Leu Pro Phe Asp Tyr
1               5                   10

<210> SEQ ID NO 176
<211> LENGTH: 11
<212> TYPE: PRT
<213> ORGANISM: Homo sapiens

<400> SEQUENCE: 176

Val Asp His Lys Trp Asp Leu Pro Phe Asp Tyr
```

<210> SEQ ID NO 177
<211> LENGTH: 11
<212> TYPE: PRT
<213> ORGANISM: Homo sapiens

<400> SEQUENCE: 177

Val Asp His Lys Trp Asp Leu Pro Phe Asp Tyr
1               5                   10

<210> SEQ ID NO 178
<211> LENGTH: 11
<212> TYPE: PRT
<213> ORGANISM: Homo sapiens

<400> SEQUENCE: 178

Val Asp His Lys Trp Asp Leu Pro Phe Asp Tyr
1               5                   10

<210> SEQ ID NO 179
<211> LENGTH: 11
<212> TYPE: PRT
<213> ORGANISM: Homo sapiens

<400> SEQUENCE: 179

Val Asp His Lys Trp Asp Leu Pro Phe Asp Tyr
1               5                   10

<210> SEQ ID NO 180
<211> LENGTH: 11
<212> TYPE: PRT
<213> ORGANISM: Homo sapiens

<400> SEQUENCE: 180

Val Asp His Lys Trp Asp Leu Pro Phe Asp Tyr
1               5                   10

<210> SEQ ID NO 181
<211> LENGTH: 11
<212> TYPE: PRT
<213> ORGANISM: Homo sapiens

<400> SEQUENCE: 181

Val Asp His Lys Trp Asp Leu Pro Phe Asp Tyr
1               5                   10

<210> SEQ ID NO 182
<211> LENGTH: 11
<212> TYPE: PRT
<213> ORGANISM: Homo sapiens

<400> SEQUENCE: 182

Val Asp His Asn Trp Asp Leu Pro Phe Asp Tyr
1               5                   10

<210> SEQ ID NO 183
<211> LENGTH: 11
<212> TYPE: PRT
<213> ORGANISM: Homo sapiens

<400> SEQUENCE: 183

Val Asp His Asn Trp Asp Leu Pro Phe Asp Tyr
1               5                   10

```
<210> SEQ ID NO 184
<211> LENGTH: 11
<212> TYPE: PRT
<213> ORGANISM: Homo sapiens

<400> SEQUENCE: 184

Val Asp His Asn Trp Asp Leu Pro Phe Asp Tyr
1               5                   10

<210> SEQ ID NO 185
<211> LENGTH: 11
<212> TYPE: PRT
<213> ORGANISM: Homo sapiens

<400> SEQUENCE: 185

Val Asp His Asn Trp Asp Leu Pro Phe Asp Tyr
1               5                   10

<210> SEQ ID NO 186
<211> LENGTH: 11
<212> TYPE: PRT
<213> ORGANISM: Homo sapiens

<400> SEQUENCE: 186

Val Asp His Asn Trp Asp Leu Pro Phe Asp Tyr
1               5                   10

<210> SEQ ID NO 187
<211> LENGTH: 12
<212> TYPE: PRT
<213> ORGANISM: Homo sapiens

<400> SEQUENCE: 187

Tyr Val Ala Asp Thr Ser Lys Asp Val Phe Asp Ile
1               5                   10

<210> SEQ ID NO 188
<211> LENGTH: 10
<212> TYPE: PRT
<213> ORGANISM: Homo sapiens

<400> SEQUENCE: 188

Val Ala Ser Thr Ala Leu Tyr Phe Asp Asn
1               5                   10

<210> SEQ ID NO 189
<211> LENGTH: 13
<212> TYPE: PRT
<213> ORGANISM: Homo sapiens

<400> SEQUENCE: 189

Gly Val Tyr Asn Trp Asn Ser Ala Ala Lys Phe Asp Tyr
1               5                   10

<210> SEQ ID NO 190
<211> LENGTH: 12
<212> TYPE: PRT
<213> ORGANISM: Homo sapiens

<400> SEQUENCE: 190

Thr Tyr Tyr Tyr Val Tyr Tyr Asn Tyr Met Asp Val
1               5                   10

<210> SEQ ID NO 191
<211> LENGTH: 11
<212> TYPE: PRT
```

<213> ORGANISM: Homo sapiens

<400> SEQUENCE: 191

Val Ala His Gly Trp His Leu Ser Phe Asp Tyr
1               5                   10

<210> SEQ ID NO 192
<211> LENGTH: 12
<212> TYPE: PRT
<213> ORGANISM: Homo sapiens

<400> SEQUENCE: 192

Ser Leu Phe Arg Val Arg Gly Val Phe Phe Asp Tyr
1               5                   10

<210> SEQ ID NO 193
<211> LENGTH: 12
<212> TYPE: PRT
<213> ORGANISM: Homo sapiens

<400> SEQUENCE: 193

Ser Leu Phe Arg Val Arg Gly Val Phe Phe Asp Tyr
1               5                   10

<210> SEQ ID NO 194
<211> LENGTH: 11
<212> TYPE: PRT
<213> ORGANISM: Homo sapiens

<400> SEQUENCE: 194

Gly Pro Ala Gly Leu Gln Leu Ser Leu Asp Ile
1               5                   10

<210> SEQ ID NO 195
<211> LENGTH: 11
<212> TYPE: PRT
<213> ORGANISM: Homo sapiens

<400> SEQUENCE: 195

Val Asp His Arg Trp Asp Leu Pro Phe Asp Tyr
1               5                   10

<210> SEQ ID NO 196
<211> LENGTH: 11
<212> TYPE: PRT
<213> ORGANISM: Homo sapiens

<400> SEQUENCE: 196

Val Asp His Lys Trp Asp Leu Pro Phe Asp Tyr
1               5                   10

<210> SEQ ID NO 197
<211> LENGTH: 11
<212> TYPE: PRT
<213> ORGANISM: Homo sapiens

<400> SEQUENCE: 197

Val Asp His Lys Trp Asp Leu Pro Phe Asp Tyr
1               5                   10

<210> SEQ ID NO 198
<211> LENGTH: 11
<212> TYPE: PRT
<213> ORGANISM: Homo sapiens

<400> SEQUENCE: 198

Val Asp His Lys Trp Asp Leu Pro Phe Asp Tyr
1               5                   10

<210> SEQ ID NO 199
<211> LENGTH: 11
<212> TYPE: PRT
<213> ORGANISM: Homo sapiens

<400> SEQUENCE: 199

Val Asp His Lys Trp Asp Leu Pro Phe Asp Tyr
1               5                   10

<210> SEQ ID NO 200
<211> LENGTH: 10
<212> TYPE: PRT
<213> ORGANISM: Homo sapiens

<400> SEQUENCE: 200

Ala Arg Asp Tyr Tyr Phe Gly Met Asp Val
1               5                   10

<210> SEQ ID NO 201
<211> LENGTH: 11
<212> TYPE: PRT
<213> ORGANISM: Homo sapiens

<400> SEQUENCE: 201

Gly Pro Ala Gly Leu Gln Leu Ser Leu Asp Ile
1               5                   10

<210> SEQ ID NO 202
<211> LENGTH: 12
<212> TYPE: PRT
<213> ORGANISM: Homo sapiens

<400> SEQUENCE: 202

Asp Arg Ser Lys Leu Asn Ala Gly Tyr Phe Asp Ser
1               5                   10

<210> SEQ ID NO 203
<211> LENGTH: 10
<212> TYPE: PRT
<213> ORGANISM: Homo sapiens

<400> SEQUENCE: 203

Thr Lys Tyr Ser Ser Ile Val Phe Asp Leu
1               5                   10

<210> SEQ ID NO 204
<211> LENGTH: 14
<212> TYPE: PRT
<213> ORGANISM: Homo sapiens

<400> SEQUENCE: 204

Phe Arg Phe Leu Val Trp Tyr Gly Glu Ala Tyr Phe Asp Tyr
1               5                   10

<210> SEQ ID NO 205
<211> LENGTH: 10
<212> TYPE: PRT
<213> ORGANISM: Homo sapiens

<400> SEQUENCE: 205

Val Arg Gly Gln Leu Leu Ala Phe Asp Ile
1               5                   10

```
<210> SEQ ID NO 206
<211> LENGTH: 11
<212> TYPE: PRT
<213> ORGANISM: Homo sapiens

<400> SEQUENCE: 206

Val Asp His Lys Trp Asp Leu Pro Phe Asp Tyr
1               5                   10

<210> SEQ ID NO 207
<211> LENGTH: 11
<212> TYPE: PRT
<213> ORGANISM: Homo sapiens

<400> SEQUENCE: 207

Val Asp His Lys Trp Asp Leu Pro Phe Asp Tyr
1               5                   10

<210> SEQ ID NO 208
<211> LENGTH: 11
<212> TYPE: PRT
<213> ORGANISM: Homo sapiens

<400> SEQUENCE: 208

Gly Pro Ala Gly Leu Gln Leu Ser Leu Asp Ile
1               5                   10

<210> SEQ ID NO 209
<211> LENGTH: 10
<212> TYPE: PRT
<213> ORGANISM: Homo sapiens

<400> SEQUENCE: 209

Thr Lys Tyr Ser Ser Ile Val Phe Asp Leu
1               5                   10

<210> SEQ ID NO 210
<211> LENGTH: 10
<212> TYPE: PRT
<213> ORGANISM: Homo sapiens

<400> SEQUENCE: 210

Ala Val Trp Asp Asp Ser Leu Asn Gly His
1               5                   10

<210> SEQ ID NO 211
<211> LENGTH: 10
<212> TYPE: PRT
<213> ORGANISM: Homo sapiens

<400> SEQUENCE: 211

Thr Lys Tyr Ser Ser Ile Val Phe Asp Leu
1               5                   10

<210> SEQ ID NO 212
<211> LENGTH: 11
<212> TYPE: PRT
<213> ORGANISM: Homo sapiens

<400> SEQUENCE: 212

Leu Asp His Lys Trp Asp Leu Pro Phe Asp Tyr
1               5                   10

<210> SEQ ID NO 213
```

```
<211> LENGTH: 11
<212> TYPE: PRT
<213> ORGANISM: Homo sapiens

<400> SEQUENCE: 213

Val Asp His Asn Trp Asp Leu Pro Phe Asp Tyr
1               5                   10

<210> SEQ ID NO 214
<211> LENGTH: 11
<212> TYPE: PRT
<213> ORGANISM: Homo sapiens

<400> SEQUENCE: 214

Glu Tyr Tyr Tyr Arg Trp Gly Ser Tyr Ala Asn
1               5                   10

<210> SEQ ID NO 215
<211> LENGTH: 11
<212> TYPE: PRT
<213> ORGANISM: Homo sapiens

<400> SEQUENCE: 215

Val Asp His Lys Trp Asp Leu Pro Phe Asp Tyr
1               5                   10

<210> SEQ ID NO 216
<211> LENGTH: 11
<212> TYPE: PRT
<213> ORGANISM: Homo sapiens

<400> SEQUENCE: 216

Val Asp His Asn Trp Asp Leu Pro Phe Asp Tyr
1               5                   10

<210> SEQ ID NO 217
<211> LENGTH: 12
<212> TYPE: PRT
<213> ORGANISM: Homo sapiens

<400> SEQUENCE: 217

Ser Leu Phe Arg Val Arg Gly Val Phe Phe Asp Tyr
1               5                   10

<210> SEQ ID NO 218
<211> LENGTH: 12
<212> TYPE: PRT
<213> ORGANISM: Homo sapiens

<400> SEQUENCE: 218

Ser Leu Phe Arg Val Arg Gly Val Phe Phe Asp Tyr
1               5                   10

<210> SEQ ID NO 219
<211> LENGTH: 12
<212> TYPE: PRT
<213> ORGANISM: Homo sapiens

<400> SEQUENCE: 219

Ser Leu Phe Arg Val Arg Gly Val Phe Phe Asp Tyr
1               5                   10

<210> SEQ ID NO 220
<211> LENGTH: 10
<212> TYPE: PRT
<213> ORGANISM: Homo sapiens
```

<400> SEQUENCE: 220

Asp Leu Gly Val Gly Arg Tyr Phe Asp Tyr
1               5                   10

<210> SEQ ID NO 221
<211> LENGTH: 10
<212> TYPE: PRT
<213> ORGANISM: Homo sapiens

<400> SEQUENCE: 221

Asp Leu Gly Val Gly Arg Tyr Phe Asp Tyr
1               5                   10

<210> SEQ ID NO 222
<211> LENGTH: 12
<212> TYPE: PRT
<213> ORGANISM: Homo sapiens

<400> SEQUENCE: 222

Ser Leu Phe Arg Val Arg Gly Val Phe Phe Asp Tyr
1               5                   10

<210> SEQ ID NO 223
<211> LENGTH: 12
<212> TYPE: PRT
<213> ORGANISM: Homo sapiens

<400> SEQUENCE: 223

Asp Arg Ser Lys Leu Asn Ala Gly Tyr Phe Asp Ser
1               5                   10

<210> SEQ ID NO 224
<211> LENGTH: 12
<212> TYPE: PRT
<213> ORGANISM: Homo sapiens

<400> SEQUENCE: 224

Asp Arg Ser Lys Leu Asn Ala Gly Tyr Phe Asp Ser
1               5                   10

<210> SEQ ID NO 225
<211> LENGTH: 11
<212> TYPE: PRT
<213> ORGANISM: Homo sapiens

<400> SEQUENCE: 225

Leu Asp His Asn Trp Asp Leu Pro Phe Asp Tyr
1               5                   10

<210> SEQ ID NO 226
<211> LENGTH: 11
<212> TYPE: PRT
<213> ORGANISM: Homo sapiens

<400> SEQUENCE: 226

Leu Asp His Asn Trp Asp Leu Pro Phe Asp Tyr
1               5                   10

<210> SEQ ID NO 227
<211> LENGTH: 11
<212> TYPE: PRT
<213> ORGANISM: Homo sapiens

<400> SEQUENCE: 227

Leu Asp His Asn Trp Asp Leu Pro Phe Asp Tyr
1               5                   10

<210> SEQ ID NO 228
<211> LENGTH: 10
<212> TYPE: PRT
<213> ORGANISM: Homo sapiens

<400> SEQUENCE: 228

Thr Lys Tyr Ser Ser Ile Val Phe Asp Leu
1               5                   10

<210> SEQ ID NO 229
<211> LENGTH: 10
<212> TYPE: PRT
<213> ORGANISM: Homo sapiens

<400> SEQUENCE: 229

Thr Lys Tyr Ser Ser Ile Val Phe Asp Leu
1               5                   10

<210> SEQ ID NO 230
<211> LENGTH: 10
<212> TYPE: PRT
<213> ORGANISM: Homo sapiens

<400> SEQUENCE: 230

Thr Lys Tyr Ser Ser Ile Val Phe Asp Leu
1               5                   10

<210> SEQ ID NO 231
<211> LENGTH: 10
<212> TYPE: PRT
<213> ORGANISM: Homo sapiens

<400> SEQUENCE: 231

Leu Asp His Asn Trp Asn Leu Pro Phe Asp
1               5                   10

<210> SEQ ID NO 232
<211> LENGTH: 9
<212> TYPE: PRT
<213> ORGANISM: Homo sapiens

<400> SEQUENCE: 232

Val Gly Gly Ala Ile Arg Phe Asp Ser
1               5

<210> SEQ ID NO 233
<211> LENGTH: 10
<212> TYPE: PRT
<213> ORGANISM: Homo sapiens

<400> SEQUENCE: 233

Ser Val Gly Arg Ser Leu Ala Phe Asp Ile
1               5                   10

<210> SEQ ID NO 234
<211> LENGTH: 11
<212> TYPE: PRT
<213> ORGANISM: Homo sapiens

<400> SEQUENCE: 234

Arg Thr Gly Asp Cys Ser Tyr Thr Ser Cys Tyr
1               5                   10

```
<210> SEQ ID NO 235
<211> LENGTH: 11
<212> TYPE: PRT
<213> ORGANISM: Homo sapiens

<400> SEQUENCE: 235

Gly Pro Ala Gly Leu Gln Leu Ser Leu Asp Ile
1               5                   10

<210> SEQ ID NO 236
<211> LENGTH: 11
<212> TYPE: PRT
<213> ORGANISM: Homo sapiens

<400> SEQUENCE: 236

Gly Pro Ala Gly Leu Gln Leu Ser Leu Asp Ile
1               5                   10

<210> SEQ ID NO 237
<211> LENGTH: 11
<212> TYPE: PRT
<213> ORGANISM: Homo sapiens

<400> SEQUENCE: 237

Val Asp His Lys Trp Asp Leu Pro Phe Asp Tyr
1               5                   10

<210> SEQ ID NO 238
<211> LENGTH: 10
<212> TYPE: PRT
<213> ORGANISM: Homo sapiens

<400> SEQUENCE: 238

Phe Thr Gly Trp Tyr Gly Ala Phe Asp Ile
1               5                   10

<210> SEQ ID NO 239
<211> LENGTH: 13
<212> TYPE: PRT
<213> ORGANISM: Homo sapiens

<400> SEQUENCE: 239

Asp Arg Tyr Asn Met Val Gly Val Leu Arg Pro Asp Ser
1               5                   10

<210> SEQ ID NO 240
<211> LENGTH: 8
<212> TYPE: PRT
<213> ORGANISM: Homo sapiens

<400> SEQUENCE: 240

Gln Ile Trp Gly Arg Phe Glu Tyr
1               5

<210> SEQ ID NO 241
<211> LENGTH: 8
<212> TYPE: PRT
<213> ORGANISM: Homo sapiens

<400> SEQUENCE: 241

Gln Ile Trp Gly Arg Phe Glu Tyr
1               5

<210> SEQ ID NO 242
<211> LENGTH: 10
```

```
<212> TYPE: PRT
<213> ORGANISM: Homo sapiens

<400> SEQUENCE: 242

Gly Tyr Asp Phe Trp Ser Gly Phe Asp Tyr
1               5                   10

<210> SEQ ID NO 243
<211> LENGTH: 7
<212> TYPE: PRT
<213> ORGANISM: Homo sapiens

<400> SEQUENCE: 243

Gly Trp Gly Val Phe Asp Met
1               5

<210> SEQ ID NO 244
<211> LENGTH: 11
<212> TYPE: PRT
<213> ORGANISM: Homo sapiens

<400> SEQUENCE: 244

Val Asp His Lys Trp Asp Leu Pro Phe Asp Phe
1               5                   10

<210> SEQ ID NO 245
<211> LENGTH: 11
<212> TYPE: PRT
<213> ORGANISM: Homo sapiens

<400> SEQUENCE: 245

Ala Arg Ala Leu Phe Arg Val Ser Gly Pro Tyr
1               5                   10

<210> SEQ ID NO 246
<211> LENGTH: 11
<212> TYPE: PRT
<213> ORGANISM: Homo sapiens

<400> SEQUENCE: 246

Asp His Pro Tyr Asn Trp Asn Tyr Phe Asp Tyr
1               5                   10

<210> SEQ ID NO 247
<211> LENGTH: 11
<212> TYPE: PRT
<213> ORGANISM: Homo sapiens

<400> SEQUENCE: 247

Gly Ala Pro Ala Val Arg His Gly Phe Asp Tyr
1               5                   10

<210> SEQ ID NO 248
<211> LENGTH: 11
<212> TYPE: PRT
<213> ORGANISM: Homo sapiens

<400> SEQUENCE: 248

Val Asp His Lys Trp Asp Leu Pro Phe Asp Tyr
1               5                   10

<210> SEQ ID NO 249
<211> LENGTH: 9
<212> TYPE: PRT
<213> ORGANISM: Homo sapiens
```

<400> SEQUENCE: 249

Phe Gly Thr Gly Ser Ser Leu Glu Val
1               5

<210> SEQ ID NO 250
<211> LENGTH: 8
<212> TYPE: PRT
<213> ORGANISM: Homo sapiens

<400> SEQUENCE: 250

Gln Ala Phe Ala Arg Phe Glu Phe
1               5

<210> SEQ ID NO 251
<211> LENGTH: 14
<212> TYPE: PRT
<213> ORGANISM: Homo sapiens

<400> SEQUENCE: 251

Asn Leu Gln Asp Ile Val Ala Thr Ile Leu Pro Phe Asp Tyr
1               5                   10

<210> SEQ ID NO 252
<211> LENGTH: 11
<212> TYPE: PRT
<213> ORGANISM: Homo sapiens

<400> SEQUENCE: 252

Val Asp His Asn Trp Asp Leu Pro Phe Asp Tyr
1               5                   10

<210> SEQ ID NO 253
<211> LENGTH: 18
<212> TYPE: PRT
<213> ORGANISM: Homo sapiens

<400> SEQUENCE: 253

Gly Asp Pro Glu Glu Leu Arg Ser Asp Ser Tyr Phe Tyr Tyr Gly Met
1               5                   10                  15

Asp Val

<210> SEQ ID NO 254
<211> LENGTH: 11
<212> TYPE: PRT
<213> ORGANISM: Homo sapiens

<400> SEQUENCE: 254

Leu Asp His Lys Trp Asp Leu Pro Phe Asp His
1               5                   10

<210> SEQ ID NO 255
<211> LENGTH: 10
<212> TYPE: PRT
<213> ORGANISM: Homo sapiens

<400> SEQUENCE: 255

Thr Lys Tyr Ser Ser Val Ala Phe Asp Leu
1               5                   10

<210> SEQ ID NO 256
<211> LENGTH: 14
<212> TYPE: PRT
<213> ORGANISM: Homo sapiens
<220> FEATURE:
<221> NAME/KEY: SITE

```
<222> LOCATION: (14)..(14)
<223> OTHER INFORMATION: Xaa can be any naturally occurring amino acid

<400> SEQUENCE: 256

Leu Leu Arg Gly Gly Ser Thr Tyr Leu Asp Ala Phe Asp Xaa
1               5                   10

<210> SEQ ID NO 257
<211> LENGTH: 14
<212> TYPE: PRT
<213> ORGANISM: Homo sapiens

<400> SEQUENCE: 257

Gly Val Tyr Gly Gly Ser Ala Gly Leu Tyr Phe Asp Val
1               5                   10

<210> SEQ ID NO 258
<211> LENGTH: 8
<212> TYPE: PRT
<213> ORGANISM: Homo sapiens

<400> SEQUENCE: 258

Gly Glu Met Ala Thr Ile Arg Tyr
1               5

<210> SEQ ID NO 259
<211> LENGTH: 11
<212> TYPE: PRT
<213> ORGANISM: Homo sapiens

<400> SEQUENCE: 259

Val Asp His Lys Trp Asp Leu Pro Phe Asp Tyr
1               5                   10

<210> SEQ ID NO 260
<211> LENGTH: 11
<212> TYPE: PRT
<213> ORGANISM: Homo sapiens

<400> SEQUENCE: 260

Val Asp His Asn Trp Asp Leu Pro Phe Asp Tyr
1               5                   10

<210> SEQ ID NO 261
<211> LENGTH: 10
<212> TYPE: PRT
<213> ORGANISM: Homo sapiens

<400> SEQUENCE: 261

Ala Ser Ser Trp Tyr Leu Val Phe Asp Ile
1               5                   10

<210> SEQ ID NO 262
<211> LENGTH: 10
<212> TYPE: PRT
<213> ORGANISM: Homo sapiens

<400> SEQUENCE: 262

Ala Ser Ser Trp Tyr Leu Val Phe Asp Ile
1               5                   10

<210> SEQ ID NO 263
<211> LENGTH: 12
<212> TYPE: PRT
<213> ORGANISM: Homo sapiens
```

```
<400> SEQUENCE: 263

Ser Leu Phe Arg Val Arg Gly Val Phe Phe Asp Tyr
1               5                   10

<210> SEQ ID NO 264
<211> LENGTH: 11
<212> TYPE: PRT
<213> ORGANISM: Homo sapiens

<400> SEQUENCE: 264

Val Asp His Asn Trp Asp Leu Pro Phe Asp Tyr
1               5                   10

<210> SEQ ID NO 265
<211> LENGTH: 11
<212> TYPE: PRT
<213> ORGANISM: Homo sapiens

<400> SEQUENCE: 265

Val Asp His Asn Trp Asp Leu Pro Phe Asp Tyr
1               5                   10

<210> SEQ ID NO 266
<211> LENGTH: 11
<212> TYPE: PRT
<213> ORGANISM: Homo sapiens

<400> SEQUENCE: 266

Val Asp Arg Arg Trp Asp Leu Pro Phe Asp Tyr
1               5                   10

<210> SEQ ID NO 267
<211> LENGTH: 11
<212> TYPE: PRT
<213> ORGANISM: Homo sapiens

<400> SEQUENCE: 267

Val Asp His Lys Trp Asp Leu Pro Phe Asp Phe
1               5                   10

<210> SEQ ID NO 268
<211> LENGTH: 11
<212> TYPE: PRT
<213> ORGANISM: Homo sapiens

<400> SEQUENCE: 268

Gly Gly Pro Pro Phe Gly Ser Ser Tyr Asp Val
1               5                   10

<210> SEQ ID NO 269
<211> LENGTH: 12
<212> TYPE: PRT
<213> ORGANISM: Homo sapiens

<400> SEQUENCE: 269

Pro Thr Tyr Gly Pro Gly Ser Phe Leu Ile Asp His
1               5                   10

<210> SEQ ID NO 270
<211> LENGTH: 10
<212> TYPE: PRT
<213> ORGANISM: Homo sapiens

<400> SEQUENCE: 270

Thr Arg Gly Tyr Ser Leu Tyr Phe Asp Ser
```

<210> SEQ ID NO 271
<211> LENGTH: 11
<212> TYPE: PRT
<213> ORGANISM: Homo sapiens

<400> SEQUENCE: 271

Val Asp His Asn Trp Asp Leu Pro Phe Asp Tyr
1               5                   10

<210> SEQ ID NO 272
<211> LENGTH: 11
<212> TYPE: PRT
<213> ORGANISM: Homo sapiens

<400> SEQUENCE: 272

Gly Pro Ala Gly Leu Gln Leu Ser Leu Asp Ile
1               5                   10

<210> SEQ ID NO 273
<211> LENGTH: 11
<212> TYPE: PRT
<213> ORGANISM: Homo sapiens

<400> SEQUENCE: 273

Gly Pro Ala Gly Leu Gln Leu Ser Leu Asp Ile
1               5                   10

<210> SEQ ID NO 274
<211> LENGTH: 11
<212> TYPE: PRT
<213> ORGANISM: Homo sapiens

<400> SEQUENCE: 274

Val Asp His Lys Trp Asp Leu Pro Phe Asp Tyr
1               5                   10

<210> SEQ ID NO 275
<211> LENGTH: 10
<212> TYPE: PRT
<213> ORGANISM: Homo sapiens

<400> SEQUENCE: 275

Ala Gly Gly Ser Ser Leu Val Phe Asp Ser
1               5                   10

<210> SEQ ID NO 276
<211> LENGTH: 9
<212> TYPE: PRT
<213> ORGANISM: Homo sapiens

<400> SEQUENCE: 276

Asp Gly Pro Ser Asn Tyr Met Asp Val
1               5

<210> SEQ ID NO 277
<211> LENGTH: 11
<212> TYPE: PRT
<213> ORGANISM: Homo sapiens

<400> SEQUENCE: 277

Val Asp His Asn Trp Asp Leu Pro Phe Asp Tyr
1               5                   10

<210> SEQ ID NO 278
<211> LENGTH: 11
<212> TYPE: PRT
<213> ORGANISM: Homo sapiens

<400> SEQUENCE: 278

Asp Gly Asp Tyr Ser Ser Ser Ser Leu Asp Tyr
1               5                   10

<210> SEQ ID NO 279
<211> LENGTH: 11
<212> TYPE: PRT
<213> ORGANISM: Homo sapiens

<400> SEQUENCE: 279

Val Arg Val Pro Gly Arg Asp Gly Met Asp Val
1               5                   10

<210> SEQ ID NO 280
<211> LENGTH: 10
<212> TYPE: PRT
<213> ORGANISM: Homo sapiens

<400> SEQUENCE: 280

Gly Ser Gly Ser Tyr Ile Ala Phe Asp Ile
1               5                   10

<210> SEQ ID NO 281
<211> LENGTH: 12
<212> TYPE: PRT
<213> ORGANISM: Homo sapiens

<400> SEQUENCE: 281

Thr Thr Val Thr Thr Glu Ser Asp Trp Phe Asp Leu
1               5                   10

<210> SEQ ID NO 282
<211> LENGTH: 11
<212> TYPE: PRT
<213> ORGANISM: Homo sapiens

<400> SEQUENCE: 282

Val Asp His Asn Trp Asp Leu Pro Phe Asp Tyr
1               5                   10

<210> SEQ ID NO 283
<211> LENGTH: 14
<212> TYPE: PRT
<213> ORGANISM: Homo sapiens

<400> SEQUENCE: 283

Gly Val Tyr Gly Gly Gly Ser Ala Gly Leu Tyr Phe Asp Val
1               5                   10

<210> SEQ ID NO 284
<211> LENGTH: 11
<212> TYPE: PRT
<213> ORGANISM: Homo sapiens

<400> SEQUENCE: 284

Gly Pro Ser Gly Leu Leu Leu Gly Leu Asp Val
1               5                   10

<210> SEQ ID NO 285
<211> LENGTH: 10
<212> TYPE: PRT

<213> ORGANISM: Homo sapiens

<400> SEQUENCE: 285

Val Ala Ser Thr Ala Leu Tyr Phe Asp Asn
1               5                   10

<210> SEQ ID NO 286
<211> LENGTH: 10
<212> TYPE: PRT
<213> ORGANISM: Homo sapiens

<400> SEQUENCE: 286

Leu Ser Gly Val Thr Leu His Met Asp Val
1               5                   10

<210> SEQ ID NO 287
<211> LENGTH: 10
<212> TYPE: PRT
<213> ORGANISM: Homo sapiens

<400> SEQUENCE: 287

Val Arg Gly Gly Asn Leu Ala Phe Asp Phe
1               5                   10

<210> SEQ ID NO 288
<211> LENGTH: 12
<212> TYPE: PRT
<213> ORGANISM: Homo sapiens

<400> SEQUENCE: 288

Ser Leu Phe Arg Val Arg Gly Val Phe Phe Asp Tyr
1               5                   10

<210> SEQ ID NO 289
<211> LENGTH: 11
<212> TYPE: PRT
<213> ORGANISM: Homo sapiens

<400> SEQUENCE: 289

Glu Asp His Lys Trp Asp Leu Pro Phe Asp Tyr
1               5                   10

<210> SEQ ID NO 290
<211> LENGTH: 8
<212> TYPE: PRT
<213> ORGANISM: Homo sapiens

<400> SEQUENCE: 290

Gly Ala Leu Ser Ser Phe Asp Ser
1               5

<210> SEQ ID NO 291
<211> LENGTH: 8
<212> TYPE: PRT
<213> ORGANISM: Homo sapiens

<400> SEQUENCE: 291

Gln Ile Trp Gly Arg Phe Glu Tyr
1               5

<210> SEQ ID NO 292
<211> LENGTH: 11
<212> TYPE: PRT
<213> ORGANISM: Homo sapiens

<400> SEQUENCE: 292

```
Ala Asp His Asn Trp Asp Leu Pro Phe Asp Tyr
1               5                   10
```

<210> SEQ ID NO 293
<211> LENGTH: 9
<212> TYPE: PRT
<213> ORGANISM: Homo sapiens

<400> SEQUENCE: 293

```
Ala His Trp Gly Ser Arg Val Asp Tyr
1               5
```

<210> SEQ ID NO 294
<211> LENGTH: 14
<212> TYPE: PRT
<213> ORGANISM: Homo sapiens

<400> SEQUENCE: 294

```
Leu Leu Arg Gly Gly Ser Thr Tyr Leu Asp Ala Phe Asp Asn
1               5                   10
```

<210> SEQ ID NO 295
<211> LENGTH: 8
<212> TYPE: PRT
<213> ORGANISM: Homo sapiens

<400> SEQUENCE: 295

```
Glu Val Gly Ser Tyr Phe Asp Tyr
1               5
```

<210> SEQ ID NO 296
<211> LENGTH: 11
<212> TYPE: PRT
<213> ORGANISM: Homo sapiens

<400> SEQUENCE: 296

```
Val Asp His Asn Trp Asp Leu Pro Phe Asp Tyr
1               5                   10
```

<210> SEQ ID NO 297
<211> LENGTH: 12
<212> TYPE: PRT
<213> ORGANISM: Homo sapiens

<400> SEQUENCE: 297

```
Ser Leu Phe Arg Val Arg Gly Val Phe Phe Asp Tyr
1               5                   10
```

<210> SEQ ID NO 298
<211> LENGTH: 11
<212> TYPE: PRT
<213> ORGANISM: Homo sapiens

<400> SEQUENCE: 298

```
Gly Pro Arg Phe Trp Thr Gly Tyr Tyr Asp Tyr
1               5                   10
```

<210> SEQ ID NO 299
<211> LENGTH: 11
<212> TYPE: PRT
<213> ORGANISM: Homo sapiens

<400> SEQUENCE: 299

```
Ala Ser Trp Asp Asp Ser Leu Asn Gly Arg Val
1               5                   10
```

<210> SEQ ID NO 300
<211> LENGTH: 11
<212> TYPE: PRT
<213> ORGANISM: Homo sapiens

<400> SEQUENCE: 300

Ala Ser Trp Asp Asp Ser Leu Lys Ser Arg Val
1               5                   10

<210> SEQ ID NO 301
<211> LENGTH: 11
<212> TYPE: PRT
<213> ORGANISM: Homo sapiens

<400> SEQUENCE: 301

Ala Ser Trp Asp Asp Ser Val Asn Gly Arg Val
1               5                   10

<210> SEQ ID NO 302
<211> LENGTH: 11
<212> TYPE: PRT
<213> ORGANISM: Homo sapiens

<400> SEQUENCE: 302

Asn Ser Arg Asp Ser Ser Gly Asn His Val Val
1               5                   10

<210> SEQ ID NO 303
<211> LENGTH: 11
<212> TYPE: PRT
<213> ORGANISM: Homo sapiens

<400> SEQUENCE: 303

Asn Ser Arg Asp Ser Ser Gly Asn His Val Val
1               5                   10

<210> SEQ ID NO 304
<211> LENGTH: 11
<212> TYPE: PRT
<213> ORGANISM: Homo sapiens

<400> SEQUENCE: 304

Asn Ser Arg Asp Ser Ser Gly Asn His Val Val
1               5                   10

<210> SEQ ID NO 305
<211> LENGTH: 11
<212> TYPE: PRT
<213> ORGANISM: Homo sapiens

<400> SEQUENCE: 305

Asn Ser Arg Asp Ser Ser Gly Asn His Val Val
1               5                   10

<210> SEQ ID NO 306
<211> LENGTH: 11
<212> TYPE: PRT
<213> ORGANISM: Homo sapiens

<400> SEQUENCE: 306

Asn Ser Arg Asp Ser Ser Gly Asn His Val Val
1               5                   10

<210> SEQ ID NO 307

```
<211> LENGTH: 11
<212> TYPE: PRT
<213> ORGANISM: Homo sapiens

<400> SEQUENCE: 307

Ala Ser Trp Asp Asp Ser Leu Asn Gly Arg Val
1               5                   10

<210> SEQ ID NO 308
<211> LENGTH: 11
<212> TYPE: PRT
<213> ORGANISM: Homo sapiens

<400> SEQUENCE: 308

Ala Ser Trp Asp Asp Ser Leu Asn Gly Arg Val
1               5                   10

<210> SEQ ID NO 309
<211> LENGTH: 11
<212> TYPE: PRT
<213> ORGANISM: Homo sapiens

<400> SEQUENCE: 309

Asn Ser Arg Asp Ser Ser Gly Asn His Val Val
1               5                   10

<210> SEQ ID NO 310
<211> LENGTH: 11
<212> TYPE: PRT
<213> ORGANISM: Homo sapiens

<400> SEQUENCE: 310

Asn Ser Arg Asp Ser Ser Gly Asn His Val Val
1               5                   10

<210> SEQ ID NO 311
<211> LENGTH: 11
<212> TYPE: PRT
<213> ORGANISM: Homo sapiens

<400> SEQUENCE: 311

Asn Ser Arg Asp Ser Ser Gly Asn His Val Val
1               5                   10

<210> SEQ ID NO 312
<211> LENGTH: 11
<212> TYPE: PRT
<213> ORGANISM: Homo sapiens

<400> SEQUENCE: 312

His Ser Arg Asp Ser Ser Gly Asn His Val Leu
1               5                   10

<210> SEQ ID NO 313
<211> LENGTH: 11
<212> TYPE: PRT
<213> ORGANISM: Homo sapiens

<400> SEQUENCE: 313

Asn Ser Arg Asp Ser Ser Gly Asn His Val Val
1               5                   10

<210> SEQ ID NO 314
<211> LENGTH: 11
<212> TYPE: PRT
<213> ORGANISM: Homo sapiens
```

<400> SEQUENCE: 314

Asn Ser Arg Asp Ser Ser Gly Asn His Val Val
1               5                   10

<210> SEQ ID NO 315
<211> LENGTH: 11
<212> TYPE: PRT
<213> ORGANISM: Homo sapiens

<400> SEQUENCE: 315

Asn Ser Arg Asp Ser Ser Gly Asn His Val Val
1               5                   10

<210> SEQ ID NO 316
<211> LENGTH: 11
<212> TYPE: PRT
<213> ORGANISM: Homo sapiens

<400> SEQUENCE: 316

Asn Ser Arg Asp Ser Ser Gly Asn His Val Val
1               5                   10

<210> SEQ ID NO 317
<211> LENGTH: 10
<212> TYPE: PRT
<213> ORGANISM: Homo sapiens

<400> SEQUENCE: 317

Ser Ser Tyr Thr Thr Arg Ser Thr Arg Val
1               5                   10

<210> SEQ ID NO 318
<211> LENGTH: 11
<212> TYPE: PRT
<213> ORGANISM: Homo sapiens

<400> SEQUENCE: 318

Asn Ser Arg Asp Ser Ser Gly Asn His Val Val
1               5                   10

<210> SEQ ID NO 319
<211> LENGTH: 11
<212> TYPE: PRT
<213> ORGANISM: Homo sapiens

<400> SEQUENCE: 319

Ala Ser Trp Asp Asp Ser Leu Asn Gly Arg Val
1               5                   10

<210> SEQ ID NO 320
<211> LENGTH: 11
<212> TYPE: PRT
<213> ORGANISM: Homo sapiens

<400> SEQUENCE: 320

Ala Ser Trp Asp Asp Ser Leu Asn Gly Arg Val
1               5                   10

<210> SEQ ID NO 321
<211> LENGTH: 11
<212> TYPE: PRT
<213> ORGANISM: Homo sapiens

<400> SEQUENCE: 321

Asn Ser Arg Asp Ser Ser Gly Asn His Val Val
1               5                   10

<210> SEQ ID NO 322
<211> LENGTH: 11
<212> TYPE: PRT
<213> ORGANISM: Homo sapiens

<400> SEQUENCE: 322

Asn Ser Arg Asp Ser Ser Gly Asn His Val Val
1               5                   10

<210> SEQ ID NO 323
<211> LENGTH: 11
<212> TYPE: PRT
<213> ORGANISM: Homo sapiens

<400> SEQUENCE: 323

Ala Ser Trp Asp Asp Ser Leu Asn Gly Arg Val
1               5                   10

<210> SEQ ID NO 324
<211> LENGTH: 11
<212> TYPE: PRT
<213> ORGANISM: Homo sapiens

<400> SEQUENCE: 324

Asn Ser Arg Asp Ser Ser Gly Asn His Val Val
1               5                   10

<210> SEQ ID NO 325
<211> LENGTH: 11
<212> TYPE: PRT
<213> ORGANISM: Homo sapiens

<400> SEQUENCE: 325

Asn Ser Arg Asp Ser Ser Gly Asn His Val Val
1               5                   10

<210> SEQ ID NO 326
<211> LENGTH: 11
<212> TYPE: PRT
<213> ORGANISM: Homo sapiens

<400> SEQUENCE: 326

Ala Ser Trp Asp Asp Ser Leu Asn Gly Arg Val
1               5                   10

<210> SEQ ID NO 327
<211> LENGTH: 11
<212> TYPE: PRT
<213> ORGANISM: Homo sapiens

<400> SEQUENCE: 327

Asn Ser Arg Asp Ser Ser Gly Asn His Val Val
1               5                   10

<210> SEQ ID NO 328
<211> LENGTH: 10
<212> TYPE: PRT
<213> ORGANISM: Homo sapiens

<400> SEQUENCE: 328

Ser Ser Tyr Thr Thr Arg Ser Thr Arg Val
1               5                   10

```
<210> SEQ ID NO 329
<211> LENGTH: 11
<212> TYPE: PRT
<213> ORGANISM: Homo sapiens

<400> SEQUENCE: 329

Asn Ser Arg Asp Ser Ser Gly Asn His Val Val
1               5                   10

<210> SEQ ID NO 330
<211> LENGTH: 11
<212> TYPE: PRT
<213> ORGANISM: Homo sapiens

<400> SEQUENCE: 330

Ala Ser Trp Asp Asp Ser Leu Asn Gly Arg Val
1               5                   10

<210> SEQ ID NO 331
<211> LENGTH: 11
<212> TYPE: PRT
<213> ORGANISM: Homo sapiens

<400> SEQUENCE: 331

Asn Ser Arg Asp Ser Ser Gly Asn His Val Val
1               5                   10

<210> SEQ ID NO 332
<211> LENGTH: 11
<212> TYPE: PRT
<213> ORGANISM: Homo sapiens

<400> SEQUENCE: 332

Asn Ser Arg Asp Ser Ser Gly Asn His Val Val
1               5                   10

<210> SEQ ID NO 333
<211> LENGTH: 11
<212> TYPE: PRT
<213> ORGANISM: Homo sapiens

<400> SEQUENCE: 333

Asn Ser Arg Asp Ser Ser Gly Asn His Val Val
1               5                   10

<210> SEQ ID NO 334
<211> LENGTH: 11
<212> TYPE: PRT
<213> ORGANISM: Homo sapiens

<400> SEQUENCE: 334

Ala Ser Trp Asp Asp Ser Leu Asn Gly Arg Val
1               5                   10

<210> SEQ ID NO 335
<211> LENGTH: 11
<212> TYPE: PRT
<213> ORGANISM: Homo sapiens

<400> SEQUENCE: 335

Asn Ser Arg Asp Ser Ser Gly Asn His Val Val
1               5                   10

<210> SEQ ID NO 336
<211> LENGTH: 11
```

```
<212> TYPE: PRT
<213> ORGANISM: Homo sapiens

<400> SEQUENCE: 336

His Ser Arg Asp Ser Ser Gly Asn His Val Leu
 1               5                  10

<210> SEQ ID NO 337
<211> LENGTH: 11
<212> TYPE: PRT
<213> ORGANISM: Homo sapiens

<400> SEQUENCE: 337

Asn Ser Arg Asp Ser Ser Gly Asn His Val Val
 1               5                  10

<210> SEQ ID NO 338
<211> LENGTH: 11
<212> TYPE: PRT
<213> ORGANISM: Homo sapiens

<400> SEQUENCE: 338

Asn Ser Arg Asp Ser Ser Gly Asn His Val Val
 1               5                  10

<210> SEQ ID NO 339
<211> LENGTH: 11
<212> TYPE: PRT
<213> ORGANISM: Homo sapiens

<400> SEQUENCE: 339

Asn Ser Arg Asp Ser Ser Gly Asn His Val Val
 1               5                  10

<210> SEQ ID NO 340
<211> LENGTH: 11
<212> TYPE: PRT
<213> ORGANISM: Homo sapiens

<400> SEQUENCE: 340

Asn Ser Arg Asp Ser Ser Gly Asn His Val Val
 1               5                  10

<210> SEQ ID NO 341
<211> LENGTH: 11
<212> TYPE: PRT
<213> ORGANISM: Homo sapiens

<400> SEQUENCE: 341

Asn Ser Arg Asp Ser Ser Gly Asn His Val Val
 1               5                  10

<210> SEQ ID NO 342
<211> LENGTH: 12
<212> TYPE: PRT
<213> ORGANISM: Homo sapiens

<400> SEQUENCE: 342

Gln Ser Tyr Asp Ser Ser Leu Gly Gly Tyr Val Ile
 1               5                  10

<210> SEQ ID NO 343
<211> LENGTH: 12
<212> TYPE: PRT
<213> ORGANISM: Homo sapiens
```

-continued

```
<400> SEQUENCE: 343

Gln Ser Tyr Asp Ser Ser Leu Gly Gly Tyr Val Ile
1               5                   10

<210> SEQ ID NO 344
<211> LENGTH: 12
<212> TYPE: PRT
<213> ORGANISM: Homo sapiens

<400> SEQUENCE: 344

Gln Ser Tyr Asp Ser Ser Leu Gly Gly Tyr Val Ile
1               5                   10

<210> SEQ ID NO 345
<211> LENGTH: 12
<212> TYPE: PRT
<213> ORGANISM: Homo sapiens

<400> SEQUENCE: 345

Gln Ser Tyr Asp Ser Ser Leu Gly Gly Tyr Val Ile
1               5                   10

<210> SEQ ID NO 346
<211> LENGTH: 12
<212> TYPE: PRT
<213> ORGANISM: Homo sapiens

<400> SEQUENCE: 346

Gln Ser Tyr Asp Ser Ser Leu Gly Gly Tyr Val Ile
1               5                   10

<210> SEQ ID NO 347
<211> LENGTH: 12
<212> TYPE: PRT
<213> ORGANISM: Homo sapiens

<400> SEQUENCE: 347

Gln Ser Tyr Asp Ser Ser Leu Gly Gly Tyr Val Ile
1               5                   10

<210> SEQ ID NO 348
<211> LENGTH: 12
<212> TYPE: PRT
<213> ORGANISM: Homo sapiens

<400> SEQUENCE: 348

Gln Ser Tyr Asp Ser Ser Leu Gly Gly Tyr Val Ile
1               5                   10

<210> SEQ ID NO 349
<211> LENGTH: 12
<212> TYPE: PRT
<213> ORGANISM: Homo sapiens

<400> SEQUENCE: 349

Gln Ser Tyr Asp Ser Ser Leu Gly Gly Tyr Val Ile
1               5                   10

<210> SEQ ID NO 350
<211> LENGTH: 12
<212> TYPE: PRT
<213> ORGANISM: Homo sapiens

<400> SEQUENCE: 350

Gln Ser Tyr Asp Ser Ser Leu Gly Gly Tyr Val Ile
```

```
1               5              10
```

<210> SEQ ID NO 351
<211> LENGTH: 12
<212> TYPE: PRT
<213> ORGANISM: Homo sapiens

<400> SEQUENCE: 351

```
Gln Ser Tyr Asp Ser Ser Leu Gly Gly Tyr Gly Ile
1               5                  10
```

<210> SEQ ID NO 352
<211> LENGTH: 11
<212> TYPE: PRT
<213> ORGANISM: Homo sapiens

<400> SEQUENCE: 352

```
His Ser Tyr Asp Ser Ser Ile Ser Gly Gly Ile
1               5                  10
```

<210> SEQ ID NO 353
<211> LENGTH: 11
<212> TYPE: PRT
<213> ORGANISM: Homo sapiens

<400> SEQUENCE: 353

```
His Ser Tyr Asp Ser Ser Ile Ser Gly Trp Ile
1               5                  10
```

<210> SEQ ID NO 354
<211> LENGTH: 11
<212> TYPE: PRT
<213> ORGANISM: Homo sapiens

<400> SEQUENCE: 354

```
His Ser Tyr Asp Ser Ser Ile Ser Gly Trp Ile
1               5                  10
```

<210> SEQ ID NO 355
<211> LENGTH: 11
<212> TYPE: PRT
<213> ORGANISM: Homo sapiens

<400> SEQUENCE: 355

```
His Ser Tyr Asp Ser Ser Ile Arg Gly Trp Ile
1               5                  10
```

<210> SEQ ID NO 356
<211> LENGTH: 11
<212> TYPE: PRT
<213> ORGANISM: Homo sapiens

<400> SEQUENCE: 356

```
His Ser Tyr Asp Ser Ser Ile Arg Gly Gly Ile
1               5                  10
```

<210> SEQ ID NO 357
<211> LENGTH: 11
<212> TYPE: PRT
<213> ORGANISM: Homo sapiens

<400> SEQUENCE: 357

```
His Ser Tyr Asp Ser Ser Ile Ser Gly Gly Ile
1               5                  10
```

```
<210> SEQ ID NO 358
<211> LENGTH: 11
<212> TYPE: PRT
<213> ORGANISM: Homo sapiens

<400> SEQUENCE: 358

His Ser Tyr Asp Ser Ser Ile Ser Ala Trp Ile
1               5                   10

<210> SEQ ID NO 359
<211> LENGTH: 11
<212> TYPE: PRT
<213> ORGANISM: Homo sapiens

<400> SEQUENCE: 359

His Ser Tyr Asp Ser Ser Ile Ser Gly Trp Ile
1               5                   10

<210> SEQ ID NO 360
<211> LENGTH: 11
<212> TYPE: PRT
<213> ORGANISM: Homo sapiens

<400> SEQUENCE: 360

His Ser Tyr Asp Ser Ser Ile Ser Gly Trp Ile
1               5                   10

<210> SEQ ID NO 361
<211> LENGTH: 11
<212> TYPE: PRT
<213> ORGANISM: Homo sapiens

<400> SEQUENCE: 361

His Ser Tyr Asp Ser Ser Ile Ser Gly Trp Ile
1               5                   10

<210> SEQ ID NO 362
<211> LENGTH: 12
<212> TYPE: PRT
<213> ORGANISM: Homo sapiens

<400> SEQUENCE: 362

Gln Ser Tyr Asp Ser Ser Leu Gly Gly Tyr Val Ile
1               5                   10

<210> SEQ ID NO 363
<211> LENGTH: 11
<212> TYPE: PRT
<213> ORGANISM: Homo sapiens

<400> SEQUENCE: 363

His Ser Tyr Asp Ser Ser Ile Ser Gly Trp Ile
1               5                   10

<210> SEQ ID NO 364
<211> LENGTH: 11
<212> TYPE: PRT
<213> ORGANISM: Homo sapiens

<400> SEQUENCE: 364

His Ser Tyr Asp Ser Ser Ile Ser Gly Trp Ile
1               5                   10

<210> SEQ ID NO 365
<211> LENGTH: 12
<212> TYPE: PRT
```

<213> ORGANISM: Homo sapiens

<400> SEQUENCE: 365

Gln Ser Tyr Asp Ser Ser Leu Gly Gly Tyr Val Ile
1               5                   10

<210> SEQ ID NO 366
<211> LENGTH: 11
<212> TYPE: PRT
<213> ORGANISM: Homo sapiens

<400> SEQUENCE: 366

His Ser Tyr Asp Ser Ser Ile Ser Gly Trp Ile
1               5                   10

<210> SEQ ID NO 367
<211> LENGTH: 11
<212> TYPE: PRT
<213> ORGANISM: Homo sapiens

<400> SEQUENCE: 367

His Ser Tyr Asp Ser Ser Ile Ser Gly Trp Ile
1               5                   10

<210> SEQ ID NO 368
<211> LENGTH: 11
<212> TYPE: PRT
<213> ORGANISM: Homo sapiens

<400> SEQUENCE: 368

His Ser Tyr Asp Ser Ser Ile Ser Gly Trp Ile
1               5                   10

<210> SEQ ID NO 369
<211> LENGTH: 12
<212> TYPE: PRT
<213> ORGANISM: Homo sapiens

<400> SEQUENCE: 369

Gln Ser Tyr Asp Ser Ser Leu Gly Gly Tyr Val Ile
1               5                   10

<210> SEQ ID NO 370
<211> LENGTH: 12
<212> TYPE: PRT
<213> ORGANISM: Homo sapiens

<400> SEQUENCE: 370

Gln Ser Tyr Asp Ser Ser Leu Gly Gly Tyr Val Ile
1               5                   10

<210> SEQ ID NO 371
<211> LENGTH: 11
<212> TYPE: PRT
<213> ORGANISM: Homo sapiens

<400> SEQUENCE: 371

His Ser Tyr Asp Ser Ser Ile Ser Gly Trp Ile
1               5                   10

<210> SEQ ID NO 372
<211> LENGTH: 11
<212> TYPE: PRT
<213> ORGANISM: Homo sapiens

<400> SEQUENCE: 372

His Ser Tyr Asp Ser Ser Ile Ser Gly Trp Ile
1               5                   10

<210> SEQ ID NO 373
<211> LENGTH: 12
<212> TYPE: PRT
<213> ORGANISM: Homo sapiens

<400> SEQUENCE: 373

Gln Ser Tyr Asp Ser Ser Leu Gly Gly Tyr Val Ile
1               5                   10

<210> SEQ ID NO 374
<211> LENGTH: 12
<212> TYPE: PRT
<213> ORGANISM: Homo sapiens

<400> SEQUENCE: 374

Gln Ser Tyr Asp Ser Ser Leu Gly Gly Tyr Val Ile
1               5                   10

<210> SEQ ID NO 375
<211> LENGTH: 11
<212> TYPE: PRT
<213> ORGANISM: Homo sapiens

<400> SEQUENCE: 375

His Ser Tyr Asp Ser Ser Ile Ser Gly Trp Ile
1               5                   10

<210> SEQ ID NO 376
<211> LENGTH: 12
<212> TYPE: PRT
<213> ORGANISM: Homo sapiens

<400> SEQUENCE: 376

Gln Ser Tyr Asp Ser Ser Leu Gly Gly Tyr Val Ile
1               5                   10

<210> SEQ ID NO 377
<211> LENGTH: 12
<212> TYPE: PRT
<213> ORGANISM: Homo sapiens

<400> SEQUENCE: 377

Gln Ser Tyr Asp Ser Glu Leu Ser Gly Ser Glu Leu
1               5                   10

<210> SEQ ID NO 378
<211> LENGTH: 11
<212> TYPE: PRT
<213> ORGANISM: Homo sapiens

<400> SEQUENCE: 378

Asn Ser Leu Asp Ser Arg Gly Gln Arg Val Ile
1               5                   10

<210> SEQ ID NO 379
<211> LENGTH: 11
<212> TYPE: PRT
<213> ORGANISM: Homo sapiens

<400> SEQUENCE: 379

Ala Leu Tyr Leu Gly Gly Gly Leu Ser Trp Val
1               5                   10

<210> SEQ ID NO 380
<211> LENGTH: 11
<212> TYPE: PRT
<213> ORGANISM: Homo sapiens

<400> SEQUENCE: 380

Ala Ala Trp Asp Asp Ser Leu Ser Ala Tyr Val
1               5                   10

<210> SEQ ID NO 381
<211> LENGTH: 12
<212> TYPE: PRT
<213> ORGANISM: Homo sapiens

<400> SEQUENCE: 381

Gln Ser Tyr Asp Ser Ser Leu Gly Gly Tyr Val Ile
1               5                   10

<210> SEQ ID NO 382
<211> LENGTH: 11
<212> TYPE: PRT
<213> ORGANISM: Homo sapiens

<400> SEQUENCE: 382

His Ser Tyr Asp Ser Ser Ile Ser Gly Trp Ile
1               5                   10

<210> SEQ ID NO 383
<211> LENGTH: 11
<212> TYPE: PRT
<213> ORGANISM: Homo sapiens

<400> SEQUENCE: 383

His Ser Tyr Asp Ser Ser Ile Ser Gly Trp Ile
1               5                   10

<210> SEQ ID NO 384
<211> LENGTH: 12
<212> TYPE: PRT
<213> ORGANISM: Homo sapiens

<400> SEQUENCE: 384

Gln Ser Tyr Asp Ser Ser Leu Gly Gly Tyr Val Ile
1               5                   10

<210> SEQ ID NO 385
<211> LENGTH: 12
<212> TYPE: PRT
<213> ORGANISM: Homo sapiens

<400> SEQUENCE: 385

Gln Ser Tyr Asp Ser Ser Leu Gly Gly Tyr Val Ile
1               5                   10

<210> SEQ ID NO 386
<211> LENGTH: 11
<212> TYPE: PRT
<213> ORGANISM: Homo sapiens

<400> SEQUENCE: 386

His Ser Tyr Asp Ser Ser Ile Ser Gly Trp Ile
1               5                   10

<210> SEQ ID NO 387

```
<211> LENGTH: 12
<212> TYPE: PRT
<213> ORGANISM: Homo sapiens

<400> SEQUENCE: 387

Gln Ser Phe Asp Asn Arg Leu Arg Gly Phe Val Val
1               5                   10

<210> SEQ ID NO 388
<211> LENGTH: 12
<212> TYPE: PRT
<213> ORGANISM: Homo sapiens

<400> SEQUENCE: 388

Gln Ser Tyr Asp Ser Ser Leu Gly Gly Tyr Val Ile
1               5                   10

<210> SEQ ID NO 389
<211> LENGTH: 12
<212> TYPE: PRT
<213> ORGANISM: Homo sapiens

<400> SEQUENCE: 389

Gln Ser Tyr Asp Ser Ser Leu Gly Gly Tyr Val Ile
1               5                   10

<210> SEQ ID NO 390
<211> LENGTH: 11
<212> TYPE: PRT
<213> ORGANISM: Homo sapiens

<400> SEQUENCE: 390

Ala Thr Trp Asp Asp Asn Leu Asn Gly Trp Val
1               5                   10

<210> SEQ ID NO 391
<211> LENGTH: 11
<212> TYPE: PRT
<213> ORGANISM: Homo sapiens

<400> SEQUENCE: 391

Ala Thr Trp Asp Asp Ser Leu Asn Gly Trp Val
1               5                   10

<210> SEQ ID NO 392
<211> LENGTH: 11
<212> TYPE: PRT
<213> ORGANISM: Homo sapiens

<400> SEQUENCE: 392

Ala Thr Trp Asp Asp Ser Leu Asn Gly Trp Val
1               5                   10

<210> SEQ ID NO 393
<211> LENGTH: 11
<212> TYPE: PRT
<213> ORGANISM: Homo sapiens

<400> SEQUENCE: 393

Ala Ala Trp Asp Asp Ser Leu Asn Gly Trp Val
1               5                   10

<210> SEQ ID NO 394
<211> LENGTH: 11
<212> TYPE: PRT
<213> ORGANISM: Homo sapiens
```

```
<400> SEQUENCE: 394

Gln Val Trp Asp Arg Ser Asn Gly His Val Val
1               5                   10

<210> SEQ ID NO 395
<211> LENGTH: 11
<212> TYPE: PRT
<213> ORGANISM: Homo sapiens

<400> SEQUENCE: 395

Gln Val Trp Asp Arg Ser Asn Gly His Val Val
1               5                   10

<210> SEQ ID NO 396
<211> LENGTH: 11
<212> TYPE: PRT
<213> ORGANISM: Homo sapiens

<400> SEQUENCE: 396

Ala Ala Trp Asp Asp Ser Leu Asp Gly Val Val
1               5                   10

<210> SEQ ID NO 397
<211> LENGTH: 11
<212> TYPE: PRT
<213> ORGANISM: Homo sapiens

<400> SEQUENCE: 397

Ser Ala Trp Asp Asp Ser Leu Asn Gly Trp Val
1               5                   10

<210> SEQ ID NO 398
<211> LENGTH: 11
<212> TYPE: PRT
<213> ORGANISM: Homo sapiens

<400> SEQUENCE: 398

Ala Ser Trp Asp Asp Leu Asn Gly Trp Val
1               5                   10

<210> SEQ ID NO 399
<211> LENGTH: 11
<212> TYPE: PRT
<213> ORGANISM: Homo sapiens

<400> SEQUENCE: 399

Ala Val Trp Asp Asp Arg Met Asn Gly Trp Glu
1               5                   10

<210> SEQ ID NO 400
<211> LENGTH: 11
<212> TYPE: PRT
<213> ORGANISM: Homo sapiens

<400> SEQUENCE: 400

Ala Ala Trp Asp Asp Ser Leu Asn Gly Trp Val
1               5                   10

<210> SEQ ID NO 401
<211> LENGTH: 11
<212> TYPE: PRT
<213> ORGANISM: Homo sapiens

<400> SEQUENCE: 401
```

```
Ala Val Trp Asp Asp Arg Leu Asn Gly Trp Glu
1               5                   10
```

<210> SEQ ID NO 402
<211> LENGTH: 10
<212> TYPE: PRT
<213> ORGANISM: Homo sapiens

<400> SEQUENCE: 402

```
Val Asp His Asn Trp Asp Leu Pro Phe Asp
1               5                   10
```

<210> SEQ ID NO 403
<211> LENGTH: 11
<212> TYPE: PRT
<213> ORGANISM: Homo sapiens

<400> SEQUENCE: 403

```
Ala Ala Trp Asp Asp Ser Leu Ser Gly Trp Met
1               5                   10
```

<210> SEQ ID NO 404
<211> LENGTH: 11
<212> TYPE: PRT
<213> ORGANISM: Homo sapiens

<400> SEQUENCE: 404

```
Ala Ser Trp Asp Asp Asp Leu Lys Ser Trp Val
1               5                   10
```

<210> SEQ ID NO 405
<211> LENGTH: 11
<212> TYPE: PRT
<213> ORGANISM: Homo sapiens

<400> SEQUENCE: 405

```
Ala Ala Trp Asp Asp Ser Leu Ser Gly Trp Val
1               5                   10
```

<210> SEQ ID NO 406
<211> LENGTH: 11
<212> TYPE: PRT
<213> ORGANISM: Homo sapiens

<400> SEQUENCE: 406

```
Ala Thr Trp Asp Asp Ser Leu Lys Gly Trp Val
1               5                   10
```

<210> SEQ ID NO 407
<211> LENGTH: 9
<212> TYPE: PRT
<213> ORGANISM: Homo sapiens

<400> SEQUENCE: 407

```
Gln Gln Ser Lys Ser Ile Pro Ile Thr
1               5
```

<210> SEQ ID NO 408
<211> LENGTH: 11
<212> TYPE: PRT
<213> ORGANISM: Homo sapiens

<400> SEQUENCE: 408

```
Val Ala Trp Asp Asp Ser Leu Asn Gly Trp Met
1               5                   10
```

<210> SEQ ID NO 409
<211> LENGTH: 11
<212> TYPE: PRT
<213> ORGANISM: Homo sapiens

<400> SEQUENCE: 409

Ala Ala Trp Asp Asp Ser Leu Ser Gly Trp Val
1               5                   10

<210> SEQ ID NO 410
<211> LENGTH: 11
<212> TYPE: PRT
<213> ORGANISM: Homo sapiens

<400> SEQUENCE: 410

Ala Ala Trp Asp Asp Ser Leu Lys Gly Trp Val
1               5                   10

<210> SEQ ID NO 411
<211> LENGTH: 11
<212> TYPE: PRT
<213> ORGANISM: Homo sapiens

<400> SEQUENCE: 411

Ser Ala Trp Asp Asp Gly Leu Ser Gly Trp Val
1               5                   10

<210> SEQ ID NO 412
<211> LENGTH: 11
<212> TYPE: PRT
<213> ORGANISM: Homo sapiens

<400> SEQUENCE: 412

Ala Thr Trp Asp Asp Ser Leu Pro Gly Leu Val
1               5                   10

<210> SEQ ID NO 413
<211> LENGTH: 11
<212> TYPE: PRT
<213> ORGANISM: Homo sapiens

<400> SEQUENCE: 413

Glu Ala Trp Asp Asp Ser Leu Ser Gly Pro Ala
1               5                   10

<210> SEQ ID NO 414
<211> LENGTH: 10
<212> TYPE: PRT
<213> ORGANISM: Homo sapiens

<400> SEQUENCE: 414

Ala Ala Trp Asp Asp Asn Leu Ser Gly Pro
1               5                   10

<210> SEQ ID NO 415
<211> LENGTH: 9
<212> TYPE: PRT
<213> ORGANISM: Homo sapiens

<400> SEQUENCE: 415

Gln Gln Thr Tyr Arg Thr Pro Ile Thr
1               5

<210> SEQ ID NO 416
<211> LENGTH: 12

```
<212> TYPE: PRT
<213> ORGANISM: Homo sapiens

<400> SEQUENCE: 416

Gly Thr Trp Asp Ser Arg Leu Tyr Val Gly Gln Val
1               5                   10

<210> SEQ ID NO 417
<211> LENGTH: 11
<212> TYPE: PRT
<213> ORGANISM: Homo sapiens

<400> SEQUENCE: 417

Ala Ala Trp Asp Asp Ser Leu Asn Gly Trp Val
1               5                   10

<210> SEQ ID NO 418
<211> LENGTH: 11
<212> TYPE: PRT
<213> ORGANISM: Homo sapiens

<400> SEQUENCE: 418

Ala Ala Trp Asp Asp Ser Leu Asn Gly Trp Val
1               5                   10

<210> SEQ ID NO 419
<211> LENGTH: 11
<212> TYPE: PRT
<213> ORGANISM: Homo sapiens

<400> SEQUENCE: 419

Ala Thr Trp Asp Asp Ser Leu Asn His Trp Val
1               5                   10

<210> SEQ ID NO 420
<211> LENGTH: 12
<212> TYPE: PRT
<213> ORGANISM: Homo sapiens

<400> SEQUENCE: 420

Ala Ala Trp Asp Asp Ser Leu Asn Gly His Trp Val
1               5                   10

<210> SEQ ID NO 421
<211> LENGTH: 11
<212> TYPE: PRT
<213> ORGANISM: Homo sapiens

<400> SEQUENCE: 421

Ala Ala Trp Asp Asp Ser Leu Ser Gly Val Leu
1               5                   10

<210> SEQ ID NO 422
<211> LENGTH: 10
<212> TYPE: PRT
<213> ORGANISM: Homo sapiens

<400> SEQUENCE: 422

Asn Ser Arg Asp Ser Ser Gly Asn Val Val
1               5                   10

<210> SEQ ID NO 423
<211> LENGTH: 11
<212> TYPE: PRT
<213> ORGANISM: Homo sapiens
```

```
<400> SEQUENCE: 423

Ala Ser Trp Asp Asp Thr Leu Lys Gly Gly Val
1               5                   10

<210> SEQ ID NO 424
<211> LENGTH: 11
<212> TYPE: PRT
<213> ORGANISM: Homo sapiens

<400> SEQUENCE: 424

Gln Ser Tyr Asp Asn Ser Leu Ser Gly Ser Glu
1               5                   10

<210> SEQ ID NO 425
<211> LENGTH: 11
<212> TYPE: PRT
<213> ORGANISM: Homo sapiens

<400> SEQUENCE: 425

Asn Ser Arg Asp Ser Ser Gly Asp Pro Val Thr
1               5                   10

<210> SEQ ID NO 426
<211> LENGTH: 11
<212> TYPE: PRT
<213> ORGANISM: Homo sapiens

<400> SEQUENCE: 426

Ser Ala Trp Asp Asp Ser Leu Lys Gly Trp Val
1               5                   10

<210> SEQ ID NO 427
<211> LENGTH: 12
<212> TYPE: PRT
<213> ORGANISM: Homo sapiens

<400> SEQUENCE: 427

Ala Ser Arg Asp Ser Ser Ala Asn Gln His Trp Val
1               5                   10

<210> SEQ ID NO 428
<211> LENGTH: 9
<212> TYPE: PRT
<213> ORGANISM: Homo sapiens

<400> SEQUENCE: 428

Gln Ser Tyr Asp Ser Ser Thr Gly Ile
1               5

<210> SEQ ID NO 429
<211> LENGTH: 11
<212> TYPE: PRT
<213> ORGANISM: Homo sapiens

<400> SEQUENCE: 429

Ala Ala Trp Asp Asp Ser Leu Asn Gly Leu Val
1               5                   10

<210> SEQ ID NO 430
<211> LENGTH: 11
<212> TYPE: PRT
<213> ORGANISM: Homo sapiens

<400> SEQUENCE: 430

Ser Thr Trp Asp Gly Ser Leu Asn Gly Trp Val
```

```
1               5                   10
```

<210> SEQ ID NO 431
<211> LENGTH: 11
<212> TYPE: PRT
<213> ORGANISM: Homo sapiens

<400> SEQUENCE: 431

```
Ala Ala Trp Asp Asp Ser Leu Asn Gly Trp Val
1               5                   10
```

<210> SEQ ID NO 432
<211> LENGTH: 11
<212> TYPE: PRT
<213> ORGANISM: Homo sapiens

<400> SEQUENCE: 432

```
Ser Thr Trp Asp Asp Ser Leu Arg Gly Val Val
1               5                   10
```

<210> SEQ ID NO 433
<211> LENGTH: 11
<212> TYPE: PRT
<213> ORGANISM: Homo sapiens

<400> SEQUENCE: 433

```
Ala Val Trp Asp Asp Ser Leu Asn Gly Trp Val
1               5                   10
```

<210> SEQ ID NO 434
<211> LENGTH: 11
<212> TYPE: PRT
<213> ORGANISM: Homo sapiens

<400> SEQUENCE: 434

```
Ala Pro Trp Asp Asp Ser Leu Asn Gly Trp Val
1               5                   10
```

<210> SEQ ID NO 435
<211> LENGTH: 11
<212> TYPE: PRT
<213> ORGANISM: Homo sapiens

<400> SEQUENCE: 435

```
Ser Ala Trp Asp Asp Ser Leu His Gly Pro Val
1               5                   10
```

<210> SEQ ID NO 436
<211> LENGTH: 11
<212> TYPE: PRT
<213> ORGANISM: Homo sapiens

<400> SEQUENCE: 436

```
Ala Ala Trp Asp Asp Ser Leu Asn Gly Val Val
1               5                   10
```

<210> SEQ ID NO 437
<211> LENGTH: 10
<212> TYPE: PRT
<213> ORGANISM: Homo sapiens

<400> SEQUENCE: 437

```
Gln Ser Tyr Asp Asn Ser Leu Ser Ala Trp
1               5                   10
```

```
<210> SEQ ID NO 438
<211> LENGTH: 11
<212> TYPE: PRT
<213> ORGANISM: Homo sapiens

<400> SEQUENCE: 438

Ala Ala Trp Asp Asp Ser Leu Asn Val Val Val
1               5                   10

<210> SEQ ID NO 439
<211> LENGTH: 12
<212> TYPE: PRT
<213> ORGANISM: Homo sapiens

<400> SEQUENCE: 439

Ser Ser Arg Asp Asn Ser Gly Asp Arg Leu Val Leu
1               5                   10

<210> SEQ ID NO 440
<211> LENGTH: 11
<212> TYPE: PRT
<213> ORGANISM: Homo sapiens

<400> SEQUENCE: 440

Ala Ala Trp Asp Asp Ser Leu Asn Gly Trp Val
1               5                   10

<210> SEQ ID NO 441
<211> LENGTH: 11
<212> TYPE: PRT
<213> ORGANISM: Homo sapiens

<400> SEQUENCE: 441

Ala Thr Trp Asp Asp Ser Leu Arg Gly Trp Val
1               5                   10

<210> SEQ ID NO 442
<211> LENGTH: 11
<212> TYPE: PRT
<213> ORGANISM: Homo sapiens

<400> SEQUENCE: 442

Ala Thr Trp Asp Asp Ser Val Arg Gly Trp Val
1               5                   10

<210> SEQ ID NO 443
<211> LENGTH: 11
<212> TYPE: PRT
<213> ORGANISM: Homo sapiens

<400> SEQUENCE: 443

Ala Thr Trp Asp Asp Ser Leu Ser Gly Trp Val
1               5                   10

<210> SEQ ID NO 444
<211> LENGTH: 11
<212> TYPE: PRT
<213> ORGANISM: Homo sapiens

<400> SEQUENCE: 444

Ala Ala Trp Asp Asp Ser Leu Asn Ala Val Leu
1               5                   10

<210> SEQ ID NO 445
<211> LENGTH: 11
<212> TYPE: PRT
```

<213> ORGANISM: Homo sapiens

<400> SEQUENCE: 445

Val Asp Arg Arg Trp Asp Leu Pro Phe Asp Tyr
1               5                   10

<210> SEQ ID NO 446
<211> LENGTH: 10
<212> TYPE: PRT
<213> ORGANISM: Homo sapiens

<400> SEQUENCE: 446

Ala Ser Trp Asp Asp Ser Leu Asn Gly Val
1               5                   10

<210> SEQ ID NO 447
<211> LENGTH: 11
<212> TYPE: PRT
<213> ORGANISM: Homo sapiens

<400> SEQUENCE: 447

Glu Ala Trp Asp Asp Ser Leu Ser Gly Pro Ala
1               5                   10

<210> SEQ ID NO 448
<211> LENGTH: 11
<212> TYPE: PRT
<213> ORGANISM: Homo sapiens

<400> SEQUENCE: 448

Gly Thr Trp Asp Ser Arg Leu Ser Ala Val Val
1               5                   10

<210> SEQ ID NO 449
<211> LENGTH: 11
<212> TYPE: PRT
<213> ORGANISM: Homo sapiens

<400> SEQUENCE: 449

Asn Ser Arg Asp Ser Ser Gly Asn Pro Val Val
1               5                   10

<210> SEQ ID NO 450
<211> LENGTH: 11
<212> TYPE: PRT
<213> ORGANISM: Homo sapiens

<400> SEQUENCE: 450

Thr Ala Trp Asp Asp Ser Leu Asn Gly Trp Val
1               5                   10

<210> SEQ ID NO 451
<211> LENGTH: 11
<212> TYPE: PRT
<213> ORGANISM: Homo sapiens

<400> SEQUENCE: 451

Ala Ala Trp Asp Asp Ile Leu Asn Gly Trp Val
1               5                   10

<210> SEQ ID NO 452
<211> LENGTH: 11
<212> TYPE: PRT
<213> ORGANISM: Homo sapiens

<400> SEQUENCE: 452

Asn Ser Arg Asp Ser Ser Gly Asn His Val Val
1               5                   10

<210> SEQ ID NO 453
<211> LENGTH: 10
<212> TYPE: PRT
<213> ORGANISM: Homo sapiens

<400> SEQUENCE: 453

Gln Ala Trp Asp Ser Ser Thr Thr Trp Glu
1               5                   10

<210> SEQ ID NO 454
<211> LENGTH: 11
<212> TYPE: PRT
<213> ORGANISM: Homo sapiens

<400> SEQUENCE: 454

Glu Thr Trp Asp Thr Ser Leu Ser Val Leu Val
1               5                   10

<210> SEQ ID NO 455
<211> LENGTH: 10
<212> TYPE: PRT
<213> ORGANISM: Homo sapiens

<400> SEQUENCE: 455

Ser Ser Arg Asp Asn Ser Gly Asp Pro Leu
1               5                   10

<210> SEQ ID NO 456
<211> LENGTH: 10
<212> TYPE: PRT
<213> ORGANISM: Homo sapiens

<400> SEQUENCE: 456

Ser Ser Arg Asp Asn Ser Gly Asp Pro Leu
1               5                   10

<210> SEQ ID NO 457
<211> LENGTH: 11
<212> TYPE: PRT
<213> ORGANISM: Homo sapiens

<400> SEQUENCE: 457

Asn Ser Arg Asp Ser Ser Gly Asn His Trp Val
1               5                   10

<210> SEQ ID NO 458
<211> LENGTH: 11
<212> TYPE: PRT
<213> ORGANISM: Homo sapiens

<400> SEQUENCE: 458

Gln Ser Tyr Asp Ser Ser Leu Ser Ala Tyr Val
1               5                   10

<210> SEQ ID NO 459
<211> LENGTH: 11
<212> TYPE: PRT
<213> ORGANISM: Homo sapiens

<400> SEQUENCE: 459

Gln Ser Tyr Asp Ser Gly Leu Ser Ala Val Val
1               5                   10

```
<210> SEQ ID NO 460
<211> LENGTH: 11
<212> TYPE: PRT
<213> ORGANISM: Homo sapiens

<400> SEQUENCE: 460

Ala Ser Trp Asp Asp Ser Leu Ser Gly Trp Val
1               5                   10

<210> SEQ ID NO 461
<211> LENGTH: 11
<212> TYPE: PRT
<213> ORGANISM: Homo sapiens

<400> SEQUENCE: 461

Ala Thr Trp Asp Asp Ser Leu Ser Gly Leu Leu
1               5                   10

<210> SEQ ID NO 462
<211> LENGTH: 11
<212> TYPE: PRT
<213> ORGANISM: Homo sapiens

<400> SEQUENCE: 462

Ala Ser Trp Asp Asp Ser Leu Lys Gly Val Val
1               5                   10

<210> SEQ ID NO 463
<211> LENGTH: 11
<212> TYPE: PRT
<213> ORGANISM: Homo sapiens

<400> SEQUENCE: 463

Ala Ala Trp Asp Asp Arg Leu Ser Gly Pro Val
1               5                   10

<210> SEQ ID NO 464
<211> LENGTH: 11
<212> TYPE: PRT
<213> ORGANISM: Homo sapiens

<400> SEQUENCE: 464

Ala Ala Trp Asp Asp Ser Leu Asn Gly Met Leu
1               5                   10

<210> SEQ ID NO 465
<211> LENGTH: 10
<212> TYPE: PRT
<213> ORGANISM: Homo sapiens

<400> SEQUENCE: 465

Ala Ala Trp Asp Asp Ser Leu Asn Gly Pro
1               5                   10

<210> SEQ ID NO 466
<211> LENGTH: 11
<212> TYPE: PRT
<213> ORGANISM: Homo sapiens

<400> SEQUENCE: 466

Ala Thr Trp Asp Asp Arg Leu Lys Gly Phe Val
1               5                   10

<210> SEQ ID NO 467
```

```
<211> LENGTH: 11
<212> TYPE: PRT
<213> ORGANISM: Homo sapiens

<400> SEQUENCE: 467

Ser Ala Trp Asp Asp Ser Leu Ser Gly Val Val
1               5                   10

<210> SEQ ID NO 468
<211> LENGTH: 12
<212> TYPE: PRT
<213> ORGANISM: Homo sapiens

<400> SEQUENCE: 468

Ala Ala Trp Asp Asp Ser Leu Asn Gly His Val Val
1               5                   10

<210> SEQ ID NO 469
<211> LENGTH: 9
<212> TYPE: PRT
<213> ORGANISM: Homo sapiens

<400> SEQUENCE: 469

Gln Thr Trp Asp Ser Thr Thr Ala Ser
1               5

<210> SEQ ID NO 470
<211> LENGTH: 11
<212> TYPE: PRT
<213> ORGANISM: Homo sapiens

<400> SEQUENCE: 470

Ser Ala Trp Asp Asp Ser Leu Asn Gly Pro Ala
1               5                   10

<210> SEQ ID NO 471
<211> LENGTH: 11
<212> TYPE: PRT
<213> ORGANISM: Homo sapiens

<400> SEQUENCE: 471

Ser Ala Trp Asp Asp Ser Leu Asn Gly Pro Ala
1               5                   10

<210> SEQ ID NO 472
<211> LENGTH: 11
<212> TYPE: PRT
<213> ORGANISM: Homo sapiens

<400> SEQUENCE: 472

Ala Thr Trp Asp Asp Thr Leu Ser Gly Leu Val
1               5                   10

<210> SEQ ID NO 473
<211> LENGTH: 11
<212> TYPE: PRT
<213> ORGANISM: Homo sapiens

<400> SEQUENCE: 473

Ala Thr Trp Asp Asp Ser Val Asn Gly Pro Ala
1               5                   10

<210> SEQ ID NO 474
<211> LENGTH: 11
<212> TYPE: PRT
<213> ORGANISM: Homo sapiens
```

-continued

```
<400> SEQUENCE: 474

Ser Ser Tyr Ala Arg Ser Asn Asn Phe Gly Val
1               5                   10

<210> SEQ ID NO 475
<211> LENGTH: 11
<212> TYPE: PRT
<213> ORGANISM: Homo sapiens

<400> SEQUENCE: 475

Ala Ala Trp Asp Asp Arg Leu Asn Gly Tyr Val
1               5                   10

<210> SEQ ID NO 476
<211> LENGTH: 11
<212> TYPE: PRT
<213> ORGANISM: Homo sapiens

<400> SEQUENCE: 476

Ala Ala Trp Asp Asp Ser Leu Asn Gly Val Val
1               5                   10

<210> SEQ ID NO 477
<211> LENGTH: 11
<212> TYPE: PRT
<213> ORGANISM: Homo sapiens

<400> SEQUENCE: 477

Gln Val Trp Asp Ser Thr Ser Asp His Arg Ile
1               5                   10

<210> SEQ ID NO 478
<211> LENGTH: 11
<212> TYPE: PRT
<213> ORGANISM: Homo sapiens

<400> SEQUENCE: 478

Ala Ala Trp Asp Asp Ser Leu Asp Gly Val Val
1               5                   10

<210> SEQ ID NO 479
<211> LENGTH: 11
<212> TYPE: PRT
<213> ORGANISM: Homo sapiens

<400> SEQUENCE: 479

Ala Ser Trp Asp Asp Ser Leu Asp Gly Trp Val
1               5                   10

<210> SEQ ID NO 480
<211> LENGTH: 11
<212> TYPE: PRT
<213> ORGANISM: Homo sapiens

<400> SEQUENCE: 480

Ser Ser Tyr Ser Gly Asp Val Asn Phe Ile Val
1               5                   10

<210> SEQ ID NO 481
<211> LENGTH: 9
<212> TYPE: PRT
<213> ORGANISM: Homo sapiens

<400> SEQUENCE: 481
```

```
Gln Gln Leu Asn Arg Tyr Pro Ser Leu
1               5
```

```
<210> SEQ ID NO 482
<211> LENGTH: 9
<212> TYPE: PRT
<213> ORGANISM: Homo sapiens

<400> SEQUENCE: 482

Gln Gln Tyr Tyr Ser Thr Pro Pro Thr
1               5
```

```
<210> SEQ ID NO 483
<211> LENGTH: 11
<212> TYPE: PRT
<213> ORGANISM: Homo sapiens

<400> SEQUENCE: 483

Ala Thr Trp Asp Asp Ser Leu Lys Gly Phe Val
1               5                   10
```

```
<210> SEQ ID NO 484
<211> LENGTH: 11
<212> TYPE: PRT
<213> ORGANISM: Homo sapiens

<400> SEQUENCE: 484

Ala Ala Trp Asp Asp Ser Leu Asn Gly Val Val
1               5                   10
```

```
<210> SEQ ID NO 485
<211> LENGTH: 11
<212> TYPE: PRT
<213> ORGANISM: Homo sapiens

<400> SEQUENCE: 485

Ser Ser Trp Asp Asp Ser Leu Asn Gly Val Val
1               5                   10
```

```
<210> SEQ ID NO 486
<211> LENGTH: 11
<212> TYPE: PRT
<213> ORGANISM: Homo sapiens

<400> SEQUENCE: 486

Gly Thr Trp Asp Ser Ser Leu Asn Thr Tyr Val
1               5                   10
```

```
<210> SEQ ID NO 487
<211> LENGTH: 11
<212> TYPE: PRT
<213> ORGANISM: Homo sapiens

<400> SEQUENCE: 487

Ser Ala Trp Asp Asp Ser Leu Asn Gly Trp Val
1               5                   10
```

```
<210> SEQ ID NO 488
<211> LENGTH: 12
<212> TYPE: PRT
<213> ORGANISM: Homo sapiens

<400> SEQUENCE: 488

Gln Ser Tyr Asp Ser Ser Leu Ser Gly Ser Trp Val
1               5                   10
```

<210> SEQ ID NO 489
<211> LENGTH: 11
<212> TYPE: PRT
<213> ORGANISM: Homo sapiens

<400> SEQUENCE: 489

Glu Ala Trp Asp Asp Ser Leu Ser Gly Pro Ala
1               5                   10

<210> SEQ ID NO 490
<211> LENGTH: 11
<212> TYPE: PRT
<213> ORGANISM: Homo sapiens

<400> SEQUENCE: 490

Ala Thr Trp Asp Asp Ser Leu Asn Gly Val Val
1               5                   10

<210> SEQ ID NO 491
<211> LENGTH: 11
<212> TYPE: PRT
<213> ORGANISM: Homo sapiens

<400> SEQUENCE: 491

Gln Val Trp Asp Arg Ser Asn Gly His Val Val
1               5                   10

<210> SEQ ID NO 492
<211> LENGTH: 9
<212> TYPE: PRT
<213> ORGANISM: Homo sapiens

<400> SEQUENCE: 492

Gln Gln Phe Lys Ser Tyr Pro Leu Thr
1               5

<210> SEQ ID NO 493
<211> LENGTH: 10
<212> TYPE: PRT
<213> ORGANISM: Homo sapiens

<400> SEQUENCE: 493

Gln Val Trp Asp Asn Ser Ser Gly Trp Val
1               5                   10

<210> SEQ ID NO 494
<211> LENGTH: 11
<212> TYPE: PRT
<213> ORGANISM: Homo sapiens

<400> SEQUENCE: 494

Ala Thr Trp Asp Asp Ser Leu Asn Gly Trp Val
1               5                   10

<210> SEQ ID NO 495
<211> LENGTH: 11
<212> TYPE: PRT
<213> ORGANISM: Homo sapiens

<400> SEQUENCE: 495

Ala Ala Trp Asp Ala Ser Leu Thr Ser Trp Val
1               5                   10

<210> SEQ ID NO 496
<211> LENGTH: 11

```
<212> TYPE: PRT
<213> ORGANISM: Homo sapiens

<400> SEQUENCE: 496

Ala Ala Trp Asp Asp Ser Leu Asn Gly Val Val
1               5                   10

<210> SEQ ID NO 497
<211> LENGTH: 11
<212> TYPE: PRT
<213> ORGANISM: Homo sapiens

<400> SEQUENCE: 497

Ala Ala Trp Asp Asp Ser Leu Asn Gly Trp Val
1               5                   10

<210> SEQ ID NO 498
<211> LENGTH: 11
<212> TYPE: PRT
<213> ORGANISM: Homo sapiens

<400> SEQUENCE: 498

Ala Ala Trp Asp Asp Ser Leu Asn Gly Trp Val
1               5                   10

<210> SEQ ID NO 499
<211> LENGTH: 13
<212> TYPE: PRT
<213> ORGANISM: Homo sapiens

<400> SEQUENCE: 499

Gly Thr Trp Asp Ser Ser Leu Ser Asp Gly Lys Val Val
1               5                   10

<210> SEQ ID NO 500
<211> LENGTH: 11
<212> TYPE: PRT
<213> ORGANISM: Homo sapiens

<400> SEQUENCE: 500

Ala Ala Trp Asp Asp Ser Leu Asn Gly Trp Val
1               5                   10

<210> SEQ ID NO 501
<211> LENGTH: 11
<212> TYPE: PRT
<213> ORGANISM: Homo sapiens

<400> SEQUENCE: 501

Ala Thr Trp Asp Asp Ser Arg Gly Gly Trp Val
1               5                   10

<210> SEQ ID NO 502
<211> LENGTH: 11
<212> TYPE: PRT
<213> ORGANISM: Homo sapiens

<400> SEQUENCE: 502

Ala Ser Trp Asp Asp Ser Val Gly Ser Trp Val
1               5                   10

<210> SEQ ID NO 503
<211> LENGTH: 11
<212> TYPE: PRT
<213> ORGANISM: Homo sapiens
```

```
<400> SEQUENCE: 503

Ala Ala Trp Asp Asp Ser Leu Asn Gly Trp Val
1               5                   10

<210> SEQ ID NO 504
<211> LENGTH: 11
<212> TYPE: PRT
<213> ORGANISM: Homo sapiens

<400> SEQUENCE: 504

Ala Ser Trp Asp Asp Leu Ser Gly Leu Val
1               5                   10

<210> SEQ ID NO 505
<211> LENGTH: 11
<212> TYPE: PRT
<213> ORGANISM: Homo sapiens

<400> SEQUENCE: 505

Ala Thr Trp Asp Asp Ser Leu Asn Gly Pro Val
1               5                   10

<210> SEQ ID NO 506
<211> LENGTH: 11
<212> TYPE: PRT
<213> ORGANISM: Homo sapiens

<400> SEQUENCE: 506

Ala Thr Trp Asp Asp Ser Leu Met Val Gly Val
1               5                   10

<210> SEQ ID NO 507
<211> LENGTH: 11
<212> TYPE: PRT
<213> ORGANISM: Homo sapiens

<400> SEQUENCE: 507

Ala Thr Trp Asp Asp Ser Leu Asn Gly Trp Val
1               5                   10

<210> SEQ ID NO 508
<211> LENGTH: 11
<212> TYPE: PRT
<213> ORGANISM: Homo sapiens

<400> SEQUENCE: 508

Ala Val Trp Asp Asp Ser Leu Asn Gly Val Ile
1               5                   10

<210> SEQ ID NO 509
<211> LENGTH: 11
<212> TYPE: PRT
<213> ORGANISM: Homo sapiens

<400> SEQUENCE: 509

Ala Ala Trp Asp Asp Asn Leu Asn Gly Val Val
1               5                   10

<210> SEQ ID NO 510
<211> LENGTH: 11
<212> TYPE: PRT
<213> ORGANISM: Homo sapiens

<400> SEQUENCE: 510

Ala Ala Trp Asp Asp Ser Leu Lys Gly Trp Val
```

```
1               5                   10
```

<210> SEQ ID NO 511
<211> LENGTH: 11
<212> TYPE: PRT
<213> ORGANISM: Homo sapiens

<400> SEQUENCE: 511

```
Ala Val Trp Asp Asp Gly Leu Ser Gly Trp Val
1               5                   10
```

<210> SEQ ID NO 512
<211> LENGTH: 9
<212> TYPE: PRT
<213> ORGANISM: Homo sapiens

<400> SEQUENCE: 512

```
Gln Gln Tyr Tyr Ser Thr Pro Ile Thr
1               5
```

<210> SEQ ID NO 513
<211> LENGTH: 11
<212> TYPE: PRT
<213> ORGANISM: Homo sapiens

<400> SEQUENCE: 513

```
Val Ala Trp Asp Asp Ser Leu Asn Gly Trp Val
1               5                   10
```

<210> SEQ ID NO 514
<211> LENGTH: 10
<212> TYPE: PRT
<213> ORGANISM: Homo sapiens

<400> SEQUENCE: 514

```
Gln Ser His Asp Asn Thr Leu Gly Glu Val
1               5                   10
```

<210> SEQ ID NO 515
<211> LENGTH: 10
<212> TYPE: PRT
<213> ORGANISM: Homo sapiens

<400> SEQUENCE: 515

```
Ala Ser Trp Asp Asp Ser Leu Thr Trp Val
1               5                   10
```

<210> SEQ ID NO 516
<211> LENGTH: 12
<212> TYPE: PRT
<213> ORGANISM: Homo sapiens

<400> SEQUENCE: 516

```
Ala Ala Trp Asp Asp Ser Leu Ser Gly Pro Val Val
1               5                   10
```

<210> SEQ ID NO 517
<211> LENGTH: 13
<212> TYPE: PRT
<213> ORGANISM: Homo sapiens

<400> SEQUENCE: 517

```
Asn Ser Arg Asp Ser Ser Gly Asn His Phe Asp Val Val
1               5                   10
```

```
<210> SEQ ID NO 518
<211> LENGTH: 11
<212> TYPE: PRT
<213> ORGANISM: Homo sapiens

<400> SEQUENCE: 518

Ala Thr Trp Asp Asp Ser Leu Asn Gly Phe Val
1               5                   10

<210> SEQ ID NO 519
<211> LENGTH: 10
<212> TYPE: PRT
<213> ORGANISM: Homo sapiens

<400> SEQUENCE: 519

Gln Val Trp Asp Asn Ser Ser Gly Trp Val
1               5                   10

<210> SEQ ID NO 520
<211> LENGTH: 11
<212> TYPE: PRT
<213> ORGANISM: Homo sapiens

<400> SEQUENCE: 520

Ala Val Trp Asp Asp Ser Leu Asn Gly Val Leu
1               5                   10

<210> SEQ ID NO 521
<211> LENGTH: 11
<212> TYPE: PRT
<213> ORGANISM: Homo sapiens

<400> SEQUENCE: 521

Ala Ala Trp Asp Asp Ser Leu Thr Gly Trp Val
1               5                   10

<210> SEQ ID NO 522
<211> LENGTH: 11
<212> TYPE: PRT
<213> ORGANISM: Homo sapiens

<400> SEQUENCE: 522

Ala Ala Trp Asp Asp Ser Leu Lys Gly Pro Val
1               5                   10

<210> SEQ ID NO 523
<211> LENGTH: 11
<212> TYPE: PRT
<213> ORGANISM: Homo sapiens

<400> SEQUENCE: 523

Ala Ala Trp Asp Asp Ser Leu Ser Gly Trp Val
1               5                   10

<210> SEQ ID NO 524
<211> LENGTH: 11
<212> TYPE: PRT
<213> ORGANISM: Homo sapiens

<400> SEQUENCE: 524

Val Thr Trp Asp Gly Ser Leu Gly Val Val Met
1               5                   10

<210> SEQ ID NO 525
<211> LENGTH: 11
<212> TYPE: PRT
```

<213> ORGANISM: Homo sapiens

<400> SEQUENCE: 525

Ala Ala Trp Asp Asp Ser Leu Lys Gly Trp Val
1               5                   10

<210> SEQ ID NO 526
<211> LENGTH: 11
<212> TYPE: PRT
<213> ORGANISM: Homo sapiens

<400> SEQUENCE: 526

Ala Ala Trp Asp Asp Ser Leu Asn Gly Trp Val
1               5                   10

<210> SEQ ID NO 527
<211> LENGTH: 11
<212> TYPE: PRT
<213> ORGANISM: Homo sapiens

<400> SEQUENCE: 527

Ala Ala Trp Asp Asp Ser Leu Asn Gly Val Val
1               5                   10

<210> SEQ ID NO 528
<211> LENGTH: 11
<212> TYPE: PRT
<213> ORGANISM: Homo sapiens

<400> SEQUENCE: 528

Ala Ala Trp Asp Asp Ser Leu Asn Gly Trp Val
1               5                   10

<210> SEQ ID NO 529
<211> LENGTH: 11
<212> TYPE: PRT
<213> ORGANISM: Homo sapiens

<400> SEQUENCE: 529

Ala Ala Trp Asp Asp Ser Leu Asn Gly Val Val
1               5                   10

<210> SEQ ID NO 530
<211> LENGTH: 11
<212> TYPE: PRT
<213> ORGANISM: Homo sapiens

<400> SEQUENCE: 530

Gln Val Trp Asp Arg Ser Asn Gly His Val Val
1               5                   10

<210> SEQ ID NO 531
<211> LENGTH: 11
<212> TYPE: PRT
<213> ORGANISM: Homo sapiens

<400> SEQUENCE: 531

Asn Ser Arg Asp Ser Ser Gly Asn Leu Trp Val
1               5                   10

<210> SEQ ID NO 532
<211> LENGTH: 11
<212> TYPE: PRT
<213> ORGANISM: Homo sapiens

<400> SEQUENCE: 532

```
<210> SEQ ID NO 532
<211> LENGTH: 11
<212> TYPE: PRT
<213> ORGANISM: Homo sapiens

<400> SEQUENCE: 532

Ala Ala Trp Asp Asp Ser Leu Asn Gly Val Val
1               5                   10

<210> SEQ ID NO 533
<211> LENGTH: 11
<212> TYPE: PRT
<213> ORGANISM: Homo sapiens

<400> SEQUENCE: 533

Ala Ala Trp Asp Asp Ser Leu Asn Gly Trp Val
1               5                   10

<210> SEQ ID NO 534
<211> LENGTH: 11
<212> TYPE: PRT
<213> ORGANISM: Homo sapiens

<400> SEQUENCE: 534

Asn Ser Arg Asp Asn Ser Gly Asn Leu Trp Val
1               5                   10

<210> SEQ ID NO 535
<211> LENGTH: 8
<212> TYPE: PRT
<213> ORGANISM: Homo sapiens

<400> SEQUENCE: 535

Gln Gln Ser Leu Thr Ala Trp Thr
1               5
```

… …

ANTIBODIES AGAINST PROTECTIVE ANTIGEN

RELATED APPLICATIONS

This application is a continuation of U.S. patent application Ser. No. 10/602,727, filed Jun. 25, 2003 (now U.S. Pat. No. 7,601,351, issued Oct. 13, 2009), which claims benefit under 35 U.S.C. §119(e) of U.S. Provisional Application Nos. 60/391,162, filed Jun. 26, 2002, 60/406,339, filed Aug. 28, 2002, 60/417,305, filed Oct. 10, 2002, 60/426,360, filed Nov. 15, 2002, 60/434,807, filed Dec. 20, 2002, 60/438,004, filed Jan. 6, 2003, 60/443,858 filed Jan. 31, 2003, 60/443,781, filed Jan. 31, 2003, 60/454,613 filed Mar. 17, 2003, and 60/468,651 filed May 8, 2003. Each of the aforementioned applications is hereby incorporated by reference in its entirety.

REFERENCE TO SEQUENCE LISTING AS TEXT FILE

This application refers to a "Sequence Listing" listed below, which is provided as a text file. The text file contains a document entitled "PF596P1C1.ST25.txt" (160,734 bytes, created Apr. 9, 2009), which is incorporated by reference in its entirety.

FIELD OF THE INVENTION

The present invention relates to antibodies and related molecules that specifically bind to the protective antigen (PA) of *Bacillus anthracis*. Such antibodies have uses, for example, in the prevention, detection and treatment of anthrax and/or anthrax related toxins. The invention also relates to nucleic acid molecules encoding anti-PA antibodies, vectors and host cells containing these nucleic acids, and methods for producing the same. The present invention relates to methods and compositions for preventing, detecting, diagnosing, treating or ameliorating anthrax and/or anthrax related toxins, comprising administering to an animal, preferably a human, an effective amount of one or more antibodies or fragments or variants thereof, or related molecules, that specifically bind to PA.

BACKGROUND OF THE INVENTION

*Bacillus anthracis* is a Gram-positive, aerobic, spore forming bacterium that is responsible for the deadly disease anthrax. There are three recognized routes of anthrax infection including cutaneous (through skin), gastrointestinal, and pulmonary (via inhalation) infection. Of the three ways to contract the disease, inhalation is the avenue that most frequently leads to the death of the patient.

Anthrax secretes a deadly three-component exotoxin which is comprised of three proteins, lethal factor (LF), edema factor (EF), and protective antigen (PA). The anthrax toxin is a bipartite toxin that contains A and B moieties, similar to that of diphtheria toxin and many clostridial toxins. The LF and EF proteins function as enzymatic A moieties of the toxin, while the PA protein functions as the B, or binding, moiety.

During the process of intoxication, PA binds to its cell surface receptor, (e.g., anthrax receptor (ATR) and/or capillary morphogenesis gene 2 (CMG2)) and is cleaved at the sequence RKKR (residues 193-196 of SEQ ID NO:2) by cell surface proteases such as furin. This cleavage releases a 20 kilodalton fragment of the PA protein, leaving a 63 kilodalton fragment of the PA protein bound to the cell surface (PA63). Some cleavage to the PA63 form may be mediated by serum proteases and occur prior to PA, in this case PA63, binding to the cell surface. Release of the 20 kilodalton PA fragment enables the PA63 fragment to multimerize into a heptameric ring structure and exposes a site on PA63 to which LF and EF bind with high affinity. The complex is then internalized by receptor-mediated endocytosis. Acidification of the vesicle causes conformational changes in the pA63 heptamer that result in transportation of LF and EF toxins across the endosomal membrane, after which they are released into the cytosol where they exert their cytotoxic effects. The edema factor (EF) component of edema toxin (EF+PA) is a calmodulin dependent adenylate cyclase whose action upsets cellular water homeostasis mechanisms, thereby resulting in swelling of infected tissues. The lethal factor (LF) moiety of lethal toxin (LF+PA) is a zinc metalloproteinase that inactivates mitogen activated protein kinase kinase in vitro. Lethal factor induces a hyperinflammatory condition in macrophages resulting in the production of proinflammatory cytokines including TNF-alpha and interleukin-1beta, which are responsible for shock and death of anthrax patients. For more detailed reviews of *Bacillus Anthracis* infection and anthrax toxin please see, e.g., *Critical Reviews in Microbiology* (2001) 27:167-200, *Medical Progress* (1999) 341:815-826, and *Microbes and Infection* (1999) 2:131-139, each of which are hereby incorporated by reference in their entireties.

There is a clear need, therefore, for identification and characterization of compositions, such as antibodies, that influence the biological activity of anthrax toxins.

SUMMARY OF THE INVENTION

The present invention encompasses antibodies (including molecules comprising, or alternatively consisting of, antibody fragments or variants thereof) that specifically bind to a PA polypeptide (SEQ ID NO:2) or polypeptide fragment or variant of PA.

The present invention relates to methods and compositions for preventing, treating or ameliorating anthrax disease and/or symptoms induced by anthrax related toxins (such as lethal toxin or edema toxin) comprising administering to an animal, preferably a human, an effective amount of one or more antibodies or fragments or variants thereof, or related molecules, that specifically bind to PA or a fragment or variant thereof. In specific embodiments, the present invention relates to methods and compositions for preventing, treating or ameliorating a disease or disorder associated with PA function, comprising administering to an animal, preferably a human, an effective amount of one or more antibodies or fragments or variants thereof, or related molecules, that specifically bind PA or a fragment or variant thereof.

In other embodiments, antibodies of the invention have a bactericidal effect on *B. anthracis* bacteria. By way of non-limiting example, antibodies of the invention may activate the classical complement pathway and/or enhance the activation of the alternative complement pathway which can lead to killing of bacterial cells. Alternatively, antibodies of the invention may opsonize *B. anthracis* bacteria. Opsonized bacteria then may be a target for antibody dependent cell-mediated cytotoxicty (ADCC). In another embodiment, antibodies of the invention may catalyze the generation of hydrogen peroxide from singlet molecular oxygen and water which chemical reaction results in the efficient killing of bacteria.

In specific embodiments, antibodies of the invention are administered in combination with other therapeutics or prophylactics such as a soluble form of an anthrax receptor (e.g., SEQ ID NO:3, described in *Nature* (2002) 414:225-229

(which is hereby incorporated by reference in its entirety), e.g., a polypeptide comprising amino acids 1-227 or 41-227 of SEQ ID NO:3) or a soluble form of the CMG2 receptor (SEQ ID NO:42, described in Scobie et al., *Proceedings of the National Academy of Sciences USA* (2003) 100:5170-5174 which is hereby incorporated by reference in its entirety, e.g., a polypeptide comprising amino acids 33-318 of SEQ ID NO:42). Other therapeutics or prophylactics that may be administered in combination with an antibody of the present invention include mutant forms of PA such as the EF/LF translocation deficient forms of PA described in International Publication Number WO01/82788 and in Science (2001) 292:695-697, both of which are hereby incorporated by reference in their entireties. Other therapeutics or prophylactics that may be administered in combination with an antibody of the present invention include peptide inhibitors that block LF binding to PA such as the P1 peptide, or its polyvalent form described in Nature Biotechnology (2002) 19:958-961 which is hereby incorporated by reference in its entirety. Still other therapeutics or prophylactics that may be administered in combination with an antibody of the present invention include, but are not limited to antibiotics, anthrax vaccines, antibodies immunoreactive with LF, EF or other protein moieties of *Bacillus anthracis*.

Another embodiment of the present invention includes the use of the antibodies of the invention as a diagnostic tool to monitor the presence of PA.

Single chain Fv's (scFvs) that specifically bind PA polypeptide (SEQ ID NOS:48-65) have been identified. Thus, the invention encompasses these scFvs, listed in Table 1. In addition, the invention encompasses cell lines engineered to express antibodies corresponding to these scFvs which are deposited with the American Type Culture Collection ("ATCC™") as of the dates listed in Table 1 and given the ATCC™ Deposit Numbers identified in Table 1. The ATCC™ is located at 10801 University Boulevard, Manassas, Va. 20110-2209, USA. The ATCC™ deposit was made pursuant to the terms of the Budapest Treaty on the International Recognition of the Deposit of Microorganisms for Purposes of Patent Procedure.

Further, the present invention encompasses the polynucleotides encoding the scFvs, as well as the amino acid sequences encoding the scFvs. Molecules comprising, or alternatively consisting of, fragments or variants of these scFvs (e.g., VH domains, VH CDRs, VL domains, or VL CDRs having an amino acid sequence of the corresponding region of the recombinant antibody expressed by a cell line contained in an ATCC™ Deposit referred to in Table 1), that specifically bind to PA or fragments or variants thereof are also encompassed by the invention, as are nucleic acid molecules that encode these antibodies and/or molecules. In specific embodiments, the present invention encompasses antibodies, or fragments or variants thereof, that bind to an epitope that comprises the RKKR sequence of amino acid residues 193 to 196 of SEQ ID NO:2). In other embodiments, the antibodies of the invention bind an epitope of PA and occlude access of proteases to the RKKR cleavage site of PA (amino acid residues 193 to 196 of SEQ ID NO:2). In other embodiments, antibodies of the invention neutralize the ability of PA to bind to a cellular anthrax receptor, e.g., ATR (SEQ ID NO:3) or CMG2 (SEQ ID NO:42). In other embodiments, antibodies of the invention neutralize the ability of the PA (particularly the PA63 form of PA) to form oligomers, and more specifically, to form heptamers. And in still other embodiments, antibodies of the invention neutralize the ability of PA (particularly the PA63 form of PA) to bind to either EF or LF (SEQ ID NOs:4 or 5, respectively).

The present invention also provides anti-PA antibodies that are coupled to a detectable label, such as an enzyme, a fluorescent label, a luminescent label, or a bioluminescent label. The present invention also provides anti-PA antibodies that are coupled to a therapeutic or cytotoxic agent. The present invention also provides anti-PA antibodies that which are coupled, directly or indirectly, to a radioactive material.

In further embodiments, the antibodies of the invention have a dissociation constant ($K_D$) of $10^{-7}$ M or less. In preferred embodiments, the antibodies of the invention have a dissociation constant ($K_D$) of $10^{-9}$ M or less.

In further embodiments, antibodies of the invention have an off rate ($k_{off}$) of $10^{-3}$/sec or less. In preferred embodiments, antibodies of the invention have an off rate ($k_{off}$) of $10^{-4}$/sec or less. In other preferred embodiments, antibodies of the invention have an off rate ($k_{off}$) of $10^{-5}$/sec or less.

The present invention also provides panels of antibodies (including molecules comprising, or alternatively consisting of, antibody fragments or variants) wherein the panel members correspond to one, two, three, four, five, ten, fifteen, twenty, or more different antibodies of the invention (e.g., whole antibodies, Fabs, F(ab')$_2$ fragments, Fd fragments, disulfide-linked Fvs (scFvs), anti-idiotypic (anti-Id) antibodies, and scFvs). The present invention further provides mixtures of antibodies, wherein the mixture corresponds to one, two, three, four, five, ten, fifteen, twenty, or more different antibodies of the invention (e.g., whole antibodies, Fabs, F(ab')$_2$ fragments, Fd fragments, disulfide-linked Fvs (sdFvs), anti-idiotypic (anti-Id) antibodies, and scFvs)). The present invention also provides for compositions comprising, or alternatively consisting of, one, two, three, four, five, ten, fifteen, twenty, or more antibodies of the present invention (including molecules comprising, or alternatively consisting of, antibody fragments or variants thereof). A composition of the invention may comprise, or alternatively consist of, one, two, three, four, five, ten, fifteen, twenty, or more amino acid sequences of one or more antibodies or fragments or variants thereof. Alternatively, a composition of the invention may comprise, or alternatively consist of, nucleic acid molecules encoding one or more antibodies of the invention.

The present invention also provides for fusion proteins comprising an antibody (including molecules comprising, or alternatively consisting of, antibody fragments or variants thereof) of the invention, and a heterologous polypeptide (i.e., a polypeptide unrelated to an antibody or antibody domain). Nucleic acid molecules encoding these fusion proteins are also encompassed by the invention. A composition of the present invention may comprise, or alternatively consist of, one, two, three, four, five, ten, fifteen, twenty or more fusion proteins of the invention. Alternatively, a composition of the invention may comprise, or alternatively consist of, nucleic acid molecules encoding one, two, three, four, five, ten, fifteen, twenty or more fusion proteins of the invention.

The present invention also provides for a nucleic acid molecule(s), generally isolated, encoding an antibody (including molecules, such as scFvs, VH domains, or VL domains, that comprise, or alternatively consist of, an antibody fragment or variant thereof) of the invention. The present invention also provides a host cell transformed with a nucleic acid molecule of the invention and progeny thereof. The present invention also provides a method for the production of an antibody (including a molecule comprising, or alternatively consisting of, an antibody fragment or variant thereof) of the invention. The present invention further provides a method of expressing an antibody (including a molecule comprising, or alternatively consisting of, an antibody fragment or variant thereof) of the invention from a nucleic acid molecule. These and other aspects of the invention are described in further detail below.

BRIEF DESCRIPTION OF THE FIGURES

FIG. 1 illustrates the ability of antibodies PWD0283 and PWD0587 to inhibit the binding of biotinylated PA to ATR.

FIG. 2 graphically depicts the binding of biotinylated-PA to CHO-K1 cells, J744.A murine macrophages, and human macrophages as determined by flow cytometry. The solid line depicts biotinylated —PA binding to cells; the dashed line depicts the background level.

FIG. 3 illustrates the ability of two antibodies PWD0283 and PWD0587 to inhibit pore formation by PA protein using the assay described in Example 5.

FIG. 4 illustrates the ability of antibodies PWD0283 and PWD0587 to inhibit lethal toxin (LT)-mediated cell killing. Data are presented as mean±SD absorbance at 490 nm.

FIG. 5 illustrates the effect of prophylactic intravenous administration of PWD0283 and PWD0587 60 minutes prior to exposure of male Fisher 344 rats to Lethal Toxin. CAT002 is an isotype-matched (IgG1) negative control antibody. A single intravenous injection of PWD0283 or PWD0587 60 minutes prior to injection of lethal toxin provided 100% survival at 24 hours with no apparent ill effects. In contrast, a single injection of the negative control mAb, CAT002, provided no protection with 0% survival and an average TTM of 100 minutes. Vehicle or no study agent also provided no protection with 0% survival and an average TTM of 99 minutes and 91 minutes, respectively.

FIG. 6 shows the 14 day survival curves of the New Zealand White Rabbits (n=12) that received:

a) no treatment (vehicle) two days prior to;

b) prophylactic treatment (1, 5, 10, or 20 mg/kg sc) two days prior to; or c) therapeutic treatment (40 mg/kg iv) within 1 hour after challenge via aerosol inhalation of approximately 195×$LD_{50}$, of B. anthracis spores. Experimental details are described more fully in Example 11. Statistical p-values were obtained from a 2-sided log-rank test. The p-values for the comparison among all groups are <0.0001, regardless of inclusion or exclusion of the 40 mg/kg iv group in the analysis. The p-values marked in the graph are for the comparison versus the vehicle control group.

FIG. 7 shows the 28 day survival curves of cynomolgus monkeys (n=10 per group) that received no treatment (vehicle) or prophylactic treatment via subcutaneous administration of anti-PA monoclonal antibody PWD0587 (10, 20 or 40 mg/kg), two days prior to challenge via aerosol inhalation of approximately 186×$LD_{50}$, of B. anthracis spores. Experimental details are described more fully in Example 12. Statistical p-values were obtained from a 2-sided log-rank test. The P values for the comparison among all groups are <0.0001. The P values marked in the graph are for the comparison versus the vehicle control group.

DETAILED DESCRIPTION OF THE INVENTION

Definitions

The term "antibody," as used herein, refers to immunoglobulin molecules and immunologically active portions of immunoglobulin molecules, i.e., molecules that contain an antigen binding site that specifically binds an antigen. As such, the term antibody encompasses not only whole antibody molecules, but also antibody multimers and antibody fragments, as well as variants (including derivatives) of antibodies, antibody multimers and antibody fragments. Examples of molecules which are described by the term "antibody" herein include, but are not limited to: single chain Fvs (scFvs), Fab fragments, Fab' fragments, F(ab')$_2$, disulfide linked Fvs (sdFvs), Fvs, and fragments comprising or alternatively consisting of, either a VL or a VH domain. The term "single chain Fv" or "scFv" as used herein refers to a polypeptide comprising a VL domain of antibody linked to a VH domain of an antibody.

Antibodies of the invention include, but are not limited to, monoclonal, multispecific, human or chimeric antibodies, single chain antibodies, Fab fragments, F(ab') fragments, anti-idiotypic (anti-Id) antibodies (including, e.g., anti-Id antibodies to antibodies of the invention), intracellularly-made antibodies (i.e., intrabodies), and epitope-binding fragments of any of the above. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Preferably, an antibody of the invention comprises, or alternatively consists of, a VH domain, VH CDR, VL domain, or VL CDR having an amino acid sequence of any one of the cell lines in the ATCC™ Deposits referred, to referred to in Table 1, or a fragment or variant thereof. In a preferred embodiment, the immunoglobulin is an IgG1 isotype. In another preferred embodiment, the immunoglobulin is an IgG4 isotype. Immunoglobulins may have both a heavy and light chain. An array of IgG, IgE, IgM, IgD, IgA, and IgY heavy chains may be paired with a light chain of the kappa or lambda forms. Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')2 fragments are tetravalent, whereas dimers of Fab fragments or scFv molecules are bivalent. Individual monomers withon an antibody multimer may be identical or different, i.e., they may be heteromeric or homomeric antibody multimers. For example, individual antibodies within a multimer may have the same or different binding specificities.

Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., Proceedings of the National Academy of Sciences USA (1997) 94:7509-7514, which is hereby incorporated by reference in its entirety. Antibody homodimers can be converted to Fab'2 homodimers through digestion with pepsin. Another way to form antibody homodimers is through the use of the autophilic T15 peptide described in Zhao and Kohler, The Journal of Immunology (2002) 25:396-404, which is hereby incorporated by reference in its entirety.

Alternatively, antibodies can be made to multimerize through recombinant DNA techniques. IgM and IgA naturally form antibody multimers through the interaction with the mature J chain polypeptide (e.g., SEQ ID NO:44). Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) Clinical Immunology 101:21-31. and Frigerio et al., (2000) Plant Physiology 123:1483-94., both of which are hereby incorporated by reference in their entireties.) IgA dimers are naturally secreted into the lumen of mucosa-lined organs. This secretion is mediated through interaction of the J chain with the polymeric IgA receptor (pIgR) on epithelial cells. If secretion of an IgA form of an antibody (or of an antibody engineered to contain a J chain interaction domain) is not desired, it can be greatly reduced by expressing the antibody molecule in association with a mutant J chain that does not interact well with pIgR (e.g., SEQ ID NOS:45-47; Johansen et al., *The Journal of Immunology* (2001) 167:5185-5192 which is hereby incorporated by reference in its entirety). Expression of an antibody with one of these mutant J chains will reduce its ability to bind to the polymeric IgA receptor on epithelial cells, thereby reducing transport of the antibody across the epithelial cell and its resultant secretion into the lumen of mucosa lined organs. ScFv dimers can also be formed through recombinant techniques known in the art; an example of the construction of scFv dimers is given in Goel et al., (2000) Cancer Research 60:6964-6971 which is hereby incorporated by reference in its entirety. Antibody multimers may be purified using any suitable method known in the art, including, but not limited to, size exclusion chromatography.

By "isolated antibody" is intended an antibody removed from its native environment. Thus, an antibody produced by, purified from and/or contained within a hybridoma and/or a recombinant host cell is considered isolated for purposes of the present invention.

Unless otherwise defined in the specification, specific binding by an antibody to PA means that an antibody binds PA but does not significantly bind to (i.e., cross react with) proteins other than PA, such as other proteins in the same family of proteins). An antibody that binds PA protein and does not cross-react with other proteins is not necessarily an antibody that does not bind said other proteins in all conditions; rather, the PA-specific antibody of the invention preferentially binds PA compared to its ability to bind said other proteins such that it will be suitable for use in at least one type of assay or treatment, i.e., give low background levels or result in no unreasonable adverse effects in treatment. It is well known that the portion of a protein bound by an antibody is known as the epitope. An epitope may either be linear (i.e., comprised of sequential amino acids residues in a protein sequences) or conformational (i.e., comprised of one or more amino acid residues that are not contiguous in the primary structure of the protein but that are brought together by the secondary, tertiary or quaternary structure of a protein). Given that PA-specific antibodies bind to epitopes of PA, an antibody that specifically binds PA may or may not bind fragments of PA and/or variants of PA (e.g., proteins that are at least 90% identical to PA) depending on the presence or absence of the epitope bound by a given PA-specific antibody in the PA fragment or variant. Likewise, PA-specific antibodies of the invention may bind species orthologues of PA (including fragments thereof) depending on the presence or absence of the epitope recognized by the antibody in the orthologue. Additionally, PA-specific antibodies of the invention may bind modified forms of PA, for example, PA fusion proteins. In such a case when antibodies of the invention bind PA fusion proteins, the antibody must make binding contact with the PA moiety of the fusion protein in order for the binding to be specific. Antibodies that specifically bind to PA can be identified, for example, by immunoassays or other techniques known to those of skill in the art, e.g., the immunoassays described in the Examples below.

Antibodies of the invention may also include multimeric forms of antibodies. For example, antibodies of the invention may take the form of antibody dimers, trimers, or higher-order multimers of monomeric immunoglobulin molecules. Dimers of whole immunoglobulin molecules or of F(ab')$_2$ fragments are tetravalent, whereas dimers of Fab fragments or scFv molecules are bivalent. Individual monomers within an antibody multimer may be identical or different, i.e., they may be heteromeric or homomeric antibody multimers. For example, individual antibodies within a multimer may have the same or different binding specificities. Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers, and other higher-order antibody multimers. Alternatively, antibody homodimers may be formed through chemical linkage techniques known in the art. For example, heterobifunctional crosslinking agents including, but not limited to, SMCC [succinimidyl 4-(maleimidomethyl)cyclohexane-1-carboxylate] and SATA [N-succinimidyl S-acethylthio-acetate] (available, for example, from Pierce Biotechnology, Inc. (Rockford, Ill.)) can be used to form antibody multimers. An exemplary protocol for the formation of antibody homodimers is given in Ghetie et al., *Proceedings of the National Academy of Sciences USA* (1997) 94:7509-7514, which is hereby incorporated by reference in its entirety. Antibody homodimers can be converted to Fab'2 homodimers through digestion with pepsin. Alternatively, antibodies can be made to multimerize through recombinant DNA techniques. IgM and IgA naturally form antibody multimers through the interaction with the J chain polypeptide. Non-IgA or non-IgM molecules, such as IgG molecules, can be engineered to contain the J chain interaction domain of IgA or IgM, thereby conferring the ability to form higher order multimers on the non-IgA or non-IgM molecules. (see, for example, Chintalacharuvu et al., (2001) *Clinical Immunology* 101:21-31 and Frigerio et al., (2000) *Plant Physiology* 123:1483-94, both of which are hereby incorporated by reference in their entireties.) ScFv dimers can also be formed through recombinant techniques known in the art; an example of the construction of scFv dimers is given in Goel et al., (2000) *Cancer Research* 60:6964-6971, which is hereby incorporated by reference in its entirety. Antibody multimers may be purified using any suitable method known in the art, including, but not limited to, size exclusion chromatography.

The term "variant" as used herein refers to a polypeptide that possesses a similar or identical amino acid sequence as a PA polypeptide, a fragment of a PA polypeptide, an anti-PA antibody or antibody fragment thereof. A variant having a similar amino acid sequence refers to a polypeptide that satisfies at least one of the following: (a) a polypeptide comprising, or alternatively consisting of, an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of PA polypeptide (SEQ ID NO:2), a fragment of a PA polypeptide, an anti-PA antibody or antibody fragment thereof (including a VH domain, VHCDR, VL domain, or VLCDR having an amino acid sequence of any one or more scFvs or recombinant antibodies expressed by the cell lines in the ATCC™ Deposits referred to in Table 1) described herein; (b) a polypeptide encoded by a nucleotide sequence, the complementary sequence of which hybridizes under stringent conditions to a nucleotide sequence encoding PA (SEQ ID NO:2), a fragment of a PA polypeptide, an anti-PA antibody or antibody fragment thereof (including a VH domain, VHCDR, VL domain, or VLCDR having an amino acid sequence of any one of the scFvs referred to in Table 1), described herein, of at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues; and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, identical to the nucleotide sequence encoding a PA polypeptide, a fragment of a PA polypeptide, an anti-PA antibody or antibody fragment thereof (including a VH domain, VHCDR, VL domain, or VLCDR having an amino acid sequence of any one or more scFvs or recombinant antibodies expressed by the cell lines in the ATCC™ Deposits referred to in Table 1), described herein. A polypeptide with similar structure to a PA polypeptide, a fragment of a PA polypeptide, an anti-PA antibody or antibody fragment thereof, described herein refers to a polypeptide that has a similar secondary, tertiary or quaternary structure of a PA polypeptide, a fragment of a PA polypeptide, an anti-PA antibody, or antibody fragment thereof, described herein. The structure of a polypeptide can determined by methods known to those skilled in the art, including but not limited to, X-ray crystallography, nuclear magnetic resonance, and crystallographic electron microscopy. Preferably, a variant PA polypeptide, a variant fragment of a PA polypeptide, or a variant anti-PA antibody and/or antibody fragment possesses similar or identical function and/or structure as the reference PA polypeptide, the reference fragment of a PA polypeptide, or the reference anti-PA antibody and/or antibody fragment, respectively.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide at the corresponding position in the second sequence, then the molecules are identical at that position. The percent identity between the two sequences is a function of the number of identical positions shared by the sequences (i.e., % identity=number of identical overlapping positions/total number of positions ×100%). In one embodiment, the two sequences are the same length.

The determination of percent identity between two sequences can be accomplished using a mathematical algorithm known to those of skill in the art. An example of a mathematical algorithm for comparing two sequences is the algorithm of Karlin and Altschul *Proc. Natl. Acad. Sci. USA* 87:2264-2268 (1990), modified as in Karlin and Altschul *Proc. Natl. Acad. Sci. USA* 90:5873-5877 (1993). The BLASTn and BLASTx programs of Altschul, et al. *J. Mol. Biol.* 215:403-410 (1990) have incorporated such an algorithm. BLAST nucleotide searches can be performed with the BLASTn program (score=100, wordlength=12) to obtain nucleotide sequences homologous to a nucleic acid molecules of the invention. BLAST protein searches can be performed with the BLASTx program (score=50, wordlength=3) to obtain amino acid sequences homologous to a protein molecules of the invention. To obtain gapped alignments for comparison purposes, Gapped BLAST can be utilized as described in Altschul et al. *Nucleic Acids Res.* 25:3589-3402 (1997). Alternatively, PSI-BLAST can be used to perform an iterated search which detects distant relationships between molecules (Id.). When utilizing BLAST, Gapped BLAST, and PSI-BLAST programs, the default parameters of the respective programs (e.g., BLASTx and BLASTn) can be used.

Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti *Comput. Appl. Biosci.*, 10:3-5 (1994); and FASTA described in Pearson and Lipman *Proc. Natl. Acad. Sci.* 85:2444-8 (1988). Within FASTA, ktup is a control option that sets the sensitivity and speed of the search.

The term "derivative" as used herein, refers to a variant polypeptide of the invention that comprises, or alternatively consists of, an amino acid sequence of a PA polypeptide, a fragment of a PA polypeptide, or an antibody of the invention that specifically binds to a PA polypeptide, which has been altered by the introduction of amino acid residue substitutions, deletions or additions. The term "derivative" as used herein also refers to a PA polypeptide, a fragment of a PA polypeptide, an antibody that specifically binds to a PA polypeptide which has been modified, e.g., by the covalent attachment of any type of molecule to the polypeptide. For example, but not by way of limitation, a PA polypeptide, a fragment of a PA polypeptide, or an anti-PA antibody, may be modified, e.g., by glycosylation, acetylation, pegylation, phosphorylation, amidation, derivatization by known protecting/blocking groups, proteolytic cleavage, linkage to a cellular ligand or other protein, etc. A derivative of a PA polypeptide, a fragment of a PA polypeptide, or an anti-PA antibody, may be modified by chemical modifications using techniques known to those of skill in the art, including, but not limited to, specific chemical cleavage, acetylation, formylation, metabolic synthesis of tunicamycin, etc. Further, a derivative of a PA polypeptide, a fragment of a PA polypeptide, or an anti-PA antibody, may contain one or more non-classical amino acids. A polypeptide derivative possesses a similar or identical function as a PA polypeptide, a fragment of a PA polypeptide, or an anti-PA antibody, described herein.

The term "fragment" as used herein refers to a polypeptide comprising an amino acid sequence of at least 5 amino acid residues, at least 10 amino acid residues, at least 15 amino acid residues, at least 20 amino acid residues, at least 25 amino acid residues, at least 30 amino acid residues, at least 35 amino acid residues, at least 40 amino acid residues, at least 45 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues, of the amino acid sequence of PA, or an anti-PA antibody (including molecules such as scFv's, that comprise, or alternatively consist of, antibody fragments or variants thereof) that specifically binds to PA.

The term "host cell" as used herein refers to the particular subject cell transfected with a nucleic acid molecule and the progeny or potential progeny of such a cell. Progeny may not be identical to the parent cell transfected with the nucleic acid molecule due to mutations or environmental influences that may occur in succeeding generations or integration of the nucleic acid molecule into the host cell genome.

Antibodies of the present invention are preferably provided in an isolated form, and preferably are substantially purified. By "isolated" is intended an antibody removed from its native environment. Thus, for example, an antibody produced and/or contained within a recombinant host cell is considered isolated for purposes of the present invention.

Antibody Structure

The basic antibody structural unit is known to comprise a tetramer. Each tetramer is composed of two identical pairs of polypeptide chains, each pair having one "light" (about 25 kilodalton) and one "heavy" chain (about 50-70 kilodalton). The amino-terminal portion of each chain includes a variable region of about 100 to 110 or more amino acids primarily responsible for antigen recognition. Herein the terms "heavy chain" and "light chain" refer to the heavy and light chains of an antibody unless otherwise specified. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact IgG antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the heavy and the light chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk, *J. Mol. Biol.* 196:901-917 (1987); Chothia et al., *Nature* 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79: 315-321 (1990), Kostelny et al. *J Immunol.* 148:1547 1553 (1992). In addition, bispecific antibodies may be formed as "diabodies" (Holliger et al. "'Diabodies': small bivalent and bispecific antibody fragments" PNAS USA 90:6444-6448 (1993)) or "Janusins" (Traunecker et al. "Bispecific single chain molecules (Janusins) target cytotoxic lymphocytes on HIV infected cells" *EMBO J.* 10:3655-3659 (1991) and Traunecker et al. "Janusin: new molecular design for bispecific reagents" *Int J Cancer Suppl* 7:51-52 (1992)).

Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Anti-PA Antibodies

Using phage display technology, single chain antibody molecules ("scFvs") that specifically bind to PA (or fragments or variants thereof) have been identified (Example 1). Molecules comprising, or alternatively consisting of, fragments or variants of these scFvs (e.g., VH domains, VH CDRs, VL domains, or VL CDRs having an amino acid sequence of the corresponding region of the antibody expressed by a cell line contained in an ATCC™ Deposit referred to in Table 1), that specifically bind to PA (or fragments or variants thereof) are also encompassed by the invention, as are nucleic acid molecules that encode these scFvs, and/or molecules.

In particular, the invention relates to scFvs comprising, or alternatively consisting of, an amino acid sequence selected from the group consisting of SEQ ID NOs: 48-56, preferably SEQ ID NOs:50 and 53 as referred to in Table 1 below. Molecules comprising, or alternatively consisting of, fragments or variants of these scFvs (e.g., VH domains, VH CDRs, VL domains, or VL CDRs having an amino acid sequence of any one of those referred to in Table 1), that specifically bind to PA are also encompassed by the invention, as are nucleic acid molecules that encode these scFvs, and/or molecules (e.g., SEQ ID NOs:57-65).

The present invention provides antibodies (including molecules comprising, or alternatively consisting of, antibody fragments or variants thereof) that specifically bind to a polypeptide or a polypeptide fragment of PA. In particular, the invention provides antibodies corresponding to the scFvs referred to in Table 1. Such scFvs may routinely be "converted" to immunoglobulin molecules by inserting, for example, the nucleotide sequences encoding the VH and/or VL domains of the scFv into an expression vector containing the constant domain sequences and engineered to direct the expression of the immunoglobulin molecule, as described in more detail in Example 6 below.

NS0 cell lines that express IgG1 antibodies that comprise the VH and VL domains of scFvs of the invention have been deposited with the American Type Culture Collection ("ATCC™") on the dates listed in Table 1 and given the ATCC™ Deposit Numbers identified in Table 1. The ATCC™ is located at 10801 University Boulevard, Manassas, Va. 20110-2209, USA. The ATCC™ deposit was made pursuant to the terms of the Budapest Treaty on the international recognition of the deposit of microorganisms for purposes of patent procedure.

Accordingly, in one embodiment, the invention provides antibodies that comprise the VH and VL domains of scFvs of the invention.

In a preferred embodiment, an antibody of the invention is the antibody expressed by cell line NS0 PA 2973 (PWD0587) #240-22 (See Table 1).

TABLE 1

Anti-PA scFvs

| scFv | scFv protein SEQ ID NO: | scFv DNA SEQ ID NO: | AAs of VH Domain | AAs of VH CDR1 | AAs of VH CDR2 | AAs of VH CDR3 | AAs of VL Domain | AAs of VL CDR1 | AAs of VL CDR2 | AAs of VL CDR3 | Cell Line Expressing antibody | ATCC Deposit Number | ATCC Deposit Date |
|---|---|---|---|---|---|---|---|---|---|---|---|---|---|
| PWB2447 | 48 | 57 | 1-125 | 26-35 | 50-66 | 99-114 | 140-248 | 162-172 | 188-194 | 227-237 | | | |
| PWC2004 | 49 | 58 | 1-123 | 26-35 | 50-66 | 99-112 | 140-251 | 162-175 | 191-197 | 230-240 | | | |
| PWD0283 | 50 | 59 | 1-118 | 26-35 | 50-66 | 99-107 | 136-246 | 158-170 | 186-192 | 225-235 | | | |
| PWD0323 | 51 | 60 | 1-117 | 26-35 | 50-66 | 99-106 | 134-244 | 156-168 | 184-190 | 223-233 | | | |
| PWD0422 | 52 | 61 | 1-117 | 26-35 | 50-66 | 99-106 | 134-244 | 156-168 | 184-190 | 223-233 | | | |
| PWD0587 | 53 | 62 | 1-117 | 26-35 | 50-66 | 99-106 | 134-244 | 156-168 | 184-190 | 223-233 | NSO PA 2973 (PWD0587) #240-22 | PTA-4796 | Nov. 11, 2002 |
| PWD0791 | 54 | 63 | 1-120 | 26-35 | 50-66 | 99-109 | 138-248 | 160-172 | 188-194 | 227-237 | | | |
| PHD2222 | 55 | 64 | 1-117 | 26-35 | 50-66 | 99-106 | 134-244 | 156-168 | 184-190 | 223-233 | | | |
| PHD2581 | 56 | 65 | 1-117 | 26-35 | 50-66 | 99-106 | 134-244 | 156-168 | 184-190 | 223-233 | | | |

The present invention encompasses antibodies (including molecules comprising, or alternatively consisting of, antibody fragments or variants thereof) that specifically bind to a PA polypeptide or a fragment, variant, or fusion protein thereof. A PA polypeptide includes, but is not limited to, PA (SEQ ID NO:2).

Protective Antigen

Antibodies of the present invention bind PA polypeptide or fragments or variants thereof. The following section describes the PA polypeptides, fragments and variants that may be bound by the antibodies of the invention in more detail.

The PA protein is a 764 amino acid protein (SEQ ID NO:2) comprising a signal sequence from amino acid residues 1-29, and a 735 amino acid secreted protein which undergoes further process upon binding to an anthrax receptor, (e.g., ATR or CMG2) on the cell surface. The 735 amino acid secreted protein, also known as PA83 because it has a molecular weight of approximately 83 kilodaltons, has a structure that is largely made up of antiparallel beta pleated sheets with only a few short alpha-helices. The protein can be divided into four domains: Domain I (amino acid residues 30-287 of SEQ ID NO:2), Domain II (amino acid residues 288-516 of SEQ ID NO:2), Domain III (amino acid residues 517-624 of SEQ ID NO:2), and Domain IV (amino acid residues 625-764) of SEQ ID NO:2). In its native form, Domain I contains two calcium ions and the protease cleavage site RKKR at amino acid residues 193-196 of SEQ ID NO:2. Thus, Domain I contains the entire 20 kilodalton fragment (PA20, amino acid residues 30-196 of SEQ ID NO:2) that is cleaved off of PA upon binding to an anthrax receptor (e.g., ATR or CMG2) at the cell surface. That portion of Domain I that remains after cleavage of PA20 forms the N terminus of active PA63 and may be involved in binding LF and EF. Domain II is the heptamerization domain and also contains a large flexible loop that is implicated in membrane insertion. Domain III, is small and its function is not clearly understood. Domain IV is the receptor binding domain.

Thus, in specific embodiments, antibodies of the invention may bind the intact 735 amino acid secreted form of PA (PA83), polypeptides that comprise or alternatively consist of the PA63 protein, the PA20 fragment, and/or any one or more of domains I, II, III, or IV. In preferred embodiments, antibodies of the invention bind PA83 and prevent its cleavage of the PA20 fragment from the PA63 fragment by proteases. In other embodiments, antibodies of the invention bind the PA63 form of PA and prevent oligomerization, and in particular heptamerization of PA63.

In certain embodiments, the antibodies of the present invention specifically bind PA polypeptide. An antibody that specifically binds PA may, in some embodiments, bind fragments, variants (including species orthologs of PA), multimers or modified forms of PA. For example, an antibody specific for PA may bind the PA moiety of a fusion protein comprising all or a portion of PA.

PA proteins may be found as monomers or multimers (i.e., dimers, trimers, tetramers, and higher multimers). Accordingly, the present invention relates to antibodies that bind PA proteins found as monomers or as part of multimers. In specific embodiments, antibodies of the invention bind PA monomers, dimers, trimers or heptamers. In additional embodiments, antibodies of the invention bind at least dimers, at least trimers, or at least tetramers containing one or more PA polypeptides.

Antibodies of the invention may bind PA homomers or heteromers. As used herein, the term homomer, refers to a multimer containing only PA proteins of the invention (including PA fragments such as PA63, variants, and fusion proteins, as described herein). These homomers may contain PA proteins having identical or different polypeptide sequences. In a specific embodiment, a homomer of the invention is a multimer containing only PA proteins having an identical polypeptide sequence. In another specific embodiment, antibodies of the invention bind PA homomers containing PA proteins having different polypeptide sequences. In specific embodiments, antibodies of the invention bind a PA homodimer (e.g., containing PA proteins having identical or different polypeptide sequences). In additional embodiments, antibodies of the invention bind at least a homodimer, at least a homotrimer, or at least a homotetramer of PA.

In specific embodiments antibodies of the present invention bind PA homoheptamers.

As used herein, the term heteromer refers to a multimer containing heterologous proteins (i.e., proteins containing polypeptide sequences that do not correspond to a polypeptide sequences encoded by the PA gene) in addition to the PA proteins of the invention. In a specific embodiment, antibodies of the invention bind a heterodimer, a heterotrimer, or a heterotetramer. In additional embodiments, the antibodies of the invention bind at least a heterodimer, at least a heterotrimer, or at least a-heterotetramer containing one or more PA polypeptides.

In specific embodiments, antibodies of the present invention bind a PA heteroheptamer.

Antibodies of the invention may bind PA multimers that are the result of hydrophobic, hydrophilic, ionic and/or covalent associations and/or may be indirectly linked, by for example, liposome formation. Thus, in one embodiment, antibodies of the invention may bind PA multimers, such as, for example, homoheptamers, that are formed when PA proteins (such as PA63 polypeptide monomers) contact one another in solution. In another embodiment, antibodies of the invention may bind heteromultimers, such as, for example, heteroheptamers, that are formed when proteins of the invention contact antibodies to the PA polypeptides (including antibodies to the heterologous polypeptide sequence in a fusion protein) in solution. In other embodiments, multimers bound by one or more antibodies of the invention are formed by covalent associations with and/or between the PA proteins of the invention. Such covalent associations may involve one or more amino acid residues contained in the polypeptide sequence of the protein (e.g., the polypeptide sequence recited in SEQ ID NO:2). In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a PA fusion protein. In one example, covalent associations are between the heterologous sequence contained in a fusion protein (see, e.g., U.S. Pat. No. 5,478,925). In a specific example, the covalent associations are between the heterologous sequence contained in a PA-Fc or PA-human serum albumin (PA-HSA) fusion protein (as described herein).

Antibodies of the invention may bind PA multimers generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers that antibodies of the invention may bind can be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins that antibodies of the invention may bind can be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer that antibodies of the invention may bind (see, e.g., U.S. Pat. No. 5,478,925, which is herein incorporated by reference in its entirety).

Alternatively, multimers that antibodies of the invention may bind can be generated using genetic engineering techniques known in the art. In one embodiment, proteins contained in multimers that may be bound by one or more antibodies of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer that may be bound by one or more antibodies of the invention are generated by ligating a polynucleotide sequence encoding a PA polypeptide to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant PA polypeptides which contain a transmembrane domain and which can be incorporated by membrane reconstitution techniques into liposomes (see, e.g., U.S. Pat. No. 5,478,925, which is herein incorporated by reference in its entirety). In another embodiment, two or more PA polypeptides are joined through synthetic linkers (e.g., peptide, carbohydrate or soluble polymer linkers). Examples include those peptide linkers described in U.S. Pat. No. 5,073,627 (hereby incorporated by reference). Proteins comprising multiple PA polypeptides separated by peptide linkers may be produced using conventional recombinant DNA technology. In specific embodiments, antibodies of the invention bind proteins comprising multiple PA polypeptides separated by peptide linkers.

Another method for preparing multimer PA polypeptides involves use of PA polypeptides fused to a leucine zipper or isoleucine polypeptide sequence. Leucine zipper domains and isoleucine zipper domains are polypeptides that promote multimerization of the proteins in which they are found. Leucine zippers were originally identified in several DNA-binding proteins (Landschulz et al., *Science* 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric PA proteins are those described in PCT application WO 94/10308, hereby incorporated by reference. Recombinant fusion proteins comprising a soluble PA polypeptide fused to a peptide that dimerizes or trimerizes in solution are expressed in suitable host cells, and the resulting soluble multimeric PA is recovered from the culture supernatant using techniques known in the art. In specific embodiments, antibodies of the invention bind PA-leucine zipper fusion protein monomers and/or PA-leucine zipper fusion protein multimers.

Antibodies that bind PA receptor polypeptides may bind them as isolated polypeptides or in their naturally occurring state. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the PA polypeptide may be substantially purified by the one-step method described in Smith and Johnson, *Gene* 67:31-40 (1988). Thus, antibodies of the present invention may bind recombinantly and/or naturally produced PA polypeptides. In a specific embodiment, antibodies of the present invention bind a PA secreted by a cell, preferably a bacterial cell, comprising a polynucleotide encoding amino acids 1 to 764 of SEQ ID NO:2 operably associated with a regulatory sequence that controls gene expression. In a specific embodiment, antibodies of the present invention bind PA purified from a bacterial cell culture, wherein said PA is encoded by a polynucleotide encoding amino acids 1 to 764 of SEQ ID NO:2 operably associated with a regulatory sequence that controls expression of said polynucleotide. In other specific embodiments, antibodies of the present invention bind a PA polypeptide expressed by a cell comprising a polynucleotide encoding amino acids 197 to 764 of SEQ ID NO:2 operably associated with a regulatory sequence that controls gene expression. In still other embodiments, antibodies of the present invention bind a PA polypeptide expressed by a cell comprising a polynucleotide encoding amino acids 625 to 764 of SEQ ID NO:2 operably associated with a regulatory sequence that controls gene expression.

Antibodies of the present invention that may bind PA polypeptide fragments comprising or alternatively, consisting of, an amino acid sequence contained in SEQ ID NO:2. Protein fragments may be "free-standing," or comprised within a larger polypeptide of which the fragment forms a part or region, most preferably as a single continuous region. Antibodies of the present invention may bind polypeptide fragments, including, for example, fragments that comprise or alternatively, consist of from about amino acid residues: 1 to 29, 30 to 59, 60 to 89, 90 to 119, 120 to 149, 150 to 175, 176 to 196, 197 to 226, 227 to 256, 257 to 287, 288 to 312, 313 to 337, 338 to 362, 363 to 387, 388 to 412, 413 to 437, 438 to 462, 463 to 487, 488 to 516, 517 to 542, 543 to 569, 570 to 569, 570 to 596, 597 to 624, 625 to 652, 653 to 680, 681 to 708, 709 to 736, and/or 737 to 764 of SEQ ID NO:2. In this context "about" includes the particularly recited value, larger or smaller by several (5, 4, 3, 2, or 1) amino acids, at either extreme or at both extremes. Moreover, polypeptide fragments that antibodies of the invention may bind can be at least about 10, 20, 30, 40, 50, 60, 70, 80, 90, 100, 110, 120, 130, 140, 150, 175 or 200 amino acids in length. In this context "about" includes the particularly recited value, larger or smaller by several (5, 4, 3, 2, or 1) amino acids, at either extreme or at both extremes.

Preferably, antibodies of the present invention bind polypeptide fragments selected from the group: a polypeptide comprising or alternatively, consisting of, the full length PA polypeptide (amino acid residues 1 to 764 in SEQ ID NO:2); a polypeptide comprising or alternatively, consisting of, the secreted form of PA (amino acid residues 30 to 764 in SEQ ID NO:2); a polypeptide comprising or alternatively, consisting of, the PA20 fragment (amino acid residues from about 30 to about 196 in SEQ ID NO:2); a polypeptide comprising or alternatively, consisting of, the PA63 fragment (amino acid residues from about 197 to about 764 in SEQ ID NO:2); a polypeptide comprising or alternatively, consisting of, PA domain I (amino acid residues 30 to 287 of SEQ ID NO:2); a polypeptide comprising or alternatively, consisting of, PA domain II (amino acid residues 288 to 516 of SEQ ID NO:2); a polypeptide comprising or alternatively, consisting of, PA domain 111 (amino acid residues 517 to 624 of SEQ ID NO:2); a polypeptide comprising or alternatively, consisting of, PA domain IV (amino acid residues 625 to 764 of SEQ ID NO:2); a polypeptide comprising or alternatively, consisting of, fragment of the predicted mature PA polypeptide; and a polypeptide comprising, or alternatively, consisting of, one, two, three, four or more, epitope bearing portions of the PA receptor protein. In additional embodiments, the polypeptide fragments of the invention comprise, or alternatively, consist of, any combination of 1, 2, 3, 4, 5, 6, 7, or all 8 of the above members. The amino acid residues constituting these domains may vary slightly (e.g., by about 1 to about 15 amino acid residues) depending on the criteria used to define each domain.

Domain I contains the proteolytic cleavage site. When the secreted form of PA is cleaved at this site, a 20 kilodalton fragment (PA20) is released from PA, generating the biologically active 63 kilodalton PA63 fragment. Thus, in specific embodiments antibodies of the invention bind an epitope at or near this cleavage site and prevent the cleavage of the secreted form of PA that results in the generation of PA20 and PA63. In specific embodiments, antibodies of the invention that prevent cleavage of PA into PA20 and PA63 may bind one or more PA peptides (as well as the native amino acid secreted form of the protein, PA83, see, e.g., Example 2) selected from the group consisting of: (a) amino acid residues 190 to 209 of SEQ ID NO:2; (b) amino acid residues 181 to 201 of SEQ ID NO:2; (c) amino acid residues 198 to 212 of SEQ ID NO:2; (d) amino acid residues 196 to 212 of SEQ ID NO:2; (e) amino acid residues 194 to 212 of SEQ ID NO:2; (f) amino acid residues 192 to 212 of SEQ ID NO:2; (g) amino acid residues 190 to 212 of SEQ ID NO:2; (h) amino acid residues 188 to 212 of SEQ ID NO:2; (i) amino acid residues 186 to 212 of SEQ ID NO:2; (j) amino acid residues 184 to 212 of SEQ ID NO:2; and (k) amino acid residues 181 to 195 of SEQ ID NO:2.

Domain IV of PA is important for interactions between PA and its receptor (e.g., ATR (SEQ ID NO:3) or CMG2 (SEQ ID NO:42)). Accordingly, in preferred embodiments, antibodies of the present invention bind PA polypeptide fragments comprising, or alternatively consisting of amino acid residues 625 to 764 of SEQ ID NO:2. In preferred embodiments, the antibodies of the invention that bind all or a portion of domain IV of PA prevent PA from binding to ATR and/or CMG2. In other preferred embodiments, the antibodies of the invention that bind all or a portion of domain IV of PA protect cells from death induced by anthrax toxins.

Antibodies of the invention may also bind fragments comprising, or alternatively, consisting of structural or functional attributes of PA. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) PA. Certain preferred regions are those set out in Table 2 and include, but are not limited to, regions of the aforementioned types identified by analysis of the amino acid sequence depicted in (SEQ ID NO:2), such preferred regions include; Garnier-Robson predicted alpha-regions, beta-regions, turn-regions, and coil-regions; Chou-Fasman predicted alpha-regions, beta-regions, and turn-regions; Kyte-Doolittle predicted hydrophilic regions; Eisenberg alpha and beta amphipathic regions; Emini surface-forming regions; and Jameson-Wolf high antigenic index regions, as predicted using the default parameters of these computer programs.

The data representing the structural or functional attributes of PA set forth in Table 2, as described above, was generated using the various modules and algorithms of the DNA*STAR set on default parameters. Column I represents the results of a Garnier-Robson analysis of alpha helical regions; Column II represents the results of a Chou-Fasman analysis of alpha helical regions; Column 111 represents the results of a Garnier Robson analysis of beta sheet regions; Column IV represents the results of a Chou-Fasman analysis of beta sheet regions; Column V represents the results of a Garnier Robson analysis of turn regions; Column VI represents the results of a Chou-Fasman analysis of turn regions; Column VII represents the results of a Garnier Robson analysis of coil regions;

Column VIII represents a Kyte-Doolittle hydrophilicity plot; Column; Column IX represents the results of an Eisenberg analysis of alpha amphipathic regions; Column X represents the results of an Eisenberg analysis of beta amphipathic regions; Column XI represents the results of a Karplus-Schultz analysis of flexible regions; Column XII represents the Jameson-Wolf antigenic index score; and Column XIII represents the Emini surface probability plot.

In a preferred embodiment, the data presented in columns VIII, XII, and XIII of Table 2 can be used to determine regions of PA which exhibit a high degree of potential for antigenicity. Regions of high antigenicity are determined from the data presented in columns VIII, XII, and/or XIII by choosing values which represent regions of the polypeptide which are likely to be exposed on the surface of the polypeptide in an environment in which antigen recognition may occur in the process of initiation of an immune response.

The above-mentioned preferred regions set out in Table 2 include, but are not limited to, regions of the aforementioned types identified by analysis of the amino acid sequence set out in SEQ ID NO:2. As set out in Table 2, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Jameson-Wolf regions of high antigenic index and Emini surface-forming regions. Among preferred polypeptide fragments bound by one or more antibodies of the invention are those that comprise regions of PA that combine several structural features, such as several (e.g., 1, 2, 3, or 4) of the same or different region features set out above and in Table 2.

TABLE 2

| Res | Position | I | II | III | IV | V | VI | VII | VIII | IX | X | XI | XII | XIII |
|---|---|---|---|---|---|---|---|---|---|---|---|---|---|---|
| Met | 1 | A | A | . | . | . | . | . | 1.59 | . | . | . | 0.75 | 2.90 |
| Lys | 2 | A | A | . | . | . | . | . | 1.12 | . | . | . | 0.75 | 4.54 |
| Lys | 3 | A | A | . | B | . | . | . | 0.70 | . | . | . | 0.75 | 2.64 |
| Arg | 4 | A | A | . | B | . | . | . | 0.20 | . | . | . | 0.75 | 2.20 |
| Lys | 5 | A | A | . | B | . | . | . | 0.38 | . | . | F | 0.75 | 0.77 |
| Val | 6 | . | A | B | B | . | . | . | 0.17 | . | . | . | 0.60 | 0.60 |
| Leu | 7 | . | A | B | B | . | . | . | -0.48 | . | . | . | -0.30 | 0.25 |
| Ile | 8 | . | A | B | B | . | . | . | -1.11 | . | . | . | -0.60 | 0.12 |
| Pro | 9 | . | A | B | B | . | . | . | -2.03 | * | . | . | -0.60 | 0.17 |
| Leu | 10 | . | A | B | B | . | . | . | -2.38 | . | * | . | -0.60 | 0.17 |
| Met | 11 | A | A | . | B | . | . | . | -1.83 | . | . | . | -0.60 | 0.32 |
| Ala | 12 | A | A | . | B | . | . | . | -1.91 | . | . | . | -0.60 | 0.30 |
| Leu | 13 | A | A | . | B | . | . | . | -1.83 | . | . | . | -0.60 | 0.26 |
| Ser | 14 | . | A | B | B | . | . | . | -2.48 | . | . | . | -0.60 | 0.21 |
| Thr | 15 | . | . | B | B | . | . | . | -1.97 | . | . | . | -0.60 | 0.16 |
| Ile | 16 | . | . | B | B | . | . | . | -1.67 | . | . | . | -0.60 | 0.25 |
| Leu | 17 | . | . | B | B | . | . | . | -1.39 | . | . | . | -0.60 | 0.25 |
| Val | 18 | . | . | B | B | . | . | . | -0.92 | . | . | . | -0.60 | 0.25 |
| Ser | 19 | . | . | B | B | . | . | . | -0.62 | . | * | F | -0.36 | 0.36 |
| Ser | 20 | . | . | . | . | . | T | C | -1.12 | . | * | F | 0.33 | 0.70 |
| Thr | 21 | . | . | . | . | . | T | C | -0.23 | . | * | F | 0.42 | 0.78 |
| Gly | 22 | . | . | . | . | . | T | C | -0.28 | . | * | F | 1.56 | 1.01 |
| Asn | 23 | . | . | . | . | . | T | C | -0.31 | . | * | F | 0.90 | 0.56 |
| Leu | 24 | A | A | . | . | . | . | . | -0.01 | . | . | . | 0.06 | 0.27 |
| Glu | 25 | A | A | . | . | . | . | . | -0.30 | . | . | . | -0.03 | 0.47 |
| Val | 26 | A | A | . | . | . | . | . | 0.01 | . | * | . | -0.12 | 0.30 |
| Ile | 27 | A | A | . | . | . | . | . | -0.50 | . | * | . | 0.39 | 0.63 |
| Gln | 28 | A | A | . | . | . | . | . | -0.46 | * | * | . | 0.30 | 0.27 |
| Ala | 29 | A | A | . | . | . | . | . | 0.36 | * | * | . | 0.30 | 0.72 |
| Glu | 30 | A | A | . | . | . | . | . | 0.36 | * | * | . | 0.45 | 1.79 |
| Val | 31 | A | A | . | . | . | . | . | 1.21 | * | * | F | 0.90 | 1.79 |
| Lys | 32 | A | A | . | . | . | . | . | 2.21 | * | * | F | 0.90 | 2.84 |
| Gln | 33 | A | A | . | . | . | . | . | 1.40 | * | * | F | 0.90 | 3.21 |
| Glu | 34 | A | A | . | . | . | . | . | 1.18 | * | * | F | 0.90 | 3.57 |
| Asn | 35 | A | A | . | . | . | . | . | 1.18 | * | * | F | 0.90 | 1.47 |
| Arg | 36 | A | A | . | . | . | . | . | 2.03 | * | * | F | 0.60 | 1.37 |
| Leu | 37 | A | A | . | . | . | . | . | 1.69 | * | . | F | 0.90 | 1.37 |
| Leu | 38 | A | A | . | . | . | . | . | 1.69 | * | . | F | 0.94 | 1.14 |
| Asn | 39 | . | . | . | . | . | T | C | 1.39 | * | . | F | 2.18 | 1.01 |
| Glu | 40 | A | . | . | . | . | T | . | 1.09 | * | . | F | 2.02 | 1.64 |
| Ser | 41 | . | . | . | . | . | T | C | 0.68 | * | . | F | 2.86 | 2.66 |
| Glu | 42 | . | . | . | . | T | T | . | 1.49 | . | . | F | 3.40 | 2.22 |
| Ser | 43 | . | . | . | . | T | T | . | 1.96 | . | . | F | 3.06 | 2.22 |
| Ser | 44 | . | . | . | . | T | T | . | 1.14 | . | . | F | 2.72 | 1.64 |
| Ser | 45 | . | . | . | . | T | T | . | 0.33 | . | . | F | 1.93 | 0.78 |
| Gln | 46 | . | . | B | . | . | T | . | 0.29 | . | . | F | 0.59 | 0.48 |
| Gly | 47 | . | . | B | B | . | . | . | 0.04 | . | . | F | -0.45 | 0.35 |
| Leu | 48 | . | . | B | B | . | . | . | 0.10 | . | . | F | -0.45 | 0.41 |
| Leu | 49 | . | . | B | B | . | . | . | -0.30 | . | . | . | -0.60 | 0.37 |
| Gly | 50 | . | . | B | B | . | . | . | -0.30 | . | . | . | -0.60 | 0.33 |
| Tyr | 51 | . | . | B | B | . | . | . | -0.30 | . | . | . | -0.60 | 0.53 |
| Tyr | 52 | . | . | B | B | . | . | . | -0.77 | . | . | . | -0.45 | 1.08 |
| Phe | 53 | . | . | B | B | . | . | . | 0.04 | . | . | . | -0.60 | 0.90 |
| Ser | 54 | . | . | B | . | . | . | . | 0.16 | . | * | . | -0.40 | 0.92 |
| Asp | 55 | . | A | B | . | . | . | . | 0.50 | . | * | . | -0.60 | 0.51 |
| Leu | 56 | . | A | B | . | . | . | . | 0.16 | . | * | . | -0.45 | 1.02 |
| Asn | 57 | . | A | . | . | T | . | . | 0.19 | . | * | . | 0.10 | 0.77 |

TABLE 2-continued

| Res | Position | I | II | III | IV | V | VI | VII | VIII | IX | X | XI | XII | XIII |
|-----|----------|---|----|----|----|---|----|----|------|----|---|----|------|------|
| Phe | 58 | . | A | . | . | T | . | . | 0.29 | . | * | . | 0.10 | 0.71 |
| Gln | 59 | A | A | . | . | . | . | . | -0.27 | . | * | . | -0.60 | 0.85 |
| Ala | 60 | . | A | B | B | . | . | . | -1.12 | . | * | . | -0.60 | 0.39 |
| Pro | 61 | . | A | B | B | . | . | . | -0.62 | . | * | . | -0.60 | 0.34 |
| Met | 62 | . | A | B | B | . | . | . | -0.92 | . | * | . | -0.60 | 0.28 |
| Val | 63 | . | A | B | B | . | . | . | -0.52 | . | . | . | -0.60 | 0.37 |
| Val | 64 | . | . | B | B | . | . | . | -0.83 | . | . | . | -0.60 | 0.32 |
| Thr | 65 | . | . | B | B | . | . | . | -0.56 | . | . | F | -0.20 | 0.47 |
| Ser | 66 | . | . | B | B | . | . | . | -0.69 | . | . | F | 0.05 | 0.92 |
| Ser | 67 | . | . | B | B | . | . | . | -0.09 | . | . | F | 0.75 | 1.22 |
| Thr | 68 | . | . | B | . | . | . | T | -0.04 | . | . | F | 2.00 | 1.42 |
| Thr | 69 | . | . | . | . | T | T | . | 0.51 | . | * | F | 2.50 | 0.87 |
| Gly | 70 | . | . | . | . | T | T | . | -0.07 | . | * | F | 2.25 | 0.87 |
| Asp | 71 | . | . | B | . | . | T | . | 0.02 | . | * | F | 1.00 | 0.42 |
| Leu | 72 | . | . | B | . | . | . | . | 0.02 | . | * | F | 0.55 | 0.45 |
| Ser | 73 | . | . | B | . | . | . | . | 0.03 | . | * | F | 0.90 | 0.61 |
| Ile | 74 | . | . | B | . | . | T | . | 0.34 | . | * | F | 0.85 | 0.49 |
| Pro | 75 | . | . | B | . | . | T | . | -0.12 | . | * | F | 1.00 | 1.04 |
| Ser | 76 | . | . | . | . | . | T | C | -0.12 | . | . | F | 1.05 | 0.64 |
| Ser | 77 | . | . | . | . | . | T | C | 0.69 | * | . | F | 1.20 | 1.57 |
| Glu | 78 | A | A | . | . | . | . | . | 0.10 | * | . | F | 0.90 | 1.64 |
| Leu | 79 | . | A | B | . | . | . | . | 0.78 | * | . | F | 0.71 | 0.86 |
| Glu | 80 | . | A | . | . | T | . | . | 0.69 | * | . | F | 1.37 | 0.99 |
| Asn | 81 | . | A | . | . | . | . | C | 0.99 | . | . | F | 1.43 | 0.76 |
| Ile | 82 | . | . | . | . | . | . | C | 1.29 | * | . | F | 2.04 | 1.61 |
| Pro | 83 | . | . | . | . | . | . | C | 1.29 | . | . | F | 2.60 | 1.49 |
| Ser | 84 | . | . | . | . | T | T | . | 1.86 | * | . | F | 2.44 | 1.61 |
| Glu | 85 | A | . | . | . | . | T | . | 1.16 | * | . | F | 1.18 | 3.59 |
| Asn | 86 | A | . | . | . | . | T | . | 1.16 | . | . | F | 0.92 | 2.01 |
| Gln | 87 | . | . | . | . | T | T | . | 1.74 | * | . | F | 1.06 | 2.60 |
| Tyr | 88 | . | . | B | B | . | . | . | 1.37 | * | . | . | -0.15 | 2.01 |
| Phe | 89 | . | . | B | B | . | . | . | 0.78 | . | . | . | -0.45 | 1.26 |
| Gln | 90 | . | . | B | B | . | . | . | 0.49 | . | . | . | -0.60 | 0.51 |
| Ser | 91 | . | . | B | B | . | . | . | 0.19 | * | . | . | -0.60 | 0.34 |
| Ala | 92 | . | . | B | B | . | . | . | -0.16 | * | . | . | -0.60 | 0.53 |
| Ile | 93 | . | . | B | B | . | . | . | -0.61 | . | . | . | -0.60 | 0.30 |
| Trp | 94 | A | . | . | . | . | T | . | -0.80 | * | * | . | -0.20 | 0.20 |
| Ser | 95 | A | . | . | . | . | T | . | -0.76 | * | * | . | -0.20 | 0.14 |
| Gly | 96 | A | . | . | . | . | T | . | -1.31 | * | * | . | -0.20 | 0.39 |
| Phe | 97 | A | . | . | . | . | T | . | -0.68 | * | * | . | -0.20 | 0.27 |
| Ile | 98 | . | A | B | B | . | . | . | 0.26 | * | * | . | 0.30 | 0.41 |
| Lys | 99 | A | A | . | B | . | . | . | 0.24 | . | * | . | 0.60 | 0.83 |
| Val | 100 | . | A | . | B | . | . | C | 0.54 | . | * | F | 1.70 | 1.28 |
| Lys | 101 | . | A | . | B | . | . | C | 0.89 | . | * | F | 2.00 | 3.05 |
| Lys | 102 | . | A | . | B | . | . | C | 1.34 | . | . | F | 2.30 | 2.64 |
| Ser | 103 | . | . | . | . | . | T | C | 1.92 | . | * | F | 3.00 | 5.57 |
| Asp | 104 | A | . | . | . | . | T | . | 1.18 | . | . | F | 2.50 | 4.02 |
| Glu | 105 | A | . | . | . | . | T | . | 1.44 | . | . | F | 2.20 | 1.74 |
| Tyr | 106 | . | . | B | . | . | T | . | 1.09 | . | . | . | 1.45 | 1.31 |
| Thr | 107 | A | . | . | B | . | . | . | 0.74 | . | . | . | 0.15 | 1.13 |
| Phe | 108 | A | . | . | B | . | . | . | 0.46 | . | . | . | -0.30 | 0.88 |
| Ala | 109 | A | . | . | B | . | . | . | 0.46 | . | . | . | -0.60 | 0.57 |
| Thr | 110 | A | . | . | B | . | . | . | 0.46 | . | . | F | 0.06 | 0.65 |
| Ser | 111 | A | . | . | . | . | T | . | 0.67 | * | . | F | 0.82 | 1.22 |
| Ala | 112 | A | . | . | . | . | T | . | 0.12 | * | . | F | 1.63 | 1.64 |
| Asp | 113 | A | . | . | . | . | T | . | 0.51 | * | . | F | 1.69 | 0.84 |
| Asn | 114 | . | . | . | . | . | T | C | 0.50 | * | . | F | 2.10 | 0.91 |
| His | 115 | . | . | . | B | . | . | C | 0.52 | * | . | . | 0.74 | 0.89 |
| Val | 116 | . | . | B | B | . | . | . | -0.03 | * | * | . | 0.03 | 0.56 |
| Thr | 117 | . | . | B | B | . | . | . | 0.56 | * | . | . | -0.18 | 0.26 |
| Met | 118 | . | . | B | B | . | . | . | 0.56 | . | . | . | -0.39 | 0.32 |
| Trp | 119 | A | . | . | B | . | . | . | 0.56 | . | . | . | -0.30 | 0.71 |
| Val | 120 | A | . | . | . | . | T | . | 0.59 | . | . | . | 0.10 | 0.86 |
| Asp | 121 | A | . | . | . | . | T | . | 0.59 | . | . | F | 1.00 | 1.50 |
| Asp | 122 | A | . | . | . | . | T | . | 0.01 | . | . | F | 1.00 | 1.06 |
| Gln | 123 | A | . | . | . | . | T | . | 0.61 | * | . | F | 1.15 | 1.00 |
| Glu | 124 | A | A | . | B | . | . | . | 0.94 | * | . | F | 0.75 | 0.96 |
| Val | 125 | A | A | . | B | . | . | . | 1.21 | . | . | . | 0.75 | 1.15 |
| Ile | 126 | A | A | . | B | . | . | . | 0.91 | * | . | . | 0.30 | 0.67 |
| Asn | 127 | A | A | . | B | . | . | . | 0.91 | . | . | . | 0.60 | 0.52 |
| Lys | 128 | A | A | . | . | . | . | . | 0.61 | * | . | F | 0.60 | 1.13 |
| Ala | 129 | A | A | . | . | . | . | . | 0.61 | * | . | F | 1.50 | 2.15 |
| Ser | 130 | . | A | . | . | . | . | C | 1.51 | * | . | F | 2.30 | 2.15 |
| Asn | 131 | . | . | . | . | . | T | C | 1.51 | . | * | F | 3.00 | 2.15 |
| Ser | 132 | . | . | . | . | . | T | C | 1.62 | . | * | F | 2.40 | 1.49 |
| Asn | 133 | A | . | . | . | . | T | . | 0.77 | . | * | F | 2.20 | 2.18 |
| Lys | 134 | . | . | B | . | . | T | . | 1.36 | . | * | F | 1.60 | 1.12 |
| Ile | 135 | . | A | B | . | . | . | . | 1.70 | . | * | F | 1.20 | 1.45 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Arg | 136 | . | A | B | . | . | . | . | 1.36 | . | * | . | 0.75 | 1.80 |
| Leu | 137 | . | A | B | . | . | . | . | 1.77 | . | * | F | 0.75 | 0.89 |
| Glu | 138 | A | A | . | . | . | . | . | 0.96 | . | * | F | 0.90 | 2.49 |
| Lys | 139 | A | A | . | . | . | . | . | 0.67 | . | * | F | 0.90 | 1.05 |
| Gly | 140 | A | . | . | B | . | . | . | 1.56 | * | . | F | 0.60 | 1.99 |
| Arg | 141 | A | . | . | B | . | . | . | 0.56 | . | . | F | 0.90 | 1.99 |
| Leu | 142 | A | . | . | B | . | . | . | 1.41 | . | * | . | 0.30 | 0.70 |
| Tyr | 143 | A | . | . | B | . | . | . | 0.52 | . | * | . | 0.45 | 1.41 |
| Gln | 144 | . | . | B | B | . | . | . | 0.48 | . | * | . | -0.30 | 0.50 |
| Ile | 145 | . | . | B | B | . | . | . | 0.58 | . | * | . | -0.45 | 1.06 |
| Lys | 146 | . | . | B | B | . | . | . | 0.47 | * | * | . | -0.45 | 1.06 |
| Ile | 147 | . | . | B | B | . | . | . | 1.39 | * | * | . | -0.15 | 1.06 |
| Gln | 148 | . | . | B | B | . | . | . | 1.63 | . | * | . | 0.45 | 2.96 |
| Tyr | 149 | . | . | B | . | . | . | . | 1.63 | . | * | . | 0.95 | 2.56 |
| Gln | 150 | . | . | B | . | . | . | . | 2.31 | . | * | F | 0.80 | 5.88 |
| Arg | 151 | . | . | . | . | . | T | . | 1.96 | . | . | F | 1.84 | 5.25 |
| Glu | 152 | . | . | . | . | . | . | C | 2.84 | . | . | F | 1.98 | 4.83 |
| Asn | 153 | . | . | . | . | . | T | C | 2.89 | . | . | F | 2.52 | 4.83 |
| Pro | 154 | . | . | . | . | . | T | C | 2.79 | . | . | F | 2.86 | 4.93 |
| Thr | 155 | . | . | . | . | T | T | . | 1.98 | . | . | F | 3.40 | 2.82 |
| Glu | 156 | A | . | . | . | . | T | . | 1.87 | . | * | F | 2.66 | 1.45 |
| Lys | 157 | A | A | . | . | . | . | . | 1.17 | . | * | F | 1.92 | 1.56 |
| Gly | 158 | A | A | . | . | . | . | . | 1.21 | . | * | F | 1.43 | 0.94 |
| Leu | 159 | A | A | . | . | . | . | . | 0.61 | . | * | . | 1.09 | 1.08 |
| Asp | 160 | A | A | . | . | . | . | . | 0.68 | . | * | . | 0.30 | 0.45 |
| Phe | 161 | . | . | B | B | . | . | . | 0.39 | . | * | . | -0.30 | 0.71 |
| Lys | 162 | . | . | B | B | . | . | . | 0.03 | . | * | . | -0.60 | 0.90 |
| Leu | 163 | . | . | B | B | . | . | . | 0.38 | . | * | . | -0.60 | 0.78 |
| Tyr | 164 | . | . | B | B | . | . | . | 0.89 | . | * | . | -0.45 | 1.50 |
| Trp | 165 | A | . | . | B | . | . | . | 0.89 | . | * | . | 0.15 | 1.01 |
| Thr | 166 | A | . | . | B | . | . | . | 1.59 | . | * | F | 0.30 | 2.11 |
| Asp | 167 | A | . | . | B | . | . | . | 1.59 | . | . | F | 0.90 | 2.17 |
| Ser | 168 | A | . | . | . | . | T | . | 2.44 | . | . | F | 2.20 | 4.12 |
| Gln | 169 | . | . | . | . | . | T | C | 2.69 | . | . | F | 3.00 | 5.71 |
| Asn | 170 | . | . | . | . | . | T | C | 2.12 | . | . | F | 2.70 | 5.93 |
| Lys | 171 | . | . | . | . | . | T | C | 1.54 | . | . | F | 2.40 | 3.28 |
| Lys | 172 | . | A | B | . | . | . | . | 1.24 | . | . | F | 1.50 | 1.33 |
| Glu | 173 | . | A | B | . | . | . | . | 1.24 | . | . | F | 1.20 | 1.11 |
| Val | 174 | . | A | B | . | . | . | . | 1.24 | . | . | F | 1.03 | 0.74 |
| Ile | 175 | . | A | B | . | . | . | . | 1.24 | . | . | F | 1.31 | 0.62 |
| Ser | 176 | . | . | B | . | . | T | . | 0.39 | . | . | F | 1.99 | 0.58 |
| Ser | 177 | . | . | B | . | . | T | . | 0.34 | . | . | F | 1.37 | 0.64 |
| Asp | 178 | . | . | . | . | T | T | . | -0.47 | . | . | F | 2.80 | 1.58 |
| Asn | 179 | . | . | . | . | . | T | C | 0.18 | . | . | F | 2.17 | 0.97 |
| Leu | 180 | A | A | . | . | . | . | . | 1.07 | . | . | . | 1.29 | 1.12 |
| Gln | 181 | A | A | . | . | . | . | . | 0.56 | . | . | . | 1.01 | 1.16 |
| Leu | 182 | A | A | . | . | . | . | . | 0.90 | . | . | . | -0.02 | 0.60 |
| Pro | 183 | A | A | . | . | . | . | . | 0.90 | . | . | F | 0.60 | 1.45 |
| Glu | 184 | A | A | . | . | . | . | . | 0.94 | . | * | F | 0.60 | 1.45 |
| Leu | 185 | A | A | . | . | . | . | . | 1.46 | . | . | F | 0.90 | 3.51 |
| Lys | 186 | A | A | . | . | . | . | . | 1.16 | * | . | F | 0.90 | 3.04 |
| Gln | 187 | A | A | . | . | . | . | . | 1.97 | * | . | F | 1.24 | 2.35 |
| Lys | 188 | A | A | . | . | . | . | . | 1.88 | . | * | F | 1.58 | 4.59 |
| Ser | 189 | A | . | . | . | . | T | . | 1.99 | * | * | F | 2.32 | 3.07 |
| Ser | 190 | A | . | . | . | . | T | . | 2.84 | . | * | F | 2.66 | 3.48 |
| Asn | 191 | . | . | . | . | T | T | . | 2.84 | . | . | F | 3.40 | 3.48 |
| Ser | 192 | . | . | . | . | T | T | . | 2.96 | . | . | F | 3.06 | 5.19 |
| Arg | 193 | . | . | . | . | T | . | . | 2.61 | . | . | F | 2.52 | 7.58 |
| Lys | 194 | . | . | . | . | T | . | . | 2.60 | . | . | F | 2.18 | 6.32 |
| Lys | 195 | . | . | . | . | T | . | . | 2.60 | . | . | F | 1.84 | 6.80 |
| Arg | 196 | . | . | B | . | . | . | . | 2.01 | . | . | F | 1.10 | 4.65 |
| Ser | 197 | . | . | B | . | . | . | . | 1.97 | . | . | F | 1.10 | 2.35 |
| Thr | 198 | . | . | B | . | . | . | . | 1.64 | . | . | F | 1.10 | 1.16 |
| Ser | 199 | . | . | . | . | T | T | . | 1.29 | . | . | F | 1.25 | 0.92 |
| Ala | 200 | . | . | . | . | . | T | C | 0.39 | * | . | F | 0.71 | 0.99 |
| Gly | 201 | . | . | . | . | . | T | C | 0.07 | * | . | F | 0.97 | 0.51 |
| Pro | 202 | . | . | B | . | . | T | . | 0.37 | * | . | F | 1.03 | 0.59 |
| Thr | 203 | . | . | B | . | . | . | . | 0.79 | . | . | F | 1.69 | 0.97 |
| Val | 204 | . | . | B | . | . | T | . | 1.09 | . | . | F | 2.60 | 1.92 |
| Pro | 205 | . | . | B | . | . | T | . | 1.68 | * | . | F | 2.34 | 2.07 |
| Asp | 206 | . | . | B | . | . | T | . | 2.02 | * | . | F | 2.42 | 2.31 |
| Arg | 207 | . | . | B | . | . | T | . | 1.89 | * | . | F | 2.50 | 5.20 |
| Asp | 208 | . | . | . | . | T | T | . | 1.31 | * | . | F | 2.98 | 3.33 |
| Asn | 209 | . | . | . | . | T | T | . | 1.96 | * | . | F | 3.06 | 1.40 |
| Asp | 210 | . | . | . | . | T | T | . | 2.17 | * | . | F | 3.40 | 1.10 |
| Gly | 211 | . | . | . | . | . | T | C | 1.87 | * | . | F | 2.86 | 1.10 |
| Ile | 212 | . | . | . | . | . | T | C | 0.94 | * | . | F | 2.37 | 0.92 |
| Pro | 213 | . | . | . | . | . | T | C | 0.94 | * | . | F | 1.73 | 0.45 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Asp | 214 | . | . | . | . | . | T | C | 0.09 | * | * | F | 1.39 | 0.79 |
| Ser | 215 | . | . | . | . | . | T | . | 0.09 | * | * | F | 0.85 | 0.84 |
| Leu | 216 | . | . | B | . | . | . | . | 0.09 | . | * | . | 0.60 | 0.94 |
| Glu | 217 | . | A | B | . | . | . | . | 0.73 | . | * | . | 0.60 | 0.56 |
| Val | 218 | A | A | . | . | . | . | . | 0.63 | . | . | . | 0.30 | 0.65 |
| Glu | 219 | A | A | . | . | . | . | . | -0.22 | . | . | . | 0.45 | 1.14 |
| Gly | 220 | A | A | . | . | . | . | . | 0.08 | . | * | . | 0.30 | 0.49 |
| Tyr | 221 | A | . | . | B | . | . | . | 0.03 | . | * | . | 0.45 | 1.10 |
| Thr | 222 | A | . | . | B | . | . | . | 0.08 | . | * | . | 0.30 | 0.47 |
| Val | 223 | A | . | . | B | . | . | . | 0.93 | . | * | . | 0.56 | 0.95 |
| Asp | 224 | A | . | . | B | . | . | . | 0.98 | . | . | . | 0.82 | 0.98 |
| Val | 225 | A | . | . | . | . | . | . | 1.43 | . | * | F | 1.88 | 1.36 |
| Lys | 226 | A | . | . | . | . | . | . | 1.37 | . | * | F | 2.14 | 3.58 |
| Asn | 227 | . | . | B | . | . | T | . | 0.98 | . | * | F | 2.60 | 3.09 |
| Lys | 228 | . | . | B | . | . | T | . | 1.02 | . | * | F | 2.34 | 3.61 |
| Arg | 229 | . | . | B | . | . | T | . | 0.72 | . | . | F | 2.08 | 1.49 |
| Thr | 230 | . | . | B | . | . | T | . | 1.37 | * | . | F | 1.52 | 1.24 |
| Phe | 231 | . | . | B | . | . | . | . | 1.03 | * | . | F | 0.91 | 0.96 |
| Leu | 232 | . | . | B | . | . | . | . | 0.14 | . | . | . | -0.40 | 0.51 |
| Ser | 233 | . | . | . | . | . | T | C | -0.20 | . | . | . | 0.00 | 0.25 |
| Pro | 234 | . | . | . | . | T | T | . | -0.31 | * | . | . | 0.20 | 0.39 |
| Trp | 235 | . | . | . | . | T | T | . | -0.89 | * | . | . | 0.20 | 0.75 |
| Ile | 236 | A | . | . | . | . | T | . | -0.22 | * | . | . | -0.20 | 0.39 |
| Ser | 237 | A | . | . | B | . | . | . | 0.59 | * | . | . | -0.60 | 0.35 |
| Asn | 238 | A | A | . | B | . | . | . | 0.93 | . | . | . | -0.60 | 0.57 |
| Ile | 239 | A | A | . | B | . | . | . | 1.19 | . | . | . | 0.45 | 1.63 |
| His | 240 | A | A | . | B | . | . | . | 1.13 | . | . | . | 0.75 | 2.44 |
| Glu | 241 | A | A | . | . | . | . | . | 1.21 | . | . | F | 0.90 | 1.50 |
| Lys | 242 | A | A | . | . | . | . | . | 1.20 | . | . | F | 0.90 | 1.76 |
| Lys | 243 | A | A | . | . | . | . | . | 1.24 | . | . | F | 0.90 | 1.87 |
| Gly | 244 | A | A | . | . | . | . | . | 1.89 | . | * | F | 0.90 | 2.16 |
| Leu | 245 | A | . | . | . | . | . | . | 1.97 | * | . | F | 1.44 | 1.69 |
| Thr | 246 | A | . | . | . | . | T | . | 1.67 | * | . | F | 1.98 | 1.69 |
| Lys | 247 | . | . | B | . | . | T | . | 1.32 | * | . | F | 2.02 | 2.29 |
| Tyr | 248 | . | . | B | . | . | T | . | 1.07 | * | * | F | 2.36 | 3.72 |
| Lys | 249 | . | . | . | . | T | T | . | 1.41 | * | . | F | 3.40 | 3.99 |
| Ser | 250 | . | . | . | . | . | . | C | 2.27 | * | . | F | 2.66 | 3.45 |
| Ser | 251 | . | . | . | . | . | T | C | 2.29 | * | * | F | 2.52 | 4.41 |
| Pro | 252 | . | . | . | . | . | T | C | 1.94 | * | * | F | 2.18 | 2.32 |
| Glu | 253 | . | . | . | . | T | T | . | 1.88 | * | . | F | 2.04 | 2.32 |
| Lys | 254 | . | . | . | . | T | T | . | 1.24 | . | . | F | 1.40 | 2.50 |
| Trp | 255 | . | . | . | . | T | . | . | 1.24 | . | . | F | 1.20 | 1.63 |
| Ser | 256 | . | . | B | . | . | . | . | 1.54 | . | . | F | 0.80 | 1.26 |
| Thr | 257 | . | . | B | . | . | . | . | 1.54 | . | . | F | 1.10 | 1.05 |
| Ala | 258 | . | . | . | . | . | T | . | 1.30 | * | . | F | 1.20 | 1.55 |
| Ser | 259 | . | . | . | . | . | . | C | 0.96 | * | . | F | 1.90 | 1.81 |
| Asp | 260 | . | . | . | . | . | T | C | 1.24 | * | . | F | 2.40 | 1.68 |
| Pro | 261 | . | . | . | . | . | T | C | 0.84 | * | . | F | 3.00 | 2.78 |
| Tyr | 262 | . | . | . | . | . | T | T | 1.16 | * | . | F | 2.60 | 1.80 |
| Ser | 263 | . | . | . | . | . | T | C | 1.79 | * | . | F | 2.40 | 1.86 |
| Asp | 264 | A | A | . | . | . | . | . | 1.23 | * | . | F | 1.50 | 2.41 |
| Phe | 265 | A | A | . | . | . | . | . | 0.92 | * | . | F | 0.90 | 1.14 |
| Glu | 266 | A | A | . | . | . | . | . | 0.79 | * | * | F | 0.90 | 1.23 |
| Lys | 267 | A | A | . | . | . | . | . | 1.14 | * | * | F | 0.75 | 0.73 |
| Val | 268 | A | A | . | . | . | . | . | 0.56 | * | * | F | 0.90 | 1.65 |
| Thr | 269 | A | . | . | B | . | . | . | 0.56 | * | * | F | 0.75 | 0.67 |
| Gly | 270 | A | . | . | B | . | . | . | 1.30 | * | * | F | 0.75 | 0.56 |
| Arg | 271 | A | . | . | B | . | . | . | 1.30 | * | * | F | 0.90 | 1.50 |
| Ile | 272 | . | . | B | B | . | . | . | 0.40 | * | * | F | 1.20 | 1.67 |
| Asp | 273 | . | . | . | . | T | T | . | 0.96 | * | * | F | 2.30 | 1.25 |
| Lys | 274 | . | . | . | . | . | T | C | 1.06 | * | * | F | 2.25 | 0.86 |
| Asn | 275 | . | . | . | . | . | T | C | 1.40 | * | * | F | 2.40 | 1.89 |
| Val | 276 | . | . | . | . | . | T | C | 0.70 | * | * | F | 3.00 | 1.96 |
| Ser | 277 | . | . | . | . | . | T | C | 1.70 | * | * | F | 2.55 | 0.99 |
| Pro | 278 | . | . | . | . | . | T | C | 1.67 | * | * | F | 2.40 | 1.21 |
| Glu | 279 | A | . | . | . | . | T | . | 1.41 | * | * | F | 1.90 | 2.21 |
| Ala | 280 | A | . | . | . | . | T | . | 0.60 | * | * | F | 1.60 | 2.56 |
| Arg | 281 | A | . | . | . | . | . | . | 0.60 | . | * | . | 0.65 | 1.36 |
| His | 282 | . | . | B | B | . | . | . | 0.31 | * | * | . | 0.30 | 0.58 |
| Pro | 283 | . | . | B | B | . | . | . | -0.07 | . | * | . | -0.30 | 0.58 |
| Leu | 284 | A | . | . | B | . | . | . | -0.31 | . | * | . | -0.30 | 0.30 |
| Val | 285 | A | . | . | B | . | . | . | 0.07 | * | * | . | -0.60 | 0.35 |
| Ala | 286 | A | . | . | B | . | . | . | -0.93 | * | . | . | -0.60 | 0.35 |
| Ala | 287 | . | . | B | B | . | . | . | -1.76 | . | . | . | -0.60 | 0.29 |
| Tyr | 288 | . | . | B | B | . | . | . | -1.58 | . | . | . | -0.60 | 0.29 |
| Pro | 289 | . | . | B | B | . | . | . | -1.62 | . | . | . | -0.60 | 0.40 |
| Ile | 290 | . | . | B | B | . | . | . | -0.77 | . | . | . | -0.60 | 0.29 |
| Val | 291 | . | . | B | B | . | . | . | -0.78 | . | * | . | -0.60 | 0.31 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| His | 292 | . | . | B | B | . | . | . | -0.19 | . | * | . | -0.60 | 0.20 |
| Val | 293 | . | . | B | B | . | . | . | 0.06 | . | . | . | -0.30 | 0.49 |
| Asp | 294 | A | . | . | B | . | . | . | -0.62 | . | . | . | 0.45 | 1.07 |
| Met | 295 | A | A | . | . | . | . | . | -0.62 | . | . | . | 0.30 | 0.55 |
| Glu | 296 | A | A | . | . | . | . | . | -0.58 | . | * | . | -0.30 | 0.52 |
| Asn | 297 | A | A | . | . | . | . | . | -0.84 | . | . | . | -0.30 | 0.26 |
| Ile | 298 | A | A | . | . | . | . | . | 0.06 | . | . | . | -0.60 | 0.35 |
| Ile | 299 | A | A | . | . | . | . | . | 0.06 | . | . | . | 0.30 | 0.40 |
| Leu | 300 | A | A | . | . | . | . | . | 0.66 | . | . | . | 0.04 | 0.40 |
| Ser | 301 | A | A | . | . | . | . | . | 0.66 | . | . | F | 1.13 | 0.99 |
| Lys | 302 | A | A | . | . | . | . | . | 0.66 | . | . | F | 1.92 | 2.36 |
| Asn | 303 | . | . | . | . | . | T | C | 1.24 | . | . | F | 2.86 | 4.95 |
| Glu | 304 | . | . | . | . | T | T | . | 1.82 | * | . | F | 3.40 | 4.95 |
| Asp | 305 | . | . | . | . | T | T | . | 2.63 | * | . | F | 3.06 | 3.57 |
| Gln | 306 | . | . | . | . | T | T | . | 2.93 | . | . | F | 2.72 | 3.85 |
| Ser | 307 | . | . | . | . | T | . | . | 2.58 | . | . | F | 2.18 | 3.57 |
| Thr | 308 | . | . | . | B | . | . | . | 2.58 | . | . | F | 1.42 | 3.09 |
| Gln | 309 | . | . | . | . | T | . | . | 2.28 | . | . | F | 1.76 | 2.98 |
| Asn | 310 | . | . | . | . | . | T | C | 2.28 | . | . | F | 2.04 | 2.98 |
| Thr | 311 | . | . | . | . | . | T | C | 1.97 | * | * | F | 2.32 | 3.57 |
| Asp | 312 | . | . | . | . | T | T | . | 2.38 | . | * | F | 2.80 | 2.98 |
| Ser | 313 | . | . | B | . | . | T | . | 2.38 | * | . | F | 2.42 | 3.62 |
| Gln | 314 | . | . | B | B | . | . | . | 1.49 | * | . | F | 1.74 | 3.62 |
| Thr | 315 | . | . | B | B | . | . | . | 1.19 | * | * | F | 1.46 | 1.52 |
| Arg | 316 | . | . | B | B | . | . | . | 1.54 | * | . | F | 0.88 | 1.52 |
| Thr | 317 | . | . | B | B | . | . | . | 1.54 | * | . | F | 0.90 | 1.76 |
| Ile | 318 | . | . | B | B | . | . | . | 1.53 | * | . | F | 0.90 | 1.96 |
| Ser | 319 | . | . | B | . | . | T | . | 1.23 | * | . | F | 1.60 | 1.44 |
| Lys | 320 | . | . | . | . | T | T | . | 1.23 | * | . | F | 2.00 | 1.34 |
| Asn | 321 | . | . | . | . | . | T | C | 0.82 | * | . | F | 2.10 | 2.76 |
| Thr | 322 | . | . | . | . | . | T | C | 1.24 | . | . | F | 2.40 | 2.76 |
| Ser | 323 | . | . | . | . | . | T | C | 1.82 | . | . | F | 3.00 | 2.70 |
| Thr | 324 | . | . | . | . | . | T | C | 2.09 | . | . | F | 2.40 | 2.42 |
| Ser | 325 | . | . | . | . | . | T | C | 1.73 | . | . | F | 2.36 | 2.29 |
| Arg | 326 | . | . | . | . | . | T | C | 1.43 | . | . | F | 2.32 | 2.46 |
| Thr | 327 | . | . | . | . | . | . | C | 1.74 | . | . | F | 2.08 | 2.29 |
| His | 328 | . | . | . | . | . | T | C | 1.19 | * | . | F | 2.54 | 2.95 |
| Thr | 329 | . | . | B | . | . | T | . | 1.47 | . | . | F | 2.60 | 1.12 |
| Ser | 330 | . | . | B | . | . | T | . | 1.42 | . | * | F | 2.04 | 1.06 |
| Glu | 331 | . | . | B | . | . | T | . | 1.31 | . | * | F | 1.63 | 0.77 |
| Val | 332 | . | . | . | . | . | . | C | 1.03 | . | * | F | 1.37 | 0.86 |
| His | 333 | . | . | . | . | . | T | C | 1.07 | . | * | F | 1.31 | 0.64 |
| Gly | 334 | . | . | . | . | . | T | C | 0.52 | . | * | . | 1.20 | 0.64 |
| Asn | 335 | A | . | . | . | . | T | . | 0.79 | . | * | . | 0.10 | 0.64 |
| Ala | 336 | A | . | . | . | . | T | . | 0.20 | . | * | . | 0.70 | 0.64 |
| Glu | 337 | A | A | . | . | . | . | . | 0.76 | . | * | . | 0.30 | 0.66 |
| Val | 338 | A | A | . | . | . | . | . | 0.09 | . | * | . | 0.30 | 0.55 |
| His | 339 | A | A | . | . | . | . | . | -0.27 | . | * | . | -0.30 | 0.47 |
| Ala | 340 | A | A | . | . | . | . | . | -0.27 | . | * | . | -0.60 | 0.24 |
| Ser | 341 | . | A | B | . | . | . | . | -0.57 | * | * | . | -0.60 | 0.53 |
| Phe | 342 | . | A | B | . | . | . | . | -0.91 | * | . | . | -0.60 | 0.27 |
| Phe | 343 | . | A | B | . | . | . | . | -0.40 | . | . | . | -0.60 | 0.27 |
| Asp | 344 | . | . | . | . | T | T | . | -0.67 | * | * | . | 0.20 | 0.20 |
| Ile | 345 | . | . | . | . | T | T | . | -0.93 | * | * | . | 0.20 | 0.30 |
| Gly | 346 | . | . | . | . | T | T | . | -0.93 | * | * | F | 0.65 | 0.26 |
| Gly | 347 | . | . | . | . | . | T | C | -0.82 | * | * | F | 1.05 | 0.21 |
| Ser | 348 | . | . | . | . | . | . | C | -0.47 | * | * | F | -0.05 | 0.30 |
| Val | 349 | . | . | B | . | . | . | . | -1.17 | * | * | F | 0.05 | 0.30 |
| Ser | 350 | . | . | B | . | . | T | . | -0.58 | * | * | . | -0.20 | 0.26 |
| Ala | 351 | . | . | B | . | . | T | . | -0.23 | . | . | . | -0.08 | 0.26 |
| Gly | 352 | . | . | B | . | . | T | . | -0.19 | . | . | . | 0.04 | 0.57 |
| Phe | 353 | . | . | B | . | . | T | . | 0.11 | . | . | F | 0.61 | 0.57 |
| Ser | 354 | . | . | . | . | . | . | C | 0.67 | . | . | F | 0.73 | 0.91 |
| Asn | 355 | . | . | . | . | . | T | C | 0.67 | . | . | F | 1.20 | 1.24 |
| Ser | 356 | . | . | . | . | . | T | C | 0.94 | . | . | F | 1.08 | 1.91 |
| Asn | 357 | . | . | . | . | . | T | C | 0.43 | . | . | F | 1.56 | 2.06 |
| Ser | 358 | . | . | . | . | . | T | C | 0.54 | . | . | F | 0.69 | 0.95 |
| Ser | 359 | . | . | . | B | . | . | C | -0.04 | . | . | F | 0.17 | 0.72 |
| Thr | 360 | . | . | B | B | . | . | . | -0.04 | . | . | F | -0.45 | 0.31 |
| Val | 361 | . | . | B | B | . | . | . | 0.22 | . | . | . | -0.30 | 0.39 |
| Ala | 362 | . | . | B | B | . | . | . | -0.08 | . | * | . | -0.30 | 0.40 |
| Ile | 363 | . | . | B | B | . | . | . | -0.59 | . | * | . | -0.30 | 0.37 |
| Asp | 364 | . | . | B | B | . | . | . | -0.59 | . | * | . | -0.30 | 0.41 |
| His | 365 | . | . | . | B | . | . | . | -1.09 | . | * | . | -0.10 | 0.54 |
| Ser | 366 | A | A | . | . | . | . | . | -0.82 | . | * | . | -0.30 | 0.64 |
| Leu | 367 | . | A | B | . | . | . | . | -0.58 | * | * | . | -0.30 | 0.38 |
| Ser | 368 | . | A | . | . | . | . | C | 0.31 | * | * | . | -0.40 | 0.28 |
| Leu | 369 | . | A | . | . | . | . | C | 0.42 | . | . | . | -0.10 | 0.36 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Ala | 370 | A | A | . | . | . | . | . | 0.14 | * | . | . | 0.30 | 0.86 |
| Gly | 371 | A | A | . | . | . | . | . | 0.16 | * | . | F | 0.75 | 0.93 |
| Glu | 372 | A | A | . | . | . | . | . | 0.38 | * | . | F | 0.00 | 1.18 |
| Arg | 373 | A | A | . | . | . | . | . | 0.68 | . | . | F | 0.60 | 1.18 |
| Thr | 374 | A | A | . | . | . | . | . | 1.18 | * | . | F | 0.90 | 2.06 |
| Trp | 375 | A | A | . | . | . | . | . | 1.17 | * | . | . | 0.75 | 1.72 |
| Ala | 376 | A | A | . | . | . | . | . | 1.17 | * | . | . | 0.30 | 0.87 |
| Glu | 377 | A | A | . | . | . | . | . | 0.36 | . | . | . | -0.60 | 0.60 |
| Thr | 378 | A | A | . | . | . | . | . | 0.24 | . | . | . | -0.60 | 0.47 |
| Met | 379 | A | A | . | . | . | . | . | 0.24 | . | . | . | -0.30 | 0.74 |
| Gly | 380 | . | A | . | . | . | . | C | -0.06 | . | . | . | -0.10 | 0.62 |
| Leu | 381 | . | A | . | . | . | . | C | 0.53 | . | . | . | -0.40 | 0.43 |
| Asn | 382 | A | A | . | . | . | . | . | 0.22 | . | . | F | -0.15 | 0.73 |
| Thr | 383 | A | A | . | . | . | . | . | -0.06 | * | . | F | 0.60 | 1.07 |
| Ala | 384 | A | A | . | . | . | . | . | 0.66 | . | * | F | 0.00 | 1.31 |
| Asp | 385 | A | A | . | . | . | . | . | 0.19 | . | * | F | 0.90 | 1.59 |
| Thr | 386 | A | A | . | . | . | . | . | 1.00 | . | * | F | 0.45 | 0.91 |
| Ala | 387 | A | A | . | . | . | . | . | 0.41 | * | * | F | 0.60 | 1.45 |
| Arg | 388 | A | A | . | . | . | . | . | 0.72 | * | * | . | 0.30 | 0.88 |
| Leu | 389 | A | A | . | . | . | . | . | 0.42 | . | * | . | 0.30 | 0.98 |
| Asn | 390 | A | . | . | . | . | T | . | 0.53 | * | * | . | 0.10 | 0.68 |
| Ala | 391 | . | . | B | . | . | T | . | 0.60 | * | * | . | 0.70 | 0.68 |
| Asn | 392 | . | . | B | . | . | T | . | 0.33 | * | * | . | -0.05 | 1.29 |
| Ile | 393 | . | . | B | . | . | T | . | 0.22 | * | * | . | 0.10 | 0.59 |
| Arg | 394 | . | . | B | B | . | . | . | 0.72 | * | * | . | -0.30 | 0.95 |
| Tyr | 395 | . | . | B | B | . | . | . | 0.38 | * | * | . | -0.30 | 0.85 |
| Val | 396 | . | . | B | B | . | . | . | 0.66 | * | * | . | -0.15 | 1.20 |
| Asn | 397 | . | . | B | . | . | T | . | 0.07 | * | * | F | 0.25 | 0.88 |
| Thr | 398 | . | . | B | . | . | T | . | 0.74 | * | * | F | -0.05 | 0.57 |
| Gly | 399 | . | . | . | . | T | T | . | -0.26 | * | . | F | 0.80 | 1.19 |
| Thr | 400 | . | . | B | . | . | T | . | -0.26 | * | . | F | -0.05 | 0.52 |
| Ala | 401 | . | . | B | B | . | . | . | 0.60 | * | . | F | -0.45 | 0.56 |
| Pro | 402 | . | . | B | B | . | . | . | -0.26 | * | . | . | -0.60 | 0.91 |
| Ile | 403 | . | . | B | B | . | . | . | -0.76 | * | . | . | -0.60 | 0.47 |
| Tyr | 404 | . | . | B | B | . | . | . | -0.62 | * | . | . | -0.60 | 0.38 |
| Asn | 405 | . | . | B | B | . | . | . | -0.62 | . | . | . | -0.60 | 0.38 |
| Val | 406 | . | . | B | B | . | . | . | -0.34 | . | . | . | -0.60 | 0.79 |
| Leu | 407 | . | . | B | B | . | . | . | -0.43 | . | . | . | -0.60 | 0.73 |
| Pro | 408 | . | . | B | . | . | T | . | -0.36 | . | . | F | -0.05 | 0.61 |
| Thr | 409 | . | . | B | . | . | T | . | -0.97 | . | . | F | -0.05 | 0.67 |
| Thr | 410 | . | . | B | . | . | T | . | -1.78 | . | . | F | -0.05 | 0.61 |
| Ser | 411 | . | . | B | . | . | T | . | -1.27 | . | . | F | -0.05 | 0.32 |
| Leu | 412 | . | . | B | B | . | . | . | -0.41 | . | . | . | -0.60 | 0.22 |
| Val | 413 | . | . | B | B | . | . | . | -0.20 | . | . | . | -0.30 | 0.31 |
| Leu | 414 | . | . | B | B | . | . | . | 0.11 | . | . | . | -0.30 | 0.37 |
| Gly | 415 | . | . | . | . | T | T | . | 0.11 | . | . | F | 0.65 | 0.77 |
| Lys | 416 | A | . | . | . | . | T | . | -0.40 | . | . | F | 0.40 | 1.50 |
| Asn | 417 | A | . | . | . | . | T | . | -0.18 | . | . | F | 0.40 | 1.50 |
| Gln | 418 | A | . | . | . | . | T | . | 0.37 | . | . | F | 1.00 | 1.54 |
| Thr | 419 | A | . | . | B | . | . | . | 0.29 | . | * | F | 0.60 | 1.11 |
| Leu | 420 | A | . | . | B | . | . | . | 0.68 | . | * | F | -0.45 | 0.48 |
| Ala | 421 | A | . | . | B | . | . | . | 0.04 | . | * | . | -0.30 | 0.56 |
| Thr | 422 | A | . | . | B | . | . | . | 0.09 | . | * | . | -0.30 | 0.39 |
| Ile | 423 | A | . | . | B | . | . | . | 0.09 | . | * | . | 0.30 | 0.95 |
| Lys | 424 | A | . | . | B | . | . | . | 0.40 | . | * | F | 0.90 | 1.62 |
| Ala | 425 | A | A | . | . | . | . | . | 1.21 | . | * | F | 0.90 | 1.81 |
| Lys | 426 | A | A | . | . | . | . | . | 0.99 | . | * | F | 0.90 | 4.47 |
| Glu | 427 | A | A | . | . | . | . | . | 1.00 | * | * | F | 0.90 | 1.84 |
| Asn | 428 | A | A | . | . | . | . | . | 1.89 | * | * | F | 0.90 | 2.44 |
| Gln | 429 | A | A | . | B | . | . | . | 0.96 | * | . | F | 0.90 | 2.12 |
| Leu | 430 | A | A | . | B | . | . | . | 0.73 | . | . | F | 0.45 | 0.86 |
| Ser | 431 | . | A | B | B | . | . | . | 0.10 | . | . | F | -0.45 | 0.44 |
| Gln | 432 | . | A | B | B | . | . | . | -0.11 | . | . | . | -0.60 | 0.26 |
| Ile | 433 | . | A | B | B | . | . | . | -0.11 | * | . | . | -0.60 | 0.48 |
| Leu | 434 | . | A | B | B | . | . | . | -0.11 | . | . | . | -0.60 | 0.58 |
| Ala | 435 | . | . | B | . | . | T | . | 0.46 | . | . | . | -0.20 | 0.54 |
| Pro | 436 | . | . | B | . | . | T | . | 0.51 | . | . | F | 0.10 | 1.20 |
| Asn | 437 | . | . | . | . | T | T | . | 0.30 | . | . | F | 0.50 | 2.27 |
| Asn | 438 | . | . | . | . | T | T | . | 0.89 | . | . | F | 0.50 | 3.48 |
| Tyr | 439 | . | . | . | . | T | . | . | 1.74 | . | . | F | 0.30 | 3.02 |
| Tyr | 440 | . | . | B | . | . | T | . | 2.33 | . | . | F | 0.40 | 3.75 |
| Pro | 441 | . | . | . | . | T | T | . | 1.73 | . | . | F | 0.80 | 3.75 |
| Ser | 442 | . | . | . | . | T | T | . | 1.14 | . | . | F | 0.50 | 1.97 |
| Lys | 443 | . | . | B | . | . | T | . | 0.93 | . | . | F | 0.40 | 1.27 |
| Asn | 444 | . | A | B | . | . | . | . | 0.29 | * | . | F | 0.60 | 1.27 |
| Leu | 445 | . | A | B | . | . | . | . | -0.06 | . | . | . | -0.30 | 0.67 |
| Ala | 446 | . | A | B | . | . | . | . | -0.66 | * | . | . | -0.30 | 0.34 |
| Pro | 447 | . | A | B | . | . | . | . | -0.36 | * | . | . | -0.60 | 0.17 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Ile | 448 | . | A | B | . | . | . | . | -0.99 | * | * | . | -0.60 | 0.34 |
| Ala | 449 | A | A | . | . | . | . | . | -0.99 | * | * | . | -0.60 | 0.34 |
| Leu | 450 | . | A | B | . | . | . | . | -0.18 | * | * | . | -0.60 | 0.38 |
| Asn | 451 | . | A | B | . | . | . | . | 0.41 | * | * | . | 0.04 | 0.90 |
| Ala | 452 | A | A | . | . | . | . | . | -0.08 | * | * | F | 1.58 | 1.48 |
| Gln | 453 | A | A | . | . | . | . | . | 0.51 | * | * | F | 1.62 | 1.56 |
| Asp | 454 | . | . | . | . | T | T | . | 0.80 | * | * | F | 3.06 | 1.30 |
| Asp | 455 | . | . | . | . | T | T | . | 1.30 | . | * | F | 3.40 | 1.72 |
| Phe | 456 | . | . | . | . | T | T | . | 1.09 | . | * | F | 3.06 | 1.43 |
| Ser | 457 | . | . | B | . | . | T | . | 0.79 | . | . | F | 2.32 | 1.33 |
| Ser | 458 | . | . | B | B | . | . | . | 0.48 | . | . | F | 0.53 | 0.56 |
| Thr | 459 | . | . | . | B | . | . | C | -0.12 | . | . | F | 0.09 | 0.93 |
| Pro | 460 | . | . | . | B | . | . | C | -0.12 | . | . | F | -0.25 | 0.69 |
| Ile | 461 | . | . | . | B | T | . | . | 0.33 | . | * | F | -0.05 | 0.82 |
| Thr | 462 | . | . | B | B | . | . | . | 0.63 | . | . | . | -0.60 | 0.89 |
| Met | 463 | . | . | B | B | . | . | . | 0.93 | . | . | . | -0.60 | 0.93 |
| Asn | 464 | . | . | B | . | . | T | . | 0.54 | * | . | . | -0.05 | 2.30 |
| Tyr | 465 | . | . | B | . | . | T | . | -0.06 | * | . | . | -0.05 | 1.38 |
| Asn | 466 | . | . | . | . | . | T | C | 0.83 | * | * | . | 0.15 | 1.15 |
| Gln | 467 | A | . | . | . | . | T | . | 0.33 | . | * | . | -0.05 | 1.24 |
| Phe | 468 | A | A | . | . | . | . | . | 0.93 | . | . | . | -0.60 | 0.65 |
| Leu | 469 | A | A | . | . | . | . | . | 0.98 | * | . | . | 0.30 | 0.70 |
| Glu | 470 | A | A | . | . | . | . | . | 0.91 | . | . | . | 0.30 | 0.81 |
| Leu | 471 | A | A | . | . | . | . | . | 0.96 | . | . | . | 0.45 | 1.35 |
| Glu | 472 | A | A | . | . | . | . | . | 0.96 | . | . | F | 0.90 | 3.27 |
| Lys | 473 | A | A | . | . | . | . | . | 0.84 | . | * | F | 0.90 | 3.27 |
| Thr | 474 | A | A | . | . | . | . | . | 1.77 | . | * | F | 0.90 | 3.27 |
| Lys | 475 | A | A | . | . | . | . | . | 0.96 | . | * | F | 0.90 | 3.70 |
| Gln | 476 | A | A | . | . | . | . | . | 1.77 | . | * | F | 0.90 | 1.53 |
| Leu | 477 | A | A | . | . | . | . | . | 1.46 | . | * | . | 0.98 | 1.77 |
| Arg | 478 | . | A | B | . | . | . | . | 1.41 | . | * | . | 1.21 | 1.27 |
| Leu | 479 | . | A | B | . | . | . | . | 1.72 | * | * | . | 1.44 | 1.23 |
| Asp | 480 | . | . | B | . | . | T | . | 0.82 | * | * | F | 2.22 | 2.58 |
| Thr | 481 | . | . | B | . | . | T | . | 0.58 | . | * | F | 2.30 | 0.98 |
| Asp | 482 | . | . | B | . | . | T | . | 1.04 | . | * | F | 1.92 | 1.86 |
| Gln | 483 | . | . | B | . | . | T | . | 0.93 | . | * | F | 1.69 | 1.10 |
| Val | 484 | . | . | B | B | . | . | . | 0.86 | . | . | . | 0.31 | 1.23 |
| Tyr | 485 | . | . | B | B | . | . | . | 0.27 | * | . | . | -0.07 | 0.52 |
| Gly | 486 | . | . | B | B | . | . | . | 0.27 | * | . | . | -0.60 | 0.30 |
| Asn | 487 | . | . | B | B | . | . | . | 0.02 | . | . | . | -0.60 | 0.58 |
| Ile | 488 | . | . | B | B | . | . | . | 0.02 | . | * | . | -0.60 | 0.58 |
| Ala | 489 | . | . | B | B | . | . | . | 0.18 | . | * | . | -0.60 | 0.95 |
| Thr | 490 | . | . | B | B | . | . | . | 0.42 | . | . | . | -0.60 | 0.51 |
| Tyr | 491 | . | . | B | . | . | . | . | 0.77 | * | . | . | -0.25 | 1.26 |
| Asn | 492 | . | . | B | . | . | . | . | 0.42 | * | . | . | 0.39 | 2.01 |
| Phe | 493 | . | . | B | . | . | T | . | 1.42 | . | . | . | 0.93 | 1.38 |
| Glu | 494 | . | . | . | . | T | T | . | 1.16 | . | * | F | 2.42 | 1.72 |
| Asn | 495 | . | . | . | . | T | T | . | 1.58 | . | * | F | 2.61 | 0.80 |
| Gly | 496 | . | . | . | . | T | T | . | 0.97 | . | * | F | 3.40 | 1.80 |
| Arg | 497 | . | . | B | B | . | . | . | 0.97 | . | * | F | 2.11 | 0.77 |
| Val | 498 | . | . | B | B | . | . | . | 1.36 | . | * | F | 1.77 | 0.80 |
| Arg | 499 | . | . | B | B | . | . | . | 1.01 | . | * | . | 1.55 | 1.17 |
| Val | 500 | . | . | B | B | . | . | . | 0.71 | . | * | F | 1.33 | 0.59 |
| Asp | 501 | . | . | B | B | . | . | . | 1.06 | . | * | F | 0.96 | 1.07 |
| Thr | 502 | . | . | . | . | . | . | C | 0.66 | . | * | F | 1.63 | 0.87 |
| Gly | 503 | . | . | . | . | . | T | C | 1.21 | . | * | F | 1.20 | 1.24 |
| Ser | 504 | . | . | . | . | . | T | C | 1.10 | . | * | F | 0.93 | 0.99 |
| Asn | 505 | . | . | . | . | . | T | C | 1.10 | * | . | F | 0.96 | 1.19 |
| Trp | 506 | . | . | . | . | . | T | C | 0.29 | * | . | F | 0.69 | 0.89 |
| Ser | 507 | . | . | . | . | . | . | C | 0.39 | * | . | F | 0.07 | 0.55 |
| Glu | 508 | . | . | B | . | . | . | . | 0.73 | * | . | . | -0.40 | 0.53 |
| Val | 509 | . | . | B | B | . | . | . | 0.14 | * | * | . | -0.60 | 0.87 |
| Leu | 510 | . | . | B | B | . | . | . | 0.14 | * | . | F | -0.15 | 0.46 |
| Pro | 511 | . | . | . | B | . | . | C | 0.43 | * | . | F | 0.05 | 0.46 |
| Gln | 512 | . | . | . | B | . | . | C | 0.42 | * | . | F | 0.20 | 1.06 |
| Ile | 513 | A | . | . | B | . | . | . | 0.11 | * | . | F | 0.00 | 1.86 |
| Gln | 514 | A | . | . | B | . | . | . | 0.38 | * | * | F | 0.60 | 1.74 |
| Glu | 515 | A | . | . | B | . | . | . | 1.30 | * | * | F | 0.60 | 1.01 |
| Thr | 516 | . | . | B | B | . | . | . | 0.62 | * | * | F | 0.60 | 2.83 |
| Thr | 517 | . | . | B | B | . | . | . | -0.27 | * | * | F | 0.60 | 1.15 |
| Ala | 518 | . | . | B | B | . | . | . | -0.08 | * | * | . | 0.30 | 0.46 |
| Arg | 519 | . | . | B | B | . | . | . | -0.08 | * | * | . | -0.60 | 0.28 |
| Ile | 520 | . | . | B | B | . | . | . | -0.42 | * | * | . | -0.60 | 0.31 |
| Ile | 521 | . | . | B | B | . | . | . | -0.07 | * | * | . | -0.36 | 0.30 |
| Phe | 522 | . | . | B | B | . | . | . | 0.24 | * | * | . | 0.78 | 0.31 |
| Asn | 523 | . | . | . | B | T | . | . | 0.02 | * | * | F | 1.57 | 0.74 |
| Gly | 524 | . | . | . | . | T | T | . | -0.09 | * | * | F | 2.21 | 0.87 |
| Lys | 525 | . | . | . | . | . | T | C | -0.01 | . | . | F | 2.40 | 1.62 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Asp | 526 | . | . | . | . | . | T | C | 0.02 | . | . | F | 2.01 | 0.83 |
| Leu | 527 | . | . | . | . | . | T | C | 0.72 | * | * | F | 1.77 | 0.62 |
| Asn | 528 | A | A | . | . | . | . | . | 0.83 | * | . | . | 1.08 | 0.54 |
| Leu | 529 | A | A | . | . | . | . | . | 1.29 | * | . | . | 0.84 | 0.63 |
| Val | 530 | A | A | . | . | . | . | . | 0.36 | * | . | . | 0.75 | 1.50 |
| Glu | 531 | A | A | . | . | . | . | . | -0.23 | * | * | . | 0.60 | 0.65 |
| Arg | 532 | A | A | . | . | . | . | . | -0.01 | * | . | . | 0.30 | 0.80 |
| Arg | 533 | A | A | . | . | . | . | . | -0.87 | * | . | . | 0.75 | 1.09 |
| Ile | 534 | . | A | B | . | . | . | . | -0.06 | * | . | . | 0.60 | 0.47 |
| Ala | 535 | . | A | B | . | . | . | . | 0.59 | * | . | . | 0.30 | 0.38 |
| Ala | 536 | . | A | B | . | . | . | . | 0.29 | * | . | . | -0.30 | 0.30 |
| Val | 537 | . | A | B | . | . | . | . | 0.18 | * | . | . | -0.30 | 0.58 |
| Asn | 538 | . | . | . | . | . | T | C | -0.14 | . | . | F | 1.65 | 0.96 |
| Pro | 539 | . | . | . | . | . | T | C | -0.07 | . | . | F | 2.10 | 1.46 |
| Ser | 540 | . | . | . | . | . | T | C | 0.52 | * | . | F | 2.40 | 1.63 |
| Asp | 541 | . | . | . | . | . | T | C | 0.80 | . | . | F | 3.00 | 1.75 |
| Pro | 542 | . | . | . | . | . | . | C | 1.34 | . | . | F | 2.50 | 1.64 |
| Leu | 543 | . | . | . | B | . | . | . | 1.39 | . | . | F | 2.00 | 1.76 |
| Glu | 544 | . | . | . | B | . | . | . | 1.39 | . | . | F | 1.70 | 2.11 |
| Thr | 545 | A | . | . | . | . | . | . | 1.69 | . | . | F | 1.10 | 2.11 |
| Thr | 546 | A | . | . | . | . | . | . | 1.09 | . | . | F | 1.10 | 4.27 |
| Lys | 547 | A | . | . | . | . | T | . | 0.99 | . | * | F | 1.30 | 2.44 |
| Pro | 548 | A | . | . | . | . | T | . | 0.99 | . | * | F | 1.00 | 2.44 |
| Asp | 549 | A | . | . | . | . | T | . | 1.03 | . | * | F | 1.00 | 1.39 |
| Met | 550 | A | . | . | . | . | T | . | 1.34 | * | * | F | 1.30 | 1.39 |
| Thr | 551 | A | A | . | . | . | . | . | 1.07 | * | * | . | 0.75 | 1.56 |
| Leu | 552 | A | A | . | . | . | . | . | 0.21 | * | * | . | 0.60 | 0.94 |
| Lys | 553 | A | A | . | . | . | . | . | 0.47 | * | * | F | 0.45 | 0.79 |
| Glu | 554 | A | A | . | . | . | . | . | -0.42 | * | * | F | 0.90 | 1.09 |
| Ala | 555 | A | A | . | . | . | . | . | -0.41 | * | * | . | 0.30 | 0.93 |
| Leu | 556 | A | A | . | . | . | . | . | -0.80 | * | * | . | 0.60 | 0.47 |
| Lys | 557 | A | A | . | . | . | . | . | -0.33 | * | * | . | -0.30 | 0.23 |
| Ile | 558 | A | A | . | . | . | . | . | -1.08 | * | * | . | -0.60 | 0.23 |
| Ala | 559 | A | A | . | . | . | . | . | -1.08 | * | * | . | -0.60 | 0.24 |
| Phe | 560 | . | A | B | . | . | . | . | -0.49 | * | * | . | -0.60 | 0.19 |
| Gly | 561 | . | A | B | . | . | . | . | 0.11 | . | * | . | -0.32 | 0.48 |
| Phe | 562 | . | . | B | . | . | . | . | 0.07 | . | * | . | 0.46 | 0.73 |
| Asn | 563 | . | . | . | . | . | . | C | 0.61 | . | . | F | 1.24 | 1.36 |
| Glu | 564 | . | . | . | . | . | T | C | 1.20 | . | . | F | 2.32 | 1.36 |
| Pro | 565 | . | . | . | . | T | T | . | 1.09 | . | * | F | 2.80 | 2.53 |
| Asn | 566 | . | . | . | . | T | T | . | 1.43 | . | * | F | 2.52 | 1.30 |
| Gly | 567 | . | . | . | . | T | T | . | 1.89 | . | * | F | 2.24 | 1.30 |
| Asn | 568 | . | . | . | . | . | . | C | 1.89 | . | * | F | 0.66 | 1.31 |
| Leu | 569 | . | . | B | . | . | . | . | 1.54 | . | * | . | 0.23 | 1.41 |
| Gln | 570 | . | . | B | . | . | . | . | 1.80 | . | * | . | 0.15 | 1.41 |
| Tyr | 571 | . | . | B | . | . | T | . | 1.80 | * | * | . | 0.85 | 1.76 |
| Gln | 572 | . | . | B | . | . | T | . | 1.26 | * | * | F | 1.80 | 3.56 |
| Gly | 573 | . | . | B | . | . | T | . | 0.94 | * | * | F | 2.00 | 1.44 |
| Lys | 574 | . | . | B | . | . | T | . | 1.76 | * | * | F | 1.80 | 1.33 |
| Asp | 575 | . | A | B | . | . | . | . | 1.06 | * | * | F | 1.50 | 1.33 |
| Ile | 576 | . | A | B | . | . | . | . | 1.30 | . | * | F | 1.30 | 1.16 |
| Thr | 577 | . | A | B | . | . | . | . | 0.60 | * | * | F | 0.95 | 0.97 |
| Glu | 578 | . | A | B | . | . | . | . | 0.94 | * | * | . | 0.30 | 0.50 |
| Phe | 579 | . | A | B | . | . | . | . | 0.20 | * | * | . | -0.15 | 1.15 |
| Asp | 580 | . | A | . | . | T | . | . | 0.20 | * | * | . | 0.10 | 0.69 |
| Phe | 581 | . | A | . | . | T | . | . | 1.09 | * | * | . | 0.70 | 0.67 |
| Asn | 582 | . | . | . | . | T | T | . | 1.40 | . | * | . | 0.65 | 1.34 |
| Phe | 583 | . | . | . | . | T | T | . | 1.09 | . | * | F | 1.40 | 1.38 |
| Asp | 584 | A | . | . | . | T | . | . | 1.49 | . | * | F | 0.40 | 2.31 |
| Gln | 585 | A | . | . | . | T | . | . | 1.49 | . | * | F | 1.28 | 1.92 |
| Gln | 586 | . | . | . | . | T | . | . | 2.19 | * | * | F | 1.76 | 3.85 |
| Thr | 587 | . | . | . | . | . | . | C | 1.30 | * | * | F | 2.14 | 3.70 |
| Ser | 588 | . | . | . | . | . | T | C | 2.04 | * | * | F | 1.72 | 1.50 |
| Gln | 589 | . | . | . | . | T | T | . | 2.04 | * | * | F | 2.80 | 1.73 |
| Asn | 590 | . | . | . | . | T | T | . | 2.04 | * | * | F | 2.52 | 1.93 |
| Ile | 591 | . | . | . | . | T | . | C | 1.23 | * | * | F | 2.04 | 2.49 |
| Lys | 592 | . | A | . | . | . | . | C | 0.96 | * | . | F | 1.36 | 1.19 |
| Asn | 593 | . | A | B | . | . | . | . | 1.26 | * | . | F | 0.13 | 0.75 |
| Gln | 594 | . | A | B | . | . | . | . | 0.44 | * | . | F | 0.60 | 1.84 |
| Leu | 595 | . | A | B | . | . | . | . | 0.44 | * | * | . | 0.30 | 0.76 |
| Ala | 596 | . | A | B | . | . | . | . | 0.74 | * | * | . | -0.30 | 0.76 |
| Glu | 597 | A | A | . | . | . | . | . | 0.39 | . | . | . | -0.30 | 0.44 |
| Leu | 598 | A | A | . | . | . | . | . | 0.39 | . | . | . | -0.30 | 0.78 |
| Asn | 599 | A | A | . | . | . | . | . | -0.50 | . | . | . | 0.45 | 1.23 |
| Ala | 600 | A | . | . | B | . | . | . | 0.07 | . | . | . | -0.30 | 0.50 |
| Thr | 601 | A | . | . | B | . | . | . | 0.34 | . | . | . | -0.60 | 0.95 |
| Asn | 602 | A | . | . | B | . | . | . | -0.51 | . | . | . | -0.60 | 0.85 |
| Ile | 603 | . | . | B | B | . | . | . | -0.51 | . | . | . | -0.60 | 0.63 |

TABLE 2-continued

| Res | Position | I | II | III | IV | V | VI | VII | VIII | IX | X | XI | XII | XIII |
|-----|----------|---|----|----|----|---|----|----|------|----|---|----|-----|------|
| Tyr | 604 | . | . | B | B | . | . | . | -0.51 | * | . | . | -0.60 | 0.36 |
| Thr | 605 | . | A | B | B | . | . | . | 0.12 | * | . | . | -0.60 | 0.37 |
| Val | 606 | . | A | B | B | . | . | . | -0.46 | * | * | . | -0.15 | 1.06 |
| Leu | 607 | A | A | . | B | . | . | . | -0.41 | * | * | . | -0.30 | 0.47 |
| Asp | 608 | A | A | . | B | . | . | . | -0.33 | * | * | F | 0.45 | 0.66 |
| Lys | 609 | A | A | . | B | . | . | . | -0.09 | * | * | F | 0.45 | 0.73 |
| Ile | 610 | A | A | . | B | . | . | . | -0.37 | * | * | F | 0.90 | 1.42 |
| Lys | 611 | A | A | . | B | . | . | . | 0.53 | * | * | F | 0.75 | 0.86 |
| Leu | 612 | A | A | . | . | . | . | . | 0.74 | . | * | F | 0.75 | 0.86 |
| Asn | 613 | A | A | . | . | . | . | . | 0.74 | . | * | . | 0.45 | 1.22 |
| Ala | 614 | A | A | . | . | . | . | . | -0.19 | . | * | . | 0.30 | 0.98 |
| Lys | 615 | A | A | . | . | . | . | . | -0.11 | . | * | . | -0.30 | 0.83 |
| Met | 616 | A | . | . | B | . | . | . | -1.04 | * | * | . | -0.30 | 0.43 |
| Asn | 617 | A | . | . | B | . | . | . | -0.12 | * | * | . | -0.60 | 0.30 |
| Ile | 618 | A | . | . | B | . | . | . | -0.12 | . | * | . | -0.30 | 0.29 |
| Leu | 619 | A | . | . | B | . | . | . | 0.51 | . | * | . | -0.30 | 0.49 |
| Ile | 620 | A | . | . | B | . | . | . | 0.58 | . | * | . | 0.60 | 0.61 |
| Arg | 621 | A | . | . | B | . | . | . | 0.48 | * | * | . | 0.75 | 1.70 |
| Asp | 622 | A | . | . | B | . | . | . | 0.44 | * | * | F | 0.90 | 1.78 |
| Lys | 623 | . | A | B | . | . | . | . | 1.09 | * | * | F | 0.90 | 3.46 |
| Arg | 624 | . | A | B | . | . | . | . | 1.90 | * | . | . | 1.03 | 2.77 |
| Phe | 625 | . | A | B | . | . | . | . | 2.90 | . | . | . | 1.31 | 2.77 |
| His | 626 | . | A | . | . | . | T | . | 2.79 | . | . | . | 1.99 | 2.71 |
| Tyr | 627 | . | A | . | . | . | T | . | 2.79 | . | * | . | 2.27 | 2.23 |
| Asp | 628 | . | . | . | . | T | T | . | 1.86 | * | . | F | 2.80 | 4.13 |
| Arg | 629 | . | . | . | . | T | T | . | 1.16 | . | * | F | 2.52 | 2.13 |
| Asn | 630 | . | . | . | . | T | T | . | 1.00 | . | . | F | 2.24 | 1.37 |
| Asn | 631 | . | . | . | . | T | T | . | 0.69 | . | . | . | 1.66 | 0.61 |
| Ile | 632 | . | . | B | B | . | . | . | 0.34 | . | * | . | -0.02 | 0.31 |
| Ala | 633 | . | . | B | B | . | . | . | 0.34 | . | * | . | -0.60 | 0.19 |
| Val | 634 | . | . | B | B | . | . | . | 0.23 | . | * | . | -0.30 | 0.20 |
| Gly | 635 | A | . | . | B | . | . | . | -0.07 | * | . | . | 0.30 | 0.50 |
| Ala | 636 | A | A | . | . | . | . | . | -0.92 | . | * | F | 0.75 | 0.66 |
| Asp | 637 | A | A | . | . | . | . | . | -0.89 | * | . | F | 0.45 | 0.66 |
| Glu | 638 | A | A | . | B | . | . | . | -0.26 | * | . | F | 0.45 | 0.49 |
| Ser | 639 | A | A | . | B | . | . | . | 0.60 | * | . | F | 0.75 | 0.98 |
| Val | 640 | A | A | . | B | . | . | . | 0.36 | * | . | F | 0.90 | 1.02 |
| Val | 641 | A | A | . | B | . | . | . | 0.91 | * | . | . | 0.60 | 0.59 |
| Lys | 642 | A | A | . | B | . | . | . | 1.02 | * | . | . | 0.30 | 0.60 |
| Glu | 643 | A | A | . | . | . | . | . | 1.02 | * | . | . | 0.75 | 1.59 |
| Ala | 644 | A | A | . | . | . | . | . | 0.47 | * | . | . | 0.75 | 3.70 |
| His | 645 | A | A | . | . | . | . | . | 0.43 | * | . | . | 0.75 | 1.37 |
| Arg | 646 | A | A | . | B | . | . | . | 1.29 | * | . | . | 0.60 | 0.56 |
| Glu | 647 | A | A | . | B | . | . | . | 0.94 | * | . | . | 0.54 | 0.89 |
| Val | 648 | A | A | . | B | . | . | . | 0.64 | * | . | . | 0.78 | 0.87 |
| Ile | 649 | A | A | . | B | . | . | . | 0.92 | * | . | . | 1.02 | 0.60 |
| Asn | 650 | . | . | . | . | . | T | C | 0.96 | * | . | F | 2.01 | 0.50 |
| Ser | 651 | . | . | . | . | . | T | C | 0.50 | * | . | F | 2.40 | 1.16 |
| Ser | 652 | . | . | . | . | . | T | C | -0.31 | * | . | F | 2.16 | 1.64 |
| Thr | 653 | . | . | . | . | . | T | C | -0.27 | . | . | F | 1.77 | 0.84 |
| Glu | 654 | A | A | . | . | . | . | . | -0.19 | . | . | F | 0.33 | 0.52 |
| Gly | 655 | A | A | . | . | . | . | . | -0.19 | . | . | F | 0.09 | 0.32 |
| Leu | 656 | A | A | . | . | . | . | . | -0.78 | . | * | . | -0.30 | 0.35 |
| Leu | 657 | A | A | . | . | . | . | . | -0.48 | * | . | . | -0.60 | 0.14 |
| Leu | 658 | A | A | . | . | . | . | . | -0.12 | * | . | . | -0.60 | 0.24 |
| Asn | 659 | A | A | . | . | . | . | . | -0.12 | * | . | . | -0.30 | 0.59 |
| Ile | 660 | A | A | . | . | . | . | . | -0.67 | * | * | F | 0.90 | 1.19 |
| Asp | 661 | A | . | . | . | . | T | . | 0.26 | * | * | F | 1.30 | 1.01 |
| Lys | 662 | A | . | . | . | . | T | . | 1.11 | * | * | F | 1.30 | 1.23 |
| Asp | 663 | A | . | . | . | . | T | . | 1.03 | * | * | F | 1.30 | 3.51 |
| Ile | 664 | A | . | . | . | . | T | . | 0.22 | * | * | F | 1.30 | 1.47 |
| Arg | 665 | . | . | B | B | . | . | . | 0.81 | * | * | F | 0.75 | 0.61 |
| Lys | 666 | . | . | B | B | . | . | . | 0.47 | * | . | F | 0.75 | 0.49 |
| Ile | 667 | . | . | B | B | . | . | . | 0.18 | * | . | . | 0.30 | 0.69 |
| Leu | 668 | . | . | B | . | . | T | . | -0.71 | * | * | . | 0.70 | 0.55 |
| Ser | 669 | . | . | B | . | . | T | . | -0.68 | * | . | . | -0.20 | 0.19 |
| Gly | 670 | . | . | B | . | . | T | . | -0.79 | * | . | . | -0.20 | 0.20 |
| Tyr | 671 | . | . | B | . | . | T | . | -1.72 | * | . | . | -0.20 | 0.43 |
| Ile | 672 | . | . | B | B | . | . | . | -0.83 | * | . | . | -0.60 | 0.22 |
| Val | 673 | . | . | B | B | . | . | . | -0.02 | * | . | . | -0.30 | 0.39 |
| Glu | 674 | . | . | B | B | . | . | . | -0.03 | . | . | . | 0.30 | 0.42 |
| Ile | 675 | . | . | B | B | . | . | . | 0.31 | . | . | . | 0.30 | 0.86 |
| Glu | 676 | . | . | . | B | . | . | . | 0.21 | . | . | F | 0.90 | 2.01 |
| Asp | 677 | A | . | . | . | . | T | . | 0.29 | . | . | F | 1.30 | 1.15 |
| Thr | 678 | A | . | . | . | . | T | . | 1.19 | . | * | F | 1.30 | 1.35 |
| Glu | 679 | A | . | . | . | . | T | . | 1.19 | . | . | F | 1.30 | 1.56 |
| Gly | 680 | A | . | . | . | . | T | . | 1.22 | * | . | F | 1.30 | 1.62 |
| Leu | 681 | A | A | . | . | . | . | . | 0.33 | * | . | F | 0.75 | 0.83 |

TABLE 2-continued

| Res | Position | I | II | III | IV | V | VI | VII | VIII | IX | X | XI | XII | XIII |
|-----|----------|---|----|----|----|---|----|----|------|----|----|----|-----|------|
| Lys | 682 | A | A | . | . | . | . | . | 0.33 | * | . | F | 0.75 | 0.34 |
| Glu | 683 | A | A | . | . | . | . | . | 0.64 | * | * | . | 0.30 | 0.55 |
| Val | 684 | A | A | . | . | . | . | . | 0.76 | * | * | . | 0.75 | 1.11 |
| Ile | 685 | A | A | . | . | . | . | . | 0.86 | * | * | . | 0.75 | 1.09 |
| Asn | 686 | A | . | . | . | . | T | . | 1.67 | * | * | . | 1.00 | 0.98 |
| Asp | 687 | A | . | . | . | . | T | . | 1.02 | * | * | . | 1.15 | 2.21 |
| Arg | 688 | A | . | . | . | . | T | . | 0.21 | * | . | . | 1.15 | 3.12 |
| Tyr | 689 | A | . | . | . | . | T | . | 1.07 | . | . | . | 1.15 | 1.60 |
| Asp | 690 | . | . | B | . | . | . | . | 1.07 | . | * | . | 0.95 | 1.54 |
| Met | 691 | . | . | B | B | . | . | . | 0.77 | . | . | . | -0.30 | 0.55 |
| Leu | 692 | . | . | B | B | . | . | . | 0.47 | . | . | . | -0.60 | 0.47 |
| Asn | 693 | . | . | B | B | . | . | . | -0.46 | . | . | . | -0.30 | 0.38 |
| Ile | 694 | . | . | B | B | . | . | . | -0.10 | . | . | . | -0.60 | 0.32 |
| Ser | 695 | . | . | B | B | . | . | . | -0.10 | . | . | F | 0.19 | 0.75 |
| Ser | 696 | . | . | B | B | . | . | . | 0.50 | . | . | F | 1.13 | 0.81 |
| Leu | 697 | . | . | B | B | . | . | . | 0.97 | * | * | F | 1.62 | 1.92 |
| Arg | 698 | A | . | . | . | . | T | . | 1.01 | * | * | F | 2.66 | 1.42 |
| Gln | 699 | . | . | . | . | T | T | . | 1.59 | * | * | F | 3.40 | 2.12 |
| Asp | 700 | . | . | . | . | T | T | . | 1.19 | * | * | F | 3.06 | 3.71 |
| Gly | 701 | . | . | . | . | T | T | . | 0.60 | * | * | F | 2.72 | 1.64 |
| Lys | 702 | . | . | B | . | . | . | . | 1.41 | * | * | F | 1.33 | 0.66 |
| Thr | 703 | . | . | B | . | . | . | . | 0.60 | * | * | F | 1.29 | 0.66 |
| Phe | 704 | . | A | B | . | . | . | . | 0.64 | * | * | . | -0.30 | 0.58 |
| Ile | 705 | . | A | B | . | . | . | . | 0.69 | * | * | . | 0.30 | 0.58 |
| Asp | 706 | A | A | . | . | . | . | . | 0.79 | * | * | . | 0.64 | 0.80 |
| Phe | 707 | A | A | . | . | . | . | . | 0.74 | * | * | . | 0.53 | 1.46 |
| Lys | 708 | A | A | . | . | . | . | . | 1.06 | * | . | F | 1.62 | 3.34 |
| Lys | 709 | . | A | . | . | . | T | . | 1.80 | * | . | F | 2.66 | 3.34 |
| Tyr | 710 | . | . | . | . | T | T | . | 1.88 | * | * | F | 3.40 | 7.72 |
| Asn | 711 | . | . | . | . | T | T | . | 1.67 | * | * | F | 3.06 | 3.18 |
| Asp | 712 | . | . | . | . | T | T | . | 1.56 | * | * | F | 2.72 | 2.46 |
| Lys | 713 | . | . | B | . | . | T | . | 1.27 | * | * | F | 1.68 | 1.29 |
| Leu | 714 | . | . | B | B | . | . | . | 0.33 | * | * | . | 0.79 | 1.26 |
| Pro | 715 | . | . | B | B | . | . | . | 0.28 | * | * | . | -0.30 | 0.53 |
| Leu | 716 | . | . | B | B | . | . | . | 0.28 | * | * | . | -0.60 | 0.35 |
| Tyr | 717 | . | . | B | B | . | . | . | 0.07 | * | . | . | -0.60 | 0.69 |
| Ile | 718 | . | . | B | B | . | . | . | 0.02 | . | * | . | -0.60 | 0.69 |
| Ser | 719 | . | . | B | B | . | . | . | 0.59 | . | * | . | -0.45 | 1.35 |
| Asn | 720 | . | . | B | . | . | T | . | 0.84 | . | * | F | 0.10 | 1.35 |
| Pro | 721 | . | . | . | . | T | T | . | 0.80 | . | * | F | 0.80 | 3.85 |
| Asn | 722 | . | . | . | . | T | T | . | 1.04 | . | * | F | 0.80 | 2.13 |
| Tyr | 723 | . | . | . | . | T | T | . | 1.08 | . | * | F | 0.80 | 2.13 |
| Lys | 724 | . | . | B | B | . | . | . | 1.13 | . | * | . | -0.15 | 1.02 |
| Val | 725 | . | . | B | B | . | . | . | 0.54 | . | * | . | -0.60 | 1.00 |
| Asn | 726 | . | . | B | B | . | . | . | -0.10 | . | * | . | -0.60 | 0.64 |
| Val | 727 | . | . | B | B | . | . | . | -0.41 | . | * | . | -0.60 | 0.24 |
| Tyr | 728 | . | . | B | B | . | . | . | -0.12 | . | * | . | -0.60 | 0.46 |
| Ala | 729 | . | . | B | B | . | . | . | -0.17 | . | * | . | -0.60 | 0.58 |
| Val | 730 | A | . | . | B | . | . | . | 0.69 | . | * | . | -0.15 | 1.35 |
| Thr | 731 | A | . | . | B | . | . | . | 0.38 | . | . | F | 0.60 | 1.38 |
| Lys | 732 | . | . | B | B | . | . | . | 0.34 | . | . | F | 0.60 | 1.97 |
| Glu | 733 | . | . | B | B | . | . | . | -0.30 | * | . | F | 0.60 | 1.86 |
| Asn | 734 | . | . | B | B | . | . | . | 0.29 | * | . | F | 0.45 | 0.91 |
| Thr | 735 | . | . | B | B | . | . | . | 0.93 | . | . | F | 0.45 | 0.73 |
| Ile | 736 | . | . | B | B | . | . | . | 0.94 | . | . | . | -0.30 | 0.65 |
| Ile | 737 | . | . | B | B | . | . | . | 0.90 | . | . | . | -0.26 | 0.54 |
| Asn | 738 | . | . | B | . | . | T | . | 0.90 | * | . | F | 0.93 | 0.65 |
| Pro | 739 | . | . | . | . | . | T | C | 0.56 | * | . | F | 2.22 | 1.49 |
| Ser | 740 | . | . | . | . | . | T | C | 0.87 | * | . | F | 2.56 | 2.11 |
| Glu | 741 | . | . | . | . | T | T | . | 1.44 | * | . | F | 3.40 | 2.19 |
| Asn | 742 | . | . | . | . | T | T | . | 2.03 | . | * | F | 3.06 | 2.04 |
| Gly | 743 | . | . | . | . | T | T | . | 1.72 | . | . | F | 2.72 | 2.04 |
| Asp | 744 | . | . | . | . | T | T | . | 1.93 | . | . | F | 2.38 | 1.70 |
| Thr | 745 | . | . | . | . | . | T | C | 1.89 | * | . | F | 1.54 | 1.70 |
| Ser | 746 | . | . | . | . | . | T | C | 1.00 | * | . | F | 1.20 | 1.70 |
| Thr | 747 | A | . | . | . | . | T | . | 1.04 | * | . | F | 0.85 | 0.71 |
| Asn | 748 | A | . | . | . | . | T | . | 1.43 | * | . | F | 0.85 | 0.99 |
| Gly | 749 | A | . | . | . | . | T | . | 0.54 | * | . | F | 1.30 | 1.48 |
| Ile | 750 | A | . | . | B | . | . | . | 0.04 | * | . | F | 0.45 | 0.72 |
| Lys | 751 | . | . | B | B | . | . | . | -0.54 | * | . | F | 0.45 | 0.37 |
| Lys | 752 | . | . | B | B | . | . | . | -0.93 | * | . | F | -0.15 | 0.26 |
| Ile | 753 | . | . | B | B | . | . | . | -1.23 | * | . | . | -0.60 | 0.32 |
| Leu | 754 | . | . | B | B | . | . | . | -0.84 | * | . | . | -0.30 | 0.22 |
| Ile | 755 | . | . | B | B | . | . | . | 0.09 | * | . | . | -0.30 | 0.22 |
| Phe | 756 | . | . | B | B | . | . | . | -0.30 | * | . | . | 0.04 | 0.62 |
| Ser | 757 | . | . | . | . | . | T | C | -0.59 | * | . | F | 1.73 | 0.74 |
| Lys | 758 | . | . | . | . | T | T | . | 0.30 | * | . | F | 1.82 | 1.65 |
| Lys | 759 | . | . | . | . | . | T | C | 0.22 | * | . | F | 2.86 | 3.30 |

TABLE 2-continued

| Res | Position | I | II | III | IV | V | VI | VII | VIII | IX | X | XI | XII | XIII |
|---|---|---|---|---|---|---|---|---|---|---|---|---|---|---|
| Gly | 760 | . | . | . | . | T | T | . | 0.77 | * | . | F | 3.40 | 1.73 |
| Tyr | 761 | . | . | . | . | T | . | . | 1.08 | * | . | F | 2.71 | 0.85 |
| Glu | 762 | . | . | B | . | . | . | . | 0.99 | * | . | . | 1.52 | 0.55 |
| Ile | 763 | . | . | B | . | . | . | . | 0.56 | * | . | . | 0.58 | 0.71 |
| Gly | 764 | . | . | B | . | . | . | . | 0.12 | . | . | . | 0.24 | 0.58 |

In another aspect, the invention provides an antibody that binds a peptide or polypeptide comprising an epitope-bearing portion of a polypeptide described herein. The epitope of this polypeptide portion is an immunogenic or antigenic epitope of a polypeptide of the invention.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 2/9:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides are therefore useful to raise antibodies, including monoclonal antibodies, that bind to a PA polypeptide of the invention. See, for instance, Wilson et al., Cell 37:767-778 (1984) at 777. Antigenic epitope-bearing peptides and polypeptides preferably contain a sequence of at least seven, more preferably at least nine and most preferably between at least about 15 to about 30 amino acids contained within the amino acid sequence of SEQ ID NO:2.

Antibodies of the invention may bind one or more antigenic PA polypeptides or peptides including, but not limited to: a polypeptide comprising amino acid residues from about 39 to about 45 of SEQ ID NO:2; a polypeptide comprising amino acid residues from about 129 to about 134 of SEQ ID NO:2; a polypeptide comprising amino acid residues from about 151 to about 157 of SEQ ID NO:2; a polypeptide comprising amino acid residues from about 168 to about 172 of SEQ ID NO:2; a polypeptide comprising amino acid residues from about 189 to about 195 of SEQ ID NO:2; a polypeptide comprising amino acid residues from about 203 to about 213 of SEQ ID NO:2; a polypeptide comprising amino acid residues from about 225 to about 230 of SEQ ID NO:2; a polypeptide comprising amino acid residues from about 246 to about 253 of SEQ ID NO:2; a polypeptide comprising amino acid residues from about 259 to about 264 of SEQ ID NO:2; a polypeptide comprising amino acid residues from about 273 to about 280 of SEQ ID NO:2; a polypeptide comprising amino acid residues from about 302 to about 307 of SEQ ID NO:2; a polypeptide comprising amino acid residues from about 309 to about 314 of SEQ ID NO:2; a polypeptide comprising amino acid residues from about 319 to about 331 of SEQ ID NO:2; a polypeptide comprising amino acid residues from about 452 to about 457 of SEQ ID NO:2; a polypeptide comprising amino acid residues from about 480 to about 483 of SEQ ID NO:2; a polypeptide comprising amino acid residues from about 494 to about 498 of SEQ ID NO:2; a polypeptide comprising amino acid residues from about 523 to about 527 of SEQ ID NO:2; a polypeptide comprising amino acid residues from about 538 to about 544 of SEQ ID NO:2; a polypeptide comprising amino acid residues from about 564 to about 567 of SEQ ID NO:2; a polypeptide comprising amino acid residues from about 572 to about 575 of SEQ ID NO:2; a polypeptide comprising amino acid residues from about 587 to about 591 of SEQ ID NO:2; a polypeptide comprising amino acid residues from about 626 to about 631 of SEQ ID NO:2; a polypeptide comprising amino acid residues from about 650 to about 653 of SEQ ID NO:2; a polypeptide comprising amino acid residues from about 697 to about 701 of SEQ ID NO:2; a polypeptide comprising amino acid residues from about 708 to about 713 of SEQ ID NO:2; a polypeptide comprising amino acid residues from about 739 to about 745 of SEQ ID NO:2; and/or a polypeptide comprising amino acid residues from about 757 to about 762 of SEQ ID NO:2. In this context "about" includes the particularly recited range, larger or smaller by several (5, 4, 3, 2, or 1) amino acids, at either terminus or at both termini. Epitope-bearing PA peptides and polypeptides may be produced by any conventional means. Houghten, R. A., "General method for the rapid solid-phase synthesis of large numbers of peptides: specificity of antigen-antibody interaction at the level of individual amino acids," *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986).

As one of skill in the art will appreciate, PA polypeptides and the epitope-bearing fragments thereof described herein can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric PA protein or protein fragment alone (Fountoulakis et al., *J Biochem* 270:3958-3964 (1995)). Thus, antibodies of the invention may bind the PA moiety of fusion proteins that comprise all or a portion of a PA polypeptide.

Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may also bind such modified PA polypeptides or PA polypeptide fragments or variants.

For instance, for many proteins, it is known in the art that one or more amino acids may be deleted from the N-terminus or C-terminus without substantial loss of biological function, or loss of the ability to be bound by a specific antibody. For instance, Ron et al., *J. Biol. Chem.*, 268:2984-2988 (1993) reported modified KGF proteins that had heparin binding activity even if 3, 8, or 27 amino-terminal amino acid residues were missing.

However, even if deletion of one or more amino acids from the N-terminus of a protein results in modification or loss of one or more biological functions of the protein, other functional activities (e.g., biological activities, ability to multimerize, ability to bind EF or LF may still be retained. For example, the ability of shortened PA polypeptides to induce and/or bind to antibodies which recognize the complete or mature forms of the PA polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a PA polypeptide with a large number of deleted N-terminal amino acid residues may retain some biological or immunogenic activities. In fact, peptides composed of as few as six PA amino acid residues may often evoke an immune response.

Accordingly, the present invention further provides antibodies that bind polypeptides having one or more residues deleted from the amino terminus of the PA amino acid sequence of SEQ ID NO:2 up to the serine residue at position number 463. In particular, the present invention provides antibodies that bind polypeptides comprising the amino acid sequence of residues $n^1$-764 of SEQ ID NO:2, where $n^1$ is an integer from 31 to 759 corresponding to the position of the amino acid residue in SEQ ID NO:2.

More in particular, the invention provides antibodies that bind polypeptides comprising, or alternatively consisting of, the amino acid sequence of residues of V-31 to G-764; K-32 to G-764; Q-33 to G-764; E-34 to G-764; N-35 to G-764; R-36 to G-764; L-37 to G-764; L-38 to G-764; N-39 to G-764; E-40 to G-764; S-41 to G-764; E-42 to G-764; S-43 to G-764; S-44 to G-764; S-45 to G-764; Q-46 to G-764; G-47 to G-764; L-48 to G-764; L-49 to G-764; G-50 to G-764; Y-51 to G-764; Y-52 to G-764; F-53 to G-764; S-54 to G-764; D-55 to G-764; L-56 to G-764; N-57 to G-764; F-58 to G-764; Q-59 to G-764; A-60 to G-764; P-61 to G-764; M-62 to G-764; V-63 to G-764; V-64 to G-764; T-65 to G-764; S-66 to G-764; S-67 to G-764; T-68 to G-764; T-69 to G-764; G-70 to G-764; D-71 to G-764; L-72 to G-764; S-73 to G-764; I-74 to G-764; P-75 to G-764; S-76 to G-764; S-77 to G-764; E-78 to G-764; L-79 to G-764; E-80 to G-764; N-81 to G-764; I-82 to G-764; P-83 to G-764; S-84 to G-764; E-85 to G-764; N-86 to G-764; Q-87 to G-764; Y-88 to G-764; F-89 to G-764; Q-90 to G-764; S-91 to G-764; A-92 to G-764; I-93 to G-764; W-94 to G-764; S-95 to G-764; G-96 to G-764; F-97 to G-764; I-98 to G-764; K-99 to G-764; V-100 to G-764; K-101 to G-764; K-102 to G-764; S-103 to G-764; D-104 to G-764; E-105 to G-764; Y-106 to G-764; T-107 to G-764; F-108 to G-764; A-109 to G-764; T-110 to G-764; S-111 to G-764; A-112 to G-764; D-113 to G-764; N-114 to G-764; H-115 to G-764; V-116 to G-764; I-117 to G-764; M-118 to G-764; W-119 to G-764; V-120 to G-764; D-121 to G-764; D-122 to G-764; Q-123 to G-764; E-124 to G-764; V-125 to G-764; I-126 to G-764; N-127 to G-764; K-128 to G-764; A-129 to G-764; S-130 to G-764; N-131 to G-764; S-132 to G-764; N-133 to G-764; K-134 to G-764; I-135 to G-764; R-136 to G-764; L-137 to G-764; E-138 to G-764; K-139 to G-764; G-140 to G-764; R-141 to G-764; L-142 to G-764; Y-143 to G-764; Q-144 to G-764; I-145 to G-764; K-146 to G-764; I-147 to G-764; Q-148 to G-764; Y-149 to G-764; Q-150 to G-764; R-151 to G-764; E-152 to G-764; N-153 to G-764; P-154 to G-764; T-155 to G-764; E-156 to G-764; K-157 to G-764; G-158 to G-764; L-159 to G-764; D-160 to G-764; F-161 to G-764; K-162 to G-764; L-163 to G-764; Y-164 to G-764; W-165 to G-764; T-166 to G-764; D-167 to G-764; S-168 to G-764; Q-169 to G-764; N-170 to G-764; K-171 to G-764; K-172 to G-764; E-173 to G-764; V-174 to G-764; I-175 to G-764; S-176 to G-764; S-177 to G-764; D-178 to G-764; N-179 to G-764; L-180 to G-764; Q-181 to G-764; L-182 to G-764; P-183 to G-764; E-184 to G-764; L-185 to G-764; K-186 to G-764; Q-187 to G-764; K-188 to G-764; S-189 to G-764; S-190 to G-764; N-191 to G-764; S-192 to G-764; R-193 to G-764; K-194 to G-764; K-195 to G-764; R-196 to G-764; S-197 to G-764; T-198 to G-764; S-199 to G-764; A-200 to G-764; G-201 to G-764; P-202 to G-764; T-203 to G-764; V-204 to G-764; P-205 to G-764; D-206 to G-764; R-207 to G-764; D-208 to G-764; N-209 to G-764; D-210 to G-764; G-211 to G-764; I-212 to G-764; P-213 to G-764; D-214 to G-764; S-215 to G-764; L-216 to G-764; E-217 to G-764; V-218 to G-764; E-219 to G-764; G-220 to G-764; Y-221 to G-764; T-222 to G-764; V-223 to G-764; D-224 to G-764; V-225 to G-764; K-226 to G-764; N-227 to G-764; K-228 to G-764; R-229 to G-764; T-230 to G-764; F-231 to G-764; L-232 to G-764; S-233 to G-764; P-234 to G-764; W-235 to G-764; I-236 to G-764; S-237 to G-764; N-238 to G-764; I-239 to G-764; H-240 to G-764; E-241 to G-764; K-242 to G-764; K-243 to G-764; G-244 to G-764; L-245 to G-764; T-246 to G-764; K-247 to G-764; Y-248 to G-764; K-249 to G-764; S-250 to G-764; S-251 to G-764; P-252 to G-764; E-253 to G-764; K-254 to G-764; W-255 to G-764; S-256 to G-764; T-257 to G-764; A-258 to G-764; S-259 to G-764; D-260 to G-764; P-261 to G-764; Y-262 to G-764; S-263 to G-764; D-264 to G-764; F-265 to G-764; E-266 to G-764; K-267 to G-764; V-268 to G-764; T-269 to G-764; G-270 to G-764; R-271 to G-764; I-272 to G-764; D-273 to G-764; K-274 to G-764; N-275 to G-764; V-276 to G-764; S-277 to G-764; P-278 to G-764; E-279 to G-764; A-280 to G-764; R-281 to G-764; H-282 to G-764; P-283 to G-764; L-284 to G-764; V-285 to G-764; A-286 to G-764; A-287 to G-764; Y-288 to G-764; P-289 to G-764; I-290 to G-764; V-291 to G-764; H-292 to G-764; V-293 to G-764; D-294 to G-764; M-295 to G-764; E-296 to G-764; N-297 to G-764; I-298 to G-764; I-299 to G-764; L-300 to G-764; S-301 to G-764; K-302 to G-764; N-303 to G-764; E-304 to G-764; D-305 to G-764; Q-306 to G-764; S-307 to G-764; T-308 to G-764; Q-309 to G-764; N-310 to G-764; T-311 to G-764; D-312 to G-764; S-313 to G-764; Q-314 to G-764; T-315 to G-764; R-316 to G-764; T-317 to G-764; I-318 to G-764; S-319 to G-764; K-320 to G-764; N-321 to G-764; T-322 to G-764; S-323 to G-764; T-324 to G-764; S-325 to G-764; R-326 to G-764; T-327 to G-764; H-328 to G-764; T-329 to G-764; S-330 to G-764; E-331 to G-764; V-332 to G-764; H-333 to G-764; G-334 to G-764; N-335 to G-764; A-336 to G-764; E-337 to G-764; V-338 to G-764; H-339 to G-764; A-340 to G-764; S-341 to G-764; F-342 to G-764; F-343 to G-764; D-344 to G-764; I-345 to G-764; G-346 to G-764; G-347 to G-764; S-348 to G-764; V-349 to G-764; S-350 to G-764; A-351 to G-764; G-352 to G-764; F-353 to G-764; S-354 to G-764; N-355 to G-764; S-356 to G-764; N-357 to G-764; S-358 to G-764; S-359 to G-764; T-360 to G-764; V-361 to G-764; A-362 to G-764; I-363 to G-764; D-364 to G-764; H-365 to G-764; S-366 to G-764; L-367 to G-764; S-368 to G-764; L-369 to G-764; A-370 to G-764; G-371 to G-764; E-372 to G-764; R-373 to G-764; T-374 to G-764; W-375 to G-764; A-376 to G-764; E-377 to G-764; T-378 to G-764; M-379 to G-764; G-380 to G-764; L-381 to G-764; N-382 to G-764; T-383 to G-764; A-384 to G-764; D-385 to G-764; T-386 to G-764; A-387 to G-764; R-388 to G-764; L-389 to G-764; N-390 to G-764; A-391 to G-764; N-392 to G-764; I-393 to G-764; R-394 to G-764; Y-395 to G-764; V-396 to G-764; N-397 to G-764; T-398 to G-764; G-399 to G-764; T-400 to G-764; A-401 to G-764; P-402 to G-764; I-403 to G-764; Y-404 to G-764; N-405 to G-764; V-406 to G-764; L-407 to G-764; P-408 to G-764; T-409 to G-764; T-410 to G-764; S-411 to G-764; L-412 to G-764; V-413 to G-764; L-414 to G-764; G-415 to G-764; K-416 to G-764; N-417 to G-764; Q-418 to G-764; T-419 to G-764; L-420 to G-764; A-421 to G-764; T-422 to G-764; I-423 to G-764; K-424 to G-764; A-425 to G-764; K-426 to G-764; E-427 to G-764; N-428 to G-764; Q-429 to G-764; L-430 to G-764; S-431 to G-764; Q-432 to G-764; I-433 to G-764; L-434 to G-764; A-435 to G-764; P-436 to G-764; N-437 to G-764; N-438 to G-764; Y-439 to G-764; Y-440 to G-764; P-441 to G-764; S-442 to G-764; K-443 to G-764; N-444 to G-764; L-445 to G-764; A-446 to G-764; P-447 to G-764; I-448 to G-764; A-449 to G-764; L-450 to G-764; N-451 to G-764; A-452 to G-764; Q-453 to G-764; D-454 to G-764; D-455 to G-764; F-456 to G-764; S-457 to G-764; S-458 to G-764; T-459 to G-764; P-460 to G-764; I-461 to G-764; T-462 to G-764; M-463 to G-764; N-464 to G-764; Y-465 to G-764; N-466 to G-764; Q-467 to G-764; F-468 to G-764; L-469 to G-764; E-470 to G-764; L-471 to G-764; E-472 to G-764; K-473 to G-764; T-474 to G-764; K-475 to G-764; Q-476 to G-764; L-477 to G-764; R-478 to G-764; L-479 to G-764; D-480 to G-764; T-481 to G-764; D-482 to G-764; Q-483 to G-764; V-484 to G-764; Y-485 to G-764; G-486 to G-764; N-487 to G-764; I-488 to G-764; A-489 to G-764; T-490 to G-764; Y-491 to G-764; N-492 to G-764; F-493 to G-764; E-494 to G-764; N-495 to G-764; G-496 to G-764; R-497 to G-764; V-498 to G-764; R-499 to G-764; V-500 to G-764; D-501 to G-764; T-502 to G-764; G-503 to G-764; S-504 to G-764; N-505 to G-764; W-506 to G-764; S-507 to G-764; E-508 to G-764; V-509 to G-764; L-510 to G-764; P-511 to G-764; Q-512 to G-764; I-513 to G-764; Q-514 to G-764; E-515 to G-764; T-516 to G-764; T-517 to G-764; A-518 to G-764; R-519 to G-764; I-520 to G-764; I-521 to G-764; F-522 to G-764; N-523 to G-764; G-524 to G-764; K-525 to G-764; D-526 to G-764; L-527 to G-764; N-528 to G-764; L-529 to G-764; V-530 to G-764; E-531 to G-764; R-532 to G-764; R-533 to G-764; I-534 to G-764; A-535 to G-764; A-536 to G-764; V-537 to G-764; N-538 to G-764; P-539 to G-764; S-540 to G-764; D-541 to G-764; P-542 to G-764; L-543 to G-764; E-544 to G-764; T-545 to G-764; T-546 to G-764; K-547 to G-764; P-548 to G-764; D-549 to G-764; M-550 to G-764; T-551 to G-764; L-552 to G-764; K-553 to G-764; E-554 to G-764; A-555 to G-764; L-556 to G-764; K-557 to G-764; I-558 to G-764; A-559 to G-764; F-560 to G-764; G-561 to G-764; F-562 to G-764; N-563 to G-764; E-564 to G-764; P-565 to G-764; N-566 to G-764; G-567 to G-764; N-568 to G-764; L-569 to G-764; Q-570 to G-764; Y-571 to G-764; Q-572 to G-764; G-573 to G-764; K-574 to G-764; D-575 to G-764; I-576 to G-764; I-577 to G-764; E-578 to G-764; F-579 to G-764; D-580 to G-764; F-581 to G-764; N-582 to G-764; F-583 to G-764; D-584 to G-764; Q-585 to G-764; Q-586 to G-764; T-587 to G-764; S-588 to G-764; Q-589 to G-764; N-590 to G-764; I-591 to G-764; K-592 to G-764; N-593 to G-764; Q-594 to G-764; L-595 to G-764; A-596 to G-764; E-597 to G-764; L-598 to G-764; N-599 to G-764; A-600 to G-764; T-601 to G-764; N-602 to G-764; I-603 to G-764; Y-604 to G-764; T-605 to G-764; V-606 to G-764; L-607 to G-764; D-608 to G-764; K-609 to G-764; I-610 to G-764; K-611 to G-764; L-612 to G-764; N-613 to G-764; A-614 to G-764; K-615 to G-764; M-616 to G-764; N-617 to G-764; I-618 to G-764; L-619 to G-764; I-620 to G-764; R-621 to G-764; D-622 to G-764; K-623 to G-764; R-624 to G-764; F-625 to G-764; H-626 to G-764; Y-627 to G-764; D-628 to G-764; R-629 to G-764; N-630 to G-764; N-631 to G-764; I-632 to G-764; A-633 to G-764; V-634 to G-764; G-635 to G-764; A-636 to G-764; D-637 to G-764; E-638 to G-764; S-639 to G-764; V-640 to G-764; V-641 to G-764; K-642 to G-764; E-643 to G-764; A-644 to G-764; H-645 to G-764; R-646 to G-764; E-647 to G-764; V-648 to G-764; I-649 to G-764; N-650 to G-764; S-651 to G-764; S-652 to G-764; T-653 to G-764; E-654 to G-764; G-655 to G-764; L-656 to G-764; L-657 to G-764; L-658 to G-764; N-659 to G-764; I-660 to G-764; D-661 to G-764; K-662 to G-764; D-663 to G-764; I-664 to G-764; R-665 to G-764; K-666 to G-764; I-667 to G-764; L-668 to G-764; S-669 to G-764; G-670 to G-764; Y-671 to G-764; I-672 to G-764; V-673 to G-764; E-674 to G-764; I-675 to G-764; E-676 to G-764; D-677 to G-764; T-678 to G-764; E-679 to G-764; G-680 to G-764; L-681 to G-764; K-682 to G-764; E-683 to G-764; V-684 to G-764; I-685 to G-764; N-686 to G-764; D-687 to G-764; R-688 to G-764; Y-689 to G-764; D-690 to G-764; M-691 to G-764; L-692 to G-764; N-693 to G-764; I-694 to G-764; S-695 to G-764; S-696 to G-764; L-697 to G-764; R-698 to G-764; Q-699 to G-764; D-700 to G-764; G-701 to G-764; K-702 to G-764; T-703 to G-764; F-704 to G-764; I-705 to G-764; D-706 to G-764; F-707 to G-764; K-708 to G-764; K-709 to G-764; Y-710 to G-764; N-711 to G-764; D-712 to G-764; K-713 to G-764; L-714 to G-764; P-715 to G-764; L-716 to G-764; Y-717 to G-764; I-718 to G-764; S-719 to G-764; N-720 to G-764; P-721 to G-764; N-722 to G-764; Y-723 to G-764; K-724 to G-764; V-725 to G-764; N-726 to G-764; V-727 to G-764; Y-728 to G-764; A-729 to G-764; V-730 to G-764; T-731 to G-764; K-732 to G-764; E-733 to G-764; N-734 to G-764; T-735 to G-764; I-736 to G-764; I-737 to G-764; N-738 to G-764; P-739 to G-764; S-740 to G-764; E-741 to G-764; N-742 to G-764; G-743 to G-764; D-744 to G-764; T-745 to G-764; S-746 to G-764; T-747 to G-764; N-748 to G-764; G-749 to G-764; I-750 to G-764; K-751 to G-764; K-752 to G-764; I-753 to G-764; L-754 to G-764; I-755 to G-764; F-756 to G-764; S-757 to G-764; K-758 to G-764; and/or K-759 to G-764; of the amino acid sequence of SEQ ID NO:2.

As mentioned above, even if deletion of one or more amino acids from the C-terminus of a protein results in modification of loss of one or more biological functions of the protein, other functional activities (e.g., biological activities, ability to multimerize, ability to bind EF or LF) may still be retained. For example, the ability of the shortened PA polypeptide to induce and/or bind to antibodies which recognize the complete or mature forms of the PA polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that a PA polypeptide with a large number of deleted C-terminal amino acid residues may retain some biological or immunogenic activities. In fact, peptides composed of as few as six PA amino acid residues may often evoke an immune response.

Accordingly, the present invention further provides antibodies that bind polypeptides having one or more residues deleted from the carboxy terminus of the amino acid sequence of the PA polypeptide sequence of SEQ ID NO:2 up to the arginine residue at position number 36. In particular, the present invention provides antibodies that bind polypeptides comprising the amino acid sequence of residues 30-$m^1$ of SEQ ID NO:2, where $m^1$ is an integer from 36 to 763 corresponding to the position of the amino acid residue in SEQ ID NO:2.

More in particular, the invention provides antibodies that bind polypeptides comprising, or alternatively consisting of, the amino acid sequence of residues E-30 to I-763; E-30 to E-762; E-30 to Y-761; E-30 to G-760; E-30 to K-759; E-30 to K-758; E-30 to S-757; E-30 to F-756; E-30 to I-755; E-30 to L-754; E-30 to I-753; E-30 to K-752; E-30 to K-751; E-30 to I-750; E-30 to G-749; E-30 to N-748; E-30 to T-747; E-30 to S-746; E-30 to T-745; E-30 to D-744; E-30 to G-743; E-30 to N-742; E-30 to E-741; E-30 to S-740; E-30 to P-739; E-30 to N-738; E-30 to I-737; E-30 to I-736; E-30 to T-735; E-30 to N-734; E-30 to E-733; E-30 to K-732; E-30 to T-731; E-30 to V-730; E-30 to A-729; E-30 to Y-728; E-30 to V-727; E-30 to N-726; E-30 to V-725; E-30 to K-724; E-30 to Y-723; E-30 to N-722; E-30 to P-721; E-30 to N-720; E-30 to S-719; E-30 to I-718; E-30 to Y-717; E-30 to L-716; E-30 to P-715; E-30 to L-714; E-30 to K-713; E-30 to D-712; E-30 to N-711; E-30 to Y-710; E-30 to K-709; E-30 to K-708; E-30 to F-707; E-30 to D-706; E-30 to I-705; E-30 to F-704; E-30 to T-703; E-30 to K-702; E-30 to G-701; E-30 to D-700; E-30 to Q-699; E-30 to R-698; E-30 to L-697; E-30 to S-696; E-30 to S-695; E-30 to I-694; E-30 to N-693; E-30 to L-692; E-30 to M-691; E-30 to D-690; E-30 to Y-689; E-30 to R-688; E-30 to D-687; E-30 to N-686; E-30 to I-685; E-30 to V-684; E-30 to E-683; E-30 to K-682; E-30 to L-681; E-30 to G-680; E-30 to E-679; E-30 to T-678; E-30 to D-677; E-30 to E-676; E-30 to I-675; E-30 to E-674; E-30 to V-673; E-30 to I-672; E-30 to Y-671; E-30 to G-670; E-30 to S-669; E-30 to L-668; E-30 to I-667; E-30 to K-666; E-30 to R-665; E-30 to I-664; E-30 to D-663; E-30 to K-662; E-30 to D-661; E-30 to I-660; E-30 to N-659; E-30 to L-658; E-30 to L-657; E-30 to L-656; E-30 to G-655; E-30 to E-654; E-30 to T-653; E-30 to S-652; E-30 to S-651; E-30 to N-650; E-30 to I-649; E-30 to V-648; E-30 to E-647; E-30 to R-646; E-30 to H-645; E-30 to A-644; E-30 to E-643; E-30 to K-642; E-30 to V-641; E-30 to V-640; E-30 to S-639; E-30 to E-638; E-30 to D-637; E-30 to A-636; E-30 to G-635; E-30 to V-634; E-30 to A-633; E-30 to I-632; E-30 to N-631; E-30 to N-630; E-30 to R-629; E-30 to D-628; E-30 to Y-627; E-30 to H-626; E-30 to F-625; E-30 to R-624; E-30 to K-623; E-30 to D-622; E-30 to R-621; E-30 to I-620; E-30 to L-619; E-30 to I-618; E-30 to N-617; E-30 to M-616; E-30 to K-615; E-30 to A-614; E-30 to N-613; E-30 to L-612; E-30 to K-611; E-30 to I-610; E-30 to K-609; E-30 to D-608; E-30 to L-607; E-30 to V-606; E-30 to T-605; E-30 to Y-604; E-30 to I-603; E-30 to N-602; E-30 to T-601; E-30 to A-600; E-30 to N-599; E-30 to L-598; E-30 to E-597; E-30 to A-596; E-30 to L-595; E-30 to Q-594; E-30 to N-593; E-30 to K-592; E-30 to I-591; E-30 to N-590; E-30 to Q-589; E-30 to S-588; E-30 to T-587; E-30 to Q-586; E-30 to Q-585; E-30 to D-584; E-30 to F-583; E-30 to N-582; E-30 to F-581; E-30 to D-580; E-30 to F-579; E-30 to E-578; E-30 to T-577; E-30 to I-576; E-30 to D-575; E-30 to K-574; E-30 to G-573; E-30 to Q-572; E-30 to Y-571; E-30 to Q-570; E-30 to L-569; E-30 to N-568; E-30 to G-567; E-30 to N-566; E-30 to P-565; E-30 to E-564; E-30 to N-563; E-30 to F-562; E-30 to G-561; E-30 to F-560; E-30 to A-559; E-30 to I-558; E-30 to K-557; E-30 to L-556; E-30 to A-555; E-30 to E-554; E-30 to K-553; E-30 to L-552; E-30 to T-551; E-30 to M-550; E-30 to D-549; E-30 to P-548; E-30 to K-547; E-30 to T-546; E-30 to T-545; E-30 to E-544; E-30 to L-543; E-30 to P-542; E-30 to D-541; E-30 to S-540; E-30 to P-539; E-30 to N-538; E-30 to V-537; E-30 to A-536; E-30 to A-535; E-30 to I-534; E-30 to R-533; E-30 to R-532; E-30 to E-531; E-30 to V-530; E-30 to L-529; E-30 to N-528; E-30 to L-527; E-30 to D-526; E-30 to K-525; E-30 to G-524; E-30 to N-523; E-30 to F-522; E-30 to I-521; E-30 to I-520; E-30 to R-519; E-30 to A-518; E-30 to T-517; E-30 to T-516; E-30 to E-515; E-30 to Q-514; E-30 to I-513; E-30 to Q-512; E-30 to P-511; E-30 to L-510; E-30 to V-509; E-30 to E-508; E-30 to S-507; E-30 to W-506; E-30 to N-505; E-30 to S-504; E-30 to G-503; E-30 to T-502; E-30 to D-501; E-30 to V-500; E-30 to R-499; E-30 to V-498; E-30 to R-497; E-30 to G-496; E-30 to N-495; E-30 to E-494; E-30 to F-493; E-30 to N-492; E-30 to Y-491; E-30 to T-490; E-30 to A-489; E-30 to I-488; E-30 to N-487; E-30 to G-486; E-30 to Y-485; E-30 to V-484; E-30 to Q-483; E-30 to D-482; E-30 to T-481; E-30 to D-480; E-30 to L-479; E-30 to R-478; E-30 to L-477; E-30 to Q-476; E-30 to K-475; E-30 to T-474; E-30 to K-473; E-30 to E-472; E-30 to L-471; E-30 to E-470; E-30 to L-469; E-30 to F-468; E-30 to Q-467; E-30 to N-466; E-30 to Y-465; E-30 to N-464; E-30 to M-463; E-30 to T-462; E-30 to I-461; E-30 to P-460; E-30 to T-459; E-30 to S-458; E-30 to S-457; E-30 to F-456; E-30 to D-455; E-30 to D-454; E-30 to Q-453; E-30 to A-452; E-30 to N-451; E-30 to L-450; E-30 to A-449; E-30 to I-448; E-30 to P-447; E-30 to A-446; E-30 to L-445; E-30 to N-444; E-30 to K-443; E-30 to S-442; E-30 to P-441; E-30 to Y-440; E-30 to Y-439; E-30 to N-438; E-30 to N-437; E-30 to P-436; E-30 to A-435; E-30 to L-434; E-30 to I-433; E-30 to Q-432; E-30 to S-431; E-30 to L-430; E-30 to Q-429; E-30 to N-428; E-30 to E-427; E-30 to K-426; E-30 to A-425; E-30 to K-424; E-30 to I-423; E-30 to T-422; E-30 to A-421; E-30 to L-420; E-30 to T-419; E-30 to Q-418; E-30 to N-417; E-30 to K-416; E-30 to G-415; E-30 to L-414; E-30 to V-413; E-30 to L-412; E-30 to S-411; E-30 to T-410; E-30 to T-409; E-30 to P-408; E-30 to L-407; E-30 to V-406; E-30 to N-405; E-30 to Y-404; E-30 to I-403; E-30 to P-402; E-30 to A-401; E-30 to T-400; E-30 to G-399; E-30 to T-398; E-30 to N-397; E-30 to V-396; E-30 to Y-395; E-30 to R-394; E-30 to I-393; E-30 to N-392; E-30 to A-391; E-30 to N-390; E-30 to L-389; E-30 to R-388; E-30 to A-387; E-30 to T-386; E-30 to D-385; E-30 to A-384; E-30 to T-383; E-30 to N-382; E-30 to L-381; E-30 to G-380; E-30 to M-379; E-30 to T-378; E-30 to E-377; E-30 to A-376; E-30 to W-375; E-30 to T-374; E-30 to R-373; E-30 to E-372; E-30 to G-371; E-30 to A-370; E-30 to L-369; E-30 to S-368; E-30 to L-367; E-30 to S-366; E-30 to H-365; E-30 to D-364; E-30 to I-363; E-30 to A-362; E-30 to V-361; E-30 to T-360; E-30 to S-359; E-30 to S-358; E-30 to N-357; E-30 to S-356; E-30 to N-355; E-30 to S-354; E-30 to F-353; E-30 to G-352; E-30 to A-351; E-30 to S-350; E-30 to V-349; E-30 to S-348; E-30 to G-347; E-30 to G-346; E-30 to I-345; E-30 to D-344; E-30 to F-343; E-30 to F-342; E-30 to S-341; E-30 to A-340; E-30 to H-339; E-30 to V-338; E-30 to E-337; E-30 to A-336; E-30 to N-335; E-30 to G-334; E-30 to H-333; E-30 to V-332; E-30 to E-331; E-30 to S-330; E-30 to T-329; E-30 to H-328; E-30 to T-327; E-30 to R-326; E-30 to S-325; E-30 to T-324; E-30 to S-323; E-30 to T-322; E-30 to N-321; E-30 to K-320; E-30 to S-319; E-30 to I-318; E-30 to T-317; E-30 to R-316; E-30 to T-315; E-30 to Q-314; E-30 to S-313; E-30 to D-312; E-30 to T-311; E-30 to N-310; E-30 to Q-309; E-30 to T-308; E-30 to S-307; E-30 to Q-306; E-30 to D-305; E-30 to E-304; E-30 to N-303; E-30 to K-302; E-30 to S-301; E-30 to L-300; E-30 to I-299; E-30 to I-298; E-30 to N-297; E-30 to E-296; E-30 to M-295; E-30 to D-294; E-30 to V-293; E-30 to H-292; E-30 to V-291; E-30 to I-290; E-30 to P-289; E-30 to Y-288; E-30 to A-287; E-30 to A-286; E-30 to V-285; E-30 to L-284; E-30 to P-283; E-30 to H-282; E-30 to R-281; E-30 to A-280; E-30 to E-279; E-30 to P-278; E-30 to S-277; E-30 to V-276; E-30 to N-275; E-30 to K-274; E-30 to D-273; E-30 to I-272; E-30 to R-271; E-30 to G-270; E-30 to T-269; E-30 to V-268; E-30 to K-267; E-30 to E-266; E-30 to F-265; E-30 to D-264; E-30 to S-263; E-30 to Y-262; E-30 to P-261; E-30 to D-260; E-30 to S-259; E-30 to A-258; E-30 to T-257; E-30 to S-256; E-30 to W-255; E-30 to K-254; E-30 to E-253; E-30 to P-252; E-30 to S-251; E-30 to S-250; E-30 to K-249; E-30 to Y-248; E-30 to K-247; E-30 to T-246; E-30 to L-245; E-30 to G-244; E-30 to K-243; E-30 to K-242; E-30 to E-241; E-30 to H-240; E-30 to I-239; E-30 to N-238; E-30 to S-237; E-30 to I-236; E-30 to W-235; E-30 to P-234; E-30 to S-233; E-30 to L-232; E-30 to F-231; E-30 to T-230; E-30 to R-229; E-30 to K-228; E-30 to N-227; E-30 to K-226; E-30 to V-225; E-30 to D-224; E-30 to V-223; E-30 to T-222; E-30 to Y-221; E-30 to G-220; E-30 to E-219; E-30 to V-218; E-30 to E-217; E-30 to L-216; E-30 to S-215; E-30 to D-214; E-30 to P-213; E-30 to I-212; E-30 to G-211; E-30 to D-210; E-30 to N-209; E-30 to D-208; E-30 to R-207; E-30 to D-206; E-30 to P-205; E-30 to V-204; E-30 to T-203; E-30 to P-202; E-30 to G-201; E-30 to A-200; E-30 to S-199; E-30 to T-198; E-30 to S-197; E-30 to R-196; E-30 to K-195; E-30 to K-194; E-30 to R-193; E-30 to S-192; E-30 to N-191; E-30 to S-190; E-30 to S-189; E-30 to K-188; E-30 to Q-187; E-30 to K-186; E-30 to L-185; E-30 to E-184; E-30 to P-183; E-30 to L-182; E-30 to Q-181; E-30 to L-180; E-30 to N-179; E-30 to D-178; E-30 to S-177; E-30 to S-176; E-30 to I-175; E-30 to V-174; E-30 to E-173; E-30 to K-172; E-30 to K-171; E-30 to N-170; E-30 to Q-169; E-30 to S-168; E-30 to D-167; E-30 to T-166; E-30 to W-165; E-30 to Y-164; E-30 to L-163; E-30 to K-162; E-30 to F-161; E-30 to D-160; E-30 to L-159; E-30 to G-158; E-30 to K-157; E-30 to E-156; E-30 to T-155; E-30 to P-154; E-30 to N-153; E-30 to E-152; E-30 to R-151; E-30 to Q-150; E-30 to Y-149; E-30 to Q-148; E-30 to I-147; E-30 to K-146; E-30 to I-145; E-30 to Q-144; E-30 to Y-143; E-30 to L-142; E-30 to R-141; E-30 to G-140; E-30 to K-139; E-30 to E-138; E-30 to L-137; E-30 to R-136; E-30 to I-135; E-30 to K-134; E-30 to N-133; E-30 to S-132; E-30 to N-131; E-30 to S-130; E-30 to A-129; E-30 to K-128; E-30 to N-127; E-30 to I-126; E-30 to V-125; E-30 to E-124; E-30 to Q-123; E-30 to D-122; E-30 to D-121; E-30 to V-120; E-30 to W-119; E-30 to M-118; E-30 to T-117; E-30 to V-116; E-30 to H-115; E-30 to N-114; E-30 to D-113; E-30 to A-112; E-30 to S-111; E-30 to T-110; E-30 to A-109; E-30 to F-108; E-30 to T-107; E-30 to Y-106; E-30 to E-105; E-30 to D-104; E-30 to S-103; E-30 to K-102; E-30 to K-101; E-30 to V-100; E-30 to K-99; E-30 to I-98; E-30 to F-97; E-30 to G-96; E-30 to S-95; E-30 to W-94; E-30 to I-93; E-30 to A-92; E-30 to S-91; E-30 to Q-90; E-30 to F-89; E-30 to Y-88; E-30 to Q-87; E-30 to N-86; E-30 to E-85; E-30 to S-84; E-30 to P-83; E-30 to I-82; E-30 to N-81; E-30 to E-80; E-30 to L-79; E-30 to E-78; E-30 to S-77; E-30 to S-76; E-30 to P-75; E-30 to I-74; E-30 to S-73; E-30 to L-72; E-30 to D-71; E-30 to G-70; E-30 to T-69; E-30 to T-68; E-30 to S-67; E-30 to S-66; E-30 to T-65; E-30 to V-64; E-30 to V-63; E-30 to M-62; E-30 to P-61; E-30 to A-60; E-30 to Q-59; E-30 to F-58; E-30 to N-57; E-30 to L-56; E-30 to D-55; E-30 to S-54; E-30 to F-53; E-30 to Y-52; E-30 to Y-51; E-30 to G-50; E-30 to L-49; E-30 to L-48; E-30 to G-47; E-30 to Q-46; E-30 to S-45; E-30 to S-44; E-30 to S-43; E-30 to E-42; E-30 to S-41; E-30 to E-40; E-30 to N-39; E-30 to L-38; E-30 to L-37; and/or E-30 to R-36 of the amino acid sequence of SEQ ID NO:2.

The invention also provides antibodies that bind polypeptides having one or more amino acids deleted from both the amino and the carboxyl termini of a PA polypeptide, which may be described generally as having residues $n^1$-$m^1$ of SEQ ID NO:2, where $n^1$ and $m^1$ are integers as described above.

It will be recognized in the art that some amino acid sequence of PA can be varied without significant effect of the structure or function of the protein. If such differences in sequence are contemplated, it should be remembered that there will be critical areas on the protein which determine activity. Such areas will usually comprise residues which make up the ligand binding site or the death domain, or which form tertiary structures which affect these domains.

Thus, the invention further includes antibodies that bind variations of the PA protein which show substantial PA protein activity or which include regions of PA such as the protein fragments discussed below. Such mutants include deletions, insertions, inversions, repeats, and type substitution. Guidance concerning which amino acid changes are likely to be phenotypically silent can be found in Bowie, J. U. et al., *Science* 247:1306-1310 (1990).

Thus, antibodies of the present invention may bind a fragment, derivative, or analog of the polypeptide of SEQ ID NO:2. Such fragments, variants or derivatives may be (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the PA protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-alpha to only one of the two known types of TNF receptors. Thus, the antibodies of the present invention may bind a PA protein that contains one or more amino acid substitutions, deletions or additions, either from natural mutations or human manipulation.

As indicated, changes are preferably of a minor nature, such as conservative amino acid substitutions that do not significantly affect the folding or activity of the protein (see Table 3).

TABLE 3

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |

TABLE 3-continued

Conservative Amino Acid Substitutions.

| | |
|---|---|
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of SEQ ID NO:2 and/or any of the polypeptides or polypeptide fragments described herein is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

In specific embodiments, the antibodies of the invention bind PA polypeptides or fragments or variants thereof that contains any one or more of the following conservative mutations in PA: M1 replaced with A, G, I, L, S, T, or V; K2 replaced with H, or R; K3 replaced with H, or R; R4 replaced with H, or K; K5 replaced with H, or R; V6 replaced with A, G, I, L, S, T, or M; L7 replaced with A, G, I, S, T, M, or V; I8 replaced with A, G, L, S, T, M, or V; L10 replaced with A, G, I, S, T, M, or V; M11 replaced with A, G, I, L, S, T, or V; A12 replaced with G, I, L, S, T, M, or V; L13 replaced with A, G, I, S, T, M, or V; S14 replaced with A, G, I, L, T, M, or V; T15 replaced with A, G, I, L, S, M, or V; I16 replaced with A, G, L, S, T, M, or V; L17 replaced with A, G, I, S, T, M, or V; V18 replaced with A, G, I, L, S, T, or M; S19 replaced with A, G, I, L, T, M, or V; S20 replaced with A, G, I, L, T, M, or V; T21 replaced with A, G, I, L, S, M, or V; G22 replaced with A, I, L, S, T, M, or V; N23 replaced with Q; L24 replaced with A, G, I, S, T, M, or V; E25 replaced with D; V26 replaced with A, G, I, L, S, T, or M; I27 replaced with A, G, L, S, T, M, or V; Q28 replaced with N; A29 replaced with G, I, L, S, T, M, or V; E30 replaced with D; V31 replaced with A, G, I, L, S, T, or M; K32 replaced with H, or R; Q33 replaced with N; E34 replaced with D; N35 replaced with Q; R36 replaced with H, or K; L37 replaced with A, G, I, S, T, M, or V; L38 replaced with A, G, I, S, T, M, or V; N39 replaced with Q; E40 replaced with D; S41 replaced with A, G, I, L, T, M, or V; E42 replaced with D; S43 replaced with A, G, I, L, T, M, or V; S44 replaced with A, G, I, L, T, M, or V; S45 replaced with A, G, I, L, T, M, or V; Q46 replaced with N; G47 replaced with A, I, L, S, T, M, or V; L48 replaced with A, G, I, S, T, M, or V; L49 replaced with A, G, I, S, T, M, or V; G50 replaced with A, I, L, S, T, M, or V; Y51 replaced with F, or W; Y52 replaced with F, or W; F53 replaced with W, or Y; S54 replaced with A, G, I, L, T, M, or V; D55 replaced with E; L56 replaced with A, G, I, S, T, M, or V; N57 replaced with Q; F58 replaced with W, or Y; Q59 replaced with N; A60 replaced with G, I, L, S, T, M, or V; M62 replaced with A, G, I, L, S, T, or V; V63 replaced with A, G, I, L, S, T, or M; V64 replaced with A, G, I, L, S, T, or M; T65 replaced with A, G, I, L, S, M, or V; S66 replaced with A, G, I, L, T, M, or V; S67 replaced with A, G, I, L, T, M, or V; T68 replaced with A, G, I, L, S, M, or V; T69 replaced with A, G, I, L, S, M, or V; G70 replaced with A, I, L, S, T, M, or V; D71 replaced with E; L72 replaced with A, G, I, S, T, M, or V; S73 replaced with A, G, I, L, T, M, or V; I74 replaced with A, G, L, S, T, M, or V; S76 replaced with A, G, I, L, T, M, or V; S77 replaced with A, G, I, L, T, M, or V; E78 replaced with D; L79 replaced with A, G, I, S, T, M, or V; E80 replaced with D; N81 replaced with Q; I82 replaced with A, G, L, S, T, M, or V; S84 replaced with A, G, I, L, T, M, or V; E85 replaced with D; N86 replaced with Q; Q87 replaced with N; Y88 replaced with F, or W; F89 replaced with W, or Y; Q90 replaced with N; S91 replaced with A, G, I, L, T, M, or V; A92 replaced with G, I, L, S, T, M, or V; I93 replaced with A, G, L, S, T, M, or V; W94 replaced with F, or Y; S95 replaced with A, G, I, L, T, M, or V; G96 replaced with A, I, L, S, T, M, or V; F97 replaced with W, or Y; I98 replaced with A, G, L, S, T, M, or V; K99 replaced with H, or R; V100 replaced with A, G, I, L, S, T, or M; K101 replaced with H, or R; K102 replaced with H, or R; S103 replaced with A, G, I, L, T, M, or V; D104 replaced with E; E105 replaced with D; Y106 replaced with F, or W; T107 replaced with A, G, I, L, S, M, or V; F108 replaced with W, or Y; A109 replaced with G, I, L, S, T, M, or V; T110 replaced with A, G, I, L, S, M, or V; S111 replaced with A, G, I, L, T, M, or V; A112 replaced with G, I, L, S, T, M, or V; D113 replaced with E; N114 replaced with Q; H115 replaced with K, or R; V116 replaced with A, G, I, L, S, T, or M; T117 replaced with A, G, I, L, S, M, or V; M118 replaced with A, G, I, L, S, T, or V; W119 replaced with F, or Y; V120 replaced with A, G, I, L, S, T, or M; D121 replaced with E; D122 replaced with E; Q123 replaced with N; E124 replaced with D; V125 replaced with A, G, I, L, S, T, or M; I126 replaced with A, G, L, S, T, M, or V; N127 replaced with Q; K128 replaced with H, or R; A129 replaced with G, I, L, S, T, M, or V; S130 replaced with A, G, I, L, T, M, or V; N131 replaced with Q; S132 replaced with A, G, I, L, T, M, or V; N133 replaced with Q; K134 replaced with H, or R; I135 replaced with A, G, L, S, T, M, or V; R136 replaced with H, or K; L137 replaced with A, G, I, S, T, M, or V; E138 replaced with D; K139 replaced with H, or R; G140 replaced with A, I, L, S, T, M, or V; R141 replaced with H, or K; L142 replaced with A, G, I, S, T, M, or V; Y143 replaced with F, or W; Q144 replaced with N; I145 replaced with A, G, L, S, T, M, or V; K146 replaced with H, or R; I147 replaced with A, G, L, S, T, M, or V; Q148 replaced with N; Y149 replaced with F, or W; Q150 replaced with N; R151 replaced with H, or K; E152 replaced with D; N153 replaced with Q; T155 replaced with A, G, I, L, S, M, or V; E156 replaced with D; K157 replaced with H, or R; G158 replaced with A, I, L, S, T, M, or V; L159 replaced with A, G, I, S, T, M, or V; D160 replaced with E; F161 replaced with W, or Y; K162 replaced with H, or R; L163 replaced with A, G, I, S, T, M, or V; Y164 replaced with F, or W; W165 replaced with F, or Y; T166 replaced with A, G, I, L, S, M, or V; D167 replaced with E; S168 replaced with A, G, I, L, T, M, or V; Q169 replaced with N; N170 replaced with Q; K171 replaced with H, or R; K172 replaced with H, or R; E173 replaced with D; V174 replaced with A, G, I, L, S, T, or M; I175 replaced with A, G, L, S, T, M, or V; S176 replaced with A, G, I, L, T, M, or V; S177 replaced with A, G, I, L, T, M, or V; D178 replaced with E; N179 replaced with Q; L180 replaced with A, G, I, S, T, M, or V; Q181 replaced with N; L182 replaced with A, G, I, S, T, M, or V; E184 replaced with D; L185 replaced with A, G, I, S, T, M, or V; K186 replaced with H, or R; Q187 replaced with N; K188 replaced with H, or R; S189 replaced with A, G, I, L, T, M, or V; S190 replaced with A, G, I, L, T, M, or V; N191 replaced with Q; S192 replaced with A, G, I, L, T, M, or V; R193 replaced with H, or K; K194 replaced with H, or R; K195 replaced with H, or R; R196 replaced with H, or K; S197 replaced with A, G, I, L, T, M, or V; T198 replaced with A, G, I, L, S, M, or V; S199 replaced with A, G, I, L, T, M, or V; A200 replaced with G, I, L, S, T, M, or V; G201 replaced with A, I, L, S, T, M, or V; T203 replaced with A, G, I, L, S, M, or V; V204 replaced with A, G, I, L, S, T, or M; D206 replaced with E; R207 replaced with H, or K; D208 replaced with E; N209 replaced with Q; D210 replaced with E; G211 replaced with A, I, L, S, T, M, or V; I212 replaced with A, G, L, S, T, M, or V; D214 replaced with E; S215 replaced with A, G, I, L, T, M, or V; L216 replaced with A, G, I, S, T, M, or V; E217 replaced with D; V218 replaced with A, G, I, L, S, T, or M; E219 replaced with D; G220 replaced with A, I, L, S, T, M, or V; Y221 replaced with F, or W; T222 replaced with A, G, I, L, S, M, or V; V223 replaced with A, G, I, L, S, T, or M; D224 replaced with E; V225 replaced with A, G, I, L, S, T, or M; K226 replaced with H, or R; N227 replaced with Q; K228 replaced with H, or R; R229 replaced with H, or K; T230 replaced with A, G, I, L, S, M, or V; F231 replaced with W, or Y; L232 replaced with A, G, I, S, T, M, or V; S233 replaced with A, G, I, L, T, M, or V; W235 replaced with F, or Y; I236 replaced with A, G, L, S, T, M, or V; S237 replaced with A, G, I, L, T, M, or V; N238 replaced with Q; I239 replaced with A, G, L, S, T, M, or V; H240 replaced with K, or R; E241 replaced with D; K242 replaced with H, or R; K243 replaced with H, or R; G244 replaced with A, I, L, S, T, M, or V; L245 replaced with A, G, I, S, T, M, or V; T246 replaced with A, G, I, L, S, M, or V; K247 replaced with H, or R; Y248 replaced with F, or W; K249 replaced with H, or R; S250 replaced with A, G, I, L, T, M, or V; S251 replaced with A, G, I, L, T, M, or V; E253 replaced with D; K254 replaced with H, or R; W255 replaced with F, or Y; S256 replaced with A, G, I, L, T, M, or V; T257 replaced with A, G, I, L, S, M, or V; A258 replaced with G, I, L, S, T, M, or V; S259 replaced with A, G, I, L, T, M, or V; D260 replaced with E; Y262 replaced with F, or W; S263 replaced with A, G, I, L, T, M, or V; D264 replaced with E; F265 replaced with W, or Y; E266 replaced with D; K267 replaced with H, or R; V268 replaced with A, G, I, L, S, T, or M; T269 replaced with A, G, I, L, S, M, or V; G270 replaced with A, I, L, S, T, M, or V; R271 replaced with H, or K; I272 replaced with A, G, L, S, T, M, or V; D273 replaced with E; K274 replaced with H, or R; N275 replaced with Q; V276 replaced with A, G, I, L, S, T, or M; S277 replaced with A, G, I, L, T, M, or V; E279 replaced with D; A280 replaced with G, I, L, S, T, M, or V; R281 replaced with H, or K; H282 replaced with K, or R; L284 replaced with A, G, I, S, T, M, or V; V285 replaced with A, G, I, L, S, T, or M; A286 replaced with G, I, L, S, T, M, or V; A287 replaced with G, I, L, S, T, M, or V; Y288 replaced with F, or W; I290 replaced with A, G, L, S, T, M, or V; V291 replaced with A, G, I, L, S, T, or M; H292 replaced with K, or R; V293 replaced with A, G, I, L, S, T, or M; D294 replaced with E; M295 replaced with A, G, I, L, S, T, or V; E296 replaced with D; N297 replaced with Q; I298 replaced with A, G, L, S, T, M, or V; I299 replaced with A, G, L, S, T, M, or V; L300 replaced with A, G, I, S, T, M, or V; S301 replaced with A, G, I, L, T, M, or V; K302 replaced with H, or R; N303 replaced with Q; E304 replaced with D; D305 replaced with E; Q306 replaced with N; S307 replaced with A, G, I, L, T, M, or V; T308 replaced with A, G, I, L, S, M, or V; Q309 replaced with N; N310 replaced with Q; T311 replaced with A, G, I, L, S, M, or V; D312 replaced with E; S313 replaced with A, G, I, L, T, M, or V; Q314 replaced with N; T315 replaced with A, G, I, L, S, M, or V; R316 replaced with H, or K; T317 replaced with A, G, I, L, S, M, or V; I318 replaced with A, G, L, S, T, M, or V; S319 replaced with A, G, I, L, T, M, or V; K320 replaced with H, or R; N321 replaced with Q; T322 replaced with A, G, I, L, S, M, or V; S323 replaced with A, G, I, L, T, M, or V; T324 replaced with A, G, I, L, S, M, or V; S325 replaced with A, G, I, L, T, M, or V; R326 replaced with H, or K; T327 replaced with A, G, I, L, S, M, or V; H328 replaced with K, or R; T329 replaced with A, G, I, L, S, M, or V; S330 replaced with A, G, I, L, T, M, or V; E331 replaced with D; V332 replaced with A, G, I, L, S, T, or M; H333 replaced with K, or R; G334 replaced with A, I, L, S, T, M, or V; N335 replaced with Q; A336 replaced with G, I, L, S, T, M, or V; E337 replaced with D; V338 replaced with A, G, I, L, S, T, or M; H339 replaced with K, or R; A340 replaced with G, I, L, S, T, M, or V; S341 replaced with A, G, I, L, T, M, or V; F342 replaced with W, or Y; F343 replaced with W, or Y; D344 replaced with E; I345 replaced with A, G, L, S, T, M, or V; G346 replaced with A, I, L, S, T, M, or V; G347 replaced with A, I, L, S, T, M, or V; S348 replaced with A, G, I, L, T, M, or V; V349 replaced with A, G, I, L, S, T, or M; S350 replaced with A, G, I, L, T, M, or V; A351 replaced with G, I, L, S, T, M, or V; G352 replaced with A, I, L, S, T, M, or V; F353 replaced with W, or Y; S354 replaced with A, G, I, L, T, M, or V; N355 replaced with Q; S356 replaced with A, G, I, L, T, M, or V; N357 replaced with Q; S358 replaced with A, G, I, L, T, M, or V; S359 replaced with A, G, I, L, T, M, or V; T360 replaced with A, G, I, L, S, M, or V; V361 replaced with A, G, I, L, S, T, or M; A362 replaced with G, I, L, S, T, M, or V; I363 replaced with A, G, L, S, T, M, or V; D364 replaced with E; H365 replaced with K, or R; S366 replaced with A, G, I, L, T, M, or V; L367 replaced with A, G, I, S, T, M, or V; S368 replaced with A, G, I, L, T, M, or V; L369 replaced with A, G, I, S, T, M, or V; A370 replaced with G, I, L, S, T, M, or V; G371 replaced with A, I, L, S, T, M, or V; E372 replaced with D; R373 replaced with H, or K; T374 replaced with A, G, I, L, S, M, or V; W375 replaced with F, or Y; A376 replaced with G, I, L, S, T, M, or V; E377 replaced with D; T378 replaced with A, G, I, L, S, M, or V; M379 replaced with A, G, I, L, S, T, or V; G380 replaced with A, I, L, S, T, M, or V; L381 replaced with A, G, I, S, T, M, or V; N382 replaced with Q; T383 replaced with A, G, I, L, S, M, or V; A384 replaced with G, I, L, S, T, M, or V; D385 replaced with E; T386 replaced with A, G, I, L, S, M, or V; A387 replaced with G, I, L, S, T, M, or V; R388 replaced with H, or K; L389 replaced with A, G, I, S, T, M, or V; N390 replaced with Q; A391 replaced with G, I, L, S, T, M, or V; N392 replaced with Q; I393 replaced with A, G, L, S, T, M, or V; R394 replaced with H, or K; Y395 replaced with F, or W; V396 replaced with A, G, I, L, S, T, or M; N397 replaced with Q; T398 replaced with A, G, I, L, S, M, or V; G399 replaced with A, I, L, S, T, M, or V; T400 replaced with A, G, I, L, S, M, or V; A401 replaced with G, I, L, S, T, M, or V; I403 replaced with A, G, L, S, T, M, or V; Y404 replaced with F, or W; N405 replaced with Q; V406 replaced with A, G, I, L, S, T, or M; L407 replaced with A, G, I, S, T, M, or V; T409 replaced with A, G, I, L, S, M, or V; T410 replaced with A, G, I, L, S, M, or V; S411 replaced with A, G, I, L, T, M, or V; L412 replaced with A, G, I, S, T, M, or V; V413 replaced with A, G, I, L, S, T, or M; L414 replaced with A, G, I, S, T, M, or V; G415 replaced with A, I, L, S, T, M, or V; K416 replaced with H, or R; N417 replaced with Q; Q418 replaced with N; T419 replaced with A, G, I, L, S, M, or V; L420 replaced with A, G, I, S, T, M, or V; A421 replaced with G, I, L, S, T, M, or V; T422 replaced with A, G, I, L, S, M, or V; I423 replaced with A, G, L, S, T, M, or V; K424 replaced with H, or R; A425 replaced with G, I, L, S, T, M, or V; K426 replaced with H, or R; E427 replaced with D; N428 replaced with Q; Q429 replaced with N; L430 replaced with A, G, I, S, T, M, or V; S431 replaced with A, G, I, L, T, M, or V; Q432 replaced with N; I433 replaced with A, G, L, S, T, M, or V; L434 replaced with A, G, I, S, T, M, or V; A435 replaced with G, I, L, S, T, M, or V; N437 replaced with Q; N438 replaced with Q; Y439 replaced with F, or W; Y440 replaced with F, or W; S442 replaced with A, G, I, L, T, M, or V; K443 replaced with H, or R; N444 replaced with Q; L445 replaced with A, G, I, S, T, M, or V; A446 replaced with G, I, L, S, T, M, or V; I448 replaced with A, G, L, S, T, M, or V; A449 replaced with G, I, L, S, T, M, or V; L450 replaced with A, G, I, S, T, M, or V; N451 replaced with Q; A452 replaced with G, I, L, S, T, M, or V; Q453 replaced with N; D454 replaced with E; D455 replaced with E; F456 replaced with W, or Y; S457 replaced with A, G, I, L, T, M, or V; S458 replaced with A, G, I, L, T, M, or V; T459 replaced with A, G, I, L, S, M, or V; I461 replaced with A, G, L, S, T, M, or V; T462 replaced with A, G, I, L, S, M, or V; M463 replaced with A, G, I, L, S, T, or V; N464 replaced with Q; Y465 replaced with F, or W; N466 replaced with Q; Q467 replaced with N; F468 replaced with W, or Y; L469 replaced with A, G, I, S, T, M, or V; E470 replaced with D; L471 replaced with A, G, I, S, T, M, or V; E472 replaced with D; K473 replaced with H, or R; T474 replaced with A, G, I, L, S, M, or V; K475 replaced with H, or R; Q476 replaced with N; L477 replaced with A, G, I, S, T, M, or V; R478 replaced with H, or K; L479 replaced with A, G, I, S, T, M, or V; D480 replaced with E; T481 replaced with A, G, I, L, S, M, or V; D482 replaced with E; Q483 replaced with N; V484 replaced with A, G, I, L, S, T, or M; Y485 replaced with F, or W; G486 replaced with A, I, L, S, T, M, or V; N487 replaced with Q; I488 replaced with A, G, L, S, T, M, or V; A489 replaced with G, I, L, S, T, M, or V; T490 replaced with A, G, I, L, S, M, or V; Y491 replaced with F, or W; N492 replaced with Q; F493 replaced with W, or Y; E494 replaced with D; N495 replaced with Q; G496 replaced with A, I, L, S, T, M, or V; R497 replaced with H, or K; V498 replaced with A, G, I, L, S, T, or M; R499 replaced with H, or K; V500 replaced with A, G, I, L, S, T, or M; D501 replaced with E; T502 replaced with A, G, I, L, S, M, or V; G503 replaced with A, I, L, S, T, M, or V; S504 replaced with A, G, I, L, T, M, or V; N505 replaced with Q; W506 replaced with F, or Y; S507 replaced with A, G, I, L, T, M, or V; E508 replaced with D; V509 replaced with A, G, I, L, S, T, or M; L510 replaced with A, G, I, S, T, M, or V; Q512 replaced with N; I513 replaced with A, G, L, S, T, M, or V; Q514 replaced with N; E515 replaced with D; T516 replaced with A, G, I, L, S, M, or V; T517 replaced with A, G, I, L, S, M, or V; A518 replaced with G, I, L, S, T, M, or V; R519 replaced with H, or K; I520 replaced with A, G, L, S, T, M, or V; I521 replaced with A, G, L, S, T, M, or V; F522 replaced with W, or Y; N523 replaced with Q; G524 replaced with A, I, L, S, T, M, or V; K525 replaced with H, or R; D526 replaced with E; L527 replaced with A, G, I, S, T, M, or V; N528 replaced with Q; L529 replaced with A, G, I, S, T, M, or V; V530 replaced with A, G, I, L, S, T, or M; E531 replaced with D; R532 replaced with H, or K; R533 replaced with H, or K; I534 replaced with A, G, L, S, T, M, or V; A535 replaced with G, I, L, S, T, M, or V; A536 replaced with G, I, L, S, T, M, or V; V537 replaced with A, G, I, L, S, T, or M; N538 replaced with Q; S540 replaced with A, G, I, L, T, M, or V; D541 replaced with E; L543 replaced with A, G, I, S, T, M, or V; E544 replaced with D; T545 replaced with A, G, I, L, S, M, or V; T546 replaced with A, G, I, L, S, M, or V; K547 replaced with H, or R; D549 replaced with E; M550 replaced with A, G, I, L, S, T, or V; I551 replaced with A, G, I, L, S, M, or V; L552 replaced with A, G, I, S, T, M, or V; K553 replaced with H, or R; E554 replaced with D; A555 replaced with G, I, L, S, T, M, or V; L556 replaced with A, G, I, S, T, M, or V; K557 replaced with H, or R; I558 replaced with A, G, L, S, T, M, or V; A559 replaced with G, I, L, S, T, M, or V; F560 replaced with W, or Y; G561 replaced with A, I, L, S, T, M, or V; F562 replaced with W, or Y; N563 replaced with Q; E564 replaced with D; N566 replaced with Q; G567 replaced with A, I, L, S, T, M, or V; N568 replaced with Q; L569 replaced with A, G, I, S, T, M, or V; Q570 replaced with N; Y571 replaced with F, or W; Q572 replaced with N; G573 replaced with A, I, L, S, T, M, or V; K574 replaced with H, or R; D575 replaced with E; I576 replaced with A, G, L, S, T, M, or V; T577 replaced with A, G, I, L, S, M, or V; E578 replaced with D; F579 replaced with W, or Y; D580 replaced with E; F581 replaced with W, or Y; N582 replaced with Q; F583 replaced with W, or Y; D584 replaced with E; Q585 replaced with N; Q586 replaced with N; T587 replaced with A, G, I, L, S, M, or V; S588 replaced with A, G, I, L, T, M, or V; Q589 replaced with N; N590 replaced with Q; I591 replaced with A, G, L, S, T, M, or V; K592 replaced with H, or R; N593 replaced with Q; Q594 replaced with N; L595 replaced with A, G, I, S, T, M, or V; A596 replaced with G, I, L, S, T, M, or V; E597 replaced with D; L598 replaced with A, G, I, S, T, M, or V; N599 replaced with Q; A600 replaced with G, I, L, S, T, M, or V; T601 replaced with A, G, I, L, S, M, or V; N602 replaced with Q; I603 replaced with A, G, L, S, T, M, or V; Y604 replaced with F, or W; T605 replaced with A, G, I, L, S, M, or V; V606 replaced with A, G, I, L, S, T, or M; L607 replaced with A, G, I, S, T, M, or V; D608 replaced with E; K609 replaced with H, or R; I610 replaced with A, G, L, S, T, M, or V; K611 replaced with H, or R; L612 replaced with A, G, I, S, T, M, or V; N613 replaced with Q; A614 replaced with G, I, L, S, T, M, or V; K615 replaced with H, or R; M616 replaced with A, G, I, L, S, T, or V; N617 replaced with Q; I618 replaced with A, G, L, S, T, M, or V; L619 replaced with A, G, I, S, T, M, or V; I620 replaced with A, G, L, S, T, M, or V; R621 replaced with H, or K; D622 replaced with E; K623 replaced with H, or R; R624 replaced with H, or K; F625 replaced with W, or Y; H626 replaced with K, or R; Y627 replaced with F, or W; D628 replaced with E; R629 replaced with H, or K; N630 replaced with Q; N631 replaced with Q; I632 replaced with A, G, L, S, T, M, or V; A633 replaced with G, I, L, S, T, M, or V; V634 replaced with A, G, I, L, S, T, or M; G635 replaced with A, I, L, S, T, M, or V; A636 replaced with G, I, L, S, T, M, or V; D637 replaced with E; E638 replaced with D; S639 replaced with A, G, I, L, T, M, or V; V640 replaced with A, G, I, L, S, T, or M; V641 replaced with A, G, I, L, S, T, or M; K642 replaced with H, or R; E643 replaced with D; A644 replaced with G, I, L, S, T, M, or V; H645 replaced with K, or R; R646 replaced with H, or K; E647 replaced with D; V648 replaced with A, G, I, L, S, T, or M; I649 replaced with A, G, L, S, T, M, or V; N650 replaced with Q; S651 replaced with A, G, I, L, T, M, or V; S652 replaced with A, G, I, L, T, M, or V; T653 replaced with A, G, I, L, S, M, or V; E654 replaced with D; G655 replaced with A, I, L, S, T, M, or V; L656 replaced with A, G, I, S, T, M, or V; L657 replaced with A, G, I, S, T, M, or V; L658 replaced with A, G, I, S, T, M, or V; N659 replaced with Q; I660 replaced with A, G, L, S, T, M, or V; D661 replaced with E; K662 replaced with H, or R; D663 replaced with E; I664 replaced with A, G, L, S, T, M, or V; R665 replaced with H, or K; K666 replaced with H, or R; I667 replaced with A, G, L, S, T, M, or V; L668 replaced with A, G, I, S, T, M, or V; S669 replaced with A, G, I, L, T, M, or V; G670 replaced with A, I, L, S, T, M, or V; Y671 replaced with F, or W; I672 replaced with A, G, L, S, T, M, or V; V673 replaced with A, G, I, L, S, T, or M; E674 replaced with D; I675 replaced with A, G, L, S, T, M, or V; E676 replaced with D; D677 replaced with E; T678 replaced with A, G, I, L, S, M, or V; E679 replaced with D; G680 replaced with A, I, L, S, T, M, or V; L681 replaced with A, G, I, S, T, M, or V; K682 replaced with H, or R; E683 replaced with D; V684 replaced with A, G, I, L, S, T, or M; I685 replaced with A, G, L, S, T, M, or V; N686 replaced with Q; D687 replaced with E; R688 replaced with H, or K; Y689 replaced with F, or W; D690 replaced with E; M691 replaced with A, G, I, L, S, T, or V; L692 replaced with A, G, I, S, T, M, or V; N693 replaced with Q; I694 replaced with A, G, L, S, T, M, or V; S695 replaced with A, G, I, L, T, M, or V; S696 replaced with A, G, I, L, T, M, or V; L697 replaced with A, G, I, S, T, M, or V; R698 replaced with H, or K; Q699 replaced with N; D700 replaced with E; G701 replaced with A, I, L, S, T, M, or V; K702 replaced with H, or R; T703 replaced with A, G, I, L, S, M, or V; F704 replaced with W, or Y; I705 replaced with A, G, L, S, T, M, or V; D706 replaced with E; F707 replaced with W, or Y; K708 replaced with H, or R; K709 replaced with H, or R; Y710 replaced with F, or W; N711 replaced with Q; D712 replaced with E; K713 replaced with H, or R; L714 replaced with A, G, I, S, T, M, or V; L716 replaced with A, G, I, S, T, M, or V; Y717 replaced with F, or W; I718 replaced with A, G, L, S, T, M, or V; S719 replaced with A, G, I, L, T, M, or V; N720 replaced with Q; N722 replaced with Q; Y723 replaced with F, or W; K724 replaced with H, or R; V725 replaced with A, G, I, L, S, T, or M; N726 replaced with Q; V727 replaced with A, G, I, L, S, T, or M; Y728 replaced with F, or W; A729 replaced with G, I, L, S, T, M, or V; V730 replaced with A, G, I, L, S, T, or M; T731 replaced with A, G, I, L, S, M, or V; K732 replaced with H, or R; E733 replaced with D; N734 replaced with Q; T735 replaced with A, G, I, L, S, M, or V; I736 replaced with A, G, L, S, T, M, or V; I737 replaced with A, G, L, S, T, M, or V; N738 replaced with Q; S740 replaced with A, G, I, L, T, M, or V; E741 replaced with D; N742 replaced with Q; G743 replaced with A, I, L, S, T, M, or V; D744 replaced with E; T745 replaced with A, G, I, L, S, M, or V; S746 replaced with A, G, I, L, T, M, or V; T747 replaced with A, G, I, L, S, M, or V; N748 replaced with Q; G749 replaced with A, I, L, S, T, M, or V; I750 replaced with A, G, L, S, T, M, or V; K751 replaced with H, or R; K752 replaced with H, or R; I753 replaced with A, G, L, S, T, M, or V; L754 replaced with A, G, I, S, T, M, or V; I755 replaced with A, G, L, S, T, M, or V; F756 replaced with W, or Y; S757 replaced with A, G, I, L, T, M, or V; K758 replaced with H, or R; K759 replaced with H, or R; G760 replaced with A, I, L, S, T, M, or V; Y761 replaced with F, or W; E762 replaced with D; I763 replaced with A, G, L, S, T, M, or V; G764 replaced with A, I, L, S, T, M, or V; of SEQ ID NO:2.

In specific embodiments, the antibodies of the invention bind PA polypeptides or fragments or variants thereof, that contains any one or more of the following non-conservative mutations in PA: M1 replaced with D, E, H, K, R, N, Q, F, W, Y, P, or C; K2 replaced with D, E, A, G, I, L, S, T, M, V, N, Q, F, W, Y, P, or C; K3 replaced with D, E, A, G, I, L, S, T, M, V, N, Q, F, W, Y, P, or C; R4 replaced with D, E, A, G, I, L, S, T, M, V, N, Q, F, W, Y, P, or C; K5 replaced with D, E, A, G, I, L, S, T, M, V, N, Q, F, W, Y, P, or C; V6 replaced with D, E, H, K, R, N, Q, F, W, Y, P, or C; L7 replaced with D, E, H, K, R, N, Q, F, W, Y, P, or C; I8 replaced with D, E, H, K, R, N, Q, F, W, Y, P, or C; P9 replaced with D, E, H, K, R, A, G, I, L, S, T, M, V, N, Q, F, W, Y, or C; L10 replaced with D, E, H, K, R, N, Q, F, W, Y, P, or C; M11 replaced with D, E, H, K, R, N, Q, F, W, Y, P, or C; A12 replaced with D, E, H, K, R, N, Q, F, W, Y, P, or C; L13 replaced with D, E, H, K, R, N, Q, F, W, Y, P, or C; S14 replaced with D, E, H, K, R, N, Q, F, W, Y, P, or C; T15 replaced with D, E, H, K, R, N, Q, F, W, Y, P, or C; I16 replaced with D, E, H, K, R, N, Q, F, W, Y, P, or C; L17 replaced with D, E, H, K, R, N, Q, F, W, Y, P, or C; V18 replaced with D, E, H, K, R, N, Q, F, W, Y, P, or C; S19 replaced with D, E, H, K, R, N, Q, F, W, Y, P, or C; S20 replaced with D, E, H, K, R, N, Q, F, W, Y, P, or C; T21 replaced with D, E, H, K, R, N, Q, F, W, Y, P, or C; G22 replaced with D, E, H, K, R, N, Q, F, W, Y, P, or C; N23 replaced with D, E, H, K, R, A, G, I, L, S, T, M, V, F, W, Y, P, or C; L24 replaced with D, E, H, K, R, N, Q, F, W, Y, P, or C; E25 replaced with H, K, R, A, G, I, L, S, T, M, V, N, Q, F, W, Y, P, or C; V26 replaced with D, E, H, K, R, N, Q, F, W, Y, P, or C; I27 replaced with D, E, H, K, R, N, Q, F, W, Y, P, or C; Q28 replaced with D, E, H, K, R, A, G, I, L, S, T, M, V, F, W, Y, P, or C; A29 replaced with D, E, H, K, R, N, Q, F, W, Y, P, or C; E30 replaced with H, K, R, A, G, I, L, S, T, M, V, N, Q, F, W, Y, P, or C; V31 replaced with D, E, H, K, R, N, Q, F, W, Y, P, or C; K32 replaced with D, E, A, G, I, L, S, T, M, V, N, Q, F, W, Y, P, or C; Q33 replaced with D, E, H, K, R, A, G, I, L, S, T, M, V, F, W, Y, P, or C; E34 replaced with H, K, R, A, G, I, L, S, T, M, V, N, Q, F, W, Y, P, or C; N35 replaced with D, E, H, K, R, A, G, I, L, S, T, M, V, F, W, Y, P, or C; R36 replaced with D, E, A, G, I, L, S, T, M, V, N, Q, F, W, Y, P, or C; L37 replaced with D, E, H, K, R, N, Q, F, W, Y, P, or C; L38 replaced with D, E, H, K, R, N, Q, F, W, Y, P, or C; N39 replaced with D, E, H, K, R, A, G, I, L, S, T, M, V, F, W, Y, P, or C; E40 replaced with H, K, R, A, G, I, L, S, T, M, V, N, Q, F, W, Y, P, or C; S41 replaced with D, E, H, K, R, N, Q, F, W, Y, P, or C; E42 replaced with H, K, R, A, G, I, L, S, T, M, V, N, Q, F, W, Y, P, or C; S43 replaced with D, E, H, K, R, N, Q, F, W, Y, P, or C; S44 replaced with D, E, H, K, R, N, Q, F, W, Y, P, or C; S45 replaced with D, E, H, K, R, N, Q, F, W, Y, P, or C; Q46 replaced with D, E, H, K, R, A, G, I, L, S, T, M, V, F, W, Y, P, or C; G47 replaced with D, E, H, K, R, N, Q, F, W, Y, P, or C; L48 replaced with D, E, H, K, R, N, Q, F, W, Y, P, or C; L49 replaced with D, E, H, K, R, N, Q, F, W, Y, P, or C; G50 replaced with D, E, H, K, R, N, Q, F, W, Y, P, or C; Y51 replaced with D, E, H, K, R, N, Q, A, G, I, L, S, T, M, V, P, or C; Y52 replaced with D, E, H, K, R, N, Q, A, G, I, L, S, T, M, V, P, or C; F53 replaced with D, E, H, K, R, N, Q, A, G, I, L, S, T, M, V, P, or C; S54 replaced with D, E, H, K, R, N, Q, F, W, Y, P, or C; D55 replaced with H, K, R, A, G, I, L, S, T, M, V, N, Q, F, W, Y, P, or C; L56 replaced with D, E, H, K, R, N, Q, F, W, Y, P, or C; N57 replaced with D, E, H, K, R, A, G, I, L, S, T, M, V, F, W, Y, P, or C; F58 replaced with D, E, H, K, R, N, Q, A, G, I, L, S, T, M, V, P, or C; Q59 replaced with D, E, H, K, R, A, G, I, L, S, T, M, V, F, W, Y, P, or C; A60 replaced with D, E, H, K, R, N, Q, F, W, Y, P, or C; P61 replaced with D, E, H, K, R, A, G, I, L, S, T, M, V, N, Q, F, W, Y, or C; M62 replaced with D, E, H, K, R, N, Q, F, W, Y, P, or C; V63 replaced with D, E, H, K, R, N, Q, F, W, Y, P, or C; V64 replaced with D, E, H, K, R, N, Q, F, W, Y, P, or C; T65 replaced with D, E, H, K, R, N, Q, F, W, Y, P, or C; S66 replaced with D, E, H, K, R, N, Q, F, W, Y, P, or C; S67 replaced with D, E, H, K, R, N, Q, F, W, Y, P, or C; T68 replaced with D, E, H, K, R, N, Q, F, W, Y, P, or C; T69 replaced with D, E, H, K, R, N, Q, F, W, Y, P, or C; G70 replaced with D, E, H, K, R, N, Q, F, W, Y, P, or C; D71 replaced with H, K, R, A, G, I, L, S, T, M, V, N, Q, F, W, Y, P, or C; L72 replaced with D, E, H, K, R, N, Q, F, W, Y, P, or C; S73 replaced with D, E, H, K, R, N, Q, F, W, Y, P, or C; I74 replaced with D, E, H, K, R, N, Q, F, W, Y, P, or C; P75 replaced with D, E, H, K, R, A, G, I, L, S, T, M, V, N, Q, F, W, Y, or C; S76 replaced with D, E, H, K, R, N, Q, F, W, Y, P, or C; S77 replaced with D, E, H, K, R, N, Q, F, W, Y, P, or C; E78 replaced with H, K, R, A, G, I, L, S, T, M, V, N, Q, F, W, Y, P, or C; L79 replaced with D, E, H, K, R, N, Q, F, W, Y, P, or C; E80 replaced with H, K, R, A, G, I, L, S, T, M, V, N, Q, F, W, Y, P, or C; N81 replaced with D, E, H, K, R, A, G, I, L, S, T, M, V, F, W, Y, P, or C; I82 replaced with D, E, H, K, R, N, Q, F, W, Y, P, or C; P83 replaced with D, E, H, K, R, A, G, I, L, S, T, M, V, N, Q, F, W, Y, or C; S84 replaced with D, E, H, K, R, N, Q, F, W, Y, P, or C; E85 replaced with H, K, R, A, G, I, L, S, T, M, V, N, Q, F, W, Y, P, or C; N86 replaced with D, E, H, K, R, A, G, I, L, S, T, M, V, F, W, Y, P, or C; Q87 replaced with D, E, H, K, R, A, G, I, L, S, T, M, V, F, W, Y, P, or C; Y88 replaced with D, E, H, K, R, N, Q, A, G, I, L, S, T, M, V, P, or C; F89 replaced with D, E, H, K, R, N, Q, A, G, I, L, S, T, M, V, P, or C; Q90 replaced with D, E, H, K, R, A, G, I, L, S, T, M, V, F, W, Y, P, or C; S91 replaced with D, E, H, K, R, N, Q, F, W, Y, P, or C; A92 replaced with D, E, H, K, R, N, Q, F, W, Y, P, or C; I93 replaced with D, E, H, K, R, N, Q, F, W, Y, P, or C; W94 replaced with D, E, H, K, R, N, Q, A, G, I, L, S, T, M, V, P, or C; S95 replaced with D, E, H, K, R, N, Q, F, W, Y, P, or C; G96 replaced with D, E, H, K, R, N, Q, F, W, Y, P, or C;

F97 replaced with D, E, H, K, R, N, Q, A, G, I, L, S, T, M, V, P, or C; I98 replaced with D, E, H, K, R, N, Q, F, W, Y, P, or C; K99 replaced with D, E, A, G, I, L, S, T, M, V, N, Q, F, W, Y, P, or C; V100 replaced with D, E, H, K, R, N, Q, F, W, Y, P, or C; K101 replaced with D, E, A, G, I, L, S, T, M, V, N, Q, F, W, Y, P, or C; K102 replaced with D, E, A, G, I, L, S, T, M, V, N, Q, F, W, Y, P, or C; S103 replaced with D, E, H, K, R, N, Q, F, W, Y, P, or C; D104 replaced with H, K, R, A, G, I, L, S, T, M, V, N, Q, F, W, Y, P, or C; E105 replaced with H, K, R, A, G, I, L, S, T, M, V, N, Q, F, W, Y, P, or C; Y106 replaced with D, E, H, K, R, N, Q, A, G, I, L, S, T, M, V, P, or C; T107 replaced with D, E, H, K, R, N, Q, F, W, Y, P, or C; F108 replaced with D, E, H, K, R, N, Q, A, G, I, L, S, T, M, V, P, or C; A109 replaced with D, E, H, K, R, N, Q, F, W, Y, P, or C; T110 replaced with D, E, H, K, R, N, Q, F, W, Y, P, or C; S111 replaced with D, E, H, K, R, N, Q, F, W, Y, P, or C; A112 replaced with D, E, H, K, R, N, Q, F, W, Y, P, or C; D113 replaced with H, K, R, A, G, I, L, S, T, M, V, N, Q, F, W, Y, P, or C; N114 replaced with D, E, H, K, R, A, G, I, L, S, T, M, V, F, W, Y, P, or C; H115 replaced with D, E, A, G, I, L, S, T, M, V, N, Q, F, W, Y, P, or C; V116 replaced with D, E, H, K, R, N, Q, F, W, Y, P, or C; T117 replaced with D, E, H, K, R, N, Q, F, W, Y, P, or C; M118 replaced with D, E, H, K, R, N, Q, F, W, Y, P, or C; W119 replaced with D, E, H, K, R, N, Q, A, G, I, L, S, T, M, V, P, or C; V120 replaced with D, E, H, K, R, N, Q, F, W, Y, P, or C; D121 replaced with H, K, R, A, G, I, L, S, T, M, V, N, Q, F, W, Y, P, or C; D122 replaced with H, K, R, A, G, I, L, S, T, M, V, N, Q, F, W, Y, P, or C; Q123 replaced with D, E, H, K, R, A, G, I, L, S, T, M, V, F, W, Y, P, or C; E124 replaced with H, K, R, A, G, I, L, S, T, M, V, N, Q, F, W, Y, P, or C; V125 replaced with D, E, H, K, R, N, Q, F, W, Y, P, or C; I126 replaced with D, E, H, K, R, N, Q, F, W, Y, P, or C; N127 replaced with D, E, H, K, R, A, G, I, L, S, T, M, V, F, W, Y, P, or C; K128 replaced with D, E, A, G, I, L, S, T, M, V, N, Q, F, W, Y, P, or C; A129 replaced with D, E, H, K, R, N, Q, F, W, Y, P, or C; S130 replaced with D, E, H, K, R, N, Q, F, W, Y, P, or C; N131 replaced with D, E, H, K, R, A, G, I, L, S, T, M, V, F, W, Y, P, or C; S132 replaced with D, E, H, K, R, N, Q, F, W, Y, P, or C; N133 replaced with D, E, H, K, R, A, G, I, L, S, T, M, V, F, W, Y, P, or C; K134 replaced with D, E, A, G, I, L, S, T, M, V, N, Q, F, W, Y, P, or C; I135 replaced with D, E, H, K, R, N, Q, F, W, Y, P, or C; R136 replaced with D, E, A, G, I, L, S, T, M, V, N, Q, F, W, Y, P, or C; L137 replaced with D, E, H, K, R, N, Q, F, W, Y, P, or C; E138 replaced with H, K, R, A, G, I, L, S, T, M, V, N, Q, F, W, Y, P, or C; K139 replaced with D, E, A, G, I, L, S, T, M, V, N, Q, F, W, Y, P, or C; G140 replaced with D, E, H, K, R, N, Q, F, W, Y, P, or C; R141 replaced with D, E, A, G, I, L, S, T, M, V, N, Q, F, W, Y, P, or C; L142 replaced with D, E, H, K, R, N, Q, F, W, Y, P, or C; Y143 replaced with D, E, H, K, R, N, Q, A, G, I, L, S, T, M, V, P, or C; Q144 replaced with D, E, H, K, R, A, G, I, L, S, T, M, V, F, W, Y, P, or C; I145 replaced with D, E, H, K, R, N, Q, F, W, Y, P, or C; K146 replaced with D, E, A, G, I, L, S, T, M, V, N, Q, F, W, Y, P, or C; I147 replaced with D, E, H, K, R, N, Q, F, W, Y, P, or C; Q148 replaced with D, E, H, K, R, A, G, I, L, S, T, M, V, F, W, Y, P, or C; Y149 replaced with D, E, H, K, R, N, Q, A, G, I, L, S, T, M, V, P, or C; Q150 replaced with D, E, H, K, R, A, G, I, L, S, T, M, V, F, W, Y, P, or C; R151 replaced with D, E, A, G, I, L, S, T, M, V, N, Q, F, W, Y, P, or C; E152 replaced with H, K, R, A, G, I, L, S, T, M, V, N, Q, F, W, Y, P, or C; N153 replaced with D, E, H, K, R, A, G, I, L, S, T, M, V, F, W, Y, P, or C; P154 replaced with D, E, H, K, R, A, G, I, L, S, T, M, V, N, Q, F, W, Y, or C; T155 replaced with D, E, H, K, R, N, Q, F, W, Y, P, or C; E156 replaced with H, K, R, A, G, I, L, S, T, M, V, N, Q, F, W, Y, P, or C; K157 replaced with D, E, A, G, I, L, S, T, M, V, N, Q, F, W, Y, P, or C; G158 replaced with D, E, H, K, R, N, Q, F, W, Y, P, or C; L159 replaced with D, E, H, K, R, N, Q, F, W, Y, P, or C; D160 replaced with H, K, R, A, G, I, L, S, T, M, V, N, Q, F, W, Y, P, or C; F161 replaced with D, E, H, K, R, N, Q, A, G, I, L, S, T, M, V, P, or C; K162 replaced with D, E, A, G, I, L, S, T, M, V, N, Q, F, W, Y, P, or C; L163 replaced with D, E, H, K, R, N, Q, F, W, Y, P, or C; Y164 replaced with D, E, H, K, R, N, Q, A, G, I, L, S, T, M, V, P, or C; W165 replaced with D, E, H, K, R, N, Q, A, G, I, L, S, T, M, V, P, or C; T166 replaced with D, E, H, K, R, N, Q, F, W, Y, P, or C; D167 replaced with H, K, R, A, G, I, L, S, T, M, V, N, Q, F, W, Y, P, or C; S168 replaced with D, E, H, K, R, N, Q, F, W, Y, P, or C; Q169 replaced with D, E, H, K, R, A, G, I, L, S, T, M, V, F, W, Y, P, or C; N170 replaced with D, E, H, K, R, A, G, I, L, S, T, M, V, F, W, Y, P, or C; K171 replaced with D, E, A, G, I, L, S, T, M, V, N, Q, F, W, Y, P, or C; K172 replaced with D, E, A, G, I, L, S, T, M, V, N, Q, F, W, Y, P, or C; E173 replaced with H, K, R, A, G, I, L, S, T, M, V, N, Q, F, W, Y, P, or C; V174 replaced with D, E, H, K, R, N, Q, F, W, Y, P, or C; I175 replaced with D, E, H, K, R, N, Q, F, W, Y, P, or C; S176 replaced with D, E, H, K, R, N, Q, F, W, Y, P, or C; S177 replaced with D, E, H, K, R, N, Q, F, W, Y, P, or C; D178 replaced with H, K, R, A, G, I, L, S, T, M, V, N, Q, F, W, Y, P, or C; N179 replaced with D, E, H, K, R, A, G, I, L, S, T, M, V, F, W, Y, P, or C; L180 replaced with D, E, H, K, R, N, Q, F, W, Y, P, or C; Q181 replaced with D, E, H, K, R, A, G, I, L, S, T, M, V, F, W, Y, P, or C; L182 replaced with D, E, H, K, R, N, Q, F, W, Y, P, or C; P183 replaced with D, E, H, K, R, A, G, I, L, S, T, M, V, N, Q, F, W, Y, or C; E184 replaced with H, K, R, A, G, I, L, S, T, M, V, N, Q, F, W, Y, P, or C; L185 replaced with D, E, H, K, R, N, Q, F, W, Y, P, or C; K186 replaced with D, E, A, G, I, L, S, T, M, V, N, Q, F, W, Y, P, or C; Q187 replaced with D, E, H, K, R, A, G, I, L, S, T, M, V, F, W, Y, P, or C; K188 replaced with D, E, A, G, I, L, S, T, M, V, N, Q, F, W, Y, P, or C; S189 replaced with D, E, H, K, R, N, Q, F, W, Y, P, or C; S190 replaced with D, E, H, K, R, N, Q, F, W, Y, P, or C; N191 replaced with D, E, H, K, R, A, G, I, L, S, T, M, V, F, W, Y, P, or C; S192 replaced with D, E, H, K, R, N, Q, F, W, Y, P, or C; R193 replaced with D, E, A, G, I, L, S, T, M, V, N, Q, F, W, Y, P, or C; K194 replaced with D, E, A, G, I, L, S, T, M, V, N, Q, F, W, Y, P, or C; K195 replaced with D, E, A, G, I, L, S, T, M, V, N, Q, F, W, Y, P, or C; R196 replaced with D, E, A, G, I, L, S, T, M, V, N, Q, F, W, Y, P, or C; S197 replaced with D, E, H, K, R, N, Q, F, W, Y, P, or C; T198 replaced with D, E, H, K, R, N, Q, F, W, Y, P, or C; S199 replaced with D, E, H, K, R, N, Q, F, W, Y, P, or C; A200 replaced with D, E, H, K, R, N, Q, F, W, Y, P, or C; G201 replaced with D, E, H, K, R, N, Q, F, W, Y, P, or C; P202 replaced with D, E, H, K, R, A, G, I, L, S, T, M, V, N, Q, F, W, Y, or C; T203 replaced with D, E, H, K, R, N, Q, F, W, Y, P, or C; V204 replaced with D, E, H, K, R, N, Q, F, W, Y, P, or C; P205 replaced with D, E, H, K, R, A, G, I, L, S, T, M, V, N, Q, F, W, Y, or C; D206 replaced with H, K, R, A, G, I, L, S, T, M, V, N, Q, F, W, Y, P, or C; R207 replaced with D, E, A, G, I, L, S, T, M, V, N, Q, F, W, Y, P, or C; D208 replaced with H, K, R, A, G, I, L, S, T, M, V, N, Q, F, W, Y, P, or C; N209 replaced with D, E, H, K, R, A, G, I, L, S, T, M, V, F, W, Y, P, or C; D210 replaced with H, K, R, A, G, I, L, S, T, M, V, N, Q, F, W, Y, P, or C; G211 replaced with D, E, H, K, R, N, Q, F, W, Y, P, or C; I212 replaced with D, E, H, K, R, N, Q, F, W, Y, P, or C; P213 replaced with D, E, H, K, R, A, G, I, L, S, T, M, V, N, Q, F, W, Y, or C; D214 replaced with H, K, R, A, G, I, L, S, T, M, V, N, Q, F, W, Y, P, or C; S215 replaced with D, E, H, K, R, N, Q, F, W, Y, P, or C; L216 replaced with D, E, H, K, R, N, Q, F, W, Y, P, or C; E217 replaced with H, K, R, A, G, I, L, S, T, M, V, N, Q, F, W, Y, P, or C; V218 replaced with D, E, H, K, R, N, Q, F, W, Y, P, or C; E219 replaced with H, K, R, A, G, I, L, S, T, M, V, N, Q, F, W, Y, P, or C; G220 replaced with D, E, H, K, R, N, Q, F, W, Y, P, or C; Y221 replaced with D, E, H, K, R, N, Q, A, G, I, L, S, T, M, V, P, or C; T222 replaced with D, E, H, K, R, N, Q, F, W, Y, P, or C; V223 replaced with D, E, H, K, R, N, Q, F, W, Y, P, or C; D224 replaced with H, K, R, A, G, I, L, S, T, M, V, N, Q, F, W, Y, P, or C; V225 replaced with D, E, H, K, R, N, Q, F, W, Y, P, or C; K226 replaced with D, E, A, G, I, L, S, T, M, V, N, Q, F, W, Y, P, or C; N227 replaced with D, E, H, K, R, A, G, I, L, S, T, M, V, F, W, Y, P, or C; K228 replaced with D, E, A, G, I, L, S, T, M, V, N, Q, F, W, Y, P, or C; R229 replaced with D, E, A, G, I, L, S, T, M, V, N, Q, F, W, Y, P, or C; T230 replaced with D, E, H, K, R, N, Q, F, W, Y, P, or C; F231 replaced with D, E, H, K, R, N, Q, A, G, I, L, S, T, M, V, P, or C; L232 replaced with D, E, H, K, R, N, Q, F, W, Y, P, or C; S233 replaced with D, E, H, K, R, N, Q, F, W, Y, P, or C; P234 replaced with D, E, H, K, R, A, G, I, L, S, T, M, V, N, Q, F, W, Y, or C; W235 replaced with D, E, H, K, R, N, Q, A, G, I, L, S, T, M, V, P, or C; I236 replaced with D, E, H, K, R, N, Q, F, W, Y, P, or C; S237 replaced with D, E, H, K, R, N, Q, F, W, Y, P, or C; N238 replaced with D, E, H, K, R, A, G, I, L, S, T, M, V, F, W, Y, P, or C; I239 replaced with D, E, H, K, R, N, Q, F, W, Y, P, or C; H240 replaced with D, E, A, G, I, L, S, T, M, V, N, Q, F, W, Y, P, or C; E241 replaced with H, K, R, A, G, I, L, S, T, M, V, N, Q, F, W, Y, P, or C; K242 replaced with D, E, A, G, I, L, S, T, M, V, N, Q, F, W, Y, P, or C; K243 replaced with D, E, A, G, I, L, S, T, M, V, N, Q, F, W, Y, P, or C; G244 replaced with D, E, H, K, R, N, Q, F, W, Y, P, or C; L245 replaced with D, E, H, K, R, N, Q, F, W, Y, P, or C; T246 replaced with D, E, H, K, R, N, Q, F, W, Y, P, or C; K247 replaced with D, E, A, G, I, L, S, T, M, V, N, Q, F, W, Y, P, or C; Y248 replaced with D, E, H, K, R, N, Q, A, G, I, L, S, T, M, V, P, or C; K249 replaced with D, E, A, G, I, L, S, T, M, V, N, Q, F, W, Y, P, or C; S250 replaced with D, E, H, K, R, N, Q, F, W, Y, P, or C; S251 replaced with D, E, H, K, R, N, Q, F, W, Y, P, or C; P252 replaced with D, E, H, K, R, A, G, I, L, S, T, M, V, N, Q, F, W, Y, or C; E253 replaced with H, K, R, A, G, I, L, S, T, M, V, N, Q, F, W, Y, P, or C; K254 replaced with D, E, A, G, I, L, S, T, M, V, N, Q, F, W, Y, P, or C; W255 replaced with D, E, H, K, R, N, Q, A, G, I, L, S, T, M, V, P, or C; S256 replaced with D, E, H, K, R, N, Q, F, W, Y, P, or C; T257 replaced with D, E, H, K, R, N, Q, F, W, Y, P, or C; A258 replaced with D, E, H, K, R, N, Q, F, W, Y, P, or C; S259 replaced with D, E, H, K, R, N, Q, F, W, Y, P, or C; D260 replaced with H, K, R, A, G, L, S, T, M, V, N, Q, F, W, Y, P, or C; P261 replaced with D, E, H, K, R, A, G, I, L, S, T, M, V, N, Q, F, W, Y, or C; Y262 replaced with D, E, H, K, R, N, Q, A, G, I, L, S, T, M, V, P, or C; S263 replaced with D, E, H, K, R, N, Q, F, W, Y, P, or C; D264 replaced with H, K, R, A, G, I, L, S, T, M, V, N, Q, F, W, Y, P, or C; F265 replaced with D, E, H, K, R, N, Q, A, G, I, L, S, T, M, V, P, or C; E266 replaced with H, K, R, A, G, I, L, S, T, M, V, N, Q, F, W, Y, P, or C; K267 replaced with D, E, A, G, I, L, S, T, M, V, N, Q, F, W, Y, P, or C; V268 replaced with D, E, H, K, R, N, Q, F, W, Y, P, or C; T269 replaced with D, E, H, K, R, N, Q, F, W, Y, P, or C; G270 replaced with D, E, H, K, R, N, Q, F, W, Y, P, or C; R271 replaced with D, E, A, G, I, L, S, T, M, V, N, Q, F, W, Y, P, or C; I272 replaced with D, E, H, K, R, N, Q, F, W, Y, P, or C; D273 replaced with H, K, R, A, G, I, L, S, T, M, V, N, Q, F, W, Y, P, or C; K274 replaced with D, E, A, G, I, L, S, T, M, V, N, Q, F, W, Y, P, or C; N275 replaced with D, E, H, K, R, A, G, I, L, S, T, M, V, F, W, Y, P, or C; V276 replaced with D, E, H, K, R, N, Q, F, W, Y, P, or C; S277 replaced with D, E, H, K, R, N, Q, F, W, Y, P, or C; P278 replaced with D, E, H, K, R, A, G, I, L, S, T, M, V, N, Q, F, W, Y, or C; E279 replaced with H, K, R, A, G, I, L, S, T, M, V, N, Q, F, W, Y, P, or C; A280 replaced with D, E, H, K, R, N, Q, F, W, Y, P, or C; R281 replaced with D, E, A, G, I, L, S, T, M, V, N, Q, F, W, Y, P, or C; H282 replaced with D, E, A, G, I, L, S, T, M, V, N, Q, F, W, Y, P, or C; P283 replaced with D, E, H, K, R, A, G, I, L, S, T, M, V, N, Q, F, W, Y, or C; L284 replaced with D, E, H, K, R, N, Q, F, W, Y, P, or C; V285 replaced with D, E, H, K, R, N, Q, F, W, Y, P, or C; A286 replaced with D, E, H, K, R, N, Q, F, W, Y, P, or C; A287 replaced with D, E, H, K, R, N, Q, F, W, Y, P, or C; Y288 replaced with D, E, H, K, R, N, Q, A, G, I, L, S, T, M, V, P, or C; P289 replaced with D, E, H, K, R, A, G, I, L, S, T, M, V, N, Q, F, W, Y, or C; I290 replaced with D, E, H, K, R, N, Q, F, W, Y, P, or C; V291 replaced with D, E, H, K, R, N, Q, F, W, Y, P, or C; H292 replaced with D, E, A, G, I, L, S, T, M, V, N, Q, F, W, Y, P, or C; V293 replaced with D, E, H, K, R, N, Q, F, W, Y, P, or C; D294 replaced with H, K, R, A, G, I, L, S, T, M, V, N, Q, F, W, Y, P, or C; M295 replaced with D, E, H, K, R, N, Q, F, W, Y, P, or C; E296 replaced with H, K, R, A, G, I, L, S, T, M, V, N, Q, F, W, Y, P, or C; N297 replaced with D, E, H, K, R, A, G, I, L, S, T, M, V, F, W, Y, P, or C; I298 replaced with D, E, H, K, R, N, Q, F, W, Y, P, or C; I299 replaced with D, E, H, K, R, N, Q, F, W, Y, P, or C; L300 replaced with D, E, H, K, R, N, Q, F, W, Y, P, or C; S301 replaced with D, E, H, K, R, N, Q, F, W, Y, P, or C; K302 replaced with D, E, A, G, I, L, S, T, M, V, N, Q, F, W, Y, P, or C; N303 replaced with D, E, H, K, R, A, G, I, L, S, T, M, V, F, W, Y, P, or C; E304 replaced with H, K, R, A, G, I, L, S, T, M, V, N, Q, F, W, Y, P, or C; D305 replaced with H, K, R, A, G, I, L, S, T, M, V, N, Q, F, W, Y, P, or C; Q306 replaced with D, E, H, K, R, A, G, I, L, S, T, M, V, F, W, Y, P, or C; S307 replaced with D, E, H, K, R, N, Q, F, W, Y, P, or C; T308 replaced with D, E, H, K, R, N, Q, F, W, Y, P, or C; Q309 replaced with D, E, H, K, R, A, G, I, L, S, T, M, V, F, W, Y, P, or C; N310 replaced with D, E, H, K, R, A, G, I, L, S, T, M, V, F, W, Y, P, or C; T311 replaced with D, E, H, K, R, N, Q, F, W, Y, P, or C; D312 replaced with H, K, R, A, G, I, L, S, T, M, V, N, Q, F, W, Y, P, or C; S313 replaced with D, E, H, K, R, N, Q, F, W, Y, P, or C; Q314 replaced with D, E, H, K, R, A, G, I, L, S, T, M, V, F, W, Y, P, or C; T315 replaced with D, E, H, K, R, N, Q, F, W, Y, P, or C; R316 replaced with D, E, A, G, I, L, S, T, M, V, N, Q, F, W, Y, P, or C; T317 replaced with D, E, H, K, R, N, Q, F, W, Y, P, or C; I318 replaced with D, E, H, K, R, N, Q, F, W, Y, P, or C; S319 replaced with D, E, H, K, R, N, Q, F, W, Y, P, or C; K320 replaced with D, E, A, G, I, L, S, T, M, V, N, Q, F, W, Y, P, or C; N321 replaced with D, E, H, K, R, A, G, I, L, S, T, M, V, F, W, Y, P, or C; T322 replaced with D, E, H, K, R, N, Q, F, W, Y, P, or C; S323 replaced with D, E, H, K, R, N, Q, F, W, Y, P, or C; T324 replaced with D, E, H, K, R, N, Q, F, W, Y, P, or C; S325 replaced with D, E, H, K, R, N, Q, F, W, Y, P, or C; R326 replaced with D, E, A, G, I, L, S, T, M, V, N, Q, F, W, Y, P, or C; T327 replaced with D, E, H, K, R, N, Q, F, W, Y, P, or C; H328 replaced with D, E, A, G, I, L, S, T, M, V, N, Q, F, W, Y, P, or C; T329 replaced with D, E, H, K, R, N, Q, F, W, Y, P, or C; S330 replaced with D, E, H, K, R, N, Q, F, W, Y, P, or C; E331 replaced with H, K, R, A, G, I, L, S, T, M, V, N, Q, F, W, Y, P, or C; V332 replaced with D, E, H, K, R, N, Q, F, W, Y, P, or C; H333 replaced with D, E, A, G, I, L, S, T, M, V, N, Q, F, W, Y, P, or C; G334 replaced with D, E, H, K, R, N, Q, F, W, Y, P, or C; N335 replaced with D, E, H, K, R, A, G, I, L, S, T, M, V, F, W, Y, P, or C; A336 replaced with D, E, H, K, R, N, Q, F, W, Y, P, or C; E337 replaced with H, K, R, A, G, I, L, S, T, M, V, N, Q, F, W, Y, P, or C; V338 replaced with D, E, H, K, R, N, Q, F, W, Y, P, or C; H339 replaced with D, E, A, G, I, L, S, T, M, V, N, Q, F, W, Y, P, or C; A340 replaced with D, E, H, K, R, N, Q, F, W, Y, P, or C; S341 replaced with D, E, H, K, R, N, Q, F, W, Y, P, or C; F342 replaced with D, E, H, K, R, N, Q, A, G, I, L, S, T, M, V, P, or C; F343 replaced with D, E, H, K, R, N, Q, A, G, I, L, S, T, M, V, P, or C; D344 replaced with H, K, R, A, G, I, L, S, T, M, V, N, Q, F, W, Y, P, or C; I345 replaced with D, E, H, K, R, N, Q, F, W, Y, P, or C; G346 replaced with D, E, H, K, R, N, Q, F, W, Y, P, or C; G347 replaced with D, E, H, K, R, N, Q, F, W, Y, P, or C; S348 replaced with D, E, H, K, R, N, Q, F, W, Y, P, or C; V349 replaced with D, E, H, K, R, N, Q, F, W, Y, P, or C; S350 replaced with D, E, H, K, R, N, Q, F, W, Y, P, or C; A351 replaced with D, E, H, K, R, N, Q, F, W, Y, P, or C; G352 replaced with D, E, H, K, R, N, Q, F, W, Y, P, or C; F353 replaced with D, E, H, K, R, N, Q, A, G, I, L, S, T, M, V, P, or C; S354 replaced with D, E, H, K, R, N, Q, F, W, Y, P, or C; N355 replaced with D, E, K, R, A, G, I, L, S, T, M, V, F, W, Y, P, or C; S356 replaced with D, E, H, K, R, N, Q, F, W, Y, P, or C; N357 replaced with D, E, H, K, R, A, G, I, L, S, T, M, V, F, W, Y, P, or C; S358 replaced with D, E, H, K, R, N, Q, F, W, Y, P, or C; S359 replaced with D, E, H, K, R, N, Q, F, W, Y, P, or C; T360 replaced with D, E, H, K, R, N, Q, F, W, Y, P, or C; V361 replaced with D, E, H, K, R, N, Q, F, W, Y, P, or C; A362 replaced with D, E, H, K, R, N, Q, F, W, Y, P, or C; I363 replaced with D, E, H, K, R, N, Q, F, W, Y, P, or C; D364 replaced with H, K, R, A, G, I, L, S, T, M, V, N, Q, F, W, Y, P, or C; H365 replaced with D, E, A, G, I, L, S, T, M, V, N, Q, F, W, Y, P, or C; S366 replaced with D, E, H, K, R, N, Q, F, W, Y, P, or C; L367 replaced with D, E, H, K, R, N, Q, F, W, Y, P, or C; S368 replaced with D, E, H, K, R, N, Q, F, W, Y, P, or C; L369 replaced with D, E, H, K, R, N, Q, F, W, Y, P, or C; A370 replaced with D, E, H, K, R, N, Q, F, W, Y, P, or C; G371 replaced with D, E, H, K, R, N, Q, F, W, Y, P, or C; E372 replaced with H, K, R, A, G, I, L, S, T, M, V, N, Q, F, W, Y, P, or C; R373 replaced with D, E, A, G, I, L, S, T, M, V, N, Q, F, W, Y, P, or C; T374 replaced with D, E, H, K, R, N, Q, F, W, Y, P, or C; W375 replaced with D, E, H, K, R, N, Q, A, G, I, L, S, T, M, V, P, or C; A376 replaced with D, E, H, K, R, N, Q, F, W, Y, P, or C; E377 replaced with H, K, R, A, G, I, L, S, T, M, V, N, Q, F, W, Y, P, or C; T378 replaced with D, E, H, K, R, N, Q, F, W, Y, P, or C; M379 replaced with D, E, H, K, R, N, Q, F, W, Y, P, or C; G380 replaced with D, E, H, K, R, N, Q, F, W, Y, P, or C; L381 replaced with D, E, H, K, R, N, Q, F, W, Y, P, or C; N382 replaced with D, E, H, K, R, A, G, I, L, S, T, M, V, F, W, Y, P, or C; T383 replaced with D, E, H, K, R, N, Q, F, W, Y, P, or C; A384 replaced with D, E, H, K, R, N, Q, F, W, Y, P, or C; D385 replaced with H, K, R, A, G, I, L, S, T, M, V, N, Q, F, W, Y, P, or C; T386 replaced with D, E, H, K, R, N, Q, F, W, Y, P, or C; A387 replaced with D, E, H, K, R, N, Q, F, W, Y, P, or C; R388 replaced with D, E, A, G, I, L, S, T, M, V, N, Q, F, W, Y, P, or C; L389 replaced with D, E, H, K, R, N, Q, F, W, Y, P, or C; N390 replaced with D, E, H, K, R, A, G, I, L, S, T, M, V, F, W, Y, P, or C; A391 replaced with D, E, H, K, R, N, Q, F, W, Y, P, or C; N392 replaced with D, E, H, K, R, A, G, I, L, S, T, M, V, F, W, Y, P, or C; I393 replaced with D, E, H, K, R, N, Q, F, W, Y, P, or C; R394 replaced with D, E, A, G, I, L, S, T, M, V, N, Q, F, W, Y, P, or C; Y395 replaced with D, E, H, K, R, N, Q, A, G, I, L, S, T, M, V, P, or C; V396 replaced with D, E, H, K, R, N, Q, F, W, Y, P, or C; N397 replaced with D, E, H, K, R, A, G, I, L, S, T, M, V, F, W, Y, P, or C; T398 replaced with D, E, H, K, R, N, Q, F, W, Y, P, or C; G399 replaced with D, E, H, K, R, N, Q, F, W, Y, P, or C; T400 replaced with D, E, H, K, R, N, Q, F, W, Y, P, or C; A401 replaced with D, E, H, K, R, N, Q, F, W, Y, P, or C; P402 replaced with D, E, H, K, R, A, G, I, L, S, T, M, V, N, Q, F, W, Y, or C; I403 replaced with D, E, H, K, R, N, Q, F, W, Y, P, or C; Y404 replaced with D, E, H, K, R, N, Q, A, G, I, L, S, T, M, V, P, or C; N405 replaced with D, E, H, K, R, A, G, I, L, S, T, M, V, F, W, Y, P, or C; V406 replaced with D, E, H, K, R, N, Q, F, W, Y, P, or C; L407 replaced with D, E, H, K, R, N, Q, F, W, Y, P, or C; P408 replaced with D, E, H, K, R, A, G, I, L, S, T, M, V, N, Q, F, W, Y, or C; T409 replaced with D, E, H, K, R, N, Q, F, W, Y, P, or C; T410 replaced with D, E, H, K, R, N, Q, F, W, Y, P, or C; S411 replaced with D, E, H, K, R, N, Q, F, W, Y, P, or C; L412 replaced with D, E, H, K, R, N, Q, F, W, Y, P, or C; V413 replaced with D, E, H, K, R, N, Q, F, W, Y, P, or C; L414 replaced with D, E, H, K, R, N, Q, F, W, Y, P, or C; G415 replaced with D, E, H, K, R, N, Q, F, W, Y, P, or C; K416 replaced with D, E, A, G, I, L, S, T, M, V, N, Q, F, W, Y, P, or C; N417 replaced with D, E, H, K, R, A, G, I, L, S, T, M, V, F, W, Y, P, or C; Q418 replaced with D, E, H, K, R, A, G, I, L, S, T, M, V, F, W, Y, P, or C; T419 replaced with D, E, H, K, R, N, Q, F, W, Y, P, or C; L420 replaced with D, E, H, K, R, N, Q, F, W, Y, P, or C; A421 replaced with D, E, H, K, R, N, Q, F, W, Y, P, or C; T422 replaced with D, E, H, K, R, N, Q, F, W, Y, P, or C; I423 replaced with D, E, H, K, R, N, Q, F, W, Y, P, or C; K424 replaced with D, E, A, G, I, L, S, T, M, V, N, Q, F, W, Y, P, or C; A425 replaced with D, E, H, K, R, N, Q, F, W, Y, P, or C; K426 replaced with D, E, A, G, I, L, S, T, M, V, N, Q, F, W, Y, P, or C; E427 replaced with H, K, R, A, G, I, L, S, T, M, V, N, Q, F, W, Y, P, or C; N428 replaced with D, E, H, K, R, A, G, I, L, S, T, M, V, F, W, Y, P, or C; Q429 replaced with D, E, H, K, R, A, G, I, L, S, T, M, V, F, W, Y, P, or C; L430 replaced with D, E, H, K, R, N, Q, F, W, Y, P, or C; S431 replaced with D, E, H, K, R, N, Q, F, W, Y, P, or C; Q432 replaced with D, E, H, K, R, A, G, I, L, S, T, M, V, F, W, Y, P, or C; I433 replaced with D, E, H, K, R, N, Q, F, W, Y, P, or C; L434 replaced with D, E, H, K, R, N, Q, F, W, Y, P, or C; A435 replaced with D, E, H, K, R, N, Q, F, W, Y, P, or C; P436 replaced with D, E, H, K, R, A, G, I, L, S, T, M, V, N, Q, F, W, Y, or C; N437 replaced with D, E, H, K, R, A, G, I, L, S, T, M, V, F, W, Y, P, or C; N438 replaced with D, E, H, K, R, A, G, I, L, S, T, M, V, F, W, Y, P, or C; Y439 replaced with D, E, H, K, R, N, Q, A, G, I, L, S, T, M, V, P, or C; Y440 replaced with D, E, H, K, R, N, Q, A, G, I, L, S, T, M, V, P, or C; P441 replaced with D, E, H, K, R, A, G, I, L, S, T, M, V, N, Q, F, W, Y, or C; S442 replaced with D, E, H, K, R, N, Q, F, W, Y, P, or C; K443 replaced with D, E, A, G, I, L, S, T, M, V, N, Q, F, W, Y, P, or C; N444 replaced with D, E, H, K, R, A, G, I, L, S, T, M, V, F, W, Y, P, or C; L445 replaced with D, E, H, K, R, N, Q, F, W, Y, P, or C; A446 replaced with D, E, H, K, R, N, Q, F, W, Y, P, or C; P447 replaced with D, E, H, K, R, A, G, I, L, S, T, M, V, N, Q, F, W, Y, or C; I448 replaced with D, E, H, K, R, N, Q, F, W, Y, P, or C; A449 replaced with D, E, H, K, R, N, Q, F, W, Y, P, or C; L450 replaced with D, E, H, K, R, N, Q, F, W, Y, P, or C; N451 replaced with D, E, H, K, R, A, G, I, L, S, T, M, V, F, W, Y, P, or C; A452 replaced with D, E, H, K, R, N, Q, F, W, Y, P, or C; Q453 replaced with D, E, H, K, R, A, G, I, L, S, T, M, V, F, W, Y, P, or C; D454 replaced with H, K, R, A, G, I, L, S, T, M, V, N, Q, F, W, Y, P, or C; D455 replaced with H, K, R, A, G, I, L, S, T, M, V, N, Q, F, W, Y, P, or C; F456 replaced with D, E, H, K, R, N, Q, A, G, I, L, S, T, M, V, P, or C; S457 replaced with D, E, H, K, R, N, Q, F, W, Y, P, or C; S458 replaced with D, E, H, K, R, N, Q, F, W, Y, P, or C; T459 replaced with D, E, H, K, R, N, Q, F, W, Y, P, or C; P460 replaced with D, E, H, K, R, A, G, I, L, S, T, M, V, N, Q, F, W, Y, or C; I461 replaced with D, E, H, K, R, N, Q, F, W, Y, P, or C; T462 replaced with D, E, H, K, R, N, Q, F, W, Y, P, or C; M463 replaced with D, E, H, K, R, N, Q, F, W, Y, P, or C; N464 replaced with D, E, H, K, R, A, G, I, L, S, T, M, V, F, W, Y, P, or C; Y465 replaced with D, E, H, K, R, N, Q, A, G, I, L, S, T, M, V, P, or C; N466 replaced with D, E, H, K, R, A, G, I, L, S, T, M, V, F, W, Y, P, or C; Q467 replaced with D, E, H, K, R, A, G, I, L, S, T, M, V, F, W, Y, P, or C; F468 replaced with D, E, H, K, R, N, Q, A, G, I, L, S, T, M, V, P, or C; L469 replaced with D, E, H, K, R, N, Q, F, W, Y, P, or C; E470 replaced with H, K, R, A, G, I, L, S, T, M, V, N, Q, F, W, Y, P, or C; L471 replaced with D, E, H, K, R, N, Q, F, W, Y, P, or C; E472 replaced with H, K, R, A, G, I, L, S, T, M, V, N, Q, F, W, Y, P, or C; K473 replaced with D, E, A, G, I, L, S, T, M, V, N, Q, F, W, Y, P, or C; T474 replaced with D, E, H, K, R, N, Q, F, W, Y, P, or C; K475 replaced with D, E, A, G, I, L, S, T, M, V, N, Q, F, W, Y, P, or C; Q476 replaced with D, E, H, K, R, A, G, I, L, S, T, M, V, F, W, Y, P, or C; L477 replaced with D, E, H, K, R, N, Q, F, W, Y, P, or C; R478 replaced with D, E, A, G, I, L, S, T, M, V, N, Q, F, W, Y, P, or C; L479 replaced with D, E, H, K, R, N, Q, F, W, Y, P, or C; D480 replaced with H, K, R, A, G, I, L, S, T, M, V, N, Q, F, W, Y, P, or C; T481 replaced with D, E, H, K, R, N, Q, F, W, Y, P, or C; D482 replaced with H, K, R, A, G, I, L, S, T, M, V, N, Q, F, W, Y, P, or C; Q483 replaced with D, E, H, K, R, A, G, I, L, S, T, M, V, F, W, Y, P, or C; V484 replaced with D, E, H, K, R, N, Q, F, W, Y, P, or C; Y485 replaced with D, E, H, K, R, N, Q, A, G, I, L, S, T, M, V, P, or C; G486 replaced with D, E, H, K, R, N, Q, F, W, Y, P, or C; N487 replaced with D, E, H, K, R, A, G, I, L, S, T, M, V, F, W, Y, P, or C; I488 replaced with D, E, H, K, R, N, Q, F, W, Y, P, or C; A489 replaced with D, E, H, K, R, N, Q, F, W, Y, P, or C; T490 replaced with D, E, H, K, R, N, Q, F, W, Y, P, or C; Y491 replaced with D, E, H, K, R, N, Q, A, G, I, L, S, T, M, V, P, or C; N492 replaced with D, E, H, K, R, A, G, I, L, S, T, M, V, F, W, Y, P, or C; F493 replaced with D, E, H, K, R, N, Q, A, G, I, L, S, T, M, V, P, or C; E494 replaced with H, K, R, A, G, I, L, S, T, M, V, N, Q, F, W, Y, P, or C; N495 replaced with D, E, H, K, R, A, G, I, L, S, T, M, V, F, W, Y, P, or C; G496 replaced with D, E, H, K, R, N, Q, F, W, Y, P, or C; R497 replaced with D, E, A, G, I, L, S, T, M, V, N, Q, F, W, Y, P, or C; V498 replaced with D, E, H, K, R, N, Q, F, W, Y, P, or C; R499 replaced with D, E, A, G, I, L, S, T, M, V, N, Q, F, W, Y, P, or C; V500 replaced with D, E, H, K, R, N, Q, F, W, Y, P, or C; D501 replaced with H, K, R, A, G, I, L, S, T, M, V, N, Q, F, W, Y, P, or C; T502 replaced with D, E, H, K, R, N, Q, F, W, Y, P, or C; G503 replaced with D, E, H, K, R, N, Q, F, W, Y, P, or C; S504 replaced with D, E, H, K, R, N, Q, F, W, Y, P, or C; N505 replaced with D, E, H, K, R, A, G, I, L, S, T, M, V, F, W, Y, P, or C; W506 replaced with D, E, H, K, R, N, Q, A, G, I, L, S, T, M, V, P, or C; S507 replaced with D, E, H, K, R, N, Q, F, W, Y, P, or C; E508 replaced with H, K, R, A, G, I, L, S, T, M, V, N, Q, F, W, Y, P, or C; V509 replaced with D, E, H, K, R, N, Q, F, W, Y, P, or C; L510 replaced with D, E, H, K, R, N, Q, F, W, Y, P, or C; P511 replaced with D, E, H, K, R, A, G, I, L, S, T, M, V, N, Q, F, W, Y, or C; Q512 replaced with D, E, H, K, R, A, G, I, L, S, T, M, V, F, W, Y, P, or C; I513 replaced with D, E, H, K, R, N, Q, F, W, Y, P, or C; Q514 replaced with D, E, H, K, R, A, G, I, L, S, T, M, V, F, W, Y, P, or C; E515 replaced with H, K, R, A, G, I, L, S, T, M, V, N, Q, F, W, Y, P, or C; T516 replaced with D, E, H, K, R, N, Q, F, W, Y, P, or C; T517 replaced with D, E, H, K, R, N, Q, F, W, Y, P, or C; A518 replaced with D, E, H, K, R, N, Q, F, W, Y, P, or C; R519 replaced with D, E, A, G, I, L, S, T, M, V, N, Q, F, W, Y, P, or C; I520 replaced with D, E, H, K, R, N, Q, F, W, Y, P, or C; I521 replaced with D, E, H, K, R, N, Q, F, W, Y, P, or C; F522 replaced with D, E, H, K, R, N, Q, A, G, I, L, S, T, M, V, P, or C; N523 replaced with D, E, H, K, R, A, G, I, L, S, T, M, V, F, W, Y, P, or C; G524 replaced with D, E, H, K, R, N, Q, F, W, Y, P, or C; K525 replaced with D, E, A, G, I, L, S, T, M, V, N, Q, F, W, Y, P, or C; D526 replaced with H, K, R, A, G, I, L, S, T, M, V, N, Q, F, W, Y, P, or C; L527 replaced with D, E, H, K, R, N, Q, F, W, Y, P, or C; N528 replaced with D, E, H, K, R, A, G, I, L, S, T, M, V, F, W, Y, P, or C; L529 replaced with D, E, H, K, R, N, Q, F, W, Y, P, or C; V530 replaced with D, E, H, K, R, N, Q, F, W, Y, P, or C; E531 replaced with H, K, R, A, G, I, L, S, T, M, V, N, Q, F, W, Y, P, or C; R532 replaced with D, E, A, G, I, L, S, T, M, V, N, Q, F, W, Y, P, or C; R533 replaced with D, E, A, G, I, L, S, T, M, V, N, Q, F, W, Y, P, or C; I534 replaced with D, E, H, K, R, N, Q, F, W, Y, P, or C; A535 replaced with D, E, H, K, R, N, Q, F, W, Y, P, or C; A536 replaced with D, E, H, K, R, N, Q, F, W, Y, P, or C; V537 replaced with D, E, H, K, R, N, Q, F, W, Y, P, or C; N538 replaced with D, E, H, K, R, A, G, I, L, S, T, M, V, F, W, Y, P, or C; P539 replaced with D, E, H, K, R, A, G, I, L, S, T, M, V, N, Q, F, W, Y, or C; S540 replaced with D, E, H, K, R, N, Q, F, W, Y, P, or C; D541 replaced with H, K, R, A, G, I, L, S, T, M, V, N, Q, F, W, Y, P, or C; P542 replaced with D, E, H, K, R, A, G, I, L, S, T, M, V, N, Q, F, W, Y, or C; L543 replaced with D, E, H, K, R, N, Q, F, W, Y, P, or C; E544 replaced with H, K, R, A, G, I, L, S, T, M, V, N, Q, F, W, Y, P, or C; T545 replaced with D, E, H, K, R, N, Q, F, W, Y, P, or C; T546 replaced with D, E, H, K, R, N, Q, F, W, Y, P, or C; K547 replaced with D, E, A, G, I, L, S, T, M, V, N, Q, F, W, Y, P, or C; P548 replaced with D, E, H, K, R, A, G, I, L, S, T, M, V, N, Q, F, W, Y, or C; D549 replaced with H, K, R, A, G, I, L, S, T, M, V, N, Q, F, W, Y, P, or C; M550 replaced with D, E, H, K, R, N, Q, F, W, Y, P, or C; T551 replaced with D, E, H, K, R, N, Q, F, W, Y, P, or C; L552 replaced with D, E, H, K, R, N, Q, F, W, Y, P, or C; K553 replaced with D, E, A, G, I, L, S, T, M, V, N, Q, F, W, Y, P, or C; E554 replaced with H, K, R, A, G, I, L, S, T, M, V, N, Q, F, W, Y, P, or C; A555 replaced with D, E, H, K, R, N, Q, F, W, Y, P, or C; L556 replaced with D, E, H, K, R, N, Q, F, W, Y, P, or C; K557 replaced with D, E, A, G, I, L, S, T, M, V, N, Q, F, W, Y, P, or C; I558 replaced with D, E, H, K, R, N, Q, F, W, Y, P, or C; A559 replaced with D, E, H, K, R, N, Q, F, W, Y, P, or C; F560 replaced with D, E, H, K, R, N, Q, A, G, I, L, S, T, M, V, P, or C; G561 replaced with D, E, H, K, R, N, Q, F, W, Y, P, or C; F562 replaced with D, E, H, K, R, N, Q, A, G, I, L, S, T, M, V, P, or C; N563 replaced with D, E, H, K, R, A, G, I, L, S, T, M, V, F, W, Y, P, or C; E564 replaced with H, K, R, A, G, I, L, S, T, M, V, N, Q, F, W, Y, P, or C; P565 replaced with D, E, H, K, R, A, G, I, L, S, T, M, V, N, Q, F, W, Y, or C; N566 replaced with D, E, H, K, R, A, G, I, L, S, T, M, V, F, W, Y, P, or C; G567 replaced with D, E, H, K, R, N, Q, F, W, Y, P, or C; N568 replaced with D, E, H, K, R, A, G, I, L, S, T, M, V, F, W, Y, P, or C; L569 replaced with D, E, H, K, R, N, Q, F, W, Y, P, or C; Q570 replaced with D, E, H, K, R, A, G, I, L, S, T, M, V, F, W, Y, P, or C; Y571 replaced with D, E, H, K, R, N, Q, A, G, I, L, S, T, M, V, P, or C; Q572 replaced with D, E, H, K, R, A, G, I, L, S, T, M, V, F, W, Y, P, or C; G573 replaced with D, E, H, K, R, N, Q, F, W, Y, P, or C; K574 replaced with D, E, A, G, I, L, S, T, M, V, N, Q, F, W, Y, P, or C; D575 replaced with H, K, R, A, G, I, L, S, T, M, V, N, Q, F, W, Y, P, or C; I576 replaced with D, E, H, K, R, N, Q, F, W, Y, P, or C; T577 replaced with D, E, H, K, R, N, Q, F, W, Y, P, or C; E578 replaced with H, K, R, A, G, I, L, S, T, M, V, N, Q, F, W, Y, P, or C; F579 replaced with D, E, H, K, R, N, Q, A, G, I, L, S, T, M, V, P, or C; D580 replaced with H, K, R, A, G, I, L, S, T, M, V, N, Q, F, W, Y, P, or C; F581 replaced with D, E, H, K, R, N, Q, A, G, I, L, S, T, M, V, P, or C; N582 replaced with D, E, H, K, R, A, G, I, L, S, T, M, V, F, W, Y, P, or C; F583 replaced with D, E, H, K, R, N, Q, A, G, I, L, S, T, M, V, P, or C; D584 replaced with H, K, R, A, G, I, L, S, T, M, V, N, Q, F, W, Y, P, or C; Q585 replaced with D, E, H, K, R, A, G, I, L, S, T, M, V, F, W, Y, P, or C; Q586 replaced with D, E, H, K, R, A, G, I, L, S, T, M, V, F, W, Y, P, or C; T587 replaced with D, E, H, K, R, N, Q, F, W, Y, P, or C; S588 replaced with D, E, H, K, R, N, Q, F, W, Y, P, or C; Q589 replaced with D, E, H, K, R, A, G, I, L, S, T, M, V, F, W, Y, P, or C; N590 replaced with D, E, H, K, R, A, G, I, L, S, T, M, V, F, W, Y, P, or C; I591 replaced with D, E, H, K, R, N, Q, F, W, Y, P, or C; K592 replaced with D, E, A, G, I, L, S, T, M, V, N, Q, F, W, Y, P, or C; N593 replaced with D, E, H, K, R, A, G, I, L, S, T, M, V, F, W, Y, P, or C; Q594 replaced with D, E, H, K, R, A, G, I, L, S, T, M, V, F, W, Y, P, or C; L595 replaced with D, E, H, K, R, N, Q, F, W, Y, P, or C; A596 replaced with D, E, H, K, R, N, Q, F, W, Y, P, or C; E597 replaced with H, K, R, A, G, I, L, S, T, M, V, N, Q, F, W, Y, P, or C; L598 replaced with D, E, H, K, R, N, Q, F, W, Y, P, or C; N599 replaced with D, E, H, K, R, A, G, I, L, S, T, M, V, F, W, Y, P, or C; A600 replaced with D, E, H, K, R, N, Q, F, W, Y, P, or C; T601 replaced with D, E, H, K, R, N, Q, F, W, Y, P, or C; N602 replaced with D, E, H, K, R, A, G, I, L, S, T, M, V, F, W, Y, P, or C; I603 replaced with D, E, H, K, R, N, Q, F, W, Y, P, or C; Y604 replaced with D, E, H, K, R, N, Q, A, G, I, L, S, T, M, V, P, or C; T605 replaced with D, E, H, K, R, N, Q, F, W, Y, P, or C; V606 replaced with D, E, H, K, R, N, Q, F, W, Y, P, or C; L607 replaced with D, E, H, K, R, N, Q, F, W, Y, P, or C; D608 replaced with H, K, R, A, G, I, L, S, T, M, V, N, Q, F, W, Y, P, or C; I0609 replaced with D, E, A, G, I, L, S, T, M, V, N, Q, F, W, Y, P, or C; I610 replaced with D, E, H, K, R, N, Q, F, W, Y, P, or C; K611 replaced with D, E, A, G, I, L, S, T, M, V, N, Q, F, W, Y, P, or C; L612 replaced with D, E, H, K, R, N, Q, F, W, Y, P, or C; N613 replaced with D, E, H, K, R, A, G, I, L, S, T, M, V, F, W, Y, P, or C; A614 replaced with D, E, H, K, R, N, Q, F, W, Y, P, or C; K615 replaced with D, E, A, G, I, L, S, T, M, V, N, Q, F, W, Y, P, or C; M616 replaced with D, E, H, K, R, N, Q, F, W, Y, P, or C; N617 replaced with D, E, H, K, R, A, G, I, L, S, T, M, V, F, W, Y, P, or C; I618 replaced with D, E, H, K, R, N, Q, F, W, Y, P, or C; L619 replaced with D, E, H, K, R, N, Q, F, W, Y, P, or C; I620 replaced with D, E, H, K, R, N, Q, F, W, Y, P, or C; R621 replaced with D, E, A, G, I, L, S, T, M, V, N, Q, F, W, Y, P, or C; D622 replaced with H, K, R, A, G, I, L, S, T, M, V, N, Q, F, W, Y, P, or C; K623 replaced with D, E, A, G, I, L, S, T, M, V, N, Q, F, W, Y, P, or C; R624 replaced with D, E, A, G, I, L, S, T, M, V, N, Q, F, W, Y, P, or C; F625 replaced with D, E, H, K, R, N, Q, A, G, I, L, S, T, M, V, P, or C; H626 replaced with D, E, A, G, I, L, S, T, M, V, N, Q, F, W, Y, P, or C; Y627 replaced with D, E, H, K, R, N, Q, A, G, I, L, S, T, M, V, P, or C; D628 replaced with H, K, R, A, G, I, L, S, T, M, V, N, Q, F, W, Y, P, or C; R629 replaced with D, E, A, G, I, L, S, T, M, V, N, Q, F, W, Y, P, or C; N630 replaced with D, E, H, K, R, A, G, I, L, S, T, M, V, F, W, Y, P, or C; N631 replaced with D, E, H, K, R, A, G, I, L, S, T, M, V, F, W, Y, P, or C; I632 replaced with D, E, H, K, R, N, Q, F, W, Y, P, or C; A633 replaced with D, E, H, K, R, N, Q, F, W, Y, P, or C; V634 replaced with D, E, H, K, R, N, Q, F, W, Y, P, or C; G635 replaced with D, E, H, K, R, N, Q, F, W, Y, P, or C; A636 replaced with D, E, H, K, R, N, Q, F, W, Y, P, or C; D637 replaced with H, K, R, A, G, I, L, S, T, M, V, N, Q, F, W, Y, P, or C; E638 replaced with H, K, R, A, G, I, L, S, T, M, V, N, Q, F, W, Y, P, or C; S639 replaced with D, E, H, K, R, N, Q, F, W, Y, P, or C; V640 replaced with D, E, H, K, R, N, Q, F, W, Y, P, or C; V641 replaced with D, E, H, K, R, N, Q, F, W, Y, P, or C; K642 replaced with D, E, A, G, I, L, S, T, M, V, N, Q, F, W, Y, P, or C; E643 replaced with H, K, R, A, G, I, L, S, T, M, V, N, Q, F, W, Y, P, or C; A644 replaced with D, E, H, K, R, N, Q, F, W, Y, P, or C; H645 replaced with D, E, A, G, I, L, S, T, M, V, N, Q, F, W, Y, P, or C; R646 replaced with D, E, A, G, I, L, S, T, M, V, N, Q, F, W, Y, P, or C; E647 replaced with H, K, R, A, G, I, L, S, T, M, V, N, Q, F, W, Y, P, or C; V648 replaced with D, E, H, K, R, N, Q, F, W, Y, P, or C; I649 replaced with D, E, H, K, R, N, Q, F, W, Y, P, or C; N650 replaced with D, E, H, K, R, A, G, I, L, S, T, M, V, F, W, Y, P, or C; S651 replaced with D, E, H, K, R, N, Q, F, W, Y, P, or C; S652 replaced with D, E, H, K, R, N, Q, F, W, Y, P, or C; T653 replaced with D, E, H, K, R, N, Q, F, W, Y, P, or C; E654 replaced with H, K, R, A, G, I, L, S, T, M, V, N, Q, F, W, Y, P, or C; G655 replaced with D, E, H, K, R, N, Q, F, W, Y, P, or C; L656 replaced with D, E, H, K, R, N, Q, F, W, Y, P, or C; L657 replaced with D, E, H, K, R, N, Q, F, W, Y, P, or C; L658 replaced with D, E, H, K, R, N, Q, F, W, Y, P, or C; N659 replaced with D, E, H, K, R, A, G, I, L, S, T, M, V, F, W, Y, P, or C; I660 replaced with D, E, H, K, R, N, Q, F, W, Y, P, or C; D661 replaced with H, K, R, A, G, I, L, S, T, M, V, N, Q, F, W, Y, P, or C; K662 replaced with D, E, A, G, I, L, S, T, M, V, N, Q, F, W, Y, P, or C; D663 replaced with H, K, R, A, G, I, L, S, T, M, V, N, Q, F, W, Y, P, or C; I664 replaced with D, E, H, K, R, N, Q, F, W, Y, P, or C; R665 replaced with D, E, A, G, I, L, S, T, M, V, N, Q, F, W, Y, P, or C; K666 replaced with D, E, A, G, I, L, S, T, M, V, N, Q, F, W, Y, P, or C; I667 replaced with D, E, H, K, R, N, Q, F, W, Y, P, or C; L668 replaced with D, E, H, K, R, N, Q, F, W, Y, P, or C; S669 replaced with D, E, H, K, R, N, Q, F, W, Y, P, or C; G670 replaced with D, E, H, K, R, N, Q, F, W, Y, P, or C; Y671 replaced with D, E, H, K, R, N, Q, A, G, I, L, S, T, M, V, P, or C; I672 replaced with D, E, H, K, R, N, Q, F, W, Y, P, or C; V673 replaced with D, E, H, K, R, N, Q, F, W, Y, P, or C; E674 replaced with H, K, R, A, G, I, L, S, T, M, V, N, Q, F, W, Y, P, or C; I675 replaced with D, E, H, K, R, N, Q, F, W, Y, P, or C; E676 replaced with H, K, R, A, G, I, L, S, T, M, V, N, Q, F, W, Y, P, or C; D677 replaced with H, K, R, A, G, I, L, S, T, M, V, N, Q, F, W, Y, P, or C; T678 replaced with D, E, H, K, R, N, Q, F, W, Y, P, or C; E679 replaced with H, K, R, A, G, I, L, S, T, M, V, N, Q, F, W, Y, P, or C; G680 replaced with D, E, H, K, R, N, Q, F, W, Y, P, or C; L681 replaced with D, E, H, K, R, N, Q, F, W, Y, P, or C; K682 replaced with D, E, A, G, I, L, S, T, M, V, N, Q, F, W, Y, P, or C; E683 replaced with H, K, R, A, G, I, L, S, T, M, V, N, Q, F, W, Y, P, or C; V684 replaced with D, E, H, K, R, N, Q, F, W, Y, P, or C; I685 replaced with D, E, H, K, R, N, Q, F, W, Y, P, or C; N686 replaced with D, E, H, K, R, A, G, I, L, S, T, M, V, F, W, Y, P, or C; D687 replaced with H, K, R, A, G, I, L, S, T, M, V, N, Q, F, W, Y, P, or C; R688 replaced with D, E, A, G, I, L, S, T, M, V, N, Q, F, W, Y, P, or C; Y689 replaced with D, E, H, K, R, N, Q, A, G, I, L, S, T, M, V, P, or C; D690 replaced with H, K, R, A, G, I, L, S, T, M, V, N, Q, F, W, Y, P, or C; M691 replaced with D, E, H, K, R, N, Q, F, W, Y, P, or C; L692 replaced with D, E, H, K, R, N, Q, F, W, Y, P, or C; N693 replaced with D, E, H, K, R, A, G, I, L, S, T, M, V, F, W, Y, P, or C; I694 replaced with D, E, H, K, R, N, Q, F, W, Y, P, or C; S695 replaced with D, E, H, K, R, N, Q, F, W, Y, P, or C; S696 replaced with D, E, H, K, R, N, Q, F, W, Y, P, or C; L697 replaced with D, E, H, K, R, N, Q, F, W, Y, P, or C; R698 replaced with D, E, A, G, I, L, S, T, M, V, N, Q, F, W, Y, P, or C; Q699 replaced with D, E, H, K, R, A, G, I, L, S, T, M, V, F, W, Y, P, or C; D700 replaced with H, K, R, A, G, I, L, S, T, M, V, N, Q, F, W, Y, P, or C; G701 replaced with D, E, H, K, R, N, Q, F, W, Y, P, or C; K702 replaced with D, E, A, G, I, L, S, T, M, V, N, Q, F, W, Y, P, or C; T703 replaced with D, E, H, K, R, N, Q, F, W, Y, P, or C; F704 replaced with D, E, H, K, R, N, Q, A, G, I, L, S, T, M, V, P, or C; I705 replaced with D, E, H, K, R, N, Q, F, W, Y, P, or C; D706 replaced with H, K, R, A, G, I, L, S, T, M, V, N, Q, F, W, Y, P, or C; F707 replaced with D, E, H, K, R, N, Q, A, G, I, L, S, T, M, V, P, or C; K708 replaced with D, E, A, G, I, L, S, T, M, V, N, Q, F, W, Y, P, or C; K709 replaced with D, E, A, G, I, L, S, T, M, V, N, Q, F, W, Y, P, or C; Y710 replaced with D, E, H, K, R, N, Q, A, G, I, L, S, T, M, V, P, or C; N711 replaced with D, E, H, K, R, A, G, I, L, S, T, M, V, F, W, Y, P, or C; D712 replaced with H, K, R, A, G, I, L, S, T, M, V, N, Q, F, W, Y, P, or C; K713 replaced with D, E, A, G, I, L, S, T, M, V, N, Q, F, W, Y, P, or C; L714 replaced with D, E, H, K, R, N, Q, F, W, Y, P, or C; P715 replaced with D, E, H, K, R, A, G, I, L, S, T, M, V, N, Q, F, W, Y, or C; L716 replaced with D, E, H, K, R, N, Q, F, W, Y, P, or C; Y717 replaced with D, E, H, K, R, N, Q, A, G, I, L, S, T, M, V, P, or C; I718 replaced with D, E, H, K, R, N, Q, F, W, Y, P, or C; S719 replaced with D, E, H, K, R, N, Q, F, W, Y, P, or C; N720 replaced with D, E, H, K, R, A, G, I, L, S, T, M, V, F, W, Y, P, or C; P721 replaced with D, E, H, K, R, A, G, I, L, S, T, M, V, N, Q, F, W, Y, or C; N722 replaced with D, E, H, K, R, A, G, I, L, S, T, M, V, F, W, Y, P, or C; Y723 replaced with D, E, H, K, R, N, Q, A, G, I, L, S, T, M, V, P, or C; K724 replaced with D, E, A, G, I, L, S, T, M, V, N, Q, F, W, Y, P, or C; V725 replaced with D, E, H, K, R, N, Q, F, W, Y, P, or C; N726 replaced with D, E, H, K, R, A, G, I, L, S, T, M, V, F, W, Y, P, or C; V727 replaced with D, E, H, K, R, N, Q, F, W, Y, P, or C; Y728 replaced with D, E, H, K, R, N, Q, A, G, I, L, S, T, M, V, P, or C; A729 replaced with D, E, H, K, R, N, Q, F, W, Y, P, or C; V730 replaced with D, E, H, K, R, N, Q, F, W, Y, P, or C; T731 replaced with D, E, H, K, R, N, Q, F, W, Y, P, or C; K732 replaced with D, E, A, G, I, L, S, T, M, V, N, Q, F, W, Y, P, or C; E733 replaced with H, K, R, A, G, I, L, S, T, M, V, N, Q, F, W, Y, P, or C; N734 replaced with D, E, H, K, R, A, G, I, L, S, T, M, V, F, W, Y, P, or C; T735 replaced with D, E, H, K, R, N, Q, F, W, Y, P, or C; I736 replaced with D, E, H, K, R, N, Q, F, W, Y, P, or C; I737 replaced with D, E, H, K, R, N, Q, F, W, Y, P, or C; N738 replaced with D, E, H, K, R, A, G, I, L, S, T, M, V, F, W, Y, P, or C; P739 replaced with D, E, H, K, R, A, G, I, L, S, T, M, V, N, Q, F, W, Y, or C; S740 replaced with D, E, H, K, R, N, Q, F, W, Y, P, or C; E741 replaced with H, K, R, A, G, I, L, S, T, M, V, N, Q, F, W, Y, P, or C; N742 replaced with D, E, H, K, R, A, G, I, L, S, T, M, V, F, W, Y, P, or C; G743 replaced with D, E, H, K, R, N, Q, F, W, Y, P, or C; D744 replaced with H, K, R, A, G, I, L, S, T, M, V, N, Q, F, W, Y, P, or C; T745 replaced with D, E, H, K, R, N, Q, F, W, Y, P, or C; S746 replaced with D, E, H, K, R, N, Q, F, W, Y, P, or C; T747 replaced with D, E, H, K, R, N, Q, F, W, Y, P, or C; N748 replaced with D, E, H, K, R, A, G, I, L, S, T, M, V, F, W, Y, P, or C; G749 replaced with D, E, H, K, R, N, Q, F, W, Y, P, or C; I750 replaced with D, E, H, K, R, N, Q, F, W, Y, P, or C; K751 replaced with D, E, A, G, I, L, S, T, M, V, N, Q, F, W, Y, P, or C; K752 replaced with D, E, A, G, I, L, S, T, M, V, N, Q, F, W, Y, P, or C; I753 replaced with D, E, H, K, R, N, Q, F, W, Y, P, or C; L754 replaced with D, E, H, K, R, N, Q, F, W, Y, P, or C; I755 replaced with D, E, H, K, R, N, Q, F, W, Y, P, or C; F756 replaced with D, E, H, K, R, N, Q, A, G, I, L, S, T, M, V, P, or C; S757 replaced with D, E, H, K, R, N, Q, F, W, Y, P, or C; K758 replaced with D, E, A, G, I, L, S, T, M, V, N, Q, F, W, Y, P, or C; K759 replaced with D, E, A, G, I, L, S, T, M, V, N, Q, F, W, Y, P, or C; G760 replaced with D, E, H, K, R, N, Q, F, W, Y, P, or C; Y761 replaced with D, E, H, K, R, N, Q, A, G, I, L, S, T, M, V, P, or C; E762 replaced with H, K, R, A, G, I, L, S, T, M, V, N, Q, F, W, Y, P, or C; I763 replaced with D, E, H, K, R, N, Q, F, W, Y, P, or C; G764 replaced with D, E, H, K, R, N, Q, F, W, Y, P, or C; of SEQ ID NO:2.

Amino acids in the PA protein that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or protein multimerization, pore formation, and toxin translocation. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)). In preferred embodiments, antibodies of the present invention bind regions of PA that are essential for PA function. In other preferred embodiments, antibodies of the present invention bind regions of PA that are essential for PA function and inhibit or abolish PA function.

Additionally, protein engineering, may be employed to improve or alter the characteristics of PA polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. Antibodies of the present invention may bind such modified PA polypeptides.

Non-naturally occurring variants of PA may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London Ser A* 317:415 (1986)).

Thus, the invention also encompasses antibodies that bind PA derivatives and analogs that have one or more amino acid residues deleted, added, and/or substituted. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognition sequences in the PA polypeptides and/or an amino acid deletion at the second position of any one or more such recognition sequences will prevent glycosylation of the PA at the modified tripeptide sequence (see, e.g., Miyajimo et al., EMBO J 5(6):1193-1197). Additionally, one or more of the amino acid residues of PA polypeptides (e.g., arginine and lysine residues) may be deleted or substituted with another residue to eliminate undesired processing by proteases such as, for example, furins or kexins.

The antibodies of the present invention also include antibodies that bind a polypeptide comprising, or alternatively, consisting of a polypeptide comprising, or alternatively, consisting of the polypeptide of SEQ ID NO:2 including the leader; a polypeptide comprising, or alternatively, consisting of the polypeptide of SEQ ID NO:2 minus the amino terminal methionine; a polypeptide comprising, or alternatively, consisting of the polypeptide of SEQ ID NO:2 minus the leader; a polypeptide comprising, or alternatively, consisting of the PA domain I; a polypeptide comprising, or alternatively, consisting of the PA domain II; a polypeptide comprising, or alternatively, consisting of the PA domain III; a polypeptide comprising, or alternatively, consisting of the PA domain IV; a polypeptide comprising, or alternatively, consisting of the PA20 fragment; a polypeptide comprising, or alternatively, consisting of the PA63 fragment; as well as polypeptides which are at least 80% identical, more preferably at least 90% or 95% identical, still more preferably at least 96%, 97%, 98% or 99% identical to the polypeptides described above (the polypeptide and polypeptide fragments of SEQ ID NO:2), and portions of such polypeptides with at least 30 amino acids and more preferably at least 50 amino acids.

By a polypeptide having an amino acid sequence at least, for example, 95% "identical" to a reference amino acid sequence of a PA polypeptide is intended that the amino acid sequence of the polypeptide is identical to the reference sequence except that the polypeptide sequence may include up to five amino acid alterations per each 100 amino acids of the reference amino acid of the PA polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to antibodies that bind proteins containing polypeptides at least 90%, 95%, 96%, 97%, 98% or 99% identical to the PA polypeptide sequence set forth herein as $n^1$-$m^1$. In preferred embodiments, the present invention encompasses antibodies that bind proteins containing polypeptides at least 90%, 95%, 96%, 97%, 98% or 99% identical to polypeptides having the amino acid sequence of the specific PA N- and C-terminal deletions recited herein.

In certain preferred embodiments, antibodies of the invention bind PA fusion proteins as described above wherein the PA portion of the fusion protein are those described as $n^1$-$m^1$ herein.

Antibodies of the Invention May Bind Modified PA Polypeptides

It is specifically contemplated that antibodies of the present invention may bind modified forms of PA proteins SEQ ID NO:2). In specific embodiments, antibodies of the present invention bind PA polypeptides (such as those described above) including, but not limited to naturally purified PA polypeptides, PA polypeptides produced by chemical synthetic procedures, and PA polypeptides produced by recombinant techniques from a prokaryotic or eukaryotic host, including, for example, bacterial, yeast, higher plant, insect and mammalian cells using, for example, the recombinant compositions and methods described above. Depending upon the host employed in a recombinant production procedure, the polypeptides may be glycosylated or non-glycosylated. In addition, PA polypeptides may also include an initial modified methionine residue, in some cases as a result of host-mediated processes.

In addition, antibodies of the present invention may bind PA proteins that were chemically synthesized using techniques known in the art (e.g., see Creighton, Proteins: Structures and Molecular Principles, W.H. Freeman & Co., N.Y. (1983), and Hunkapiller, et al., *Nature* 310:105-111(1984)). For example, a peptide corresponding to a fragment of a PA polypeptide can be synthesized by use of a peptide synthesizer. Furthermore, if desired, nonclassical amino acids or chemical amino acid analogs can be introduced as a substitution or addition into the PA polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention additionally encompasses antibodies that bind PA polypeptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH$_4$, acetylation, formylation, oxidation, reduction, metabolic synthesis in the presence of tunicamycin; etc.

Additional post-translational modifications to PA polypeptides for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein.

Also provided by the invention are antibodies that bind chemically modified derivatives of PA polypeptides which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kilodalton and about 100 kilodalton (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kilodalton.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol* 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride (ClSO$_2$CH$_2$CF$_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each PA polypeptide (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

As mentioned the antibodies of the present invention may bind PA polypeptides that are modified by either natural processes, such as posttranslational processing, or by chemical modification techniques which are well known in the art. It will be appreciated that the same type of modification may be present in the same or varying degrees at several sites in a given PA polypeptide. PA polypeptides may be branched, for example, as a result of ubiquitination, and they may be cyclic, with or without branching. Cyclic, branched, and branched cyclic PA polypeptides may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation. GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., *Meth Enzymol* 182:626-646 (1990); Rattan et al., *Ann NY Acad Sci* 663:48-62 (1992)).

Anti-PA Antibodies

In one embodiment, the invention provides antibodies (e.g., antibodies comprising two heavy chains and two light chains linked together by disulfide bridges) that specifically bind PA (SEQ ID NO:2) or fragments or variants thereof, wherein the amino acid sequence of the heavy chain and the amino acid sequence of the light chain are the same as the amino acid sequence of a heavy chain and a light chain of one or more scFvs or cell lines referred to in Table 1. In another embodiment, the invention provides antibodies (each consisting of two heavy chains and two light chains linked together by disulfide bridges to form an antibody) that specifically bind PA or fragments or variants thereof, wherein the amino acid sequence of the heavy chain or the amino acid sequence of the light chain are the same as the amino acid sequence of a heavy chain or a light chain of one or more scFvs or cell lines referred to in Table 1. Immunospecific binding to PA polypeptides may be determined by immunoassays known in the art or described herein for assaying specific antibody-antigen binding. Molecules comprising, or alternatively consisting of, fragments or variants of these antibodies that specifically bind to PA are also encompassed by the invention, as are nucleic acid molecules encoding these antibodies molecules, fragments and/or variants (SEQ ID NOS:57-65).

In one embodiment of the present invention, antibodies that specifically bind to a PA or a fragment or variant thereof, comprise a polypeptide having the amino acid sequence of a heavy chain of at least one of the scFvs referred to in Table 1 or cell lines contained in the ATCC™ Deposits referred to in Table 1 and/or a light chain of at least one of the scFvs referred to in Table 1 or cell lines contained in the ATCC™ Deposits referred to in Table 1.

In another embodiment of the present invention, antibodies that specifically bind to PA or a fragment or variant thereof, comprise a polypeptide having the amino acid sequence of any one of the VH domains of at least one of the scFvs referred to in Table 1 or at least one of the recombinant antibodies expressed by the cell lines contained in the ATCC™ Deposits referred to in Table 1 and/or any one of the VL domains of at least one of the scFvs referred to in Table 1 or at least one of the recombinant antibodies expressed by the cell lines contained in the ATCC™ Deposits referred to in Table 1. In preferred embodiments, antibodies of the present invention comprise the amino acid sequence of a VH domain and VL domain from a single scFv referred to in Table 1 or single recombinant antibody expressed by a cell line contained in an ATCC™ Deposit referred to in Table 1. In alternative embodiments, antibodies of the present invention comprise the amino acid sequence of a VH domain and a VL domain from different scFvs referred to in Table 1 or different recombinant antibodies expressed by the cell lines contained in the ATCC™ Deposits referred to in Table 1. Molecules comprising, or alternatively consisting of, antibody fragments or variants of the VH and/or VL domains of at least one of the scFvs referred to in Table 1 or at least one of the recombinant antibodies expressed by the cell lines contained in the ATCC™ Deposits referred to in Table 1 that specifically bind to PA are also encompassed by the invention, as are nucleic acid molecules encoding the VH and VL domains, molecules, fragments and/or variants (SEQ ID NOS:57-65).

The present invention also provides antibodies that specifically bind to a polypeptide, or polypeptide fragment or variant of PA, wherein said antibodies comprise, or alternatively consist of, a polypeptide having an amino acid sequence of any one, two, three, or more of the VH CDRs contained in a VH domain of one or more scFvs referred to in Table 1 or at least one of the recombinant antibodies expressed by the cell lines contained in the ATCC™ Deposits referred to in Table 1. In particular, the invention provides antibodies that specifically bind PA or fragments or variants thereof, comprising, or alternatively consisting of, a polypeptide having the amino acid sequence of a VH CDR1 contained in a VH domain of one or more scFvs or at least one of the recombinant antibodies expressed by the cell lines contained in the ATCC™ Deposits referred to in Table 1. In another embodiment, antibodies that specifically bind PA, comprise, or alternatively consist of, a polypeptide having the amino acid sequence of a VH CDR2 contained in a VH domain of one or more scFvs referred to in Table 1 or one or more recombinant antibodies expressed by the cell lines contained in the ATCC™ Deposits referred to in Table 1. In a preferred embodiment, antibodies that specifically bind PA or fragments or variants thereof, comprise, or alternatively consist of a polypeptide having the amino acid sequence of a VH CDR3 contained in a VH domain of one or more scFvs referred to in Table 1 or one or more recombinant antibodies expressed by the cell lines contained in the ATCC™ Deposits referred to in Table 1. Molecules comprising, or alternatively consisting of, these antibodies, or antibody fragments or variants thereof, that specifically bind to PA or a PA fragment or variant thereof are also encompassed by the invention, as are nucleic acid molecules encoding these antibodies, molecules, fragments and/or variants (SEQ ID NOS:57-65).

The present invention also provides antibodies that specifically bind to a PA polypeptide or a polypeptide fragment or variant of PA, wherein said antibodies comprise, or alternatively consist of, a polypeptide having an amino acid sequence of any one, two, three, or more of the VL CDRs contained in a VL domain of one or more scFvs referred to in Table 1 or one or more recombinant antibodies expressed by the cell lines contained in the ATCC™ Deposits referred to in Table 1. In particular, the invention provides antibodies that specifically bind PA or a fragment or variant thereof, comprising, or alternatively consisting of, a polypeptide having the amino acid sequence of a VL CDR1 contained in a VL domain of one or more scFvs referred to in Table 1 or one or more recombinant antibodies expressed by the cell lines contained in the ATCC™ Deposits referred to in Table 1. In another embodiment, antibodies that specifically bind PA or a fragment or variant thereof, comprise, or alternatively consist of, a polypeptide having the amino acid sequence of a VL CDR2 contained in a VL domain of one or more scFvs referred to in Table 1 or one or more recombinant antibodies expressed by the cell lines contained in the ATCC™ Deposits referred to in Table 1. In a preferred embodiment, antibodies that specifically bind PA or a fragment or variant thereof, comprise, or alternatively consist of a polypeptide having the amino acid sequence of a VL CDR3 contained in a VL domain of one or more scFvs referred to in Table 1 or one or more recombinant antibodies expressed by the cell lines contained in the ATCC™ Deposits referred to in Table 1. Molecules comprising, or alternatively consisting of, these antibodies, or antibody fragments or variants thereof, that specifically bind to PA or a PA fragment or variant thereof are also encompassed by the invention, as are nucleic acid molecules encoding these antibodies, molecules, fragments and/or variants (SEQ ID NOS:57-65).

The present invention also provides antibodies (including molecules comprising, or alternatively consisting of, antibody fragments or variants) that specifically bind to PA polypeptide or a fragment or variant of a PA, wherein said antibodies comprise, or alternatively consist of, one, two, three, or more VH CDRs and one, two, three or more VL CDRs, as contained in a VH domain or VL domain of one or more scFvs referred to in Table 1 or one or more recombinant antibodies expressed by the cell lines contained in the ATCC™ Deposits referred to in Table 1. In particular, the invention provides for antibodies that specifically bind to a PA polypeptide or polypeptide fragment or variant of PA, wherein said antibodies comprise, or alternatively consist of, a VH CDR1 and a VL CDR1, a VH CDR1 and a VL CDR2, a VH CDR1 and a VL CDR3, a VH CDR2 and a VL CDR1, VH CDR2 and VL CDR2, a VH CDR2 and a VL CDR3, a VH CDR3 and a VH CDR1, a VH CDR3 and a VL CDR2, a VH CDR3 and a VL CDR3, or any combination thereof, of the VH CDRs and VL CDRs contained in a VH domain or VL domain of one or more scFvs referred to in Table 1 or one or more recombinant antibodies expressed by the cell lines contained in the ATCC™ Deposits referred to in Table 1. In a preferred embodiment, one or more of these combinations are from the same scFv or the same recombinant antibody expressed by cell line contained in an ATCC™ deposit as disclosed in Table 1. Molecules comprising, or alternatively consisting of, fragments or variants of these antibodies, that specifically bind to PA or a fragment or variant thereof are also encompassed by the invention, as are nucleic acid molecules encoding these antibodies, molecules, fragments or variants (SEQ ID NOS: 57-65).

Nucleic Acid Molecules Encoding Anti-PA Antibodies

The present invention also provides for nucleic acid molecules, generally isolated, encoding an antibody of the invention (including molecules comprising, or alternatively consisting of, antibody fragments or variants thereof).

In a specific embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 or at least one of the recombinant antibodies expressed by the cell lines contained in the ATCC™ Deposits referred to in Table 1 and a VL domain having an amino acid sequence of VL domain of at least one of the scFvs referred to in Table 1 or at least one of the recombinant antibodies expressed by the cell lines contained in the ATCC™ Deposits referred to in Table 1. In another embodiment, a nucleic acid molecule of the invention encodes an antibody (including molecules comprising, or alternatively consisting of, antibody fragments or variants thereof), comprising, or alternatively consisting of, a VH domain having an amino acid sequence of any one of the VH domains of at least one of the scFvs referred to in Table 1 or at least one of the recombinant antibodies expressed by the cell lines contained in the ATCC™ Deposits referred to in Table 1 or a VL domain having an amino acid sequence of a VL domain of at least one of the scFvs referred to in Table 1 or at least one of the recombinant antibodies expressed by the cell lines contained in the ATCC™ Deposits referred to in Table 1.

The present invention also provides antibodies that comprise, or alternatively consist of, variants (including derivatives) of the antibody molecules (e.g., the VH domains and/or VL domains) described herein, which antibodies specifically bind to PA or a fragment or variant thereof. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH domain, VHCDR1, VHCDR2, VHCDR3, VL domain, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind PA).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g, improvements in antigen binding activity or change in antibody specificity). Following mutagenesis, the encoded protein may routinely be expressed and the functional and/or biological activity of the encoded protein, (e.g., ability to specifically bind PA) can be determined using techniques described herein or by routinely modifying techniques known in the art.

In a specific embodiment, an antibody of the invention (including a molecule comprising, or alternatively consisting of, an antibody fragment or variant thereof), that specifically binds PA or a fragment or variant thereof, comprises, or alternatively consists of, an amino acid sequence encoded by a nucleotide sequence that hybridizes to a nucleotide sequence that is complementary to that encoding one of the VH or VL domains of one or more scFvs referred to in Table 1 or one or more recombinant antibodies expressed by the cell lines contained in the ATCC™ Deposits referred to in Table 1 under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/0.2% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3). The nucleic acid molecules encoding these antibodies are also encompassed by the invention.

It is well known within the art that polypeptides, or fragments or variants thereof, with similar amino acid sequences often have similar structure and many of the same biological activities. Thus, in one embodiment, an antibody (including a molecule comprising, or alternatively consisting of, an antibody fragment or variant thereof), that specifically binds to PA or fragments or variants of PA, comprises, or alternatively consists of, a VH domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VH domain of at least one of the scFvs referred to in Table 1 or at least one of the recombinant antibodies expressed by the cell lines contained in the ATCC™ Deposits referred to in Table 1.

In another embodiment, an antibody (including a molecule comprising, or alternatively consisting of, an antibody fragment or variant thereof), that specifically binds to PA or a fragment or variant of PA, comprises, or alternatively consists of, a VL domain having an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical, to the amino acid sequence of a VL domain of at least one of the scFvs referred to in Table 1 or at least one of the recombinant antibodies expressed by the cell lines contained in the ATCC™ Deposits referred to in Table 1.

Methods of Producing Antibodies

Antibodies in accordance with the invention were prepared via the utilization of a phage scFv display library. Technologies utilized for achieving the same are disclosed in the patents, applications, and references disclosed herein.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues) or synthetic cDNA libraries. The DNA encoding the VH and VL domains are joined together by an scFv linker by PCR and cloned into a phagemid vector (e.g., pCANTAB 6 or pComb 3 HSS). The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to an antigen of interest (i.e., a PA polypeptide or a fragment thereof) can be selected or identified with antigen, e.g., using labeled antigen or antigen bound or captured to a solid surface or bead. Examples of phage display methods that can be used to make the antibodies of the present invention include, but are not limited to, those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/O1 134; PCT publications WO 90/02809; WO 91/10737; WO 92/01047; WO 92/18719; WO 93/1 1236; WO 95/15982; WO 95/20401; WO97/13844; and U.S. Pat. Nos. 5,698,426; 5,223,409; 5,403,484; 5,580,717; 5,427,908; 5,750,753; 5,821,047; 5,571,698; 5,427,908; 5,516,717; 5,780,225; 5,658,727; 5,735,743 and 5,969,108; each of which is incorporated herein by reference in its entirety.

For some uses, such as for in vitro affinity maturation of an antibody of the invention, it may be useful to express the VH and VL domains of one or more scFvs referred to in Table 1 or one or more recombinant antibodies expressed by the cell lines contained in the ATCC™ Deposits referred to in Table 1 as single chain antibodies or Fab fragments in a phage display library. For example, the cDNAs encoding the VH and VL domains of the scFvs referred to in Table 1 or recombinant antibodies expressed by the cell lines contained in the ATCC™ Deposits referred to in Table 1 may be expressed in all possible combinations using a phage display library, allowing for the selection of VH/VL combinations that bind PA polypeptides with preferred binding characteristics such as improved affinity or improved off rates. Additionally, VH and VL segments—and in particular, the CDR regions of the VH and VL domains of the scFvs referred to in Table 1 or recombinant antibodies expressed by the cell lines contained in the ATCC™ Deposits referred to in Table 1, in particular, may be mutated in vitro. Expression of VH and VL domains with "mutant" CDRs in a phage display library allows for the selection of VH/VL combinations that bind PA polypeptides with preferred binding characteristics such as improved affinity or improved off rates.

In particular embodiments, antibodies of the invention comprise the VH and VL domains of the PWD0587 scFv wherein the V11 domain contains one or more of the following mutations (using amino acid numbering according to that of SEQ ID NO:53): Q13R, S31W, I100V, and/or E105D. An antibody comprising the PWD0587 VH domain with the Q13R, S31W and I100V mutations and the PWD0587 VL domain, had an approximately 11 fold increase in affinity for the PA antigen compared to an antibody comprising the PWD0587 heavy and light chains. Thus, in specific embodiments, an antibody of the invention comprises the PWD0587 VH domain with the Q13R, S31W and I100V mutations and the PWD0587 VL domain.

An antibody comprising the PWD0587 VH domain with the Q13R and S31W mutations and the PWD0587 VL domain, had an approximately 68 fold increase in affinity for the PA antigen compared to an antibody comprising the PWD0587 heavy and light chains. Thus, in specific embodiments, an antibody of the invention comprises the PWD0587 VH domain with the Q13R and S31W mutations and the PWD0587 VL domain.

An antibody comprising the PWD0587 VH domain with the Q13R, S31W, I100V and E105D mutations and the PWD0587 VL domain, had an approximately 121 fold increase in affinity for the PA antigen compared to an antibody comprising the PWD0587 heavy and light chains. Thus, in specific embodiments, an antibody of the invention comprises the PWD0587 VH domain with the Q13R, S31W, 1100V and E105D mutations and the PWD0587 VL domain.

An antibody comprising the PWD0587 VH domain with the Q13R, S31W and E105D mutations and the PWD0587 VL domain, had an approximately 665 fold increase in affinity for the PA antigen compared to an antibody comprising the PWD0587 heavy and light chains. Thus in specific embodiment an antibody of the invention comprises the PWD0587 VH domain with the Q13R, S31W and E105D mutations and the PWD0587 VL domain.

Preliminary testing of the four mutant forms of the PWD0587 antibody with increased affinities for PA compared to the parental PWD0587 (unmutated) antibody, indicated that the mutant PWD0587 antibodies behaved comparably to the parental PWD0587 antibody in, for example, a rubidium release assay (e.g., similar to the assays described in Example 5). In a rat lethal toxin challenge model (similar to the assays described in Example 9) an antibody comprising the PWD0587 VH domain with the Q13R, S31 W and E105D mutations and the PWD0587 VL domain was slightly more effective than the parental PWD0587 antibody in preventing lethal toxin induced death.

Additional Methods of Producing Antibodies

Antibodies of the invention (including antibody fragments or variants) can be produced by any method known in the art. For example, it will be appreciated that antibodies in accordance with the present invention can be expressed in cell lines including, but not limited to, myeloma cell lines and hybridoma cell lines. Sequences encoding the cDNAs or genomic clones for the particular antibodies can be used for transformation of a suitable mammalian or nonmammalian host cells or to generate phage display libraries, for example. Additionally, polypeptide antibodies of the invention may be chemically synthesized or produced through the use of recombinant expression systems.

One way to produce the antibodies of the invention would be to clone the VH and/or VL domains of an scFv referred to in Table 1 or recombinant antibody expressed by the cell lines contained in the ATCC™ Deposits referred to in Table 1. In order to isolate the VH and VL domains from bacteria transfected with a vector containing the scFv, PCR primers complementary to VH or VL nucleotide sequences (See Example 6), may be used to amplify the VH and VL sequences. The PCR products may then be cloned using vectors, for example, which have a PCR product cloning site consisting of a 5' and 3' single T nucleotide overhang, that is complementary to the overhanging single adenine nucleotide added onto the 5' and 3' end of PCR products by many DNA polymerases used for PCR reactions. The VH and VL domains can then be sequenced using conventional methods known in the art. Alternatively, the VH and VL domains may be amplified using vector specific primers designed to amplify the entire scFv, (i.e. the VH domain, linker and VL domain.)

The cloned VH and VL genes may be placed into one or more suitable expression vectors. By way of non-limiting example, PCR primers including VH or VL nucleotide sequences, a restriction site, and a flanking sequence to protect the restriction site may be used to amplify the VH or VL sequences. Utilizing cloning techniques known to those of skill in the art, the PCR amplified VH domains may be cloned into vectors expressing the appropriate immunoglobulin constant region, e.g., the human IgG1 or IgG4 constant region for VH domains, and the human kappa or lambda constant regions for kappa and lambda VL domains, respectively. Preferably, the vectors for expressing the VH or VL domains comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL domains may also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol. Methods 184:177-86 (1995) which are herein incorporated in their entireties by reference).

The invention provides polynucleotides comprising, or alternatively consisting of, a nucleotide sequence encoding an antibody of the invention (including molecules comprising, or alternatively consisting of, antibody fragments or variants thereof). The invention also encompasses polynucleotides that hybridize under high stringency, or alternatively, under intermediate or lower stringency hybridization conditions, e.g., as defined supra, to polynucleotides complementary to nucleic acids having a polynucleotide sequence that encodes an antibody of the invention or a fragment or variant thereof.

The polynucleotides may be obtained, and the nucleotide sequence of the polynucleotides determined, by any method known in the art. If the amino acid sequences of the VH domains, VL domains and CDRs thereof, are known, nucleotide sequences encoding these antibodies can be determined using methods well known in the art, i.e., the nucleotide codons known to encode the particular amino acids are assembled in such a way to generate a nucleic acid that encodes the antibody, of the invention. Such a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody (including molecules comprising, or alternatively consisting of, antibody fragments or variants thereof) may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells or Epstein Barr virus transformed B cell lines that express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody (including molecules comprising, or alternatively consisting of, antibody fragments or variants thereof) is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, VH and VL domains of one or more scFvs referred to in Table 1 or one or more recombinant antibodies expressed by the cell lines contained in the ATCC™ Deposits referred to in Table 1, or fragments or variants thereof, are inserted within framework regions using recombinant DNA techniques known in the art. In a specific embodiment, one, two, three, four, five, six, or more of the CDRs of a VH and/or a VL domain of one or more scFvs referred to in Table 1 or one or more recombinant antibodies expressed by the cell lines contained in the ATCC™ Deposits referred to in Table 1, or fragments or variants thereof, are inserted within framework regions using recombinant DNA techniques known in the art. The framework regions may be naturally occurring or consensus framework regions, and preferably human framework regions (see, e.g., Chothia et al., J. Mol. Biol. 278: 457-479 (1998) for a listing of human framework regions, the contents of which are hereby incorporated by reference in its entirety). Preferably, the polynucleotides generated by the combination of the framework regions and CDRs encode an antibody (including molecules comprising, or alternatively consisting of, antibody fragments or variants thereof) that specifically binds to a PA polypeptide. Preferably, as discussed supra, polynucleotides encoding variants of antibodies or antibody fragments having one or more amino acid substitutions may be made within the framework regions, and, preferably, the amino acid substitutions do not significantly alter binding of the antibody to its antigen. Additionally, such methods may be used to make amino acid substitutions or deletions of one or more variable region cysteine residues participating in an intrachain disulfide bond to generate antibody molecules, or antibody fragments or variants, lacking one or more intrachain disulfide bonds. Other alterations to the polynucleotide are encompassed by the present invention and fall within the ordinary skill of the art.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B cell development. Furthermore, such a strategy could provide an ideal source for production of fully human monoclonal antibodies (mAbs) an important milestone towards fulfilling the promise of antibody therapy in human disease.

Fully human antibodies are expected to minimize the immunogenic and allergic responses intrinsic to mouse or mouse-derivatized Monoclonal antibodies and thus to increase the efficacy and safety of the administered antibodies. The use of fully human antibodies can be expected to provide a substantial advantage in the treatment of chronic and recurring human diseases, such as cancer, which require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Monoclonal antibodies with the desired specificity could be readily produced and selected.

This general strategy was demonstrated in connection with the generation of the first XENOMOUSE™ transgenic mouse system strains as published in 1994. See Green et al. *Nature Genetics* 7:13-21 (1994). The XENOMOUSE™ transgenic mouse system strains were engineered with yeast artificial chromosomes (YACS) containing germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human monoclonal antibodies. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XENOMOUSE™ transgenic mouse system mice. See Mendez et al. *Nature Genetics* 15:146-156 (1997), Green and Jakobovits *J. Exp. Med.* 188:483-495 (1998), Green, *Journal of Immunological Methods* 231:11-23 (1999) and U.S. patent application Ser. No. 08/759,620, filed Dec. 3, 1996, the disclosures of which are hereby incorporated by reference.

Such approach is further discussed and delineated in U.S. patent application Ser. Nos. 07/466,008, filed Jan. 12, 1990, 07/710,515, filed Nov. 8, 1990, 07/919,297, filed Jul. 24, 1992, 07/922,649, filed Jul. 30, 1992, filed 08/031,801, filed Mar. 15, 1993, 08/112,848, filed Aug. 27, 1993, 08/234,145, filed Apr. 28, 1994, 08/376,279, filed Jan. 20, 1995, 08/430, 938, Apr. 27, 1995, 08/464,584, filed Jun. 5, 1995, 08/464, 582, filed Jun. 5, 1995, 08/471,191, filed Jun. 5, 1995, 08/462, 837, filed Jun. 5, 1995, 08/486,853, filed Jun. 5, 1995, 08/486, 857, filed Jun. 5, 1995, 08/486,859, filed Jun. 5, 1995, 08/462, 513, filed Jun. 5, 1995, 08/724,752, filed Oct. 2, 1996, and 08/759,620, filed Dec. 3, 1996. See also Mendez et al. *Nature Genetics* 15:146-156 (1997) and Green and Jakobovits *J. Exp. Med.* 188:483 495 (1998). See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, and WO 98/24893, published Jun. 11, 1998. The disclosures of each of the above-cited patents, applications, and references are hereby incorporated by reference in their entirety.

Human anti-mouse antibody (HAMA) responses have led the industry to prepare chimeric or otherwise humanized antibodies. While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against PA polypeptides in order to vitiate concerns and/or effects of HAMA or HACA responses.

Monoclonal antibodies specific for PA polypeptides may be prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 571-681 (1981)). Briefly, XENOMOUSE™ transgenic mouse system mice may be immunized with PA polypeptides. After immunization, the splenocytes of such mice are extracted and fused with a suitable myeloma cell line. Any suitable myeloma cell line, such as the myeloma cell line (SP2O), available from the ATCC™, may be employed in accordance with the present invention; however, it is preferable to employ the parent myeloma cell line (SP2O), available from the ATCC™. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the PA polypeptides.

For some uses, including in vivo use of antibodies in humans and in vitro detection assays, it may be preferable to use human or chimeric antibodies. Completely human antibodies are particularly desirable for therapeutic treatment of human patients. See also, U.S. Pat. Nos. 4,444,887 and 4,716, 111; and PCT publications WO 98/46645, WO 98/50435, WO 98/24893, WO98/16654, WO 96/34096, WO 96/35735, and WO 91/10741; each of which is incorporated herein by reference in its entirety. In a specific embodiment, antibodies of the present invention comprise one or more VH and VL domains of the invention and constant regions from another immunoglobulin molecule, preferably a human immunoglobulin molecule. In a specific embodiment, antibodies of the present invention comprise one or more CDRs corresponding to the VH and VL domains of the invention and framework regions from another immunoglobulin molecule, preferably a human immunoglobulin molecule. In other embodiments, an antibody of the present invention comprises one, two, three, four, five, six or more VL CDRs or VH CDRs corresponding to one or more of the VH or VL domains of one or more scFvs referred to in Table 1 or one or more recombinant antibodies expressed by the cell lines contained in the ATCC™ Deposits referred to in Table 1, or fragments or variants thereof, and framework regions (and, optionally one or more CDRs not present in the scFvs referred to in Table 1 or recombinant antibodies expressed by the cell lines contained in the ATCC™ Deposits referred to in Table 1) from a human immunoglobulin molecule. In a preferred embodiment, an antibody of the present invention comprises a VH CDR3, VL CDR3, or both, corresponding to the same recombinant antibody, or different recombinant antibodies selected from the recombinant antibodies expressed by the cell lines contained in the ATCC™ Deposits referred to in Table 1, or fragments or variants thereof, and framework regions from a human immunoglobulin.

A chimeric antibody is a molecule in which different portions of the antibody are derived from different immunoglobulin molecules such as antibodies having a human variable region and a non-human (e.g., murine) immunoglobulin constant region or vice versa. Methods for producing chimeric antibodies are known in the art. See e.g., Morrison, Science 229:1202 (1985); Oi et al., BioTechniques 4:214 (1986); Gillies et al., J. Immunol. Methods 125:191-202 (1989); U.S. Pat. Nos. 5,807,715; 4,816,567; and 4,816,397, which are incorporated herein by reference in their entirety. Chimeric antibodies comprising one or more CDRs from human species and framework regions from a non-human immunoglobulin molecule (e.g., framework regions from a murine, canine or feline immunoglobulin molecule) (or vice versa) can be produced using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska et al., PNAS 91:969-973 (1994)), and chain shuffling (U.S. Pat. No. 5,565,352). In a preferred embodiment, chimeric antibodies comprise a human CDR3 having an amino acid sequence of any one of the VH CDR3s or VL CDR3s of a VH or VL domain of one or more of the scFvs referred to in Table 1, or a variant thereof, and non-human framework regions or human framework regions different from those of the frameworks in the corresponding scFv disclosed in Table 1. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 352:323 (1988), which are incorporated herein by reference in their entireties.)

Intrabodies are antibodies, often scFvs, that are expressed from a recombinant nucleic acid molecule and engineered to be retained intracellularly (e.g., retained in the cytoplasm, endoplasmic reticulum, or periplasm). Intrabodies may be used, for example, to ablate the function of a protein to which the intrabody binds. The expression of intrabodies may also be regulated through the use of inducible promoters in the nucleic acid expression vector comprising the intrabody. Intrabodies of the invention can be produced using methods known in the art, such as those disclosed and reviewed in Chen et al., *Hum. Gene Ther.* 5:595-601 (1994); Marasco, W. A., *Gene Ther.* 4:11-15 (1997); Rondon and Marasco, *Annu. Rev. Microbiol.* 51:257-283 (1997); Proba et al., *J. Mol. Biol.* 275:245-253 (1998); Cohen et al., *Oncogene* 17:2445-2456 (1998); Ohage and Steipe, *J. Mol. Biol.* 291:1119-1128 (1999); Ohage et al., *J. Mol. Biol.* 291:1129-1134 (1999); Wirtz and Steipe, *Protein Sci.* 8:2245-2250 (1999); Zhu et al., *J. Immunol. Methods* 231:207-222 (1999); and references cited therein.

Recombinant expression of an antibody of the invention (including antibody fragments or variants thereof (e.g., a heavy or light chain of an antibody of the invention), requires construction of an expression vector(s) containing a polynucleotide that encodes the antibody. Once a polynucleotide encoding an antibody molecule (e.g., a whole antibody, a heavy or light chain of an antibody, or portion thereof (preferably, but not necessarily, containing the heavy or light chain variable domain)), of the invention has been obtained, the vector(s) for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464, the contents of each of which are hereby incorporated by reference in its entirety) and the variable domain of the antibody may be cloned into such a vector for expression of the entire heavy chain, the entire light chain, or both the entire heavy and light chains.

The expression vector(s) is(are) transferred to a host cell by conventional techniques and the transfected cells are then cultured by conventional techniques to produce an antibody of the invention. Thus, the invention includes host cells containing polynucleotide(s) encoding an antibody of the invention (e.g., whole antibody, a heavy or light chain thereof, or portion thereof, or a single chain antibody, or a fragment or variant thereof), operably linked to a heterologous promoter. In preferred embodiments, for the expression of entire antibody molecules, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, bacteriophage particles engineered to express antibody fragments or variants thereof (single chain antibodies), microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3, NS0 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990); Bebbington et al., Bio/Techniques 10:169 (1992); Keen and Hale, Cytotechnology 18:207 (1996)). These references are incorporated in their entireties by reference herein.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) may be used as a vector to express foreign genes. The virus grows in *Spodoptera frugiperda* cells. Antibody coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, Proc. Natl. Acad. Sci. USA 8 1:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERY, BHK, HeLa, COS, NSO, MDCK, 293, 3T3, W138, and in particular, breast cancer cell lines such as, for example, BT483, Hs578T, HTB2, BT2O and T47D, and normal mammary gland cell line such as, for example, CRL7O3O and Hs578Bst.

For long-term, high-yield production of recombinant proteins, stable expression is preferred. For example, cell lines which stably express the antibody may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk-, hgprt- or aprt-cells, respectively. Also, antimetabolite resistance can be used as the basis of selection for the following genes: dhfr, which confers resistance to methotrexate (Wigler at al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260: 926-932 (1993); and Morgan and Anderson, Ann. Rev. Biochem. 62: 191-217 (1993); TIB TECH 11(5):155-2 15 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel at al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli at al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells" in *DNA Cloning, Vol.* 3. (Academic Press, New York, 1987)). When a marker in the vector system expressing antibody is amplifiable, increase in the level of inhibitor present in culture of host cell will increase the number of copies of the marker gene. Since the amplified region is associated with the coding sequence of the antibody, production of the antibody will also increase (Crouse et al., Mol. Cell. Biol. 3:257 (1983)).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g. Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/01036; WO89/10404; and WO91/06657 which are incorporated in their entireties by reference herein. Additionally, glutamine synthase expression vectors that may be used according to the present invention are commercially available from suppliers, including, for example Lonza Biologics, Inc. (Portsmouth, N.H.). Expression and production of monoclonal antibodies using a GS expression system in murine myeloma cells is described in Bebbington et al., *Bio/technology* 10:169 (1992) and in Biblia and Robinson *Biotechnol. Prog.* 11:1 (1995) which are incorporated in their entireties by reference herein.

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain (Proudfoot, Nature 322:52 (1986); Kohler, Proc. Natl. Acad. Sci. USA 77:2 197 (1980)). The coding sequences for the heavy and light chains may comprise cDNA or genomic DNA.

Once an antibody molecule of the invention (including molecules comprising, or alternatively consisting of, antibody fragments or variants thereof) has been chemically synthesized or recombinantly expressed, it may be purified by any method known in the art for purification of an immunoglobulin molecule, or more generally, a protein molecule, such as, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art, to facilitate purification.

Antibodies of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the antibodies of the present invention may be glycosylated or may be non-glycosylated. In addition, antibodies of the invention may also include an initial modified methionine residue, in some cases as a result of host-mediated processes.

Antibodies of the invention can be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). For example, a peptide corresponding to a fragment of an antibody of the invention can be synthesized by use of a peptide synthesizer. Furthermore, if desired, nonclassical amino acids or chemical amino acid analogs can be introduced as a substitution or addition into the antibody polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses antibodies which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antibodies may also be modified with a detectable label, such as an enzymatic, fluorescent, radioisotopic or affinity label to allow for detection and isolation of the antibody.

Examples of suitable enzymes include horseradish peroxidase, alkaline phosphatase, beta-galactosidase, glucose oxidase or acetylcholinesterase; examples of suitable prosthetic group complexes include streptavidin/biotin and avidin/biotin; examples of suitable fluorescent materials include biotin, umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include a radioactive metal ion, e.g., alpha-emitters such as, for example, 213Bi, or other radioisotopes such as, for example, iodine (131I, 125I, 123I, 121I), carbon (14C), sulfur (35S), tritium (3H), indium (115mIn, 113mIn, 112In, 111In), and technetium (99Tc, 99 mTc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin.

In specific embodiments, antibodies of the invention may be labeled with Europium. For example, antibodies of the invention may be labelled with Europium using the DELFIA Eu-labeling kit (catalog #1244-302, Perkin Elmer Life Sciences, Boston, Mass.) following manufacturer's instructions.

In specific embodiments, antibodies of the invention are attached to macrocyclic chelators useful for conjugating radiometal ions, including but not limited to, 111In, 177Lu, 90Y, 166Ho, 153Sm, 215Bi and 225Ac to polypeptides. In a preferred embodiment, the radiometal ion associated with the macrocyclic chelators attached to antibodies of the invention is 111In. In another preferred embodiment, the radiometal ion associated with the macrocyclic chelator attached to antibodies polypeptides of the invention is 90Y. In specific embodiments, the macrocyclic chelator is 1,4,7,10-tetraazacyclododecane-N,N',N'',N'''-tetraacetic acid (DOTA). In specific embodiments, the macrocyclic chelator is α-(5-isothiocyanato-2-methoxyphenyl)-1,4,7,10-tetraaza-cyclododecane-1,4,7,10-tetraacetic acid. In other specific embodiments, the DOTA is attached to the antibody of the invention via a linker molecule. Examples of linker molecules useful for conjugating a macrocyclic chelator such as DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al, Nucl. Med. Biol. 26(8):943-50, 1999 which are hereby incorporated by reference in their entirety. In addition, U.S. Pat. Nos. 5,652,361 and 5,756,065, which disclose chelating agents that may be conjugated to antibodies, and methods for making and using them, are hereby incorporated by reference in their entireties.

In one embodiment, antibodies of the invention are labeled with biotin. In other related embodiments, biotinylated antibodies of the invention may be used, for example, as an imaging agent or as a means of identifying one or more TRAIL receptor coreceptor or ligand molecules.

Also provided by the invention are chemically modified derivatives of antibodies of the invention which may provide additional advantages such as increased solubility, stability and in vivo or in vitro circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The antibodies may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

The polyethylene glycol molecules (or other chemical moieties) should be attached to the antibody with consideration of effects on functional or antigenic domains of the antibody. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include, for example, lysine residues and the N-terminal amino acid residues; those having a free carboxyl group may include aspartic acid residues, glutamic acid residues, and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins, e.g., antibodies, via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire antibodies chemically modified at the N-terminus of either the heavy chain or the light chain or both. Using polyethylene glycol as an illustration, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective chemical modification at the N-terminus may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the antibodies of the invention may be accomplished by any number of means. For example, polyethylene glycol may be attached to the antibody either directly or by an intervening linker. Linkerless systems for attaching polyethylene glycol to proteins are described in Delgado et al., Crit. Rev. Thera. Drug Carrier Sys. 9:249-304 (1992); Francis et al., Intern. J. of Hematol. 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of antibodies without an intervening linker employs tresylated MPEG, which is produced by the modification of monmethoxy polyethylene glycol (MPEG) using tresylchloride (CISO2CH2CF3). Upon reaction of protein with tresylated MPEG, polyethylene glycol is directly attached to amine groups of the protein. Thus, the invention includes antibody-polyethylene glycol conjugates produced by reacting antibodies of the invention with a polyethylene glycol molecule having a 2,2,2-trifluoreothane sulphonyl group.

Polyethylene glycol can also be attached to antibodies using a number of different intervening linkers. For example, U.S. Pat. No. 5,612,460, the entire disclosure of which is incorporated herein by reference, discloses urethane linkers for connecting polyethylene glycol to proteins. Antibody-polyethylene glycol conjugates wherein the polyethylene glycol is attached to the antibody by a linker can also be produced by reaction of antibodies with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated antibody products produced using the reaction chemistries set out herein are included within the scope of the invention.

The number of polyethylene glycol moieties attached to each antibody of the invention (i.e., the degree of substitution) may also vary. For example, the pegylated antibodies of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per antibody molecule. Methods for determining the degree of substitution are discussed, for example, in Delgado et al., Crit. Rev. Thera. Drug Carrier Sys. 9:249-304 (1992).

Characterization of Anti-PA Antibodies

Antibodies of the present invention (including molecules comprising, or alternatively consisting of, antibody fragments or variants thereof) may also be described or specified in terms of their binding to PA polypeptides or fragments or variants of PA polypeptides. In specific embodiments, antibodies of the invention bind PA polypeptides, or fragments or variants thereof, with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind PA polypeptides or fragments or variants thereof with a dissociation constant or $K_D$ less than or equal to $5\times10^{-6}$ M, $10^{-6}$ M, $5\times10^{-7}$ M, $10^{-7}$M, $5\times10^{-8}$ M, or $10^{-8}$ M. Even more preferably, antibodies of the invention bind PA polypeptides or fragments or variants thereof with a dissociation constant or $K_D$ less than or equal to $5\times10^{-9}$ M, $5\times10^{-9}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. The invention encompasses antibodies that bind PA polypeptides with a dissociation constant or $K_D$ that is within any one of the ranges that are between each of the individual recited values.

In specific embodiments, antibodies of the invention bind PA polypeptides or fragments or variants thereof with an off rate ($k_{off}$) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, antibodies of the invention bind PA polypeptides or fragments or variants thereof with an off rate ($k_{off}$) less than or equal to $5\times10^{-4}$ sec$^{-1}$, $10^{-4}$ sec$^{-1}$, $5\times10^{-5}$ sec$^{-1}$, or $10^{-5}$ sec$^{-1}$, $5\times10^{-6}$ sec$^{-1}$, $10^{-6}$ sec$^{-1}$, $5\times10^{-7}$ sec$^{-1}$ or $10^{-7}$ sec$^{-1}$. The invention encompasses antibodies that bind PA polypeptides with an off rate ($k_{off}$) that is within any one of the ranges that are between each of the individual recited values.

In other embodiments, antibodies of the invention bind PA polypeptides or fragments or variants thereof with an on rate ($k_{on}$) of greater than or equal to $10^3$ M$^{-1}$ sec$^{-1}$, $5\times10^3$ M$^{-1}$ sec$^{-1}$, $10^4$ M$^{-1}$ sec$^{-1}$ or $5\times10^4$ M$^{-1}$ sec$^{-1}$. More preferably, antibodies of the invention bind PA polypeptides or fragments or variants thereof with an on rate ($k_{on}$) greater than or equal to $10^5$ M$^{-1}$ sec$^{-1}$, $5\times10^5$ M$^{-1}$ sec$^{-1}$, $10^6$ M$^{-1}$ sec$^{-1}$, or $5\times10^6$ M$^{-1}$ sec$^{-1}$ or $10^7$M$^{-1}$ sec$^{-1}$. The invention encompasses antibodies that bind PA polypeptides with on rate ($k_{on}$) that is within any one of the ranges that are between each of the individual recited values.

In preferred embodiments, the antibodies of the present invention (including molecules comprising, or alternatively consisting of, antibody fragments or variants thereof), specifically bind to PA polypeptides and do not cross-react with any other antigens. In preferred embodiments, the antibodies of the invention specifically bind to PA polypeptides (e.g., SEQ ID NO:2 or fragments or variants thereof) and do not cross-react with other bacterial binary toxins (A-B toxins) such as those from *Clostridum difficile, Clostridium perfringens, Clostridium spiroforme, Clostridium botulinum, Bacillus cereus* and/or *Bacillus thuringiensis*.

In another embodiment, the antibodies of the present invention (including molecules comprising, or alternatively consisting of, antibody fragments or variants thereof), specifically bind to PA polypeptides and cross-react with other antigens. In other embodiments, the antibodies of the invention specifically bind to PA polypeptides (e.g., SEQ ID NO:2 or fragments or variants thereof) and cross-react with other bacterial binary toxins (A-B toxins) such as those from *Clostridum difficile, Clostridium perfringens, Clostridium spiroforme, Clostridium botulinum, Bacillus cereus* and/or *Bacillus thuringiensis*.

In a preferred embodiment, antibodies of the invention preferentially bind PA (SEQ ID NO:2), or fragments and variants thereof relative to their ability to bind other antigens (e.g., other bacterial binary toxins (A-B toxins) such as those from *Clostridum difficile, Clostridium perfringens, Clostridium spiroforme, Clostridium botulinum, Bacillus cereus* and/or *Bacillus thuringiensis*). An antibody's ability to preferentially bind one antigen compared to another antigen may be determined using any method known in the art.

By way of non-limiting example, an antibody may be considered to bind a first antigen preferentially if it binds said first antigen with a dissociation constant ($K_D$) that is less than the antibody's $K_D$ for the second antigen.

In another non-limiting embodiment, an antibody may be considered to bind a first antigen preferentially if it binds said first antigen with an affinity (i.e., $K_D$) that is at least one order of magnitude less than the antibody's $K_D$ for the second antigen. In another non-limiting embodiment, an antibody may be considered to bind a first antigen preferentially if it binds said first antigen with an affinity (i.e., $K_D$) that is at least two orders of magnitude less than the antibody's $K_D$ for the second antigen.

In another non-limiting embodiment, an antibody may be considered to bind a first antigen preferentially if it binds said first antigen with an off rate ($k_{off}$) that is less than the antibody's $k_{off}$ for the second antigen. In another non-limiting embodiment, an antibody may be considered to bind a first antigen preferentially if it binds said first antigen with a $k_{off}$ that is at least one order of magnitude less than the antibody's $k_{off}$ for the second antigen. In another non-limiting embodiment, an antibody may be considered to bind a first antigen preferentially if it binds said first antigen with a $k_{off}$ that is at least two orders of magnitude less than the antibody's $k_{off}$ for the second antigen.

The invention also encompasses antibodies (including molecules comprising, or alternatively consisting of, antibody fragments or variants thereof) that have one or more of the same biological characteristics as one or more of the antibodies described herein. By "biological characteristics" is meant, the in vitro or in vivo activities or properties of the antibodies, such as, for example, the ability to bind to PA polypeptides (e.g., either the PA83 or PA63 form of PA); or the ability to inhibit the cleavage of the PA83 into PA20 and PA63 by proteases such as trypsin or furin. Additionally, antibodies of the invention may: prevent oligomerization of PA63, especially heptamerization of PA63; inhibit or abolish the ability of PA63 to bind to an anthrax receptor, e.g., ATR and/or CMG2 (See Example 3); inhibit or abolish the ability of PA63 to bind LF or EF; inhibit or abolish the ability of PA63 to form pores in membranes (see Example 5); inhibit or abolish the ability of lethal toxin (LT) to kill cells, such as macrophages (see Example 8), or animals (see Examples 9-12); or inhibit or abolish the ability of PA heptamers to translocate LF or EF across a membrane (see Example 13). Optionally, the antibodies of the invention will bind to the same epitope as at least one of the antibodies specifically referred to herein. Such epitope binding can be routinely determined using assays known in the art.

The present invention also provides for antibodies (including molecules comprising, or alternatively consisting of, antibody fragments or variants thereof), that inhibit or abolish biological activities of PA. By "biological activities of PA" is meant, for example, the ability of PA83 to be cleaved by proteases into PA20 and PA63 fragments; the ability of PA to bind to ATR and/or CMG2; the ability of PA or PA63 to oligomerize, especially to heptamerize; the ability of PA63 to bind LF or EF; the ability of PA63 heptamers to form pores in a membrane; and/or the ability of PA heptamers to translocate EF or LF across a membrane. In one embodiment, an antibody that inhibits or abolishes biological activities of PA comprises, or alternatively consists of a VH and/or a VL domain of at least one of the scFvs referred to in Table 1 or recombinant antibodies expressed by the cell lines referred to in Table 1, or a fragment or variant thereof. In a specific embodiment, an antibody that inhibits or abolishes biological activities of PA comprises, or alternatively consists of a VH and a VL domain of any one of the scFvs referred to in Table 1 or recombinant antibodies expressed by the cell lines referred to in Table 1, or a fragment or variant thereof. Nucleic acid molecules encoding these antibodies are also encompassed by the invention.

The present invention also provides for antibodies (including molecules comprising, or alternatively consisting of, antibody fragments or variants thereof), that inhibit the cleavage of the PA83 into PA20 and PA63 by proteases such as trypsin or furin. See, e.g., Example 2 wherein an antibody that binds peptides that span the RKKR (residues 193-196 of SEQ ID NO:2) cleavage site of PA may be predictive of an antibody's ability to inhibit the cleavage of PA by proteases. Alternatively, a PA cleavage assay is described in J. Biol. Chem. (1992), 267:16396-402, which is hereby incorporated by reference in its entirety. In one embodiment, an antibody that inhibits the cleavage of the PA83 into PA20 and PA63 comprises, or alternatively consists of a VH and/or a VL domain of at least one of the scFvs referred to in Table 1 or recombinant antibodies expressed by the cell lines referred to in Table 1, or a fragment or variant thereof. In a specific embodiment, an antibody that inhibits the cleavage of the PA83 into PA20 and PA63 comprises, or alternatively consists of a VH and a VL domain of any one of the scFvs referred to in Table 1 or recombinant antibodies expressed by the cell lines referred to in Table 1, or a fragment or variant thereof. Nucleic acid molecules encoding these antibodies are also encompassed by the invention.

The present invention also provides for antibodies (including molecules comprising, or alternatively consisting of, antibody fragments or variants thereof), that block or inhibit the binding of PA to ATR and/or CMG2 (e.g., see Example 3). In one embodiment, an antibody that blocks or inhibits the binding of PA to ATR and/or CMG2 comprises, or alternatively consists of a VH and/or a VL domain of at least one of the scFvs referred to in Table 1 or at least one of the recombinant antibodies expressed by the cell lines contained in the ATCC™ Deposits referred to in Table 1, or a fragment or variant thereof. In a specific embodiment, an antibody that blocks or inhibits the binding of PA to ATR and/or CMG2 comprises, or alternatively consists of a VH and a VL domain of any one of the scFvs referred to in Table 1 or any one of the recombinant antibodies expressed by the cell lines contained in the ATCC™ Deposits referred to in Table 1, or a fragment or variant thereof. Nucleic acid molecules encoding these antibodies are also encompassed by the invention.

The present invention also provides for antibodies (including molecules comprising, or alternatively consisting of, antibody fragments or variants thereof), that block or inhibit the ability of PA or PA63 to heptamerize. In one embodiment, an antibody that blocks or inhibits the ability of PA or PA63 to heptamerize comprises, or alternatively consists of a VH and/or a VL domain of at least one of the scFvs referred to in Table 1 or at least one of the recombinant antibodies expressed by the cell lines contained in the ATCC™ Deposits referred to in Table 1, or a fragment or variant thereof. In a specific embodiment, an antibody that blocks or inhibits the ability of PA63 to heptamerize comprises, or alternatively consists of a VH and a VL domain of any one of the scFvs referred to in Table 1 or any one of the recombinant antibodies expressed by the cell lines contained in the ATCC™ Deposits referred to in Table 1, or a fragment or variant thereof. Nucleic acid molecules encoding these antibodies are also encompassed by the invention.

The present invention also provides for antibodies (including molecules comprising, or alternatively consisting of, antibody fragments or variants thereof), that block or inhibit the ability of PA63 to bind EF or LF. In one embodiment, an antibody that blocks or inhibits the ability of PA63 to bind EF or LF comprises, or alternatively consists of a VH and/or a VL domain of at least one of the scFvs referred to in Table 1 or at least one of the recombinant antibodies expressed by the cell lines contained in the ATCC™ Deposits referred to in Table 1, or a fragment or variant thereof. In a specific embodiment, an antibody that blocks or inhibits the ability of PA63 to bind EF or LF comprises, or alternatively consists of a VH and a VL domain of any one of the scFvs referred to in Table 1 or any one of the recombinant antibodies expressed by the cell lines contained in the ATCC™ Deposits referred to in Table 1, or a fragment or variant thereof. Nucleic acid molecules encoding these antibodies are also encompassed by the invention.

The present invention also provides for antibodies (including molecules comprising, or alternatively consisting of, antibody fragments or variants thereof), that block or inhibit the ability of PA63 heptamers to form pores in membranes. In one embodiment, an antibody that blocks or inhibits the ability of PA63 heptamers to form pores in membranes comprises, or alternatively consists of a VH and/or a VL domain of at least one of the scFvs referred to in Table 1 or at least one of the recombinant antibodies expressed by the cell lines contained in the ATCC™ Deposits referred to in Table 1, or a fragment or variant thereof. In a specific embodiment, an antibody that blocks or inhibits the ability of PA63 heptamers to form pores in membranes comprises, or alternatively consists of a VH and a VL domain of any one of the scFvs referred to in Table 1 or any one of the recombinant antibodies expressed by the cell lines contained in the ATCC™ Deposits referred to in Table 1, or a fragment or variant thereof. Nucleic acid molecules encoding these antibodies are also encompassed by the invention.

The present invention also provides for antibodies (including molecules comprising, or alternatively consisting of, antibody fragments or variants thereof), that block or inhibit the ability of PA63 heptamers to translocate EF or LF across membranes. In one embodiment, an antibody that blocks or inhibits the ability of PA63 heptamers to translocate EF or LF across membranes comprises, or alternatively consists of a VH and/or a VL domain of at least one of the scFvs referred to in Table 1 or at least one of the recombinant antibodies expressed by the cell lines contained in the ATCC™ Deposits referred to in Table 1, or a fragment or variant thereof. In a specific embodiment, an antibody that blocks or inhibits the ability of PA63 heptamers to translocate EF or LF across membranes comprises, or alternatively consists of a VH and a VL domain of any one of the scFvs referred to in Table 1 or any one of the recombinant antibodies expressed by the cell lines contained in the ATCC™ Deposits referred to in Table 1, or a fragment or variant thereof. Nucleic acid molecules encoding these antibodies are also encompassed by the invention.

The present invention also provides for antibodies (including molecules comprising, or alternatively consisting of, antibody fragments or variants thereof), that block or inhibit the ability of anthrax lethal toxin to kill cells or animals. In one embodiment, an antibody that blocks or inhibits the ability of anthrax lethal toxin to kill cells or animals comprises, or alternatively consists of a VH and/or a VL domain of at least one of the scFvs referred to in Table 1 or at least one of the recombinant antibodies expressed by the cell lines contained in the ATCC™ Deposits referred to in Table 1, or a fragment or variant thereof. In a specific embodiment, an antibody that blocks or inhibits the ability of anthrax lethal toxin to kill cells or animals comprises, or alternatively consists of a VH and a VL domain of any one of the scFvs referred to in Table 1 or any one of the recombinant antibodies expressed by the cell lines contained in the ATCC™ Deposits referred to in Table 1, or a fragment or variant thereof. Nucleic acid molecules encoding these antibodies are also encompassed by the invention.

The present invention also provides for fusion proteins comprising, or alternatively consisting of, an antibody (including molecules comprising, or alternatively consisting of, antibody fragments or variants thereof), that specifically bind to PA fused to a heterologous polypeptide. Preferably, the heterologous polypeptide to which the antibody is fused is useful for function or is useful to target the fusion protein to cells with surface bound PA molecules. In specific embodiments the invention encompasses bispecific antibodies in which one antibody binding site is specific for PA and the second antibody binding site is specific for a heterologous polypeptide. In one embodiment, a fusion protein of the invention comprises, or alternatively consists of, a polypeptide having the amino acid sequence of any one or more of the VH domains of an antibody of the invention or the amino acid sequence of any one or more of the VL domains of an antibody of the invention or fragments or variants thereof, and a heterologous polypeptide sequence. In another embodiment, a fusion protein of the present invention comprises, or alternatively consists of, a polypeptide having the amino acid sequence of any one, two, three, or more of the VH CDRs of an antibody of the invention, or the amino acid sequence of any one, two, three, or more of the VL CDRs of an antibody of the invention, or fragments or variants thereof, and a heterologous polypeptide sequence. In a preferred embodiment, the fusion protein comprises, or alternatively consists of, a polypeptide having the amino acid sequence of, a VH CDR3 of an antibody of the invention, or fragment or variant thereof, and a heterologous polypeptide sequence, which fusion protein specifically binds to PA. In another embodiment, a fusion protein comprises, or alternatively consists of a polypeptide having the amino acid sequence of at least one VH domain of an antibody of the invention and the amino acid sequence of at least one VL domain of an antibody of the invention or fragments or variants thereof, and a heterologous polypeptide sequence. Preferably, the VH and VL domains of the fusion protein correspond to a single antibody (or scFv or Fab fragment) of the invention. In yet another embodiment, a fusion protein of the invention comprises, or alternatively consists of a polypeptide having the amino acid sequence of any one, two, three or more of the VH CDRs of an antibody of the invention and the amino acid sequence of any one, two, three or more of the VL CDRs of an antibody of the invention, or fragments or variants thereof, and a heterologous polypeptide sequence. Preferably, two, three, four, five, six, or more of the VHCDR(s) or VLCDR(s) correspond to single antibody (or scFv or Fab fragment) of the invention. Nucleic acid molecules encoding these fusion proteins are also encompassed by the invention.

Antibodies of the present invention (including antibody fragments or variants thereof) may be characterized in a variety of ways. In particular, antibodies and related molecules of the invention may be assayed for the ability to specifically bind to PA or a fragment or variant of PA, using techniques described herein or routinely modifying techniques known in the art. Assays for the ability of the antibodies of the invention to specifically bind PA or a fragment or variant of PA, may be performed in solution (e.g., Houghten, Bio/Techniques 13:412-421 (1992)), on beads (e.g., Lam, Nature 354:82-84 (1991)), on chips (e.g., Fodor, Nature 364:555-556 (1993)), on bacteria (e.g., U.S. Pat. No. 5,223,409), on spores (e.g., U.S. Pat. Nos. 5,571,698; 5,403,484; and 5,223,409), on plasmids (e.g., Cull et al., Proc. Natl. Acad. Sci. USA 89:1865-1869 (1992)) or on phage (e.g., Scott and Smith, Science 249:386-390 (1990); Devlin, Science 249:404-406 (1990); Cwirla et al., Proc. Natl. Acad. Sci. USA 87:7178-7182 (1990); and Felici, J. Mol. Biol. 222:301-310 (1991)) (each of these references is incorporated herein in its entirety by reference). Antibodies that have been identified to specifically bind to PA or a fragment or variant of PA can then be assayed for their specificity and affinity for PA using or routinely modifying techniques described herein or otherwise known in the art (see, e.g., Examples 1 and 2).

The antibodies of the invention may be assayed for specific binding to PA polypeptides and cross-reactivity with other antigens by any method known in the art. Immunoassays which can be used to analyze specific binding and cross-reactivity include, but are not limited to, competitive and non-competitive assay systems using techniques such as BIAcore analysis, FACS (fluorescence activated cell sorter) analysis, immunofluorescence, immunocytochemistry, radioimmunoassays, ELISA (enzyme linked immunosorbent assay), "sandwich" immunoassays, immunoprecipitation assays, western blots, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

ELISAs comprise preparing antigen, coating the well of a 96-well microtiter plate with the antigen, washing away antigen that did not bind the wells, adding the antibody of interest conjugated to a detectable compound such as an enzymatic substrate (e.g., horseradish peroxidase or alkaline phosphatase) to the wells and incubating for a period of time, washing away unbound antibodies or non-specifically bound antibodies, and detecting the presence of the antibodies specifically bound to the antigen coating the well. In ELISAs, the antibody of interest does not have to be conjugated to a detectable compound; instead, a second antibody (which recognizes the antibody of interest) conjugated to a detectable compound may be added to the well. Alternatively, the antigen need not be directly coated to the well; instead the ELISA plates may be coated with an anti-Ig Fc antibody, and the antigen in the form or a PA-Fc fusion protein, may be bound to the anti-Ig Fc coated to the plate. This may be desirable so as to maintain the antigen protein (e.g., the PA polypeptides) in a more native conformation than it may have when it is directly coated to a plate. In another alternative, instead of coating the well with the antigen, the antibody may be coated to the well. In this case, the detectable molecule could be the antigen conjugated to a detectable compound such as an enzymatic substrate (e.g., horseradish peroxidase or alkaline phosphatase). One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody (including an scFv or other molecule comprising, or alternatively consisting of, antibody fragments or variants thereof) to an antigen and the off-rate of an antibody-antigen interaction can be determined by competitive binding assays. One example of a competitive binding assay is a radioimmunoassay comprising the incubation of labeled antigen (e.g., antigen labeled with $^3$H or $^{125}$I), or fragment or variant thereof with the antibody of interest in the presence of increasing amounts of unlabeled antigen, and the detection of the antibody bound to the labeled antigen. The affinity of the antibody of the present invention for PA and the binding off-rates can be determined from the data by Scatchard plot analysis. Competition with a second antibody can also be determined using radioimmunoassays. In this case, a PA polypeptide is incubated with an antibody of the present invention conjugated to a labeled compound (e.g., compound labeled with $^3$H or $^{125}$I) in the presence of increasing amounts of an unlabeled second anti-PA antibody. Assays for determining the ability of one antibody to competitively inhibit the binding of another antibody are known in the art (See, for example, Harlow, Ed & David Lane, *Antibodies: A Laboratoiy Manual*, New York: Cold Spring Harbor Laboratory, 1988. pp. 567-569.) This kind of competitive assay between two antibodies, may also be used to determine if two antibodies bind the same, closely associated (e.g., overlapping) or different epitopes.

In a preferred embodiment, BIAcore kinetic analysis is used to determine the binding on and off rates of antibodies (including antibody fragments or variants thereof) to PA, or fragments of PA.

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40 degrees C., adding protein A and/or protein G sepharose beads to the cell lysate, incubating for about an hour or more at 40 degrees C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

Antibody Conjugates

The present invention encompasses antibodies (including antibody fragments or variants thereof), recombinantly fused or chemically conjugated (including both covalent and non-covalent conjugations) to a heterologous polypeptide (or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. For example, antibodies of the invention may be used to target heterologous polypeptides to particular cell types (e.g., cancer cells), either in vitro or in vivo, by fusing or conjugating the heterologous polypeptides to antibodies of the invention that are specific for particular cell surface antigens or which bind antigens that bind particular cell surface receptors. Antibodies of the invention may also be fused to albumin (including but not limited to recombinant human serum albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)), resulting in chimeric polypeptides, In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention. Such fusion proteins may, for example, facilitate purification and may increase half-life in vivo. Antibodies fused or conjugated to heterologous polypeptides may also be used in in vitro immunoassays and purification methods using methods known in the art. See e.g., Harbor et al., supra, and PCT publication WO 93/2 1232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising, or alternatively consisting of, heterologous polypeptides fused or conjugated to antibody fragments. For example, the heterologous polypeptides may be fused or conjugated to a Fab fragment, Fd fragment, Fv fragment, F(ab), fragment, or a portion thereof. Methods for fusing or conjugating polypeptides to antibody portions are known in the art. See, e.g., U.S. Pat. Nos. 5,356,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88: 10535-10539 (1991); Zheng et al., J. Immunol. 154:5590-5600 (1995); and Vil et al., Proc. Natl. Acad. Sci. USA 89:11357-11341 (1992) (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of antibodies (including molecules comprising, or alternatively consisting of, antibody fragments or variants thereof), such methods can be used to generate antibodies with altered activity (e.g., antibodies with higher affinities and lower dissociation rates). See, generally, U.S. Pat. Nos. 5,605,793; 5,811,238; 5,830,721; 5,834,252; and 5,837,458, and Patten et al., Curr. Opinion Biotechnol. 8:724-35 (1997); Harayama, Trends Biotechnol. 16(2):76-82 (1998); Hansson, et al., J. Mol. Biol. 287: 265-76 (1999); and Lorenzo and Blasco, Biotechniques 24(2):308-13 (1998) (each of these patents and publications are hereby incorporated by reference in its entirety). In one embodiment, polynucleotides encoding antibodies of the invention may be altered by being subjected to random mutagenesis by error-prone PCR, random nucleotide insertion or other methods prior to recombination. In another embodiment, one or more portions of a polynucleotide encoding an antibody which portions specifically bind to PA may be recombined with one or more components, motifs, sections, parts, domains, fragments, etc. of one or more heterologous molecules.

Moreover, the antibodies of the present invention (including antibody fragments or variants thereof), can be fused to marker sequences, such as a polypeptides to facilitate purification. In preferred embodiments, the marker amino acid sequence is a hexa-histidine polypeptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., Cell 37:767 (1984)) and the FLAG® tag (Stratagene, La Jolla, Calif.).

The present invention further encompasses antibodies (including antibody fragments or variants thereof), conjugated to a diagnostic or therapeutic agent. The antibodies can be used, for example, as part of a clinical testing procedure to, e.g., determine the safety or efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include, but are not limited to, horseradish peroxidase, alkaline phosphatase, beta-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotri-azinylamine fluorescein, dansyl chloride or phycoerythrin; an example of a luminescent material includes, but is not limited to, luminol; examples of bioluminescent materials include, but are not limited to, luciferase, luciferin, and aequorin; and examples of suitable radioactive material include, but are not limited to, iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti, gallium ($^{68}$Ga, $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$Pm, $^{140}$La, $^{175}$YB, $^{166}$Ho, $^{90}$Y, $^{47}$Sc, $^{186}$Re, $^{188}$Re, $^{142}$Pr, $^{105}$Rh, and $^{97}$Ru.

Further, an antibody of the invention (including an scFv or other molecule comprising, or alternatively consisting of, antibody fragments or variants thereof), may be coupled or conjugated to a therapeutic moiety such as a cytotoxin, e.g., a cytostatic or cytocidal agent, a therapeutic agent or a radioactive metal ion, e.g., alpha-emitters such as, for example, $^{213}$Bi, or other radioisotopes such as, for example, $^{103}$Pd, $^{135}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Y, $^{117}$Tin, $^{186}$Re, $^{188}$Re and $^{166}$Ho. In specific embodiments, an antibody or fragment thereof is attached to macrocyclic chelators that chelate radiometal ions, including but not limited to, $^{177}$Lu, $^{90}$Y, $^{166}$Ho, and $^{153}$Sm, to polypeptides. In specific embodiments, the macrocyclic chelator is 1,4,7,10-tetraazacyclododecane-N,N',N'',N'''-tetraacetic acid (DOTA). In other specific embodiments, the DOTA is attached to the an antibody of the invention or fragment thereof via a linker molecule. Examples of linker molecules useful for conjugating DOTA to a polypeptide are commonly known in the art—see, for example, DeNardo et al., Clin Cancer Res. 4(10):2483-90, 1998; Peterson et al., Bioconjug. Chem. 10(4):553-7, 1999; and Zimmerman et al., Nucl. Med. Biol. 26(8):943-50, 1999 which are hereby incorporated by reference in their entirety.

A cytotoxin or cytotoxic agent includes any agent that is detrimental to cells. Examples include, but are not limited to, paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, thymidine kinase, endonuclease, RNAse, and puromycin and fragments, variants or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques known in the art may be applied to label antibodies of the invention. Such techniques include, but are not limited to, the use of bifunctional conjugating agents (see e.g., U.S. Pat. Nos. 5,756,065; 5,714,711; 5,696,239; 5,652,371; 5,505,931; 5,489,425; 5,435,990; 5,428,139; 5,342,604; 5,274,119; 4,994,560; and 5,808,003; the contents of each of which are hereby incorporated by reference in its entirety) and direct coupling reactions (e.g., Bolton-Hunter and Chloramine-T reaction).

The antibodies of the invention which are conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, but are not limited to, for example, a toxin such as abrin, ricin A, alpha toxin, pseudomonas exotoxin, or diphtheria toxin, saporin, momordin, gelonin, pokeweed antiviral protein, alpha-sarcin and cholera toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (see, International Publication No. WO 97/35899), AIM II (see, International Publication No. WO 97/34911), Fas Ligand (Takahashi et al., *Int. Immunol.*, 6:1567-1574 (1994)), VEGI (see, International Publication No. WO 99/23105), a thrombotic agent or an anti-angiogenic agent, e.g., angiostatin or endostatin; or, biological response modifiers such as, for example, lymphokines, interleukin-1 (IL-1), interleukin-2 (IL-2), interleukin-6 (IL-6), granulocyte macrophage colony stimulating factor (GM-CSF), granulocyte colony stimulating factor (G-CSF), or other growth factors.

Antibodies of the invention (including antibody fragments or variants thereof), may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating a therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody of the invention can be conjugated to a second antibody to form an antibody heteroconjugate as described by Segal in U.S. Pat. No. 4,676,980, which is incorporated herein by reference in its entirety.

An antibody of the invention (including an other molecules comprising, or alternatively consisting of, an antibody fragment or variant thereof), with or without a therapeutic moiety conjugated to it, administered alone or in combination with cytotoxic factor(s) and/or cytokine(s) can be used as a therapeutic.

Uses of Antibodies of the Invention

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of PA polypeptides in biological and non-biological samples. See, e.g., Harlow et al., Antibodies: A Laboratory Manual, (Cold Spring Harbor Laboratory Press, 2nd ed. 1988) (incorporated by reference herein in its entirety). By way of another non-limiting example, antibodies of the invention may be administered to individuals as a form of passive immunization.

Prophylactic or therapeutic treatment with anti-PA antibodies has advantages over other anti-anthrax agents, such as antibiotics, in that anti-PA antibodies provide protection against drug resistant strains; anti-PA antibodies can be given as either a single dose treatment or can be given in multiple doses (e.g., bi-weekly or monthly dosing); individual doses of anti-PA antibodies will have a relatively long duration of effect; can be administered subcutaneously in addition to other routes of administration (e.g., intravenously), and will be useful in re-exposure or flare situations. Given that the anti-PA antibodies provided herein are fully human antibodies, the risk of side effects due to anti-PA treatment will be minimal when administered as fully human antibodies.

Epitope Mapping

The present invention provides antibodies (including antibody fragments or variants thereof), that can be used to identify epitopes of a PA polypeptide (e.g., SEQ ID NO:2)) using techniques described herein or otherwise known in the art. Fragments which function as epitopes may be produced by any conventional means. (See, e.g., Houghten, Proc. Natl. Acad. Sci. USA 82:5131-5135 (1985), further described in U.S. Pat. No. 4,711,211.) Identified epitopes of antibodies of the present invention may, for example, be used as vaccine candidates, i.e., to immunize an individual to elicit antibodies against the naturally occurring forms of PA polypeptides.

Diagnostic Uses of Antibodies

Labeled antibodies of the invention (including molecules comprising, or alternatively consisting of, antibody fragments or variants thereof) which specifically bind to a PA polypeptide can be used for diagnostic purposes to detect, diagnose, prognose, or monitor the presence of the intact *Bacillus anthracis* spore or organism, or simply the components of anthrax toxin. In specific embodiments, labeled antibodies of the invention (including molecules comprising, or alternatively consisting of, antibody fragments or variants thereof) which specifically bind to a PA polypeptide can be used for diagnostic purposes to detect, diagnose, prognose, or monitor the course of anthrax infection.

The invention provides for the detection of expression of a PA polypeptide comprising: (a) assaying the expression of a PA polypeptide in a (biological—or non-biological) sample from an individual using one or more antibodies of the invention that specifically binds to PA; and (b) detecting the presence of PA polypeptide in the sample.

The invention provides for the detection of aberrant expression of a PA polypeptide comprising: (a) assaying the expression of a PA polypeptide in from one strain of *Bacillus anthracis* using one or more antibodies of the invention that specifically binds to PA; and (b) comparing the level of a PA polypeptide in the biological sample with a standard level of a PA polypeptide, e.g., in a reference strain of *Bacillus anthracis*, whereby an increase or decrease in the assayed level of a PA polypeptide compared to the standard level of a PA polypeptide is indicative of aberrant expression.

By "biological sample" is intended any fluids and/or cells obtained from an individual, body fluid, body tissue, body cell, cell line, tissue culture, bacterial culture, or other source which may contain a PA polypeptide protein or mRNA. Body fluids include, but are not limited to, sera, plasma, urine, synovial fluid, pleural fluid, edema fluid, spinal fluid, saliva, and mucous. Tissues samples may be taken from virtually any tissue in the body. Tissue samples may also be obtained from autopsy material. Methods for obtaining tissue biopsies and body fluids from mammals are well known in the art. Where the biological sample is to include mRNA, a tissue biopsy is the preferred source.

One aspect of the invention is the detection and diagnosis of a disease or disorder associated with *Bacillus anthracis* or anthrax toxins in an animal, preferably a mammal and most preferably a human.

Therapeutic and Prophylactic Uses of Antibodies

One or more antibodies of the present invention (including molecules comprising, or alternatively consisting of, antibody fragments or variants thereof) that specifically bind to PA may be used locally or systemically in the body as a prophylactic or a therapeutic. The present invention is further directed to antibody-based therapies which involve administering antibodies of the invention (including molecules comprising, or alternatively consisting of, antibody fragments or variants thereof) to an animal, preferably a mammal, and most preferably a human, for treating individuals infected with *Bacillus anthracis* bacteria and/or *B. anthracis* spores or individuals that have been exposed to *B. anthracis* bacteria, *B. anthracis* spores and/or anthrax toxins. Anthrax infection occurs when an animal has *B. anthracis* bacteria and/or *B. anthracis* spores within its body or in contact with the surface of its body. An animal may be considered as poisoned with anthrax toxin when it has within its body or in contact with the surface of its body, lethal toxin, edema toxin, lethal factor or edema factor.

Therapeutic compounds of the invention include, but are not limited to, antibodies of the invention and nucleic acids encoding antibodies of the invention as described herein. The treatment and/or prevention of anthrax infection and/or anthrax toxin poisoning includes alleviating or preventing symptoms associated with anthrax infection and/or anthrax toxin poisoning.

For example, bacteremia occurs in almost all cases of anthrax that progress to a fatal outcome. Antibodies of the invention may be used to prevent the development of bacteremia in anthrax patients or to treat patients that have developed bacteremia associated with anthrax infection. In specific embodiments, anti-PA antibodies of the invention which activate the complement cascade, i.e. IgG1, IgG2, IgG3, and IgA1 and IgM antibodies, are used to prevent the development of bacteremia in anthrax patients or to treat patients that have developed bacteremia associated with anthrax infection.

In other embodiments, antibodies of the invention may have a bactericidal and or bacteriostatic effect on *B. anthracis* bacteria. By way of non-limiting example, antibodies of the invention may activate the classical complement pathway and/or enhance the activation of the alternative complement pathway. Alternatively, antibodies of the invention may opsonize *B. anthracis* bacteria. Opsonized bacteria then may be a target for antibody dependent cell-mediated cytotoxicty (ADCC). In another embodiment, antibodies of the invention may catalyze the generation of hydrogen peroxide from singlet molecular oxygen and water which chemical reaction results in the efficient killing of bacteria. Armed with the teachings provided herein, one of ordinary skill in the art will know how to use the antibodies of the present invention for diagnostic, monitoring or therapeutic purposes without undue experimentation.

Antibodies of the invention may be provided in pharmaceutically acceptable compositions as known in the art or as described herein.

Therapeutic/Prophylactic Compositions and Administration

The invention provides methods of treatment, inhibition and prophylaxis by administration to a subject of an effective amount of antibody (or fragment or variant thereof) or pharmaceutical composition of the invention, preferably an antibody of the invention. In a preferred aspect, an antibody or fragment or variant thereof is substantially purified (i.e., substantially free from substances that limit its effect or produce undesired side-effects). The subject is preferably an animal, including but not limited to, animals such as cows, pigs, horses, chickens, cats, dogs, etc., and is preferably a mammal, and most preferably a human.

Formulations and methods of administration that can be employed when the compound comprises a nucleic acid or an immunoglobulin are described above; additional appropriate formulations and routes of administration can be selected from among those described herein below.

Various delivery systems are known and can be used to administer antibody or fragment or variant thereof of the invention, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of introduction include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

The preferred route of administration for antibodies of the invention will depend, in part, on the time of administration relative to the time of exposure or potential exposure to anthrax bacterium, anthrax spores, and/or anthrax derived toxins such as lethal toxin and edema toxin. For example, if administration of the antibody to an individual occurs after an actual or suspected exposure to anthrax bacterium, anthrax spores, and/or anthrax derived toxins, it would be most expedient to deliver the antibodies via a route which will provide the quickest time to maximum concentration (Tmax) and/or the greatest maximum concentration (Cmax) of serum anti- PA antibody levels. The shortest Tmax in serum is achieved using intravenous administration, because the antibody is delivered directly to the serum. It has also been shown in pharmacokinetic studies using rabbits and cynomolgus monkeys, that intramuscular administration results in a slightly higher Cmax and a slightly faster Tmax as compared to subcutaneous administration. Thus, post-exposure administration of antibodies of the invention is preferably performed intravenously. However, due to the time, materials and facilities required for intravenous administration, other routes of administration (such as intramuscular or subcutaneous administration) may be preferable for post-exposure administration of anti-PA antibodies especially in mass exposure events, exposure events in isolated areas or in battlefield conditions, or other similar situations.

On the other hand, if the time the antibody stays in the body (residence time) is the greatest clinical consideration, it may be preferable to administer the antibody via a route that provides for a relatively long terminal half life of the antibody in serum and a long residence time. If antibodies are being administered prophylactically, prior to exposure or potential exposure to anthrax bacterium, anthrax spores, and/or anthrax derived toxins, it would be desirable to ensure the greatest longevity of the efficacy of the prophylactic antibody treatment by administering the antibodies via the route that provides for a relatively long terminal half life of the antibody in serum and a long residence time. It has been shown in pharmacokinetic studies using rabbits and cynomolgus monkeys, that that intramuscular or subcutaneous administration gives a longer terminal half life and/or residence time compared to intravenous administration. Thus, pre-exposure administration of anti-PA antibodies of the invention is preferably performed intramuscularly or subcutaneously.

In a preferred embodiment the antibody of the invention is formulated in 10 mM sodium citrate, 1.8% glycine, 1.0% sucrose, 0.02% polysorbate 80 (w/v), pH 6.5. In another preferred embodiment, the antibody of the invention is formulated in 10 mM sodium citrate, 1.8% glycine, 1.0% sucrose, 0.02% polysorbate 80 (w/v), pH 6.5 for subcutaneous, intramuscular and/or intravenous administration. Of course, any formulation suitable for clinical administration may be used.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the composition can be delivered in a vesicle, in particular a liposome (see Langer, Science 249:1527-1535 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 3 17-327; see generally ibid.).

In yet another embodiment, the composition can be delivered in a controlled release system. In one embodiment, a pump may be used (see Langer, supra; Sefton, CRC Crit. Ref. Biomed. Eng. 14:20 1 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:71 (1983); see also Levy et al., Science 228: 190 (1985); During et al., Ann. Neurol. 25:35 1 (1989); Howard et al., J. Neurosurg. 7 1:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1535 (1990)).

In a specific embodiment where the composition of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of an antibody or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 50 mg/kg of the patient's body weight. In specific embodiments, the dosage administered to a patient is exactly or about 1 mg/kg of the patient's body weight. In specific embodiments, the dosage administered to a patient is exactly or about 3 mg/kg of the patient's body weight. In specific embodiments, the dosage administered to a patient is exactly or about 5 mg/kg of the patient's body weight. In specific embodiments, the dosage administered to a patient is exactly or about 10 mg/kg of the patient's body weight. In specific embodiments, the dosage administered to a patient is exactly or about 20 mg/kg of the patient's body weight. In specific embodiments, the dosage administered to a patient is exactly or about 30 mg/kg of the patient's body weight. In specific embodiments, the dosage administered to a patient is exactly or about 40 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of therapeutic or pharmaceutical compositions of the invention may be reduced by enhancing uptake and tissue penetration (e.g., into the brain) of the antibodies by modifications such as, for example, lipidation.

Because bacteria and/or toxin will already be present when a patient is to be treated therapeutically, therapeutic dosages generally will be greater than prophylactic dosages. In specific embodiments, a therapeutic dosage of anti-PA antibodies of the invention will be in the range of 1 to 100 mg/kg of the patient's body weight. In preferred embodiments, a therapeutic dosage of anti-PA antibodies of the invention will be in the range of 10 to 40 mg/kg of the patient's body weight. In specific preferred embodiments, a therapeutic dosage of anti-PA antibodies of the invention will be exactly or about 10 mg/kg of the patient's body weight. In specific preferred embodiments, a therapeutic dosage of anti-PA antibodies of the invention will be exactly or about 20 mg/kg of the patient's body weight. In specific preferred embodiments, a therapeutic dosage of anti-PA antibodies of the invention will be exactly or about 30 mg/kg of the patient's body weight. In specific preferred embodiments, a therapeutic dosage of anti-PA antibodies of the invention will be exactly or about 40 mg/kg of the patient's body weight.

In specific embodiments, a prophylactic dose of anti-PA antibodies of the invention will be in the range of 0.1 to 20 mg/kg of the patient's body weight. In preferred embodiments, a prophylactic dose of anti-PA antibodies of the invention will be in the range of 1 to 10 mg/kg of the patient's body weight. In specific preferred embodiments, a prophylactic dose of anti-PA antibodies of the invention will be exactly or about 1 mg/kg of the patient's body weight. In specific preferred embodiments, a prophylactic dose of anti-PA antibodies of the invention will be exactly or about 3 mg/kg of the patient's body weight. In specific preferred embodiments, a prophylactic dose of anti-PA antibodies of the invention will be exactly or about 5 mg/kg of the patient's body weight. In specific preferred embodiments, a prophylactic dose of anti-PA antibodies of the invention will be exactly or about 10 mg/kg of the patient's body weight.

Generally, administration of products of a species origin or species reactivity (in the case of antibodies) that is the same species as that of the patient is preferred. Thus, in a preferred embodiment, human antibodies, fragments, or variants, (e.g., derivatives), or nucleic acids, are administered to a human patient for therapy or prophylaxis.

It is preferred to use high affinity and/or potent in vivo inhibiting and/or neutralizing antibodies of the invention (including molecules comprising, or alternatively consisting of, antibody fragments or variants thereof) that specifically bind to PA, or polynucleotides encoding antibodies that specifically bind to PA, for both immunoassays and administration to patients. Such antibodies will preferably have an affinity for PA and/or PA polypeptide fragments. Preferred binding affinities include those with a dissociation constant or $K_D$ of less than or equal to $5\times10^{-2}$ M, $10^{-2}$ M, $5\times10^{-3}$ M, $10^{-3}$ M, $5\times10^{-4}$ M, $10^{-4}$ M, $5\times10^{-5}$ M, or $10^{-5}$ M. More preferably, antibodies of the invention bind PA polypeptides or fragments or variants thereof with a dissociation constant or $K_D$ less than or equal to $5\times10^{-6}$ M, $10^{-6}$ M, $5\times10^{-7}$ M, $10^{-7}$ M, $5\times10^{-8}$ M, or $10^{-8}$ M. Even more preferably, antibodies of the invention bind PA polypeptides or fragments or variants thereof with a dissociation constant or $K_D$ less than or equal to $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

As discussed in more detail below, the antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibody and antibody compositions of the invention may be administered alone or in combination with other therapeutic agents, including but not limited to antibiotics, antivirals, anti-retroviral agents, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In some embodiments, antibodies of the invention that are administered to an animal, preferably a human, for therapeutic or prophylactic uses are multimeric antibodies. In specific embodiments, antibodies of the invention are homodimeric IgG molecules. In other specific embodiments, antibodies of the invention are homodimeric IgG1 molecules. In specific embodiments, antibodies of the invention are homotrimeric IgG molecules. In other specific embodiments, antibodies of the invention are trimeric IgG1 molecules. In other specific embodiments, antibodies of the invention are higher-order multimers of IgG molecules (e.g., tetramers, penatmers and hexamers]. In still further specific embodiments, antibodies of the IgG molecules comprising the higher order multimers of IgG molecules are IgG1 molecules.

Alternatively, antibodies of the invention for therapeutic or prophylactic uses may be administered in combination with crosslinking agents known in the art, including but not limited to anti-IgG antibodies.

Combination Administration with Antibiotics, Other Anti-Anthrax Agents, or Other Anti-Bioterorrism Agents The antibodies of the invention (including molecules comprising, or alternatively consisting of, antibody fragments or variants thereof) may be administered alone or in combination with other therapeutic or prophylactic regimens (e.g., radiation therapy, chemotherapy, hormonal therapy, immunotherapy, anti-tumor agents, anti-angiogenesis and anti-inflammatory agents). In specific embodiments, antibodies of the invention are administered in combination with one or more anti-anthrax agents. An anti-anthrax agent is a substance that is used to treat or prevent anthrax infection and/or anthrax toxin-poisoning. Such combinatorial therapy may be administered sequentially and/or concomitantly.

The antibodies of the invention may be administered prophylactically or therapeutically. It is specifically contemplated that the antibodies of the invention may be administered to provide protection against anthrax infection and/or anthrax toxin exposure as a supplementary or supportive measure in addition to other prophylactic or therapeutic regimens. For example, conventional treatment for known or suspected anthrax infection and/or anthrax toxin exposure typically includes immunization with an anthrax vaccine and/ or administration of antibiotics. However, it takes significant time both for an individual or animal to build up antibody titers against anthrax following immunization, and for antibiotic treatment regimens to effectively control an anthrax infection. During these time periods, conventional treatment does little to offset the clinical effect of anthrax toxins on the patient. In one embodiment of the invention, the antibodies of the invention may be administered as a form of passive immunization or supportive therapy during the time period following immunization with an anthrax vaccine, in order to prevent or lessen the effect of anthrax toxins prior to development of protective levels of anti-anthrax antibody titers. Another exemplary use of the antibodies of the invention is as supportive or supplemental therapy for an individual undergoing antibiotic treatment for anthrax exposure, in order to prevent or lessen the effect of anthrax toxins while the antibiotic treatment regimen is given time to eliminate the anthrax infection.

In specific embodiments, anti-PA antibodies of the invention may be administered in combination with other anti-PA antibodies, or other antibodies reactive with different protein components of Bacillus anthracis or anthrax toxin components (including EF and LF).

In specific embodiments, anti-PA antibodies of the invention may be administered in combination with one or more antibiotic agents. In a particular embodiment, anti-PA antibodies of the invention may be administered in combination with the antibiotic Ciprofloxacin Hydrochloride (Cipro). In other embodiments, anti-PA antibodies of the invention may be administered in combination with the antibiotic doxycycline. In other embodiments, anti-PA antibodies of the invention may be administered in combination with the antibiotic penicillin G procaine. In other embodiments, anti-PA antibodies of the invention may be administered in combination with the antibiotic amoxicillin. In other embodiments, anti-PA antibodies of the invention may be administered in combination with the antibiotic ofloxacin. In other embodiments, anti-PA antibodies of the invention may be administered in combination with the antibiotic penicillin levofloxacin.

Other antibiotics that may be administered in combination with anti-PA antibodies of the invention include, but are not limited to, aminoglycosides, beta-lactam (glycopeptide), beta-lactamases, Clindamycin, chloramphenicol, cephalosporins, erythromycin, fluoroquinolones, macrolides, metronidazole, cephalothin, cefazolin, penicillins, quinolones, rifampin, streptomycin, sulfonamide, tetracyclines, imipenem, clarithromycin, gentamycin, and vancomycin.

In specific embodiments, antibodies of the invention are administered in combination with other therapeutics or prophylactics such as a soluble form of an anthrax receptor (e.g., SEQ ID NO:3 described in Nature (2002) 414:225-229 which is hereby incorporated by reference in its entirety, e.g., a polypeptide comprising amino acids 1 to 227 of 41-227 SEQ ID NO:3), a soluble for of the CMG2 receptor (described in Scobie et al., Proceedings of the National Academy of Sciences USA (2003) 100:5170-5174 which is hereby incorporated by reference in its entirety) or anti-ATR or anti-CMG2 antibodies that block binding of PA to ATR or CMG2, respectively. Other therapeutics or prophylactics that may be administered in combination with an antibody of the present invention include mutant forms of PA such as the EF/LF translocation deficient forms of PA described in International Publication Number WO01/82788 and in Science (2001) 292:695-697, both of which are hereby incorporated by reference in their entireties. Other therapeutics or prophylactics that may be administered in combination with an antibody of the present invention include peptide inhibitors that block LF binding to PA such as the P1 peptide, or its polyvalent form described in Nature Biotechnology (2002) 19:958-961 which is hereby incorporated by reference in its entirety. Still other therapeutics or prophylactics that may be administered in combination with an antibody of the present invention include, but are not limited to antibiotics, anthrax vaccines, antibodies immunoreactive with LF, EF or other protein moieties of *Bacillus anthracis*.

In specific embodiments, antibodies of the invention are administered in combination with anthrax vaccines, including but not limited to vaccines such as Anthrax Vaccine Adsorbed (AVA, also known as MDPH-PA and BioThrax), manufactured by BioPort Corporation, Lansing, Mich.; the vaccine manufactured by the Center for Applied Microbiology & Research (CAMR), Porton Down, Salisbury, England; vaccines utilizing recombinantly expressed anthrax PA, LF and/or EF proteins, whether wild-type or mutated (including both naturally occurring and artificially generated mutants); and other anthrax vaccines, including live, modified live, and killed vaccines.

In another specific embodiment, antibodies and antibody compositions of the invention are administered in combination with protease inhibitors. In specific embodiments, antibodies and antibody compositions of the invention are administered in combination with furin inhibitors.

Additional Combination Therapies

In other embodiments, antibody and antibody compositions of the invention may be administered in combination with anti-opportunistic infection agents. Anti-opportunistic agents that may be administered in combination with the antibody and antibody compositions of the invention, include, but are not limited to, dapsone, pentamidine, atovaquone, isoniazid, rifampin, pyrazinamide, ethambutol, rifabutin, clarithromycin, azithromycin, ganciclovir, foscarnet, cidofovir, fluconazol, itraconazole, ketoconazole, acyclovir, famcicolvir, pyrimethamine, leucovorin, (filgrastim/G-CSF), and LEUKINE™ (sargramostim/GM-CSF). In a specific embodiment, antibody and antibody compositions of the invention are used in any combination with trimethoprim-sulfamethoxazole, dapsone, pentamidine, and/or atovaquone to prophylactically treat, prevent, and/or diagnose an opportunistic *Pneumocystis carinii* pneumonia infection. In another specific embodiment, antibody and antibody compositions of the invention are used in any combination with isoniazid, rifampin, pyrazinamide, and/or ethambutol to prophylactically treat, prevent, and/or diagnose an opportunistic *Mycobacterium avium* complex infection. In another specific embodiment, antibody and antibody compositions of the invention are used in any combination with rifabutin, clarithromycin, and/or azithromycin to prophylactically treat, prevent, and/or diagnose an opportunistic *Mycobacterium tuberculosis* infection. In another specific embodiment, antibody and antibody compositions of the invention are used in any combination with ganciclovir, foscarnet, and/or cidofovir to prophylactically treat, prevent, and/or diagnose an opportunistic cytomegalovirus infection. In another specific embodiment, antibody and antibody compositions of the invention are used in any combination with fluconazole, itraconazole, and/or ketoconazole to prophylactically treat, prevent, and/or diagnose an opportunistic fungal infection. In another specific embodiment, antibody and antibody compositions of the invention are used in any combination with acyclovir and/or famcicolvir to prophylactically treat, prevent, and/or diagnose an opportunistic herpes simplex virus type I and/or type II infection. In another specific embodiment, antibody and antibody compositions of the invention are used in any combination with pyrimethamine and/or leucovorin to prophylactically treat, prevent, and/or diagnose an opportunistic *Toxoplasma gondii* infection. In another specific embodiment, antibody and antibody compositions of the invention are used in any combination with leucovorin and/or NEUPOGEN™ (filgrastim/G-CSF) to prophylactically treat, prevent, and/or diagnose an opportunistic bacterial infection.

In a further embodiment, the antibody and antibody compositions of the invention are administered in combination with an antiviral agent. Antiviral agents that may be administered with the antibody and antibody compositions of the invention include, but are not limited to, acyclovir, ribavirin, amantadine, and remantidine.

In certain embodiments, Therapeutics of the invention are administered in combination with antiretroviral agents, nucleoside/nucleotide reverse transcriptase inhibitors (NRTIs), non-nucleoside reverse transcriptase inhibitors (NNRTIs), and/or protease inhibitors (PIs). NRTIs that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). NNRTIs that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In a specific embodiment, compositions of the invention are administered in combination with a chemotherapeutic agent. Chemotherapeutic agents that may be administered with the compositions of the invention include, but are not limited to, antibiotic derivatives (e.g., doxorubicin (adriamycin), bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, etoposide, Topotecan, 5-Fluorouracil, paclitaxel (Taxol), Cisplatin, Cytarabine, and IFN-gamma, irinotecan (Camptosar, CPT-11), irinotecan analogs, and gemcitabine (GEMZAR™)).

In a specific embodiment, antibody and antibody compositions of the invention are administered in combination with CHOP (cyclophosphamide, doxorubicin, vincristine, and prednisone) or any combination of the components of CHOP. In another embodiment, antibody and antibody compositions of the invention are administered in combination with Rituximab. In a further embodiment, antibody and antibody compositions of the invention are administered with Rituximab and CHOP, or Rituximab and any combination of the components of CHOP.

In additional preferred embodiments, the compositions of the invention are administered in combination with TRAIL polypeptides or fragments or variants thereof, particularly of the extracellular soluble domain of TRAIL.

In one embodiment, the compositions of the invention are administered in combination with other members of the TNF family or antibodies specific for TNF receptor family members. In specific embodiments Antibodies and antibody compositions of the invention are administered in combination with anti-TNF-alpha and/or anti-IL-1Beta antibodies. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), TRAIL, AIM-II (International Publication No. WO 97/34911), APRIL (J. Exp. Med. 188(6):1185-1190), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/35904), TR5 (International Publication No. WO 98/30693), TR6 (International Publication No. WO 98/30694), TR7 (International Publication No. WO 98/41629), TRANK, TR9 (International Publication No. WO 98/56892) TR10 (International Publication No. WO 98/54202), 312C2 (International Publication No. WO 98/06842), and TR12, and soluble forms CD154, CD70, and CD153.

In a more preferred embodiment, the antibody and antibody compositions of the invention are administered in combination with an antimalarial, methotrexate, anti-TNF antibody, ENBREL™ (etanercept) and/or suflasalazine. In one embodiment, the antibody and antibody compositions of the invention are administered in combination with methotrexate. In another embodiment, the antibody and antibody compositions of the invention are administered in combination with anti-TNF antibody. In another embodiment, the antibody and antibody compositions of the invention are administered in combination with methotrexate and anti-TNF antibody. In another embodiment, the antibody and antibody compositions of the invention are administered in combination with suflasalazine. In another specific embodiment, the antibody and antibody compositions of the invention are administered in combination with methotrexate, anti-TNF antibody, and suflasalazine. In another embodiment, the antibody and antibody compositions of the invention are administered in combination ENBREL™ (etanercept). In another embodiment, the antibody and antibody compositions of the invention are administered in combination with ENBREL™ (etanercept) and methotrexate. In another embodiment, the antibody and antibody compositions of the invention are administered in combination with ENBREL™ (etanercept), methotrexate and suflasalazine. In another embodiment, the antibody and antibody compositions of the invention are administered in combination with ENBREL™ (etanercept), methotrexate and suflasalazine. In other embodiments, one or more antimalarials is combined with one of the above-recited combinations. In a specific embodiment, the antibody and antibody compositions of the invention are administered in combination with an antimalarial (e.g., hydroxychloroquine), ENBREL™ (etanercept), methotrexate and suflasalazine. In another specific embodiment, the antibody and antibody compositions of the invention are administered in combination with an antimalarial (e.g., hydroxychloroquine), sulfasalazine, anti-TNF antibody, and methotrexate.

Conventional nonspecific immunosuppressive agents, that may be administered in combination with the antibody and antibody compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells.

In specific embodiments, antibody and antibody compositions of the invention are administered in combination with immunosuppressants. Immunosuppressants preparations that may be administered with the antibody and antibody compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the antibody and antibody compositions of the invention are administered in combination with steroid therapy. Steroids that may be administered in combination with the antibody and antibody compositions of the invention, include, but are not limited to, oral corticosteroids, prednisone, and methylprednisolone (e.g., IV methylprednisolone). In a specific embodiment, antibody and antibody compositions of the invention are administered in combination with prednisone. In a further specific embodiment, the antibody and antibody compositions of the invention are administered in combination with prednisone and an immunosuppressive agent. Immunosuppressive agents that may be administered with the antibody and antibody compositions of the invention and prednisone are those described herein, and include, but are not limited to, azathioprine, cylophosphamide, and cyclophosphamide IV. In another specific embodiment, antibody and antibody compositions of the invention are administered in combination with methylprednisolone. In a further specific embodiment, the antibody and antibody compositions of the invention are administered in combination with methylprednisolone and an immunosuppressive agent. Immunosuppressive agents that may be administered with the antibody and antibody compositions of the invention and methylprednisolone are those described herein, and include, but are not limited to, azathioprine, cylophosphamide, and cyclophosphamide IV.

The invention also encompasses combining the polynucleotides and/or polypeptides of the invention (and/or agonists or antagonists thereof) with other proposed or conventional hematopoietic therapies. Thus, for example, the polynucleotides and/or polypeptides of the invention (and/or agonists or antagonists thereof) can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations of the antibody and antibody compositions of the invention with compounds generally used to treat aplastic anemia, such as, for example, methenolene, stanozolol, and nandrolone; to treat iron-deficiency anemia, such as, for example, iron preparations; to treat malignant anemia, such as, for example, vitamin $B_{12}$ and/or folic acid; and to treat hemolytic anemia, such as, for example, adrenocortical steroids, e.g., corticoids. See e.g., Resegotti et al., Panminerva Medica, 23:243-248 (1981); Kurtz, FEBS Letters, 14a:105-

108 (1982); McGonigle et al., Kidney Int., 25:437-444 (1984); and Pavlovic-Kantera, Expt. Hematol., 8 (supp. 8) 283-291 (1980), the contents of each of which are hereby incorporated by reference in their entireties.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Kalmani, Kidney Int., 22:383-391 (1982); Shahidi, New Eng. J. Med., 289:72-80 (1973); Urabe et al., J. Exp. Med., 149:1314-1325 (1979); Billat et al., Expt. Hematol., 10:135-140 (1982); Naughton et al., Acta Haemat, 69:171-179 (1983); Cognote et al. in abstract 364, Proceedings 7th Intl. Cong. of Endocrinology (Quebec City, Quebec, Jul. 1-7, 1984); and Rothman et al., 1982, J. Surg. Oncol., 20:105-108 (1982). Methods for stimulating hematopoiesis comprise administering a hematopoietically effective amount (i.e., an amount which effects the formation of blood cells) of a pharmaceutical composition containing polynucleotides and/or polypeptides of the invention to a patient. The polynucleotides and/or polypeptides of the invention are administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin $B_{12}$, folic acid and/or adrenocortical steroids.

In an additional embodiment, the antibody and antibody compositions of the invention are administered in combination with hematopoietic growth factors. Hematopoietic growth factors that may be administered with the antibody and antibody compositions of the invention include, but are not limited to, LEUKINE™ (sargramostim/GM-CSF) and NEUPOGEN™ (filgrastim/G-CSF).

In an additional embodiment, the antibody and antibody compositions of the invention are administered alone or in combination with an anti-angiogenic agent(s). Anti-angiogenic agents that may be administered with the antibody and antibody compositions of the invention include, but are not limited to, Angiostatin (Entremed, Rockville, Md.), Troponin-1 (Boston Life Sciences, Boston, Mass.), anti-Invasive Factor, retinoic acid and derivatives thereof, paclitaxel (Taxol), Suramin, Tissue Inhibitor of Metalloproteinase-1, Tissue Inhibitor of Metalloproteinase-2, VEGI, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include, but are not limited to, platelet factor 4; protamine sulphate; sulphated chitin derivatives (prepared from queen crab shells), (Murata et al., Cancer Res. 51:22-26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321-17326, 1992); Chymostatin (Tomkinson et al., Biochem J. 286:475-480, 1992); Cyclodextrin Tetradecasulfate; Eponemycin; Camptothecin; Fumagillin (Ingber et al., Nature 348:555-557, 1990); Gold Sodium Thiomalate ("GST"; Matsubara and Ziff, J. Clin. Invest. 79:1440-1446, 1987); anticollagenase-serum; alpha2-antiplasmin (Holmes et al., J. Biol. Chem. 262(4):1659-1664, 1987); Bisantrene (National Cancer Institute); Lobenzarit disodium (N-(2)-carboxyphenyl-4-chloroanthronilic acid disodium or "CCA"; (Takeuchi et al., Agents Actions 36:312-316, 1992); and metalloproteinase inhibitors such as BB94.

Additional anti-angiogenic factors that may also be utilized within the context of the present invention include Thalidomide, (Celgene, Warren, N.J.); Angiostatic steroid; AGM-1470 (H. Brem and J. Folkman *J Pediatr. Surg.* 28:445-51 (1993)); an integrin alpha v beta 3 antagonist (C. Storgard et al., *J. Clin. Invest.* 103:47-54 (1999)); carboxynaminolmidazole; Carboxyamidotriazole (CAI) (National Cancer Institute, Bethesda, Md.); Conbretastatin A-4 (CA4P) (OXiGENE, Boston, Mass.); Squalamine (Magainin Pharmaceuticals, Plymouth Meeting, Pa.); TNP-470, (Tap Pharmaceuticals, Deerfield, Ill.); ZD-0101 AstraZeneca (London, UK); APRA (CT2584); Benefin, Byrostatin-1 (SC359555); CGP-41251 (PKC 412); CM101; Dexrazoxane (ICRF187); DMXAA; Endostatin; Flavopridiol; Genestein; GTE; ImmTher; Iressa (ZDI 839); Octreotide (Somatostatin); Panretin; Penacillamine; Photopoint; PI-88; Prinomastat (AG-3540) Purlytin; Suradista (FCE26644); Tamoxifen (Nolvadex); Tazarotene; Tetrathiomolybdate; Xeloda (Capecitabine); and 5-Fluorouracil.

Anti-angiogenic agents that may be administered in combination with the compounds of the invention may work through a variety of mechanisms including, but not limited to, inhibiting proteolysis of the extracellular matrix, blocking the function of endothelial cell-extracellular matrix adhesion molecules, by antagonizing the function of angiogenesis inducers such as growth factors, and inhibiting integrin receptors expressed on proliferating endothelial cells. Examples of anti-angiogenic inhibitors that interfere with extracellular matrix proteolysis and which may be administered in combination with the antibody and antibody compositions of the invention include, but are not limited to, AG-3540 (Agouron, La Jolla, Calif.), BAY-12-9566 (Bayer, West Haven, Conn.), BMS-275291 (Bristol Myers Squibb, Princeton, N.J.), CGS-27032A (Novartis, East Hanover, N.J.), Marimastat (British Biotech, Oxford, UK), and Metastat (Aeterna, St-Foy, Quebec). Examples of anti-angiogenic inhibitors that act by blocking the function of endothelial cell-extracellular matrix adhesion molecules and which may be administered in combination with the antibody and antibody compositions of the invention include, but are not limited to, EMD-121974 (Merck KcgaA Darmstadt, Germany) and Vitaxin (Ixsys, La Jolla, Calif./Medimmune, Gaithersburg, Md.). Examples of anti-angiogenic agents that act by directly antagonizing or inhibiting angiogenesis inducers and which may be administered in combination with the antibody and antibody compositions of the invention include, but are not limited to, Angiozyme (Ribozyme, Boulder, Colo.), Anti-VEGF antibody (Genentech, S. San Francisco, Calif.), PTK-787/ZK-225846 (Novartis, Basel, Switzerland), SU-101 (Sugen, S. San Francisco, Calif.), SU-5416 (Sugen/Pharmacia Upjohn, Bridgewater, N.J.), and SU-6668 (Sugen). Other anti-angiogenic agents act to indirectly inhibit angiogenesis. Examples of indirect inhibitors of angiogenesis which may be administered in combination with the antibody and antibody compositions of the invention include, but are not limited to, IM-862 (Cytran, Kirkland, Wash.), Interferon-alpha, IL-12 (Roche, Nutley, N.J.), and Pentosan polysulfate (Georgetown University, Washington, D.C.).

In particular embodiments, the use of antibody and antibody compositions of the invention in combination with anti-angiogenic agents is contemplated for the treatment, prevention, and/or amelioration of cancers and other hyperproliferative disorders.

In a preferred embodiment, the antibody and antibody compositions of the invention are administered in combination with CD40 ligand (CD40L), a soluble form of CD40L (e.g., avrend), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In another embodiment, antibody and antibody compositions of the invention are administered in combination with an anticoagulant. Anticoagulants that may be administered with the antibody and antibody compositions of the invention include, but are not limited to, heparin, warfarin, and aspirin. In a specific embodiment, antibody and antibody compositions of the invention are administered in combination with heparin and/or warfarin. In another specific embodiment, antibody and antibody compositions of the invention are administered in combination with warfarin. In another specific embodiment, antibody and antibody compositions of the invention are administered in combination with warfarin and aspirin. In another specific embodiment, antibody and antibody compositions of the invention are administered in combination with heparin. In another specific embodiment, antibody and antibody compositions of the invention are administered in combination with heparin and aspirin.

In another embodiment, antibody and antibody compositions of the invention are administered in combination with an agent that suppresses the production of anticardiolipin antibodies. In specific embodiments, the polynucleotides of the invention are administered in combination with an agent that blocks and/or reduces the ability of anticardiolipin antibodies to bind phospholipid-binding plasma protein beta 2-glycoprotein I (b2GPI).

In a preferred embodiment, the antibody and antibody compositions of the invention are administered in combination with an antimalarial. Antimalarials that may be administered with the antibody and antibody compositions of the invention include, but are not limited to, hydroxychloroquine, chloroquine, and/or quinacrine.

In a preferred embodiment, the antibody and antibody compositions of the invention are administered in combination with an NSAID.

In a nonexclusive embodiment, the antibody and antibody compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-714 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-671 (Merck), ST-1482 (Sigma-Tau), and butixocort propionate (WarnerLambert).

In a preferred embodiment, the antibody and antibody compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, LJP 394 (La Jolla Pharmaceutical Company, San Diego, Calif.) and prednisolone.

In an additional embodiment, antibody and antibody compositions of the invention are administered alone or in combination with one or more intravenous immune globulin preparations. Intravenous immune globulin preparations that may be administered with the antibody and antibody compositions of the invention include, but not limited to, GAMMAR™ (immune serum globulin), IVEEGAM™ (immune serum globulin), SANDOGLOBULFN™ (immune globulin), GAMMAGARD S/D™ (immunoglobulin), and GAMIMUNE™ (immune serum globulin). In a specific embodiment, antibody and antibody compositions of the invention are administered in combination with intravenous immune globulin preparations in transplantation therapy (e.g., bone marrow transplant).

CD40 ligand (CD40L), a soluble form of CD40L (e.g., avrend), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the antibody and antibody compositions of the invention are administered in combination with cytokines. Cytokines that may be administered with the antibody and antibody compositions of the invention include, but are not limited to, GM-CSF, G-CSF, IL2, IL3, IL4, IL5, IL6, IL7, IL10, IL12, IL13, IL15, anti-CD40, CD40L, IFN-alpha, IFN-beta, IFN-gamma, TNF-alpha, and TNF-beta. In preferred embodiments, antibody and antibody compositions of the invention are administered with TRAIL receptor. In another embodiment, antibody and antibody compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22. In preferred embodiments, the antibody and antibody compositions of the invention are administered in combination with IL4 and IL10.

In one embodiment, the antibody and antibody compositions of the invention are administered in combination with one or more chemokines. In specific embodiments, the antibody and antibody compositions of the invention are administered in combination with an α(C×C) chemokine selected from the group consisting of gamma-interferon inducible protein-10 (γIP-10), interleukin-8 (IL-8), platelet factor-4 (PF4), neutrophil activating protein (NAP-2), GRO-α, GRO-β, GRO-γ, neutrophil-activating peptide (ENA-78), granulocyte chemoattractant protein-2 (GCP-2), and stromal cell-derived factor-1 (SDF-1, or pre-B cell stimulatory factor (PBSF)); and/or a β(CC) chemokine selected from the group consisting of: RANTES (regulated on activation, normal T expressed and secreted), macrophage inflammatory protein-1 alpha (MIP-1β), macrophage inflammatory protein-1 beta (MIP-1α), monocyte chemotactic protein-1 (MCP-1), monocyte chemotactic protein-2 (MCP-2), monocyte chemotactic protein-3 (MCP-3), monocyte chemotactic protein-4 (MCP-4) macrophage inflammatory protein-1 gamma (MIP-1γ), macrophage inflammatory protein-3 alpha (MIP-3α), macrophage inflammatory protein-3 beta (MIP-3β), macrophage inflammatory protein-4 (MIP-4/DC-CK-1/PARC), eotaxin, Exodus, and I-309; and/or the γ(C) chemokine, lymphotactin.

In another embodiment, the antibody and antibody compositions of the invention are administered with chemokine beta-8, chemokine beta-1, and/or macrophage inflammatory protein-4. In a preferred embodiment, the antibody and antibody compositions of the invention are administered with chemokine beta-8.

In an additional embodiment, the antibody and antibody compositions of the invention are administered in combination with an IL-4 antagonist. IL-4 antagonists that may be administered with the antibody and antibody compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the antibody and antibody compositions of the invention are administered in combination with fibroblast growth factors. Fibroblast growth factors that may be administered with the antibody and antibody compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Demonstration of Therapeutic or Prophylactic Utility of a Composition

The compounds of the invention are preferably tested in vitro, and then in vivo for the desired therapeutic or prophylactic activity, prior to use in humans. For example, in vitro assays which can be used to determine whether administration of a specific antibody or composition of the present invention is indicated, include in vitro cell culture assays in which a patient tissue sample is grown in culture, and exposed to or otherwise administered an antibody or composition of the present invention, and the effect of such an antibody or composition of the present invention upon the tissue sample is observed. In various specific embodiments, in vitro assays can be carried out with representative cells of cell types involved in a patient's disorder, to determine if an antibody or composition of the present invention has a desired effect upon such cell types. Preferably, the antibodies or compositions of the invention are also tested in in vitro assays and animal model systems prior to administration to humans.

Antibodies or compositions of the present invention for use in therapy can be tested for their toxicity in suitable animal model systems, including but not limited to rats, mice, chicken, cows, monkeys, and rabbits. For in vivo testing of an antibody or composition's toxicity any animal model system known in the art may be used.

Antibodies or compositions of the invention can also be tested for their ability to reduce bacterial numbers in in vitro and in vivo assays known to those of skill in the art. Antibodies or compositions of the invention can also be tested for their ability to alleviate of one or more symptoms associated with anthrax disease or anthrax toxin poisoning. Antibodies or antibody compositions of the invention can also be tested for their ability to decrease the time course of the infectious disease. Further, antibodies or compositions of the invention can be tested for their ability to increase the survival period of animals suffering from anthrax or anthrax toxin poisoning. Techniques known to those of skill in the art can be used to analyze the function of the antibodies or compositions of the invention in vivo.

Efficacy in treating or preventing bacterial (e.g. *Bacillus anthracis*) infection may be demonstrated by detecting the ability of an antibody or composition of the invention to inhibit the replication of the bacteria, to inhibit transmission or prevent the bacteria from establishing itself in its host, or to prevent, ameliorate or alleviate the symptoms of disease progression. The treatment is considered therapeutic if there is, for example, a reduction in bacterial load, amelioration of one or more symptoms, or a decrease in mortality and/or morbidity following administration of an antibody or composition of the invention.

Panels/Mixtures

The present invention also provides for mixtures of antibodies (including scFvs and other molecules comprising, or alternatively consisting of, antibody fragments or variants thereof) that specifically bind to PA or a fragment or variant thereof, wherein the mixture has at least one, two, three, four, five or more different antibodies of the invention. In specific embodiments, the invention provides mixtures of at least 2, preferably at least 4, at least 6, at least 8, at least 10, at least 12, at least 15, at least 20, or at least 25 different antibodies that specifically bind to PA or fragments or variants thereof, wherein at least 1, at least 2, at least 4, at least 6, or at least 10, antibodies of the mixture is an antibody of the invention. In a specific embodiment, each antibody of the mixture is an antibody of the invention.

The present invention also provides for panels of antibodies (including scFvs and other molecules comprising, or alternatively consisting of, antibody fragments or variants thereof) that specifically bind to PA or a fragment or variant thereof, wherein the panel has at least one, two, three, four, five or more different antibodies of the invention. In specific embodiments, the invention provides for panels of antibodies that have different affinities for PA, different specificities for PA, or different dissociation rates. The invention provides panels of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000, antibodies. Panels of antibodies can be used, for example, in 96 well plates for assays such as ELISAs.

The present invention further provides for compositions comprising, one or more antibodies (including molecules comprising, or alternatively consisting of antibody fragments or variants of the invention). In one embodiment, a composition of the present invention comprises, one, two, three, four, five, or more antibodies that comprise or alternatively consist of, a polypeptide having an amino acid sequence of any one or more of the VH domains of a one or more of the scFvs referred to in Table 1 or recombinant antibodies expressed by the cell lines referred to in Table 1, or a variant thereof. In another embodiment, a composition of the present invention comprises, one, two, three, four, five, or more antibodies that comprise, or alternatively consist of, a polypeptide having an amino acid sequence of any one or more of the VH CDR1s of a VH domain of one or more of the scFvs referred to in Table 1 or recombinant antibodies expressed by the cell lines referred to in Table 1, or a variant thereof. In another embodiment, a composition of the present invention comprises, one, two, three, four, five or more antibodies that comprise, or alternatively consist of, a polypeptide having an amino acid sequence of any one or more of the VH CDR2s of a VH domain of one or more of the scFvs referred to in Table 1 or recombinant antibodies expressed by the cell lines referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VH CDR3s as of a VH domain of one or more of the scFvs or recombinant antibodies expressed by the cell lines referred to in Table 1, or a variant thereof.

Other embodiments of the present invention providing for compositions comprising, one or more antibodies (including molecules comprising, or alternatively consisting of antibody fragments or variants of the invention) are listed below. In another embodiment, a composition of the present invention comprises, one, two, three, four, five, or more antibodies that comprise, or alternative consist of, a polypeptide having an amino acid sequence of any one or more of the VL domains of one or more of the scFvs referred to in Table 1 or recombinant antibodies expressed by the cell lines referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR1s domains of one or more of the scFvs referred to in Table 1 or recombinant antibodies expressed by the cell lines referred to in Table 1, or a variant thereof. In another embodiment, a composition of the present invention comprises, one, two, three, four, five, or more antibodies that comprise, or alternatively consist of, a polypeptide having an amino acid sequence of any one or more of the VL CDR2s of one or more of the scFvs referred to in Table 1 or recombinant antibodies expressed by the cell lines referred to in Table 1, or a variant thereof. In a preferred embodiment, a composition of the present invention comprises, one, two, three, four, five, or more antibodies that comprise, or alternatively consist of, a polypeptide having an amino acid sequence of any one or more of the VL CDR3s domains of one or more of the scFvs referred to in Table 1 or recombinant antibodies expressed by the cell lines referred to in Table 1, or a variant thereof.

Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises an antibody of the invention, preferably a purified antibody, in one or more containers. In an alternative embodiment, a kit comprises an antibody fragment that specifically binds to PA polypeptides or fragments or variants thereof. In a specific embodiment, the kits of the present invention contain a substantially isolated PA polypeptide or fragment or variant thereof as a control. Preferably, the kits of the present invention further comprise a control antibody which does not react with PA polypeptides or fragments or variants thereof. In another specific embodiment, the kits of the present invention contain a means for detecting the binding of an antibody to PA polypeptides (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized PA polypeptide. The PA provided in the kit may also be attached to a solid support. In a more specific embodiment the detecting means of the above-described kit includes a solid support to which PA is attached. Such a kit may also include a non-attached reporter-labeled anti-human antibody. In this embodiment, binding of the antibody to PA can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with PA polypeptides, and means for detecting the binding of PA polypeptides to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In specific embodiments, a kit of the invention comprises a means for administering an antibody to an animal, preferably a human. Means for administering an antibody to an animal include a syringe.

Gene Therapy

In a specific embodiment, nucleic acids comprising sequences encoding antibodies or functional derivatives thereof, are administered to treat, inhibit or prevent a anthrax or anthrax toxin poisoning, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 1 1(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, a composition of the invention comprises, or alternatively consists of, nucleic acids encoding an antibody, said nucleic acids being part of an expression vector that expresses the antibody or fragments or chimeric proteins or heavy or light chains thereof in a suitable host. In particular, such nucleic acids have promoters, preferably heterologous promoters, operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is an scFv; alternatively, the nucleic acid sequences include sequences encoding both the heavy and light chains, or fragments or variants thereof, of an antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06 180; WO 92/22715; WO92/203 16; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention or fragments or variants thereof are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:29 1-302 (1994), which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Klein et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, macrocell-mediated gene transfer, spheroplast fusion, etc. Numerous techniques are known in the art for the introduction of foreign genes into cells (see, e.g., Loeffler and Behr, Meth. Enzymol. 217:599-718 (1993); Cohen et al., Meth. Enzymol. 217:718-644 (1993); Clin. Pharma. Ther. 29:69-92m (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody or fragment thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 7 1:973-985 (1992); Rheinwald, Meth. Cell Bio. 21A:229 (1980); and Pittelkow and Scott, Mayo Clinic Proc. 71:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

EXAMPLES

Example 1

Isolation and Characterization of scFvs Referred to in Table 1

Maxisorp tubes (Nunc) were coated overnight with 10 micrograms/ml of PA83 protein in PBS at 4° C. Unbound PA was removed by washing the tubes with 1×PBST and 1×PBS followed by filling the tubes with a 3% milk solution in 1×PBS for one hour to block any exposed tube surface. Approximately $10^{13}$ TU of phage from phage display libraries available from Cambridge Antibody Technology (Cambridgshire, United Kingdom) diluted in 3% milk/1×PBS was applied to the tube and incubated for at least 60 minutes at room temperature. Tubes were washed 10 times with PBS 0.1% Tween-20 and 10 times with PBS. Phage are eluted by adding 1 ml of 100 mM triethylamine with gentle shaking after which the solution is immediately neutralized with 0.5 ml of 1.0M Tris-HCl, pH 7.4. Phage were then used to infect 10 ml of mid-log *E. coli* TG1 by incubating eluted phage with bacteria for 30 minutes at 37° C. The *E. coli* were then plated on 2XYT plates containing 2% glucose and 100 micrograms/ml ampicillin. The resulting bacterial library was then rescued with delta gene 3 helper phage to prepare phage for a subsequent round of selection. This process is usually repeated for a total of 2-4 rounds of affinity purification. Specific enrichment of PA binding phage can be monitored during the selection process. Individual clones from both the second and the third rounds of selections were screened for the ability to bind to PA protein using the assay protocol described below.

PA Binding Assay Protocol for scFv-Phage Library Screening

Purified full-length PA protein (PA83) was labeled with Biotin-LC-Sulfo—NHS (Pierce) at a molar challenge ratio of 8:1 in PBS, 8.0 for 60 minutes at 23° C. Protein was separated from free label using a NAP 5 gel filtration column (Amersahm-Pharmacia Biotech) following manufacturer's protocol. A polyclonal antibody specific for the M13 phage coat (Amersham-Pharmacia Biotech) was labeled with the electrochemi-luminescent reporter Origen-TAG-NHS ((Ori-TAG), IGEN International, Inc.) at a molar challenge ratio of 5:1 in PBS, 8.0 buffer for 60 minutes at 23° C. Protein was separated from free label using a NAP 5 gel filtration column (Amersham-Pharmacia Biotech) following manufacturer's protocol. The amount of incorporated Origen-TAG label was determined by measuring the absorbance of the undiluted labeling reaction at 455 nm in a 1 cm cuvette and dividing by 13,700 (extinction coefficient of Ori-TAG label) to obtain the Ori-TAG label concentration in moles per liter. This number was divided by the moles per liter IgG concentration in the labeling reaction. Label concentrations used in the assay ranged from 3 to 5 labels per IgG molecule. The biotinylated-PA83 and Origen-TAG labeled anti-M13 antibody were used to screen phage clones for PA binding as described below.

Individual *E. coli* colonies containing phagemid were inoculated into 96 well plates containing 100 microliters 2×TY+100 micrograms/ml ampicillin+2% glucose per well. Plates were incubated 37 C for 4 hours, shaking. M13K07 helper phage was added to each well at a multiplicity of infection (MOI) of 2 to 10 and the plates were incubated for a further 1 hour at 37 C. The plates were centrifuged in a benchtop centrifuge at 2000 rpm for 10 minutes. The supernatant was removed and cell pellets were resuspended in 100 microliters 2×TY+100 micrograms/ml ampicillin+50 micrograms/ml kanamycin and incubated at 30 C overnight, with vigorous shaking. The next day, plates were centrifuged at 2000 rpm for 10 min and 100 microliters of phage-containing supernatant from each well carefully transferred into a fresh 96-well plate.

The supernatants containing scFv-phage were screened for binding to PA83 using the following protocol: In a 96 well plate, 5 microliters of scFv-phage were combined with 150 microliters of 0.5 micrograms/ml Biotin-PA83 and 0.5 micrograms/ml Origen-Tag labeled anti-M13 polyclonal antibody and 20 micrograms of Streptavidin coated magnetic beads (Dynal M280 beads). The plate was sealed and mixed vigorously for 60 minutes at room temperature. The electrochemiluminescent (ECL) signal was measured in each well of the plate using an Origen M8 series ECL analyzer (IGEN International, Inc). Wells that showed ECL signals that were 5-fold above the assay background were scored as positive PA binders and submitted for sequencing.

The complete nucleotide sequence of the scFv insert from 980 PA positive binding phage clones was determined and a numerical summary of the sequence diversity and ability to bind PA in the above-described-PA Binding Assay is presented in the Table 4 below.

TABLE 4

Summary of ScFv Groups and CDR 3 Sequences for
PA-Binding Phage Clones

| Group | HC group, LC group | Representative scFv clone | HC CDR 3 Seq. | SEQ ID NO: | LC CDR 3 Seq. | SEQ ID NO: | PA Binding Pos/Neg |
|---|---|---|---|---|---|---|---|
| 1 | HC group 115, LC group 122: | PWB2001 | HSPGDYAFDY | 66 | ASWDDSLNGRV | 299 | + |
| 2 | HC group 115, LC group 135: | PWB2855 | HSPGDYAFDY | 67 | ASWDDSLKSRV | 300 | + |
| 3 | HC group 115, LC group 137: | PWB2916 | HSPGDYAFDY | 68 | ASWDDSVNGRV | 301 | + |
| 4 | HC group 116, LC group 123: | PWB2002 | AGRRTQLQPRDFLFEY | 69 | NSRDSSGNHVV | 302 | + |
| 5 | HC group 116, LC group 127: | PWB2175 | AGRRTQLQPRDFLFEY | 70 | NSRDSSGNHVV | 303 | + |
| 6 | HC group 116, LC group 131: | PWB2362 | AGRRTQLQPRDFLFEY | 71 | NSRDSSGNHVV | 304 | + |
| 7 | HC group 116, LC group 132: | PWB2447 | AGRRTQLQPRDFLFEY | 72 | NSRDSSGNHVV | 305 | + |
| 8 | HC group 116, LC group 134: | PWB2754 | AGRRTQLQPRDFLFEY | 73 | NSRDSSGNHVV | 306 | + |
| 9 | HC group 117, LC group 122: | PWB2006 | HSPGDYAFDY | 74 | ASWDDSLNGRV | 307 | + |
| 10 | HC group 118, LC group 124: | PWB2008 | HSPGDYAFDY | 75 | ASWDDSLNGRV | 308 | + |
| 11 | HC group 119, LC group 123: | PWB2016 | ASYLSTSSSLDY | 76 | NSRDSSGNHVV | 309 | + |
| 12 | HC group 119, LC group 133: | PWB2562 | ASYLSTSSSLDY | 77 | NSRDSSGNHVV | 310 | + |
| 13 | HC group 120, LC group 123: | PWB2018 | AGRRTQLQPRDFLFEY | 78 | NSRDSSGNHVV | 311 | + |
| 14 | HC group 121, LC group 125 | PWB2043 | DLDSSTIPHREYGMDV | 79 | HSRDSSGNHVL | 312 | + |
| 15 | HC group 122, LC group 123: | PWB2061 | AGRRTQLQPRDFLFEY | 80 | NSRDSSGNHVV | 313 | + |
| 16 | HC group 123, LC group 123: | PWB2144 | AGRRTQLQPRDFLFEY | 81 | NSRDSSGNHVV | 314 | + |
| 17 | HC group 124, LC group 126: | PWB2153 | AGRRTQLQPRDFLFEY | 82 | NSRDSSGNHVV | 315 | + |
| 18 | HC group 125, LC group 123: | PWB2202 | ASNLSTSSSLDY | 83 | NSRDSSGNHVV | 316 | + |
| 19 | HC group 126, LC group 128: | PWB2216 | SGSSWSHFDF | 84 | SSYTTRSTRV | 317 | + |
| 20 | HC group 127, LC group 129: | PWB2281 | GSPTGDLNVDVFDY | 85 | NSRDSSGNHVV | 318 | + |
| 21 | HC group 128, LC group 130: | PWB2301 | HSPGDYAFDY | 86 | ASWDDSLNGRV | 319 | + |
| 22 | HC group 129, LC group 122: | PWB2323 | VRDIRPGDYAFDY | 87 | ASWDDSLNGRV | 320 | + |
| 23 | HC group 130, LC group 123: | PWB2325 | AGRRTQLQPRDFLFEY | 88 | NSRDSSGNHVV | 321 | + |
| 24 | HC group 131, LC group 123: | PWB2334 | Not Determined |  | NSRDSSGNHVV | 322 | + |
| 25 | HC group 132, LC group 122: | PWB2341 | HSPGDYAFDY | 89 | ASWDDSLNGRV | 323 | + |
| 26 | HC group 133, LC group 123: | PWB2353 | ASYLSTSPSLDY | 90 | NSRDSSGNHVV | 324 | + |
| 27 | HC group 134, LC group 123: | PWB2363 | AGRRTQLQPRDFLFEY | 91 | NSRDSSGNHVV | 325 | + |
| 28 | HC group 135, LC group 122: | PWB2364 | HSPGDYAFDY | 92 | ASWDDSLNGRV | 326 | + |
| 29 | HC group 136, LC group 123: | PWB2376 | AGRRTQLQPRDFLFEY | 93 | NSRDSSGNHVV | 327 | + |
| 30 | HC group 137, LC group 128: | PWB2435 | SGSSWSHFDF | 94 | SSYTTRSTRV | 328 | + |
| 31 | HC group 138, LC group 123: | PWB2456 | AGRRTQLPPRDFLFEH | 95 | NSRDSSGNHVV | 329 | + |
| 32 | HC group 139, LC group 122: | PWB2466 | HSPGDYAFDY | 96 | ASWDDSLNGRV | 330 | + |
| 33 | HC group 140, LC group 123: | PWB2502 | ASNLSTSPSLDY | 97 | NSRDSSGNHVV | 331 | + |
| 34 | HC group 141, LC group 123: | PWB2532 | AGRRTQLQPIDFLFEY | 98 | NSRDSSGNHVV | 332 | + |
| 35 | HC group 142, LC group 123: | PWB2617 | AGRRTQLQPRDFLFEY | 99 | NSRDSSGNHVV | 333 | + |
| 36 | HC group 143, LC group 122: | PWB2756 | HSPGDYAFDY | 100 | ASWDDSLNGRV | 334 | + |

TABLE 4-continued

Summary of ScFv Groups and CDR 3 Sequences for
PA-Binding Phage Clones

| Group | HC group, LC group | Representative scFv clone | HC CDR 3 Seq. | SEQ ID NO: | LC CDR 3 Seq. | SEQ ID NO: | PA Binding Pos/Neg |
|---|---|---|---|---|---|---|---|
| 37 | HC group 144, LC group 123: | PWB2849 | AGRRTQLQP RDFLFEY | 101 | NSRDSSGN HVV | 335 | + |
| 38 | HC group 145, LC group 136: | PWB2873 | GSGYSGYDFP YYYGMDV | 102 | HSRDSSGN HVL | 336 | + |
| 39 | HC group 146, LC group 123: | PWB2878 | AGRRTQLQP RDFLFEY | 103 | NSRDSSGN HVV | 337 | + |
| 40 | HC group 147, LC group 123: | PWB2955 | Not Determined | | NSRDSSGN HVV | 338 | + |
| 41 | HC group 2, LC group 2: | PWC2008 | AGRRTQLQP RDFLFEY | 104 | NSRDSSGN HVV | 339 | + |
| 42 | HC group 2, LC group 163: | PWC2065 | AGRRTQLQP RDFLFEY | 105 | NSRDSSGN HVV | 340 | + |
| 43 | HC group 2, LC group 188: | PWC2963 | AGRRTQLQP RDFLFEY | 106 | NSRDSSGN HVV | 341 | + |
| 44 | HC group 140, LC group 155: | PWC2002 | DSSSGWFFIDY | 107 | QSYDSSLG GYVI | 342 | + |
| 45 | HC group 140, LC group 160: | PWC2043 | ARDSSSGWFF IDY | 108 | QSYDSSLG GYVI | 343 | + |
| 46 | HC group 140, LC group 165: | PWC2302 | DSSSGWFFIDY | 109 | QSYDSSLG GYVI | 344 | + |
| 47 | HC group 140, LC group 166: | PWC2308 | DSSSGWFFIDY | 110 | QSYDSSLG GYVI | 345 | + |
| 48 | HC group 140, LC group 167: | PWC2310 | DSSSGWFFIDY | 111 | QSYDSSLG GYVI | 346 | + |
| 49 | HC group 140, LC group 169: | PWC2361 | DSSSGWFFIDY | 112 | QSYDSSLG GYVI | 347 | + |
| 50 | HC group 140, LC group 172: | PWC2461 | DSSSGWFFIDY | 113 | QSYDSSLG GYVI | 348 | + |
| 51 | HC group 140, LC group 175: | PWC2616 | DSSSGWFFIDY | 114 | QSYDSSLG GYVI | 349 | + |
| 52 | HC group 140, LC group 176: | PWC2632 | DSSSGWFFIDY | 115 | | | + |
| 53 | HC group 140, LC group 179: | PWC2678 | DSSSGWFFIDY | 116 | QSYDSSLG GYVI | 350 | + |
| 54 | HC group 140, LC group 183: | PWC2748 | DSSSGWFFIDY | 117 | QSYDSSLG GYGI | 351 | + |
| 55 | HC group 141, LC group 156: | PWC2004 | SRYSSSPFRG GLDV | 118 | HSYDSSISG GI | 352 | + |
| 56 | HC group 141, LC group 157: | PWC2007 | SRYSSSPFRG GLDV | 119 | HSYDSSISG WI | 353 | + |
| 57 | HC group 141, LC group 158: | PWC2010 | SRYSSSPFRG GLDV | 120 | HSYDSSISG WI | 354 | + |
| 58 | HC group 141, LC group 159: | PWC2021 | SRYSSSPFRG GLDV | 121 | HSYDSSIR GWI | 355 | + |
| 59 | HC group 141, LC group 161: | PWC2046 | SRYSSSPFRG GLDV | 122 | HSYDSSIR GGI | 356 | + |
| 60 | HC group 141, LC group 162: | PWC2057 | SRYSSSPFRG GLDV | 123 | HSYDSSISG GI | 357 | + |
| 61 | HC group 141, LC group 164: | PWC2093 | SRYSSSPFRG GLDV | 124 | HSYDSSISA WI | 358 | + |
| 62 | HC group 141, LC group 170: | PWC2375 | SRYSSSPFRG GLDV | 125 | HSYDSSISG WI | 359 | + |
| 63 | HC group 141, LC group 178: | PWC2652 | SRYSSSPFRG GLDV | 126 | HSYDSSISG WI | 360 | + |
| 64 | HC group 141, LC group 187: | PWC2939 | SRYSSSPFRG GLDV | 127 | HSYDSSISG WI | 361 | + |
| 65 | HC group 142, LC group 160: | PWC2068 | SSSGCLFIDY | 128 | QSYDSSLG GYVI | 362 | + |
| 66 | HC group 143, LC group 157: | PWC2131 | SRYSSSPFRG GLDV | 129 | HSYDSSISG WI | 363 | + |
| 67 | HC group 143, LC group 158: | PWC2892 | SRYSSSPFRG GLDV | 130 | HSYDSSISG WI | 364 | ++ |
| 68 | HC group 144, LC group 155: | PWC2151 | DSSSGWFFIDY | 131 | QSYDSSLG GYVI | 365 | + |
| 69 | HC group 145, LC group 157: | PWC2156 | SRYSSSPFRG GLDV | 132 | HSYDSSISG WI | 366 | + |
| 70 | HC group 146, LC group 157: | PWC2321 | SRYSSSPFRG GLDV | 133 | HSYDSSISG WI | 367 | + |
| 71 | HC group 147, LC group 157: | PWC2332 | SRYSSSPFRG GLDV | 134 | HSYDSSISG WI | 368 | + |
| 72 | HC group 148, LC group 168: | PWC2350 | DSSSGWFFI | 135 | QSYDSSLG GYVI | 369 | + |

TABLE 4-continued

Summary of ScFv Groups and CDR 3 Sequences for PA-Binding Phage Clones

| Group | HC group, LC group | Representative scFv clone | HC CDR 3 Seq. | SEQ ID NO: | LC CDR 3 Seq. | SEQ ID NO: | PA Binding Pos/Neg |
|---|---|---|---|---|---|---|---|
| 73 | HC group 149, LC group 155: | PWC2386 | SSSGWLFIDY | 136 | QSYDSSLG GYVI | 370 | + |
| 74 | HC group 150, LC group 171: | PWC2393 | SRYSSSPFRG GLDV | 137 | HSYDSSISG WI | 371 | + |
| 75 | HC group 151, LC group 157: | PWC2412 | SRYSSSPFRG GLDV | 138 | HSYDSSISG WI | 372 | + |
| 76 | HC group 152, LC group 155: | PWC2424 | DSSSGWFFIDY | 139 | QSYDSSLG GYVI | 373 | + |
| 77 | HC group 153, LC group 155: | PWC2431 | DSSSGWFFIDY | 140 | QSYDSSLG GYVI | 374 | + |
| 78 | HC group 154, LC group 157: | PWC2436 | SRYSSSPFRG GLDV | 141 | HSYDSSISG WI | 375 | + |
| 79 | HC group 155, LC group 155: | PWC2444 | DSSSGWFFIDY | 142 | QSYDSSLG GYVI | 376 | + |
| 80 | HC group 156, LC group 173: | PWC2590 | TYPYGGGTY AFDY | 143 | QSYDSELS GSEL | 377 | - |
| 81 | HC group 157, LC group 174: | PWC2606 | NAFDY | 144 | NSLDSRGQ RVI | 378 | + |
| 82 | HC group 158, LC group 177: | PWC2643 | SAKSGWKST FDV | 145 | ALYLGGGL SWV | 379 | - |
| 83 | HC group 159, LC group 180: | PWC2682 | No seq. | | AAWDDSL SAYV | 380 | - |
| 84 | HC group 160, LC group 181: | PWC2691 | DSSSGWLFIDY | 146 | QSYDSSLG GYVI | 381 | + |
| 85 | HC group 161, LC group 157: | PWC2710 | SRYSSSPFRG GLDV | 147 | HSYDSSISG WI | 382 | + |
| 86 | HC group 161, LC group 182: | PWC2722 | SRYSSSPFRG GLDV | 148 | HSYDSSISG WI | 383 | + |
| 87 | HC group 162, LC group 184: | PWC2758 | DSSSGWLFIDY | 149 | QSYDSSLG GYVI | 384 | + |
| 88 | HC group 163, LC group 185: | PWC2771 | DSSSGWLFIDY | 150 | QSYDSSLG GYVI | 385 | + |
| 89 | HC group 164, LC group 157: | PWC2792 | SRYSSSPFRG GLDV | 151 | HSYDSSISG WI | 386 | + |
| 90 | HC group 165, LC group 186: | PWC2901 | QMIMAARC | 152 | QSFDNRLR GFVV | 387 | - |
| 91 | HC group 166, LC group 155: | PWC2972 | DSSSGWFFI | 153 | QSYDSSLG GYVI | 388 | + |
| 92 | HC group 167, LC group 155: | PWC2980 | DSSSGWFFI | 154 | QSYDSSLG GYVI | 389 | + |
| 93 | HC group 148 LC group 138 | PWD0103 | VDHKWDLPF DY | 155 | ATWDDNL NGWV | 390 | + |
| 94 | HC group 148, LC group 194: | PWD0332 | VDHKWDLPF DY | 156 | ATWDDSL NGWV | 391 | + |
| 95 | HC group 148, LC group 249: | PWD0853 | VDHKWDLPF DY | 157 | ATWDDSL NGWV | 392 | + |
| 96 | HC group 148, LC group 272: | PWD1070 | VDHKWDLPF DY | 158 | AAWDDSL NGWV | 393 | + |
| 97 | HC group 149, LC group 139: | PWD0104 | LLRGGSTYLD AFDN | 159 | QVWDRSN GHVV | 394 | + |
| 98 | HC group 149, LC group 199: | PWD0384 | LLRGGSTYLD AFDN | 160 | QVWDRSN GHVV | 395 | + |
| 99 | HC group 150, LC group 140: | PWD0106 | GWGVFDI | 161 | AAWDDSL DGVV | 396 | + |
| 100 | HC group 151, LC group 141: | PWD0108 | VDHNWDLPF DY | 162 | SAWDDSL NGWV | 397 | + |
| 101 | HC group 151, LC group 143: | PWD0111 | VDHNWDLPF DY | 163 | ASWDDDL NGWV | 398 | + |
| 102 | HC group 151, LC group 195: | PWD0336 | VDHNWDLPF DY | 164 | AVWDDRM NGWE | 399 | + |
| 103 | HC group 151, LC group 208: | PWD0435 | VDHNWDLPF DY | 165 | AAWDDSL NGWV | 400 | + |
| 104 | HC group 151, LC group 234: | PWD0757 | VDHNWDLPF DY | 166 | AVWDDRL NGWE | 401 | + |
| 105 | HC group 151, LC group 248: | PWD0848 | VDHNWDLPF DY | 167 | VDHNWDL PFD | 402 | + |
| 106 | HC group 151, LC group 253: | PWD0875 | VDHNWDLPF DY | 168 | AAWDDSL SGWM | 403 | + |
| 107 | HC group 151, LC group 257: | PWD0925 | VDHNWDLPF DY | 169 | ASWDDDL KSWV | 404 | + |
| 108 | HC group 151, LC group 269: | PWD1048 | VDHNWDLPF DY | 170 | AAWDDSL SGWV | 405 | + |

TABLE 4-continued

Summary of ScFv Groups and CDR 3 Sequences for PA-Binding Phage Clones

| Group | HC group, LC group | Representative scFv clone | HC CDR 3 Seq. | SEQ ID NO: | LC CDR 3 Seq. | SEQ ID NO: | PA Binding Pos/Neg |
|---|---|---|---|---|---|---|---|
| 109 | HC group 152, LC group 142: | PWD0109 | VDHNWDLPFDY | 171 | ATWDDSLKGWV | 406 | + |
| 110 | HC group 152, LC group 164: | PWD0171 | VDHNWDLPFDY | 172 | QQSKSIPIT | 407 | − |
| 111 | HC group 152, LC group 197: | PWD0366 | VDHNWDLPFDY | 173 | VAWDDSLNGWM | 408 | + |
| 112 | HC group 152, LC group 214: | PWD0470 | VDHNWDLPFDY | 174 | AAWDDSLSGWV | 409 | + |
| 113 | HC group 153, LC group 144: | PWD0112 | VDHKWDLPFDY | 175 | AAWDDSLKGWV | 410 | + |
| 114 | HC group 153, LC group 227: | PWD0679 | VDHKWDLPFDY | 176 | SAWDDGLSGWV | 411 | + |
| 115 | HC group 154, LC group 145: | PWD0114 | VDHKWDLPFDY | 177 | ATWDDSLPGLV | 412 | + |
| 116 | HC group 154, LC group 215: | PWD0526 | VDHKWDLPFDY | 178 | EAWDDSLSGPA | 413 | + |
| 117 | HC group 154, LC group 239: | PWD0810 | VDHKWDLPFDY | 179 | AAWDDNLSGP | 414 | − |
| 118 | HC group 154, LC group 267: | PWD1012 | VDHKWDLPFDY | 180 | QQTYRTPIT | 415 | + |
| 119 | HC group 154, LC group 270: | PWD1050 | VDHKWDLPFDY | 181 | GTWDSRLYVGQV | 416 | + |
| 120 | HC group 155, LC group 146: | PWD0118 | VDHNWDLPFDY | 182 | AAWDDSLNGWV | 417 | + |
| 121 | HC group 155, LC group 172: | PWD0205 | VDHNWDLPFDY | 183 | AAWDDSLNGWV | 418 | + |
| 122 | HC group 155, LC group 241: | PWD0813 | VDHNWDLPFDY | 184 | ATWDDSLNHWV | 419 | + |
| 123 | HC group 155, LC group 244: | PWD0827 | VDHNWDLPFDY | 185 | AAWDDSLNGHWV | 420 | + |
| 124 | HC group 155, LC group 271: | PWD1063 | VDHNWDLPFDY | 186 | AAWDDSLSGVL | 421 | + |
| 125 | HC group 156, LC group 147: | PWD0121 | YVADTSKDVFDI | 187 | NSRDSSGNVV | 422 | + |
| 126 | HC group 157, LC group 148: | PWD0123 | VASTALYFDN | 188 | ASWDDTLKGGV | 423 | + |
| 127 | HC group 158, LC group 149: | PWD0124 | GVYNWNSAAKFDY | 189 | QSYDNSLSGSE | 424 | + |
| 128 | HC group 159, LC group 150: | PWD0127 | TYYYVYYNYMDV | 190 | NSRDSSGDPVT | 425 | + |
| 129 | HC group 160, LC group 151: | PWD0130 | VAHGWHLSFDY | 191 | SAWDDSLKGWV | 426 | + |
| 130 | HC group 161, LC group 152: | PWD0133 | SLFRVRGVFFDY | 192 | ASRDSSANQHWV | 427 | + |
| 131 | HC group 161, LC group 158: | PWD0150 | SLFRVRGVFFDY | 193 | QSYDSSTGIDY | 428 | + |
| 132 | HC group 162, LC group 153: | PWD0135 | GPAGLQLSLDI | 194 | AAWDDSLNGLV | 429 | + |
| 133 | HC group 163, LC group 154: | PWD0136 | VDHRWDLPFDY | 195 | STWDGSLNGWV | 430 | + |
| 134 | HC group 164, LC group 155: | PWD0139 | VDHKWDLPFDY | 196 | AAWDDSLNGWV | 431 | + |
| 135 | HC group 164, LC group 163: | PWD0169 | VDHKWDLPFDY | 197 | STWDDSLRGVV | 432 | + |
| 136 | HC group 164, LC group 181: | PWD0254 | VDHKWDLPFDY | 198 | AVWDDSLNGWV | 433 | + |
| 137 | HC group 164, LC group 240: | PWD0811 | VDHKWDLPFDY | 199 | APWDDSLNGWV | 434 | + |
| 138 | HC group 165, LC group 156: | PWD0146 | ARDYYFGMDV | 200 | SAWDSLHGPV | 435 | + |
| 139 | HC group 166, LC group 157: | PWD0147 | GPAGLQLSLDI | 201 | AAWDDSLNGVV | 436 | + |
| 140 | HC group 167, LC group 159: | PWD0151 | DRSKLNAGYFDS | 202 | QSYDNSLSAW | 437 | + |
| 141 | HC group 168, LC group 160: | PWD0154 | TKYSSIVFDL | 203 | AAWDDSLNVVV | 438 | + |
| 142 | HC group 169, LC group 161: | PWD0157 | FRFLVWYGEAYFDY | 204 | SSRDNSGDRLVL | 439 | + |
| 143 | HC group 170, LC group 162: | PWD0164 | VRGQLLAFDI | 205 | AAWDDSLNGWV | 440 | + |
| 144 | HC group 171, LC group 165: | PWD0175 | VDHKWDLPFDY | 206 | ATWDDSLRGWV | 441 | + |

TABLE 4-continued

Summary of ScFv Groups and CDR 3 Sequences for PA-Binding Phage Clones

| Group | HC group, LC group | Representative scFv clone | HC CDR 3 Seq. | SEQ ID NO: | LC CDR 3 Seq. | SEQ ID NO: | PA Binding Pos/Neg |
|---|---|---|---|---|---|---|---|
| 145 | HC group 171, LC group 182: | PWD0258 | VDHKWDLPFDY | 207 | ATWDDSVRGWV | 442 | + |
| 146 | HC group 172, LC group 166: | PWD0176 | GPAGLQLSLDI | 208 | ATWDDSLSGWV | 443 | +/- |
| 147 | HC group 173, LC group 167: | PWD0177 | TKYSSIVFDL | 209 | AAWDDSLNAVL | 444 | + |
| 148 | HC group 174, LC group 168: | PWD0183 | AVWDDSLNGH | 210 | VDRRWDLPFDY | 445 | + |
| 149 | HC group 175, LC group 169: | PWD0187 | TKYSSIVFDL | 211 | ASWDDSLNGV | 446 | + |
| 150 | HC group 176, LC group 170: | PWD0189 | LDHKWDLPFDY | 212 | EAWDDSLSGPA | 447 | +/- |
| 151 | HC group 177, LC group 171: | PWD0190 | VDHNWDLPFDY | 213 | GTWDSRLSAVV | 448 | + |
| 152 | HC group 178, LC group 173: | PWD0211 | EYYYRWGSYAN | 214 | NSRDSSGNPVV | 449 | +/- |
| 153 | HC group 179, LC group 174: | PWD0218 | VDHKWDLPFDY | 215 | TAWDDSLNGWV | 450 | + |
| 154 | HC group 180, LC group 175: | PWD0228 | VDHNWDLPFDY | 216 | AAWDDILNGWV | 451 | + |
| 155 | HC group 181, LC group 176: | PWD0229 | SLFRVRGVFFDY | 217 | NSRDSSGNHVV | 452 | + |
| 156 | HC group 181, LC group 193: | PWD0329 | SLFRVRGVFFDY | 218 | QAWDSSTTWE | 453 | + |
| 157 | HC group 181, LC group 233: | PWD0754 | SLFRVRGVFFDY | 219 | ETWDTSLSVLV | 454 | + |
| 158 | HC group 182, LC group 177: | PWD0233 | DLGVGRYFDY | 220 | SSRDNSGDPL | 455 | + |
| 159 | HC group 182, LC group 223: | PWD0611 | DLGVGRYFDY | 221 | SSRDNSGDPL | 456 | + |
| 160 | HC group 183, LC group 178: | PWD0243 | SLFRVRGVFFDY | 222 | NSRDSSGNHWV | 457 | + |
| 161 | HC group 184, LC group 179: | PWD0246 | DRSKLNAGYFDS | 223 | QSYDSSLSAYV | 458 | + |
| 162 | HC group 184, LC group 263: | PWD0968 | DRSKLNAGYFDS | 224 | QSYDSGLSAVV | 459 | + |
| 163 | HC group 185, LC group 180: | PWD0248 | LDHNWDLPFDY | 225 | ASWDDSLSGWV | 460 | + |
| 164 | HC group 185, LC group 207: | PWD0427 | LDHNWDLPFDY | 226 | ATWDDSLSGLL | 461 | + |
| 165 | HC group 185, LC group 235: | PWD0766 | LDHNWDLPFDY | 227 | ASWDDSLKGVV | 462 | + |
| 166 | HC group 186, LC group 183: | PWD0259 | TKYSSIVFDL | 228 | AAWDDRLSGPV | 463 | + |
| 167 | HC group 186, LC group 210: | PWD0441 | TKYSSIVFDL | 229 | AAWDDSLNGML | 464 | + |
| 168 | HC group 186, LC group 243: | PWD0824 | TKYSSIVFDL | 230 | AAWDDSLNGP | 465 | +/- |
| 169 | HC group 187, LC group 184: | PWD0268 | LDHNWNLPFD | 231 | ATWDDRLKGFV | 466 | + |
| 170 | HC group 188, LC group 185: | PWD0283 | VGGAIRFDS | 232 | SAWDDSLSGVV | 467 | + |
| 171 | HC group 189, LC group 186: | PWD0288 | SVGRSLAFDI | 233 | AAWDDSLNGHVV | 468 | + |
| 172 | HC group 190, LC group 187: | PWD0291 | RTGDCSYTSCY | 234 | QTWDSTTAS | 469 | + |
| 173 | HC group 191, LC group 188: | PWD0294 | GPAGLQLSLDI | 235 | SAWDDSLNGPA | 470 | + |
| 174 | HC group 191, LC group 209: | PWD0440 | GPAGLQLSLDI | 236 | SAWDDSLNGPA | 471 | + |
| 175 | HC group 192, LC group 189: | PWD0305 | VDHKWDLPFDY | 237 | ATWDDTLSGLV | 472 | + |
| 176 | HC group 193, LC group 190: | PWD0308 | FTGWYGAFDI | 238 | ATWDDSVNGPA | 473 | + |
| 177 | HC group 194, LC group 191: | PWD0318 | DRYNMVGVLRPDS | 239 | SSYARSNNFGV | 474 | - |
| 178 | HC group 195, LC group 192: | PWD0323 | QIWGRFEY | 240 | AAWDDRLNGYV | 475 | + |
| 179 | HC group 195, LC group 219: | PWD0587 | QIWGRFEY | 241 | AAWDDSLNGVV | 476 | + |
| 180 | HC group 196, LC group 196: | PWD0339 | GYDFWSGFDY | 242 | QVWDSTSDHRI | 477 | + |

TABLE 4-continued

Summary of ScFv Groups and CDR 3 Sequences for PA-Binding Phage Clones

| Group | HC group, LC group | Representative scFv clone | HC CDR 3 Seq. | SEQ ID NO: | LC CDR 3 Seq. | SEQ ID NO: | PA Binding Pos/Neg |
|---|---|---|---|---|---|---|---|
| 181 | HC group 197, LC group 140: | PWD0355 | GWGVFDM | 243 | AAWDDSL DGVV | 478 | + |
| 182 | HC group 198, LC group 198: | PWD0369 | VDHKWDLPF DF | 244 | ASWDDSL DGWV | 479 | +/− |
| 183 | HC group 199, LC group 200: | PWD0389 | ARALFRVSGPY | 245 | SSYSGDVN FIV | 480 | + |
| 184 | HC group 200, LC group 201: | PWD0391 | DHPYNWNYF DY | 246 | QQLNRYPSL | 481 | − |
| 185 | HC group 201, LC group 202: | PWD0392 | GAPAVRHGF DY | 247 | QQYYSTPPT | 482 | − |
| 186 | HC group 202, LC group 203: | PWD0412 | VDHKWDLPF DY | 248 | ATWDDSL KGFV | 483 | + |
| 187 | HC group 203, LC group 204: | PWD0416 | FGTGSSLEV | 249 | AAWDDSL NGVV | 484 | + |
| 188 | HC group 204, LC group 205: | PWD0422 | QAFARFEF | 250 | SSWDDSLN GVV | 485 | + |
| 189 | HC group 205, LC group 206: | PWD0424 | NLQDIVATIL PFDY | 251 | GTWDSSLN TYV | 486 | − |
| 190 | HC group 206, LC group 141: | PWD0436 | VDHNWDLPF DY | 252 | SAWDDSL NGWV | 487 | + |
| 191 | HC group 207, LC group 211: | PWD0451 | GDPEELRSDS YFYYGMDV | 253 | QSYDSSLS GSWV | 488 | − |
| 192 | HC group 208, LC group 212: | PWD0454 | LDHKWDLPF DH | 254 | EAWDDSLS GPA | 489 | + |
| 193 | HC group 209, LC group 213: | PWD0469 | TKYSSVAFDL | 255 | ATWDDSL NGVV | 490 | + |
| 194 | HC group 210, LC group 139: | PWD0525 | LLRGGSTYLD AFDX | 256 | QVWDRSN GHVV | 491 | + |
| 195 | HC group 211, LC group 216: | PWD0541 | Not Determined | | QQFKSYPLT | 492 | − |
| 196 | HC group 212, LC group 217: | PWD0542 | GVYGGGSAG LYFDV | 257 | QVWDNSS GWV | 493 | + |
| 197 | HC group 213, LC group 218: | PWD0568 | GEMATIRY | 258 | ATWDDSL NGWV | 494 | + |
| 198 | HC group 214, LC group 220: | PWD0588 | VDHKWDLPF DY | 259 | AAWDASL TSWV | 495 | + |
| 199 | HC group 215, LC group 221: | PWD0593 | VDHNWDLPF DY | 260 | AAWDDSL NGVV | 496 | + |
| 200 | HC group 216, LC group 222: | PWD0605 | ASSWYLVFDI | 261 | AAWDDSL NGWV | 497 | + |
| 201 | HC group 216, LC group 259: | PWD0929 | ASSWYLVFDI | 262 | AAWDDSL NGWV | 498 | + |
| 202 | HC group 217, LC group 224: | PWD0615 | SLFRVRGVFF DY | 263 | GTWDSSLS DGKVV | 499 | + |
| 203 | HC group 218, LC group 146: | PWD0635 | VDHNWDLPF DY | 264 | AAWDDSL NGWV | 500 | + |
| 204 | HC group 219, LC group 225: | PWD0638 | VDHNWDLPF DY | 265 | ATWDDSR GGWV | 501 | + |
| 205 | HC group 220, LC group 226: | PWD0648 | VDRRWDLPF DY | 266 | ASWDDSV GSWV | 502 | + |
| 206 | HC group 221, LC group 228: | PWD0706 | VDHKWDLPF DF | 267 | AAWDDSL NGWV | 503 | + |
| 207 | HC group 222, LC group 229: | PWD0709 | GGPPFGSSYDV | 268 | ASWDDDL SGLV | 504 | + |
| 208 | HC group 223, LC group 230: | PWD0718 | PTYGPGSFLI DH | 269 | ATWDDSL NGPV | 505 | + |
| 209 | HC group 224, LC group 231: | PWD0721 | TRGYSLYFDS | 270 | ATWDDSL MVGV | 506 | + |
| 210 | HC group 225, LC group 232: | PWD0730 | VDHNWDLPF DY | 271 | ATWDDSL NGWV | 507 | + |
| 211 | HC group 226, LC group 236: | PWD0773 | GPAGLQLSLDI | 272 | AVWDDSL NGVI | 508 | + |
| 212 | HC group 227, LC group 237: | PWD0776 | GPAGLQLSLDI | 273 | AAWDDNL NGVV | 509 | +/− |
| 213 | HC group 228, LC group 144: | PWD0791 | VDHKWDLPF DY | 274 | AAWDDSL KGWV | 510 | + |
| 214 | HC group 229, LC group 238: | PWD0808 | AGGSSLVFDS | 275 | AVWDDGL SGWV | 511 | + |
| 215 | HC group 230, LC group 242: | PWD0821 | DGPSNYMDV | 276 | QQYYSTPIT | 512 | − |
| 216 | HC group 231, LC group 245: | PWD0830 | VDHNWDLPF DY | 277 | VAWDDSL NGWV | 513 | + |

TABLE 4-continued

Summary of ScFv Groups and CDR 3 Sequences for PA-Binding Phage Clones

| GroupLC | HC group, LC group | Representative scFv clone | HC CDR 3 Seq. | SEQ ID NO: | LC CDR 3 Seq. | SEQ ID NO: | PA Binding Pos/Neg |
|---|---|---|---|---|---|---|---|
| 217 | HC group 232, LC group 246: | PWD0834 | DGDYSSSSLDY | 278 | QSHDNTLCEV | 514 | − |
| 218 | HC group 233, LC group 247: | PWD0838 | VRVPGRDGMDV | 279 | ASWDDSLTWV | 515 | −/+ |
| 219 | HC group 234, LC group 250: | PWD0858 | GSGSYIAFDI | 280 | AAWDDSLSGPVV | 516 | + |
| 220 | HC group 235, LC group 251: | PWD0864 | TTVTTESDWFDL | 281 | NSRDSSGNHFDVV | 517 | −/+ |
| 221 | HC group 236, LC group 252: | PWD0871 | VDHNWDLPFDY | 282 | ATWDDSLNGFV | 518 | + |
| 222 | HC group 237, LC group 217: | PWD0876 | GVYGGGSAGLYFDV | 283 | QVWDNSSGWV | 519 | + |
| 223 | HC group 238, LC group 254: | PWD0880 | GPSGLLLGLDV | 284 | AVWDDSLNGVL | 520 | + |
| 224 | HC group 239, LC group 255: | PWD0884 | VASTALYFDN | 285 | AAWDDSLTGWV | 521 | + |
| 225 | HC group 240, LC group 256: | PWD0914 | LSGVTLHMDV | 286 | AAWDDSLKGPV | 522 | + |
| 226 | HC group 241, LC group 258: | PWD0928 | VRGGNLAFDF | 287 | AAWDDSLSGWV | 523 | + |
| 227 | HC group 242, LC group 260: | PWD0934 | SLFRVRGVFFDY | 288 | VTWDGSLGVVM | 524 | + |
| 228 | HC group 243, LC group 144: | PWD0948 | EDHKWDLPFDY | 289 | AAWDDSLKGWV | 525 | + |
| 229 | HC group 244, LC group 261: | PWD0949 | GALSSFDS | 290 | AAWDDSLNGWV | 526 | + |
| 230 | HC group 245, LC group 262: | PWD0953 | QIWGRFEY | 291 | AAWDDSLNGVV | 527 | + |
| 231 | HC group 246, LC group 146: | PWD0963 | ADHNWDLPFDY | 292 | AAWDDSLNGWV | 528 | + |
| 232 | HC group 247, LC group 264: | PWD0991 | AHWGSRVDY | 293 | AAWDDSLNGVV | 529 | + |
| 233 | HC group 248, LC group 265: | PWD0995 | LLRGGSTYLDAFDN | 294 | QVWDRSNGHVV | 530 | + |
| 234 | HC group 249, LC group 266: | PWD1003 | Not Determined | | NSRDSSGNLWV | 531 | − |
| 235 | HC group 250, LC group 268: | PWD1038 | EVGSYFDY | 295 | AAWDDSLNGVV | 532 | + |
| 236 | HC group 251, LC group 273: | PWD1072 | VDHNWDLPFDY | 296 | AAWDDSLNGWV | 533 | + |
| 237 | HC group 252, LC group 274: | PWD1077 | SLFRVRGVFFDY | 297 | NSRDNSGNLWV | 534 | + |
| 238 | HC group 253, LC group 275: | PWD1079 | GPRFWTGYYDY | 298 | QQSLTAWT | 535 | + |

Example 2

Affinity Ranking of mAbs to PA and PA Cleavage Site Peptide ELISA

Theoretical considerations suggest that under ideal circumstances antibody concentration at half-maximal antigen binding (EC50) is a measure of affinity. In practical terms it can be used to rank the affinities of antibodies to quickly identify best binders. The lower the antibody concentration required for 50% of plateau binding, the higher is the affinity of the antibody for antigen. In the approach described below, a conventional ELISA is used to generate binding isotherms for PA antibodies in order to derive their EC-50 values. Additionally, antibodies may be tested for their ability to bind peptides that span the RKKR (residues 193-196 of SEQ ID NO:2) cleavage site in PA.
EC-50 ELISA Direct Plate Coating with PA: 50 microliters of PA solution (0.2 μg/ml in PBS) is dispensed to individual wells of 96-well plates (Immulon-2, Dynex) sealed with Plate sealers (Advanced Genetic cat. #48461) and incubated overnight at 4° C. Next day the coating solution is removed, plates are washed 4 times with PBS with 0.1% Tween-20 and blocked by incubation with 200 microliters of blocking buffer (PBS, 3% BSA) for 1 hr at room temperature.

Serial dilutions of anti-PA antibodies are prepared in diluent buffer (PBS, 0.1% Tween-20, 0.1% BSA). Human IgG2 (Sigma, cat # I-4139) is used as a negative control. Two 50 microliter aliquots of each dilution are dispensed into individual wells of coated and blocked plates. The plates are sealed and incubated for 2 hours at room temperature.

Next, plates are washed 4 times with PBST (PBS, 0.1% Tween-20) and 50 microliters of HRP labeled anti-human IgG (Vector, cat# PI-3000) at concentration 1 microgram/milliliter in diluent buffer is dispensed to individual wells. Plates are sealed and incubated for 1 hr at room temperature. In the meantime substrate solution is prepared by dissolving 1 tablet of TMB (Sigma cat# T3405) in 5 ml of water. After the tablet is dissolved, 5 ml of the substrate buffer (0.1 M $Na_2PO_4$, 0.05 M Citric acid) and 2 microliters of 30% $H_2O_2$ is added.

Plates are washed 4 times with PBST and 100 microliters of substrate is added to each well. Plates are incubated for 10 min at room temperature and the Absorption at 450 nm is measured on SpectraMax 3000 (Molecular Devices).

Data analysis Data is analyzed using SofMaxPro 3.0. Binding curves (on OD 450 versus concentration graphs) are generated using the four parameter fit model. EC-50 values are calculated automatically as the concentration of the antibody that provides 50% of the maximum binding (maximum binding is characterized by parameter D in the four parameter fit equation).

Cleavage Site Peptide ELISA:

Indirect coating of biotinylated peptides to streptavidin coated plates: One hundred microliters of Streptavidin (Sigma S-4762) solution (1 mg/ml in PBS) is dispensed into individual wells of 96-well plates (Immulon-4, Dynex) sealed with Plate sealers (Advanced Genetic Cat. #48461) and incubated overnight at 4° C. The next day the coating solution is removed, plates are washed 4 times with PBS+0.1% Tween-20 and blocked by incubation with 200 ml of blocking buffer (PBS, 3% BSA) for 1 hour at room temperature.

After blocking, the blocking solution is removed, plates are washed 4 times with PBS+0.1% Tween-20 and 100 microliters per well of biotinylated peptides (1 mg/ml diluted in 0.1% BSA in PBS) is incubated for 1 hour at room temperature. The biotinylated peptides are: sp-186: biotin-SNSRKKRST-SAGPTVPDRDN (amino acids 190-206 of SEQ ID NO:2); sp-187: biotin-QLPELKQKSSNSRKKRSTSAG (amino acids 181-201 of SEQ ID NO:2); and sp-189: biotin-QLPELKQKSSNSRKK (amino acids 181-195 of SEQ ID NO:2). The plates are then washed 4 times with PBST.

100 microliters of 3 dilutions (10 micrograms/ml, 1.0 micrograms/ml and 0.1 micrograms/ml) of purified antibody in duplicate are dispensed into the 96-well plate. The plates are sealed and incubated for 2 hours at room temperature. Plates are washed 4 times with PBST and 100 microliters of HRP-labeled goat anti human IgG (H+L) (Vector, Cat# PI-3000) are dispensed into individual wells (1 mg/ml in 0.1% BSA in PBST). Plates are sealed and incubated for 1 hour at room temperature. In the meantime, substrate solution is prepared by dissolving 1 tablet of TMB (Sigma, Cat# T3405) in 5 ml of water. After the tablet is dissolved, 5 ml of the substrate buffer (0.1 M $Na_2PO_4$, 0.05 M Citric acid) and 2 ml of 30% $H_2O_2$ are added. Plates are washed 4 times with PBST and 100 microliters of substrate is added to each well. Plates are incubated for 15 minutes at room temperature and the absorption (at 450 nm) is measured on SpectraMaxPlus (Molecular Devices).

Example 3

Inhibition of Biotinylated PA Binding to Anthrax Receptors

The following protocol may be used to test whether an antibody is able to inhibit the binding of biotinylated PA protein to the anthrax receptor protein (SEQ ID NO:3).

Preparation of ATR Protein

ATR protein was produced by cloning the first 227 amino acid residues of the ATR protein gene (SEQ ID NO:3, Bradley et al, (2001) Nature 414:225-229) linked to a polynucleotide encoding the FLAG® tag (Stratagene, La Jolla, Calif.) (amino acid residues DYKDDDDK, SEQ ID NO:43) into a mammalian expression vector (Lonza Biologics). Recombinant soluble ATR protein was expressed from 293T cells by transient transfection. Three days after transfection, conditioned media were collected and the ATR protein with a flag-tag at the carboxy terminus was purified from the media sample by passing it through an anti-flag monoclonal antibody affinity column (Sigma).

Preparation of PA Protein

PA protein was produced from a synthetic gene encoding the B. anthracis PA which was constructed using a combination of overlapping oligonucleotides and polymerase chain reaction (PCR). The synthetic gene encoding the B. anthracis PA residues E30-G764 of mature PA (SEQ ID NO:2) was codon-optimized for expression in the bacterium, Escherichia coli. Subsequent PCR amplification reactions were performed to add a heterologous signal peptide to the N-terminus of mature PA (E30-G764). PA was produced in E. coli K-12 cells and extracted from the cell paste upon periplasmic shock. The PA protein was purified using Q-sepharose-HP and hydroxyapatite chromatography. PA purity was confirmed by native- and SDS-PAGE silver staining, N-terminal protein sequencing, RP-HPLC and SEC-HPLC and was determined to be 96-98% pure.

To assess the proper function of the PA protein, the ability of the PA protein to form heptamers after enzymatic cleavage was evaluated. PA binds to its cell surface receptor and is cleaved by a furin-like protease to eliminate the N-terminal 20 kilodalton region. This cleavage permits the PA63 fragment to polymerize and form a heptameric pore in the membrane. PA63 can also be obtained in vitro by trypsin digestion (Benson et al, (1998) Biochemistry 37:3941-3948; Ahuja et al, (2001) Biochem. Biophys. Res. Comm. 286:6-11, each of which are herein incorporated by reference in their entireties). Purified PA (83 kilodaltons) was subjected to trypsin digestion to determine if the purified PA was capable of being cleaved to PA63 and if the cleaved PA63 fragments could form heptamers. The trypsin-treated PA protein was analyzed via SDS-PAGE and transferred to a membrane for protein sequencing. SDS-PAGE analysis indicated the trypsin-treated PA protein yielded a 63 kilodalton protein. Subsequent N-terminal sequence analysis confirmed the correct cleavage position. Moreover, native-PAGE analysis and mass spectrometry indicated that the 63 kilodalton subunits formed multimers. Heptameric PA63 was also captured on a Q-sepharose-HP column.

Inhibition of PA Binding to ATR Assay

The assay buffer for this assay consists of 1×PBS (pH7.4, without calcium and Magnesium; catalogue #17-516 from BioWhittaker), 2% BSA (Sigma, A-0336, stock 30% solution), 1 mM $CaCl_2$, 1 mM $MgCl_2$, 0.1% Tween-20. Calcium and magnesium need to be added to assay buffer at the time of assay. Biotinylated PA protein (final concentration 300 ng/ml; biotinylation was performed using EZ-Link™ Sulfo-NHS-LC-Biotin available from Pierce Biotechnology) is pre-incubated with antibody preparations (phage expressing scFv, purified scFv or whole antibody molecules, such as IgG molecules, comprising the VH and VL domains of specific scFvs) in assay buffer for 45 minutes, at room temperature with gentle shaking. Flag-tagged ATR protein (amino acids 1-227 of SEQ ID NO:3) is then added to the mixture and incubated for an additional 20 minutes.

Next, 2.5 microliters of streptavidin coated beads (Dynabeads M-280, Dynal Biotech) is added to each well along with anti-flag antibody (Sigma, catalogue # F3165) (1 microgram/milliliter final concentration) that has been labeled with ORI-TAG® (IGEN International) according to the manufacturer's directions. The mixture is then incubated for 45 minutes at room temperature with gentle shaking. Electrochemiluminescence is then measured using the M8 ECL unit (IGEN, International).

The protein concentrations given in the above-described assay can be modified by one of skill in the art to optimize assay performance, as necessary. Additionally, this assay may be modified to test an antibody's ability to block binding of PA to its receptor on other primary cells or cell lines, such as macrophage cell lines.

FIG. 1 shows results for the ability of antibodies PWD0283 and PWD0587 to inhibit the binding of biotinylated PA to ATR.

Inhibition of PA Binding to CMG2

In an assay similar to the one described above antibody PWD0587 was tested for its ability to block binding of PA to a flag tagged version of CMG2 protein that also acts as an anthrax receptor (see, Scobie et al., (2003) *Proceedings of the National Academy of Sciences* 100:5170-5174). The CMG2 protein used consisted of amino acids 33-318 of SEQ ID NO:42 fused to a flag tag (SEQ ID NO:43). Using this assay, it was shown that an IgG1 format of the PWD0587 antibody also inhibits the binding of PA to CMG2.

Example 4

Detection of Biotinylated PA binding to PA Receptor by Flow Cytometry

In preparation for a series of in vitro studies to test if anti-PA monoclonal antibodies of the invention can inhibit the action of PA, flow cytometry analysis of binding of biotinylated PA protein to CHO-K1 cells, J774A.1 cells, and human macrophages was performed. CHO-K1 cells are a cell line that have functional ATR protein on their surface. Both the J774A.1 cells (a murine macrophage cell line) and human macrophages also possess PA binding proteins on their surface. For flow cytometry analysis, PA protein was biotinylated as described above (Example 3) and added to cells in culture and incubated for 10-20 minutes at room temperature. The cells were washed and pelleted by centrifugation. Streptavidin PE was then added to the cell pellets and incubated briefly at room temperature. After washing, the cells were first resuspended in propidium iodide to discriminate between live and dead cells, and then were analyzed on a FACScan. Data were acquired and analyzed using CellQuest software (Becton Dickinson). As shown in FIG. 2, biotinylated PA binds specifically to CHO-K1 cells, J774A.1 murine macrophages, and human macrophages, indicating that these cells have ATR protein on their surface.

Example 5

$^{86}$Rubidium Release Assay

PA has been shown to interact with the ATR on CHO-K1 cells (Escuyer and Collier, (1991) *Infect. Immunol.* 59:3381-3386, which is hereby incorporated by reference in its entirety. Following binding of PA to the ATR, a 20 kilodalton peptide is cleaved from the PA and the remaining PA63 molecules aggregate into heptamers and form a pore on the cell surface. One assay that has been developed to measure PA63-mediated pore formation monitors the release of intracellular $^{86}$Rubidium ($^{86}$Rb) from cells that have been pre-loaded with $^{86}$Rb. The following protocol may be used to test whether an antibody is able to inhibit the ability of PA63 to form pores in membranes.

$^{86}$Rubidium Release Assay Using CHO-K1 Cells 2.0×10$^5$ CHO-K1 cells (ATCC™#CCL 61, which express PA Receptor on their surface, see Example 4) are plated in a 24 well plate in 1 milliliter of culture medium (Ham's F12K medium with 2 mM L-glutamine adjusted to contain 2.5 g/L sodium bicarbonate., 90%; fetal bovine serum, 10%). The cells are incubated for 24 hours at 37° C., 5% CO$_2$. Medium is aspirated and replaced with milliliter of fresh culture medium containing $^{86}$Rb at a concentration 1 microCurie/milliliter. Cells are incubated on ice for 30 minutes after which the medium is removed and the cells are washed two times with 750 µl of cold PBS. Next, 1 milliliter of medium containing PA alone or PA which has been pre-incubated (for 1 hour at 37 degrees on a rotator) with anti-PA antibody is added to the cells which are then incubated for 1.5 hours on ice. At the end of the incubation period, the cells are again washed twice with 750 µl of cold PBS. 500 microliters of cold MES-gluconate buffer, pH4.9 is then added and incubated on ice for 30 minutes. 100 microliters of supernatant is removed from cell supernatant and added to 2.0 ml of Supermix OptiPhase scintillant (Perkin-Elmer Life Sciences) and the radioactivity is counted using a Wallac Microbeta TRILUX Liquid Scintillation and Luminescence Counter (Perkin-Elmer). Radioactivity in the medium is indicative of pore formation by PA63.

To determine the optimal amount of PA to use in the $^{86}$Rb release assay, PA was titrated by measuring $^{86}$Rb release with different concentrations of PA (18, 6, 2, 0.67, 0.22, 0.074, 0.025, and 0 nM) were added to the assay. Based on this titration, 5 nM PA was chosen for the subsequent assays.

In this assay PATD, a mutant of PA which is defective in pore formation is used as a positive control for inhibition of pore formation. PATD is identical to wildtype PA with the exception that it has two amino acid mutations, K426D and D454K using the numbering of SEQ ID NO:2. PATD is described in Sellman et al., *J. Biol. Chem.* (2001), 276:8371-6, Sellman et al., *Science* 292:695-697, and in International Patent Publication WO01/82788 each of which is hereby incorporated by reference in its entirety.

FIG. 3 shows the ability of two antibodies PWD0283 and PWD0587 in whole IgG1 format to inhibit pore formation by PA protein using the above described assay.

$^{86}$Rubidium Release Assay Using Human Macrophages

The systemic shock and death from anthrax results primarily from the effects of high levels of cytokines produced by and released from macrophages that have been affected by the anthrax lethal toxin. Consequently, it was of interest to evaluate whether anti-PA antibodies of the invention could inhibit PA-mediated release of $^{86}$Rb from human macrophages.

Preparation of Human Macrophages

For the preparation of human macrophages, peripheral blood mononuclear cells (PBMC) were isolated from various human donors by Ficoll-Hypaque density gradient centrifugation. PBMC were incubated with anti-CD14-labeled paramagnetic microbeads (Miltenyi Biotec). After magnetic labeling, the cells were passed through a separation column placed in a strong permanent magnet. The magnetically-labeled cells retained in the column were then eluted, washed, and counted. CD14+ cells were then placed in 6-well culture dishes for 10-12 days in medium containing granulocyte-macrophage colony-stimulating factor (GM-CSF). Medium was replenished every 3 days until the cells were used in the assay.

Inhibition of $^{86}$Rb Release from Human Macrophages by Anti-PA Monoclonal Antibodies The $^{86}$Rb release assay was performed as described above, except for using human macrophages in place of the CHO-K1 cells. Anti-PA monoclonal antibodies PWD0283 and PWD0587 fully inhibited PA-mediated $^{86}$Rb release at antibody concentration of about 5 nM.

Example 6

Identification and Cloning of VH and VL Domains

One method to identify and clone VH and VL domains from cell lines expressing a particular antibody is to perform PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may lysed in the TRIzol™ reagent (Life Technologies, Rockville. MD) and extracted with one fifth volume of chloroform. After addition of chloroform, the solution is allowed to incubate at room temperature for 10 minutes, and the centrifuged at 14,000 rpm for 15 minutes at 4° C. in a tabletop centrifuge. The supernatant is collected and RNA is precipitated using an equal volume of isopropanol. Precipitated RNA is pelleted by centrifuging at 14,000 rpm for 15 minutes at 4° C. in a tabletop centrifuge. Following centrifugation, the supernatant is discarded and washed with 75% ethanol. Following washing, the RNA is centrifuged again at 800 rpm for 5 minutes at 4° C. The supernatant is discarded and the pellet allowed to air dry. RNA is the dissolved in DEPC water and heated to 60° C. for 10 minutes. Quantities of RNA can determined using optical density measurements.

cDNA may be synthesized, according to methods well-known in the art, from 1.5-2.5 micrograms of RNA using reverse transcriptase and random hexamer primers. cDNA is then used as a template for PCR amplification of VH and VL domains. Primers used to amplify VH and VL genes are shown in Table 6. Typically a PCR reaction makes use of a single 5' primer and a single 3' primer. Sometimes, when the amount of available RNA template is limiting, or for greater efficiency, groups of 5' and/or 3' primers may be used. For example, sometimes all five VH-5' primers and all JH3' primers are used in a single PCR reaction. The PCR reaction is carried out in a 50 microliter volume containing 1×PCR buffer, 2 mM of each dNTP, 0.7 units of High Fidelity Taq polymerase, 5' primer mix, 3' primer mix and 7.5 microliters of cDNA. The 5' and 3' primer mix of both VH and VL can be made by pooling together 22 pmole and 28 pmole, respectively, of each of the individual primers. PCR conditions are: 96° C. for 5 minutes; followed by 25 cycles of 94° C. for 1 minute, 50° C. for 1 minute, and 72° C. for 1 minute; followed by an extension cycle of 72° C. for 10 minutes. After the reaction is completed, sample tubes were stored 4° C.

TABLE 5

Primer Sequences Used to Amplify VH and VL domains.

| Primer name | SEQ ID NO | Primer Sequence (5'-3') |
|---|---|---|
| VH Primers | | |
| Hu VH1-5' | 6 | CAGGTGCAGCTGGTGCAGTCTGG |
| Hu VH2-5' | 7 | CAGGTCAACTTAAGGGAGTCTGG |
| Hu VH3-5' | 8 | GAGGTGCAGCTGGTGGAGTCTGG |
| Hu VH4-5' | 9 | CAGGTGCAGCTGCAGGAGTCGGG |
| Hu VH5-5' | 10 | GAGGTGCAGCTGTTGCAGTCTGC |
| Hu VH6-5' | 11 | CAGGTACAGCTGCAGCAGTCAGG |
| Hu JH1,2-5' | 12 | TGAGGAGACGGTGACCAGGGTGCC |
| Hu JH3-5' | 13 | TGAAGAGACGGTGACCATTGTCCC |
| Hu JH4,5-5' | 14 | TGAGGAGACGGTGACCAGGGTTCC |
| Hu JH6-5' | 15 | TGAGGAGACGGTGACCGTGGTCCC |
| VL Primers | | |
| Hu Vkappa1-5' | 16 | GACATCCAGATGACCCAGTCTCC |
| Hu Vkappa2a-5' | 17 | GATGTTGTGATGACTCAGTCTCC |
| Hu Vkappa2b-5' | 18 | GATATTGTGATGACTCAGTCTCC |
| Hu Vkappa3-5' | 19 | GAAATTGTGTTGACGCAGTCTCC |
| Hu Vkappa4-5' | 20 | GACATCGTGATGACCCAGTCTCC |
| Hu Vkappa5-5' | 21 | GAAACGACACTCACGCAGTCTCC |
| Hu Vkappa6-5' | 22 | GAAATTGTGCTGACTCAGTCTCC |
| Hu Vlambda1-5' | 23 | CAGTCTGTGTTGACGCAGCCGCC |
| Hu Vlambda2-5' | 24 | CAGTCTGCCCTGACTCAGCCTGC |
| Hu Vlambda3-5' | 25 | TCCTATGTGCTGACTCAGCCACC |
| Hu Vlambda3b-5' | 26 | TCTTCTGAGCTGACTCAGGACCC |
| Hu Vlambda4-5' | 27 | CACGTTATACTGACTCAACCGCC |
| Hu Vlambda5-5' | 28 | CAGGCTGTGCTCACTCAGCCGTC |
| Hu Vlambda6-5' | 29 | AATTTTATGCTGACTCAGCCCCA |
| Hu Jkappa1-3' | 30 | ACGTTTGATTTCCACCTTGGTCCC |
| Hu Jkappa2-3' | 31 | ACGTTTGATCTCCAGCTTGGTCCC |
| Hu Jkappa3-3' | 32 | ACGTTTGATATCCACTTTGGTCCC |
| Hu Jkappa4-3' | 33 | ACGTTTGATCTCCACCTTGGTCCC |
| Hu Jkappa5-3' | 34 | ACGTTTAATCTCCAGTCGTGTCCC |
| Hu Jlambda1-3' | 35 | CAGTCTGTGTTGACGCAGCCGCC |
| Hu Jlambda2-3' | 36 | CAGTCTGCCCTGACTCAGCCTGC |
| Hu Jlambda3--3' | 37 | TCCTATGTGCTGACTCAGCCACC |
| Hu Jlambda3b-3' | 38 | TCTTCTGAGCTGACTCAGGACCC |
| Hu Jlambda4-3' | 39 | CACGTTATACTGACTCAACCGCC |
| Hu Jlambda5-3' | 40 | CAGGCTGTGCTCACTCAGCCGTC |
| Hu Jlambda6-3' | 41 | AATTTTATGCTGACTCAGCCCCA |

PCR samples are then electrophoresed on a 1.3% agarose gel. DNA bands of the expected sizes (~506 base pairs for VH domains, and 344 base pairs for VL domains) can be cut out of the gel and purified using methods well known in the art. Purified PCR products can be ligated into a PCR cloning vector (TA vector from Invitrogen Inc., Carlsbad, Calif.). Individual cloned PCR products can be isolated after transfection of E. coli and blue/white color selection. Cloned PCR products may then be sequenced using methods commonly known in the art.

Example 7

Kinetics of PA binding Analyzed by BIACORE

For BIAcore analysis, PA and PA heptamer were immobilized on individual flow cells of a BIAcore CM5 sensor chip. The PA monoclonal antibodies, PWD0283 and PWD0587 (IgG1 format), were diluted from 50 μg/mL (333 nM) to 0.625 μg/mL (4.1 nM). Each concentration was in contact with the PA proteins during a 4-minute association phase. The off-rate of the anti-PA monoclonal antibodies was determined by washing the complex in the presence of buffer for 5 minutes. The binding data were analyzed using the BIAevaluation software, Version 3.1. The kinetics of anti-PA monoclonal antibody binding to PA and to PA heptamer are summarized in Tables 6 and 7, respectively. Both PWD0283 and PWD0587 antibodies showed high affinity binding to both PA and its heptamer.

TABLE 6

Kinetics of anti-PA monoclonal antibody binding to PA

| Anti-PA mAb | ka (1/Ms) | kd (1/s) | KD (M) |
|---|---|---|---|
| PWD0283 | $4.46 \times 10^6$ | $1.03 \times 10^{-3}$ | $2.32 \times 10^{-10}$ |
| PWD0587 | $2.44 \times 10^5$ | $5.30 \times 10^{-4}$ | $2.17 \times 10^{-9}$ | ka (1/Ms, association rate constant; kd (1/s), dissociation rate constant; KD (M)

TABLE 7

Kinetics of anti-PA monoclonal antibody binding to PA heptamer

| Anti-PA mAb | ka (1/Ms) | kd (1/s) | KD (M) |
|---|---|---|---|
| PWD0283 | $2.28 \times 10^6$ | $4.26 \times 10^{-4}$ | $1.87 \times 10^{-10}$ |
| PWD0587 | $3.23 \times 10^5$ | $6.50 \times 10^{-5}$ | $2.01 \times 10^{-10}$ | ka (1/Ms, association rate constant; kd (1/s), dissociation rate constant; KD (M)

Example 8

Inhibition of Lethal Toxin Mediated Cell Killing by Anti-PA Antibodies

The ability of anti-PA antibodies to inhibit cell killing caused by lethal toxin (PA/LF) was evaluated using J774A.1, murine macrophage cell line (Quinn et al, (1991) *J. Biol. Chem.* 266:20124-20130, herein incorporated by reference in its entirety). The cells were seeded in a 96-well micro titer plate and incubated overnight. The next day, fresh medium containing 100 ng/mL PA was added. Then, 20 μL of DMEM (containing 100 ng/mL PA) and 50 ng/mL LF was added. Cells were incubated for 3 hrs. To detect viable cells after lethal toxin treatment, 20 μL of CellTiter 96 $AQ_{ueous}$ One Solution Reagent (Promega) was added to each well and cells were incubated for 2.5 hrs. Plates were then read at 490 nm using SpectraMax250 (Molecular Devices). CellTiter 96 $AQ_{ueous}$ One Solution Reagent contains a tetrazolium compound which is bioreduced by metabolically active cells into a soluble colored formazan product. The quantity of formazan product as measured by absorbance at 490 nm is directly proportional to the number of living cells.

The ability of PA mAb, PWD0283 and PWD05687, to inhibit cell killing was compared with a negative control IgG1 mAb (CAT002). As shown in FIG. 4, PWD0283 and PWD0587 both inhibited lethal toxin-induced cell killing in a dose-dependent manner.

Example 9

Prophylactic Use of Anti-PA Antibodies

Fisher 344 rats are highly susceptible to the lethal effects of systemic doses of lethal toxin (Sellman et al., (2001) *Science* 292:695-697 and Ivins et al., (1989) *Applied and Environmental Microbiology* 55:2098-2100, both of which are herein incorporated by reference in their entireties). Lethal toxin is the combination of the receptor-binding component, PA and the metalloprotease, LF, of *B. anthracis*. The following studies were performed to examine the ability of anti-PA antibodies to act prophylactically by intravenous (IV), subcutaneous (SC) or intramuscular (IM) administration when administered at various times before single or multiple injections of lethal toxin (also referred to as "PA/LF" in this example and Example 10). In these studies, the time to morbundity (TTM) was measured and the number of animals surviving at 24 hours were counted. The average TTM following injection of lethal toxin is approximately 90 minutes. Animals that survived past 24 hours were euthanized. PA (83 kilodaltons) was formulated at a concentration of 0.45 mg/mL in a buffer containing 50 mM $NaPO_4$ and then diluted with phosphate-buffered normal saline to concentrations of 0.1125 mg/mL and 0.2 mg/mL. A volume of 0.2 mL delivered 0.0225 mg or 0.04 mg of PA. Doses of 0.09 mg/kg or 0.16 mg/kg were used. The dose 0.09 mg/kg was based on the lowest concentration needed to produce 100% lethality. The doses of PA monoclonal antibody and control monoclonal antibody used were in 10-fold molar excess of the PA dose.

Recombinant lethal factor (LF) from *B. anthracis*; List Biological Laboratories, Inc. (408.866.6363); Lot 1721B was provided as a lyophilized powder. When reconstituted with 1 mL sterile water for injection, the solution contained 1.0 mg LF in a buffer of 5 mM HEPES and 50 mM NaCl. It was then diluted with phosphate-buffered normal saline to a concentration of 0.040 mg/mL. A volume of 0.2 mL delivered 0.008 mg of LF. A dose of 0.032 mg/kg was used. This dose was based on the lowest concentration needed to produce 100% lethality.

Prophylactic Study 1: IV Administration of Anti-PA Antibodies 60 Minutes Prior to Injection of Lethal Toxin In this study, the effects of PA mAb administered 60 minutes prior to a single intravenous injection of PA/LF were examined. Male Fisher 344 rats (n=5/treatment) were assigned to the groups shown in Table 8. Sixty minutes before intravenous injection of PA/LF, animals received either anti-PA monoclonal antibodies (PWD0283 or PWD0587 in IgG1 format), a negative IgG1 control monoclonal antibody (CAT002), vehicle, or no study agent by intravenous injection.

As shown in Table 8 and FIG. 5, a single intravenous injection of PWD0283 or PWD0587 60 minutes prior to injection of lethal toxin provided 100% survival at 24 hours with no apparent ill effects. In contrast, a single injection of the negative control mAb, CAT002, provided no protection with 0% survival and an average TTM of 100 minutes. Vehicle or no study agent also provided no protection with 0% survival and an average TTM of 99 minutes and 91 minutes, respectively. In a separate study, rats receiving mAb alone without PA/LF showed no adverse effects.

TABLE 8

| Group | n | Time of Study Agent relative to PA/LF (min) | Study Agent (3 mg/kg) | PA (mg/kg) | LF (mg/kg) | % Survival | TTM (minutes) |
|---|---|---|---|---|---|---|---|
| 1 | 5 | −60 | PWD0283 | 0.16 | 0.032 | 100 | — |
| 2 | 5 | −60 | PWD0587 | 0.16 | 0.032 | 100 | — |
| 3 | 5 | −60 | CAT002 | 0.16 | 0.032 | 0 | 100 |
| 4 | 5 | −60 | vehicle | 0.16 | 0.032 | 0 | 99 |
| 5 | 5 | — | — | 0.16 | 0.032 | 0 | 91 |

Prophylactic Study 2: SC and IM Administration of anti-PA Antibodies 60 Minutes Prior to Injection of Lethal Toxin Because intravenous administration of anti-PA antibodies given 1 hour prior to lethal toxin was completely protective against lethal toxin, the experiment was repeated giving the anti-PA antibodies by SC or IM administration 60 minutes prior to the lethal toxin to examine these routes of PA mAb administration. Male Fisher 344 rats (n=5/treatment) were assigned to the groups shown in Table 9. Sixty minutes before administration of PA/LF, animals received either PA mAb (PWD0283 or PWD0587), or a negative control antibody (CAT002).

SC administration of PWD0283 or PWD0587 (Table 9) 1 hour prior to lethal toxin administration provided no protection with 0% survival and an average TTM of 105 minutes and 145 minutes, respectively. IM administration of PWD0283 or PWD0587 (Table 9) 1 hour prior to lethal toxin administration provided 80% survival. The TTM's of the non-surviving animals were 240 minutes and 124 minutes, respectively, for the anti-PA monoclonal antibodies. Administration of CAT002 by either route of administration as a negative control provided no protection against the lethal effects of systemic lethal toxin. All rats in the route-matched control groups exhibited the expected SYMPTOMS of animals exposed to toxic levels of PA/LF. TTM in the control animals ranged from 85 to 93 minutes.

TABLE 9

| Group | N | Time of Study Agent relative to PA/LF (min) | Study Agent (3 mg/kg) | Route of Administration | PA (mg/kg) | LF (mg/kg) | % Survival | TTM (minutes) |
|---|---|---|---|---|---|---|---|---|
| 1 | 5 | −60 | PWD0283 | SC | 0.09 | 0.032 | 0 | 145 |
| 2 | 5 | −60 | PWD0283 | IM | 0.09 | 0.032 | 80 | 240 |
| 3 | 5 | −60 | PWD0587 | SC | 0.09 | 0.032 | 0 | 105 |
| 4 | 5 | −60 | PWD0587 | IM | 0.09 | 0.032 | 80 | 124 |
| 5 | 5 | −60 | CAT002 | SC | 0.09 | 0.032 | 0 | 85 |
| 6 | 5 | −60 | CAT002 | IM | 0.09 | 0.032 | 0 | 93 |

Prophylactic Study 3: IV, SC and 1M Administration of Anti-PA Antibodies 24 Hours Prior to Injection of Lethal Toxin Because administration of anti-PA antibodies given SC or IM 1 hour prior to lethal toxin was only partially protective, the experiment was repeated giving the anti-PA antibodies 24 hours prior to the lethal toxin, to allow the antibody more time to distribute in the animals. In this study, anti-PA antibodies were administered by SC, IM or IV injection 24 hours prior to a single intravenous injection of PA/LF. Male Fisher 344 rats (n=5/treatment) were assigned to the groups shown in Table 10 Twenty-four hours before administration of PA/LF, animals received either PA mAb (PWD0283 or PWD0587), or a negative control mAb (CAT002).

As shown in Table 10, a single SC, IM or IV injection of PWD0283 or PWD0587 24 hours prior to injection of lethal toxin provided 100% survival at 24 hours with no apparent ill effects. In contrast, a single injection of the negative control mAb, CAT002, regardless of route of administration, provided no protection with 0% survival and an average TTM of 100 minutes. In a separate study, rats receiving anti-PA antibodies alone without PA/LF showed no adverse effects.

TABLE 10

| Group | N | Time of Study Agent relative to PA/LF (min) | Study Agent (3 mg/kg) | Route of Administration | PA (mg/kg) | LF (mg/kg) | % Survival | TTM (minutes) |
|---|---|---|---|---|---|---|---|---|
| 1 | 5 | −24 | PWD0283 | SC | 0.09 | 0.032 | 100 | — |
| 2 | 5 | −24 | PWD0283 | IM | 0.09 | 0.032 | 100 | — |
| 3 | 5 | −24 | PWD0283 | IV | 0.09 | 0.032 | 100 | — |
| 4 | 5 | −24 | PWD0587 | SC | 0.09 | 0.032 | 100 | — |
| 5 | 5 | −24 | PWD0587 | IM | 0.09 | 0.032 | 100 | — |
| 6 | 5 | −24 | PWD0587 | IV | 0.09 | 0.032 | 100 | — |
| 7 | 5 | −24 | CAT002 | SC | 0.09 | 0.032 | 0 | 88 |
| 8 | 5 | −24 | CAT002 | IM | 0.09 | 0.032 | 0 | 90 |
| 9 | 5 | −24 | CAT002 | | 0.09 | 0.032 | 0 | 92 |

Prophylactic Study 4: Duration of Protective Effect of a Single IV Administration of Anti-PA Antibodies Against Multiple Lethal Toxin Challenge The previous studies established that prophylactic administration of PWD0587 and PWD0283 protected Fisher 344 rats exposed to a lethal dose of anthrax toxin. The following study was designed to establish if administration of anti-PA antibodies would provide protection with recurrent multi-day administrations of lethal toxin.

Male Fisher 344 Rats (F344) were randomly assigned to groups of 5 as shown in Table 11. One injection of PWD0283 or PWD0587 was injected intravenously 1 hour prior to the first PA/LF injection on Day 1. The dose of antibody administered was approximately 10-fold higher than the PA in a single dose of lethal toxin on a molar basis. To provide sufficient control animals for the duration of the experiment 65 rats received CAT002 on Day 1. To assure lethality of the toxin, 5 rats from the CAT002 group were dosed each day parallel to the dosing of the PA mAb groups. Lethal toxin was administered on subsequent days to the animals surviving from the previous day. This study reports the data for 11 injections of lethal toxin through 15 days.

On Day 1, a single injection of PWD0283 or PWD0587 60 minutes prior to injection of lethal toxin provided 100% survival, replicating the results observed in the previous studies. Moreover, the single injection of PWD0283 or PWD0587 continued to provide 100% protection after 11 subsequent lethal toxin injections over 15 days (Table 11). Administration of the negative control mAb, CAT002, provided no protection 0% survival) in any of the day-matched control groups. The TTM in the day-matched controls ranged from 79 to 113 minutes.

TABLE 11

| Group | N | Time of Study Agent relative to PA/LF (min) | Study Agent (3 mg/kg) | Route of Administration | PA (mg/kg) | LF (mg/kg) | Day/ No. of PA/LF challenges | % Survival | TTM (minutes) |
|---|---|---|---|---|---|---|---|---|---|
| 1 | 5 | −24 | PWD0283 | IV | 0.09 | 0.032 | 15/11 | 100 | — |
| 2 | 5 | −24 | PWD0587 | IV | 0.09 | 0.032 | 15/11 | 100 | — |
| 3 | 65 | −24 | CAT002 | IV | 0.09 | 0.032 | 15/1* | 0 | 79-113 |

*Each set of 5 rats in Group 3, only received 1 challenge

Importantly, this study does not establish the maximum duration of the protective effect. Furthermore, repeated administration of PA/LF may have allowed the animals to develop their own protective immune response against PA. Indeed, daily administration of PA only, but not of LF only, for 14 consecutive days, allows rats to survive a PA/LF challenge at day 14 (data not shown). This result is likely explained by the rats' generation of endogenous protective titers of neutralizing anti-PA antibodies.

Prophylactic Study 5: Protective duration of single IV administration of anti-PA monoclonal antibodies The following study was designed to establish the duration of time which a single IV administration of anti-PA antibody would be protective against a single lethal toxin challenge.

Male Fisher 344 Rats (F344) were randomly assigned to groups of 5. Three, seven or fourteen days prior to PA/LF challenge, rats were given a single IV administration of PWD0283. Alternatively, seven, fourteen or twenty-one days prior to PA/LF challenge, rats were given a single IV administration of PWD0587. The dose of antibody administered was 1.5 mg/kg, which is approximately 10-fold higher than the PA in a single dose of lethal toxin on a molar basis. Control rats were given the an isotype-matched, non-PA-binding, control antibody (CAT002). PWD0283 fully protected (100% survival) rats from PA/LF when given three days prior to lethal toxin challenge, and protected 60% of animals (as measured 24 hours following PA/LF challenge) when administered seven days prior to challenge. Administration of PWD0283 14 days prior to PA/LF challenge was not protective. PWD0587 fully protected (100% survival) rats from PA/LF (as measured 24 hours following PA/LF challenge) when administered seven, fourteen or twenty-one days prior to challenge. Control antibody was not protective at any time point.

Together, the results of prophylactic studies 4 and 5 demonstrate that in addition to being protective against single or multiple challenges of PA/LF, the antibodies of the present invention are useful, for example, as passive immunotherapy, until such time as an individual can develop endogenous protective anti-PA antibody titers through vaccination or infection.

Example 10

Dose Response of Prophylactic Monoclonal Antibody Treatment

Using the experimental approach defined in Example 8, Prophylactic Study 1 (with the exception that 0.09 mg/kg, rather than 0.16 mg/kg, of PA was injected in the PA/LF injection), the quantity of anti-PA antibody administered was titrated to determine the minimum amount of antibody that would be protective. It was determined that doses of antibody equal to 10×, 1×, 0.75×, and 0.5× the molarity of PA injected allowed for 100% survival of animals, as measured 24 hours post PA/LF challenge. That is, doses as little as 0.075 mg/kg (0.136 nanomoles) of either PWD0283 or PWD0587 were fully protective when the PA/LF challenge comprised 0.09 mg/kg of PA (0.0272 nanomoles) and 0.032 mg/kg of LF (0.089 nanomoles). Doses of PWD0283 and PWD0587 antibody at one-quarter the molarity (0.038 mg/kg) of PA injected allowed 80% and 60% of the animals challenged to survive at least 24 hours (n=5/group). Doses of antibody one-tenth the molarity (0.015 mg/kg) of PA injected were not protective, although TTM was slightly extended to approximately 150 minutes compared to animals injected with the control antibody, CAT002, where TTM was approximately 100 minutes.

Example 11

Efficacy of Anti-PA Monoclonal Antibody Against Aerosolized Anthrax in The Rabbit Model The following study was designed to test the efficacy of an anti-PA antibody, administered as either a prophylactic or a therapeutic, of preventing or delaying death due to inhalational exposure to *Bacillus anthracis*.

New Zealand White Rabbits (2.5-3.5 kg from Covance, Inc.) were randomly assigned to six groups, each containing 12 animals evenly divided between male and female. Animals in each group were each challenged aerosol inhalation of anthrax spores, either after or prior to receiving anti-PA antibody or vehicle control. Group I was a control group that received no antibody treatment. Groups II-IV received a single prophylactic dose of 1, 5, 10, or 20 mg/kg of anti-PA antibody (PWD0587), respectively, administered subcutaneously 2 days prior to *B. anthracis* spore challenge. Group IV received a single therapeutic dose of 40 mg/kg of anti-PA antibody (PWD0587) administered intravenously one hour after *B. anthracis* spore challenge. Animals were exposed via aerosolization to a target dose of 100×LD$_{50}$ of *B. anthracis* spores. Post-exposure measurements indicated that animals were actually exposed to spore challenge dose of 196×LD$_{50}$.

Observations: Clinical observations were recorded twice daily from receipt of rabbits until death. Body weights were recorded twice pre-dose, at dosing and at necropsy (data not shown). Food consumption (ad libitum) was confirmed by visual inspection. All animals that died or were euthanized due to moribundity had gross necropsy performed and recorded.

Blood collection: Blood collections were taken on days—7, 7, and 14 for hematology and serum chemistry as well as for determination of serum PA protein and anti-PA Antibody levels (results not shown). Serum PA protein and anti-PA antibody levels were also determined for blood collections taken at days 1, 2 and 4 (data not shown). Bacteremia was determined at Days 2, 7, 14 and at death (see below).

Study Termination: 14 days post-challenge, following blood collection, surviving animals were euthanized and a complete necropsy was performed and recorded. Tissue samples from all deaths (scheduled or unscheduled) were collected from liver, lung, mediastinal lymph node, spleen, kidney and brain.

Results: The efficacy of the treatments was assessed in three ways. First, the number of animals surviving at least 14 days post-challenge was recorded. Second, if animals died within the two weeks post challenge, the time to death was recorded. Third, the bacteremia of the blood at 2, 7 and 14 days post-challenge and at death was also assessed.

Results of this experiment are shown in FIG. 6 and Table 1 below. All statistical tests are 2-sided and performed at the 5% level of significance.

The percentage of animals surviving to 14 days post-challenge among the vehicle control and PA mAb treated groups were compared using the Fisher's exact test. The survival at 14 days post-challenge is significantly different among the vehicle control and PA mAb treated groups (p-value <0.0001, Table 1). Compared with the vehicle control group (survival at Day 14=0%), the survival at Day 14 is significantly higher in the 5.0 mg/kg sc group (42%, p-value=0.0373), in both 10 mg/kg sc and 20 mg/kg sc groups (83%, p-value <0.0001), and in the 40 mg/kg iv group (100%, p-value <0.0001).

TABLE 12

Summary of the survival at Day 14 among all rabbits (N = 12 per group)

| Treatment | Survivors | P-value vs. Control[a] |
|---|---|---|
| Vehicle | 0 (0%) | |
| 1 mg/kg sc | 0 (0%) | NA |
| 5 mg/kg sc | 5 (42%) | 0.0373 |
| 10 mg/kg sc | 10 (83%) | <0.0001 |
| 20 mg/kg sc | 10 (83%) | <0.0001 |
| 40 mg/kg iv | 12 (100%) | <0.0001 |

[a]obtained from a 2-sided Fisher's exact test. The p-values for the comparison among all groups are <0.0001, regardless of the inclusion or exclusion of the 40 mg/kg iv group in the analysis.

The Cochran-Armitage test was used to examine the dose response trend of the survival at 14 days post-challenge among the vehicle control and PA mAb sc treated groups. There is a significant dose-response trend with respect to the survival at day 14 (p-value <0.0001). The percentage of animals of surviving to day 14 increase significantly as the dose level of PA mAb (PWD 0587) increases.

The survival time from spore challenge to death was analyzed using a log-rank test. The survival time for the rabbits that survived at the end of follow-up is censored at the 14-day study period. The survival time of the rabbits is significantly different among the vehicle control and PA mAb treated groups (p-value <0.0001, FIG. 1). Compared with the vehicle control group (median survival time=2 days), the median survival times are 3 days in the 1 mg/kg sc group (p-value=0.0002), 6.5 days in the 5 mg/kg sc group (value <0.0001), and more than 14 days in the 10 mg/kg sc, 20 mg/kg sc, and 40 mg/kg iv groups (all values <0.0001), respectively.

The incidence of bacteremia in blood samples was also analyzed (See Table 13).

TABLE 13

Number of Animals with Bacteremia at Day 2, Day 7 or at Death

| Treatment | Day 2 | Day 7[A] | Death (see FIG. 6) |
|---|---|---|---|
| Vehicle | 12/12 | NA | 11/12 animals died on Day 2; 1 animal survived to Day 3 |
| 1 mg/kg sc | 0/12 | NA | 12/12 animals died prior to Day 7; 10/12 animals were bacteremic at death |
| 5 mg/kg sc | 0/12 | 0/5 | 7/12 animals died on or prior to Day 7. 5 of those 7 animals were bacteremic at death |
| 10 mg/kg sc | 0/12 | 1/10 | One animal died at day 6. A second animal died at day 7. Neither of these animals were bacteremic at death. |
| 20 mg/kg sc | 1/12[B] | 1/10 | One animal died at day 5. A second animal died at day 7. One of the animals was bacteremic at death. |
| 40 mg/kg iv | 0/12 | 0/12 | 12/12 animals survived to Day 14. No bacteremia was observed in 12/12 animals. |

[A]Bacteremia of surviving animals indicated.
[B]Bacteremic animal at day 2 survived.

In summary, subcutaneous administration of anti-PA monoclonal antibody 2 days prior to lethal challenge with anthrax spores significantly prolongs time to death and/or increases the survival rate of challenged animals. Bacteremia was most often associated with found dead or moribund necropsied rabbits. Preliminary results showed no evidence of gross pathology at terminal necropsy.

Example 12

Cynomolgus Monkey Inhalation Spore Challenge Study

The following study was designed to examine the efficacy of an anti-PA monoclonal antibody, administered as a prophylactic treatment, against lethality due to inhalational exposure to *Bacillus anthracis* in cynomolgus monkeys.

40 cynomolgus monkeys were randomly assigned to four groups, each containing 10 animals. Animals in each group were each challenged via aerosol inhalation of anthrax spores, 2 days after receiving anti-PA antibody (PWD0587) at 10, 20 or 40 mg/kg or vehicle control. Animals were exposed via aerosolization to a target dose of 100×$LD_{50}$ of *B. anthracis* spores. Post-exposure measurements indicated that animals were actually exposed to spore challenge dose of 186×$LD_{50}$.

Statistical Methods

The primary efficacy endpoint is survival at Day 28 following spore challenge. Difference in 28-day survival between any one of the PA mAb treated groups and the vehicle control group are evaluated by 2-tailed Fisher's exact test. The secondary efficacy endpoint is survival time, defined as the time from spore challenge to death during the 28-day study. The Cochran-Armitage test is used to examine the dose response trend among the groups.

The survival time from spore challenge to death was analyzed using a log-rank test. The survival time for the monkeys that survived at the end of follow-up is censored at the 28-day study period. All statistical tests are 2-sided and performed at the 5% level of significance.

Results

FIG. 7 shows the percent survival of cynomolgus monkeys prophylactically treated with anti-PA monoclonal antibody PWD0587 (IgG1 format) and challenged with a lethal aerosolized dose of *B. anthracis* spores. Survival is significantly different among the vehicle control and PA mAb treated groups (P value=0.0002). Compared with the vehicle control group, survival is significantly higher in the 10 mg/kg group (60%, P value=0.0108), the 20 mg/kg group (70%, P value=0.0031), and 40 mg/kg group (90%, P value=0.0001) (Table 14). There is a significant dose-response trend with respect to survival (P value=0.0002). The survival at Day 28 increases significantly as the dose level of PWD0587 increases.

TABLE 14

| Survival in monkey study | | |
|---|---|---|
| Treatment | Survivors | P Value vs. Control[a] |
| Vehicle | 0 (0%) | |
| 10 mg/kg | 6 (60%) | 0.0108 |
| 20 mg/kg | 7 (70%) | 0.0031 |
| 40 mg/kg | 9 (90%) | 0.0001 |

[a]obtained from a 2-sided Fisher's exact test. The P value = 0.0002 for the comparison among all groups.

The survival time of the monkeys is significantly different among the vehicle control and PA mAb treated groups (P value <0.0001, FIG. 7). Compared with the vehicle control group (median survival time=4 days), the median survival times in all 3 PWD0587 treatment groups are significantly longer (more than 28 days; all P values ≦0.0005), FIG. 7. None of the surviving PA mAb-treated animals had positive (bacteremic) blood cultures at Days 7, 14, or 21 or 28.

Example 13

Detection of Neutralizing Antibodies Against Anthrax Protective Antigen by Edema Factor-Mediated cAMP Induction Assay As described above, antibodies that neutralize the biological activity of PA protein can be identified by using a rubidium release assay such as the one described in Example 5 and/or a lethal toxin mediated cell killing assay such as the one described in Example 8. An additional assay which can be used to identify neutralizing antibodies against PA is an edema factor-mediated cAMP induction assay. This bioassay is based upon the ability of edema factor, a bacterial adenylate cyclase dependent upon PA for entry into cells, to bind PA and enter cells leading to a measurable increase in cAMP. In the presence of antibodies that neutralize PA, edema factor (EF) is inhibited from entering cells and reduced cAMP levels are observed.

Briefly, cells expressing anthrax receptor are exposed to edema toxin (PA+EF). Levels of cAMP in the cells are measured by any method known in the art, for example by ELISA using an anti-cAMP antibody. The ability of an antibody to inhibit edema toxin mediated increases in intracellular levels cAMP can be assayed by pre-incubating the edema toxin with a test antibody and then exposing the cells expressing anthrax receptor with the antibody/edema toxin mixture.

By way of non-limiting example, cAMP levels induced by edema factor, and the inhibition of same by anti-PA antibodies of the invention, can be measured using the following assay. 4000 Chinese Hamster Ovary cells in 100 microliters of CHO culture medium (CCM; F-12K growth medium (Invitrogen, Carlsbad, Calif.) supplemented with 10% fetal bovine serum, 100 units/ml penicillin and 100 micrograms/ml streptomycin) are seeded into cAMP-Direct ELISA plates (Applied Biosystems, Foster City, Calif.; Cat No. T1507). Cells are incubated at 37° C., 5% $CO_2$, greater than 85% relative humidity while test samples are prepared.

In a separate assay plate, test antibodies starting at a concentration of 60 micrograms/milliliter in CCM/IBMX (CCM supplemented with 250 micromoles 3-isobutyl-1 methylxanthine) are diluted 3-fold for a total 10 serial dilutions in CCM/IBMX. 75 microliters of each dilution of antibody is then added to 75 microliters of PA/EF solution (1200 nanograms/milliliter PA and 100 nanograms/milliliter EF in CCM/IBMX). anti-PA/edema toxin mixture is incubated at 37° C., 5% $CO_2$ for one hour.

At the end of the hour, the cell culture medium supernatant from the cAMP-Direct ELISA plates onto which CHO cells have been plated (described above), is removed. Then 100 microliters of the anti-PA/edema toxin mixture is added to the wells containing the cells which are then incubated at 37° C., 5% $CO_2$ for one hour. At the end of the hour, the anti-PA/edema toxin mixture is removed and 60 microliters of lysis buffer is added to the cells. From this point forward, the cAMP-Direct ELISA is completed according to the manufacturer's instructions. In the absence of neutralizing antibody, cAMP levels induced by edema toxin are approximately 100 fold greater than that induced by controls (e.g. samples containing no EF).

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, in both computer and paper forms, is hereby incorporated by reference in its entirety.

The entire disclosure (including the specification, sequence listing, and drawings) of each of U.S. patent application Ser. No. 10/602,727, filed Jun. 25, 2003 and U.S. Provisional Application Nos. 60/391,162, filed Jun. 26, 2002, 60/406,339, filed Aug. 28, 2002, 60/417,305, filed Oct. 10, 2002, 60/426,360, filed Nov. 15, 2002, 60/434,807, filed Dec. 20, 2002, 60/438,004, filed Jan. 6, 2003, 60/443,858 filed Jan. 31, 2003, 60/443,781, filed Jan. 31, 2003, 60/454,613 filed Mar. 17, 2003, and 60/468,651 filed May 8, 2003 is herein incorporated by reference in its entirety.

The invention claimed is:

1. A composition comprising a monoclonal antibody produced by the cell line contained in ATCC Deposit Number PTA-4796 and a carrier.

2. A pharmaceutical composition comprising the composition of claim 1, wherein said carrier is a pharmaceutically acceptable carrier.

3. The pharmaceutical composition of claim 2 wherein said pharmaceutically acceptable carrier further comprises sodium citrate, sucrose, glycine, and polysorbate 80.

4. The pharmaceutical composition of claim 2 wherein said composition has a pH of 6.5.

5. A method of treatment of anthrax infection or anthrax toxin poisoning comprising administering the pharmaceutical composition of claim 2 to a human patient.

6. The method of claim 5 wherein said antibody is administered intravenously at 40 mg/kg of the patient's body weight.

7. The method of claim 5 further comprising the administration of an antibiotic.

8. The method of claim 7 wherein the antibiotic is ciprofloxacin.

9. The method of claim 7 wherein the antibiotic is doxycycline.

10. The method of claim 7 wherein the antibiotic is levofloxacin.

11. A method of treating or reducing bacteremia associated with anthrax infection comprising administering the pharmaceutical composition of claim 2 to a human patient.

12. The method of claim 11 wherein said antibody is administered intravenously at 40 mg/kg of the patient's body weight.

13. The method of claim 11 further comprising the administration of an antibiotic.

14. The method of claim 13 wherein the antibiotic is ciprofloxacin.

15. The method of claim 13 wherein the antibiotic is doxycycline.

16. The method of claim 13 wherein the antibiotic is levofloxacin.

17. A monoclonal antibody having the amino acid sequence of the monoclonal antibody produced by the cell line contained in ATCC Deposit Number PTA-4796.

18. A pharmaceutical composition comprising the antibody of claim 17 and a pharmaceutically acceptable carrier.

19. The pharmaceutical composition of claim 18 wherein said pharmaceutically acceptable carrier further comprises sodium citrate, sucrose, glycine, and polysorbate 80.

20. The pharmaceutical composition of claim 18 wherein said composition has a pH of 6.5.

21. A method of treatment of anthrax infection or anthrax toxin poisoning comprising administering the pharmaceutical composition of claim 18 to a human patient.

22. The method of claim 21 wherein said antibody is administered intravenously at 40 mg/kg of the patient's body weight.

23. The method of claim 21 further comprising the administration of an antibiotic.

24. The method of claim 23 wherein the antibiotic is ciprofloxacin.

25. The method of claim 23 wherein the antibiotic is doxycycline.

26. The method of claim 23 wherein the antibiotic is levofloxacin.

27. A method of treating or reducing bacteremia associated with anthrax infection comprising administering the pharmaceutical composition of claim 18 to a human patient.

28. The method of claim 27 wherein said antibody is administered intravenously at 40 mg/kg of the patient's body weight.

29. The method of claim 27 further comprising the administration of an antibiotic.

30. The method of claim 29 wherein the antibiotic is ciprofloxacin.

31. The method of claim 29 wherein the antibiotic is doxycycline.

32. The method of claim 29 wherein the antibiotic is levofloxacin.

33. A pharmaceutical composition comprising:
(a) a monoclonal antibody having the amino acid sequence of the monoclonal antibody produced by the cell line contained in ATCC Deposit Number PTA-4796; and
(b) a pharmaceutically acceptable carrier comprising sodium citrate, sucrose, glycine, and polysorbate 80; wherein said composition has a pH of 6.5.

34. A method of treatment of anthrax infection or anthrax toxin poisoning comprising administering a pharmaceutical composition to a human patient, wherein said composition comprises:
(a) a monoclonal antibody having the amino acid sequence of the monoclonal antibody produced by the cell line contained in ATCC Deposit Number PTA-4796; and
(b) a pharmaceutically acceptable carrier comprising sodium citrate, sucrose, glycine, and polysorbate 80; wherein said composition has a pH of 6.5, and wherein said pharmaceutical composition is administered intravenously at 40 mg of said antibody per kg of the patient's body weight.

35. The method of claim 34 further comprising the administration of an antibiotic.

36. The method of claim 35 wherein the antibiotic is ciprofloxacin.

37. The method of claim 35 wherein the antibiotic is doxycycline.

38. The method of claim 35 wherein the antibiotic is levofloxacin.

39. A method of treating or reducing bacteremia associated with anthrax infection comprising administering a pharmaceutical composition to a human patient, wherein said composition comprises:
(a) a monoclonal antibody having the amino acid sequence of the monoclonal antibody produced by the cell line contained in ATCC Deposit Number PTA-4796; and
(b) a pharmaceutically acceptable carrier comprising sodium citrate, sucrose, glycine, and polysorbate 80; wherein said composition has a pH of 6.5, and wherein said pharmaceutical composition is administered intravenously at 40 mg of said antibody per kg of the patient's body weight.

40. The method of claim 39 further comprising the administration of an antibiotic.

41. The method of claim 40 wherein the antibiotic is ciprofloxacin.

42. The method of claim 40 wherein the antibiotic is doxycycline.

43. The method of claim 40 wherein the antibiotic is levofloxacin.

44. A composition comprising the human monoclonal antibody of claim 17 and a carrier.

* * * * *